(12) United States Patent
Scanlan et al.

(10) Patent No.: US 7,355,079 B2
(45) Date of Patent: Apr. 8, 2008

(54) THYRONAMINE DERIVATIVES AND ANALOGS AND METHODS OF USE THEREOF

(75) Inventors: Thomas S. Scanlan, San Francisco, CA (US); Matthew E. Hart, San Francisco, CA (US); David K. Grandy, Portland, OR (US); James R. Bunzow, Portland, OR (US); Motonori Miyakawa, South San Francisco, CA (US); Edwin Saavedra Tan, San Francisco, CA (US); Katherine L. Suchland, Portland, OR (US)

(73) Assignees: The Regents of the University of California, Oakland, CA (US); Oregon Health & Science University, Portland, OR (US)

( * ) Notice: Subject to any disclaimer, the term of this patent is extended or adjusted under 35 U.S.C. 154(b) by 286 days.

(21) Appl. No.: 11/099,959

(22) Filed: Apr. 5, 2005

(65) Prior Publication Data

US 2006/0035980 A1    Feb. 16, 2006

Related U.S. Application Data

(63) Continuation-in-part of application No. 10/825,881, filed on Apr. 16, 2004, which is a continuation-in-part of application No. 10/418,399, filed on Apr. 18, 2003, now Pat. No. 6,979,750.

(51) Int. Cl.
*C07C 211/27* (2006.01)
*A61K 31/135* (2006.01)

(52) U.S. Cl. .............. 564/374; 564/316; 564/336; 564/347; 514/648; 514/649; 514/651; 514/654

(58) Field of Classification Search ............. None
See application file for complete search history.

(56) References Cited

U.S. PATENT DOCUMENTS

| | | | |
|---|---|---|---|
| 3,791,932 A | 2/1974 | Schuurs et al. | 435/7.8 |
| 3,817,837 A | 6/1974 | Rubenstein et al. | 435/7.9 |
| 3,839,153 A | 10/1974 | Schuurs et al. | 435/7.93 |
| 3,850,578 A | 11/1974 | McConnell | 436/536 |
| 3,850,752 A | 11/1974 | Schuurs et al. | 435/7.93 |
| 3,853,987 A | 12/1974 | Dreyer | 424/1.37 |
| 3,867,517 A | 2/1975 | Ling | 436/531 |
| 3,879,262 A | 4/1975 | Schuurs et al. | 435/7.93 |
| 3,901,654 A | 8/1975 | Gross | 436/172 |
| 3,935,074 A | 1/1976 | Rubenstein et al. | 435/7.9 |
| 3,984,533 A | 10/1976 | Uzgiris | 436/516 |
| 3,996,345 A | 12/1976 | Ullman et al. | 436/537 |
| 4,034,074 A | 7/1977 | Miles | 436/518 |
| 4,098,876 A | 7/1978 | Piasio et al. | 436/500 |
| 4,366,241 A | 12/1982 | Tom et al. | 435/7.91 |
| 4,376,110 A | 3/1983 | David et al. | 435/5 |
| 4,391,904 A | 7/1983 | Litman et al. | 435/7.91 |
| 4,486,530 A | 12/1984 | David et al. | 435/7.91 |
| 4,517,288 A | 5/1985 | Giegel et al. | 435/5 |
| 4,634,664 A | 1/1987 | Oestberg | 435/70.21 |
| 4,634,666 A | 1/1987 | Engleman et al. | 435/70.21 |
| 4,837,168 A | 6/1989 | de Jaeger et al. | 436/533 |
| 5,225,539 A | 7/1993 | Winter | 530/387.3 |
| 5,530,101 A | 6/1996 | Queen et al. | 530/387.3 |
| 5,565,332 A | 10/1996 | Hoogenboom et al. | 435/69.1 |
| 5,585,089 A | 12/1996 | Queen et al. | 424/133.1 |
| 5,693,761 A | 12/1997 | Queen et al. | 536/23.53 |
| 5,693,762 A | 12/1997 | Queen et al. | 530/387.3 |
| 5,733,743 A | 3/1998 | Johnson et al. | 435/69.1 |
| 5,837,242 A | 11/1998 | Holliger et al. | 424/136.1 |
| 5,858,657 A | 11/1998 | Winter et al. | 435/6 |
| 5,871,907 A | 2/1999 | Winter et al. | 435/6 |
| 5,877,218 A | 3/1999 | Herzig et al. | 514/617 |
| 5,914,241 A | 6/1999 | Valkirs | 435/7.4 |
| 5,965,375 A | 10/1999 | Valkirs | 435/7.2 |
| 5,969,108 A | 10/1999 | McCafferty et al. | 530/387.3 |
| 5,994,519 A | 11/1999 | Osbourn et al. | 530/413 |
| 6,172,197 B1 | 1/2001 | McCafferty et al. | 530/387.3 |
| 6,180,336 B1 | 1/2001 | Osbourn et al. | 435/5 |
| 2005/0096485 A1 | 5/2005 | Scanlan et al. | 564/162 |

FOREIGN PATENT DOCUMENTS

| | | |
|---|---|---|
| JP | 11-302235 | 11/1999 |
| WO | WO 90/07861 | 7/1990 |
| WO | WO 90/14334 | 11/1990 |
| WO | WO 91/17271 | 11/1991 |
| WO | WO 92/01047 | 1/1992 |
| WO | WO 92/22653 | 12/1992 |
| WO | WO 98/27972 | 7/1998 |
| WO | WO 00/72811 | 12/2000 |
| WO | WO 01/56989 | 8/2001 |
| WO | WO 02/060375 | 8/2002 |
| WO | WO 03/002078 | 1/2003 |
| WO | WO 03/106380 | 12/2003 |
| WO | WO 2004/020415 | 3/2004 |
| WO | WO 2005/000309 | 1/2005 |

OTHER PUBLICATIONS

Database CAPLUS on STN, Acc. No. 1966:4055, Furukawa, Yakugaku Zasshi (1965), 85(9), p. 850-4 (abstract).*

(Continued)

*Primary Examiner*—Brian J. Davis
(74) *Attorney, Agent, or Firm*—Woodcock Washburn LLP

(57) ABSTRACT

Thyronamine derivatives and analogs, methods of using such compounds, and pharmaceutical compositions containing them are disclosed. Methods of preparing such compounds are also disclosed.

17 Claims, 22 Drawing Sheets

OTHER PUBLICATIONS

Akerstrom, B. et al., "Protein G: A Powerful Tool for Binding and Detection of Monoclonal and Polyclonal Antibodies," *J. Immunol.*, 1985, 135(4), 2589-2592.

Biondi, B., et al., "Effects of Subclinical Thyroid Dysfunction on the Heart", *Ann Intern Med.*, 137: 904-914, 2002.

Boissier, J.R., et al., "Differential Inotropic-Chronotropic Action of Thyronamine", *Eur. J. Pharmacol.* 22: 141-149, 1973.

Borowsky, B., et al., "Trace amines: Indentification of a family of mammalian G protein-coupled receptors", *Proc. Natl. Acad. Sci.* 98: 8966-8971, 2001.

Bunzow, J.R., et al., "Amphetamine, 3,4-Methylenedioxymethamphetamine, Lysergic Acid Diethylamide, and Metabolites of the Catecholamine Neurotransmitters are Agonists of a Rat Trace Amine Receptor", *Mol. Pharmacol.* 60: 1181-1188, 2001.

Buu-Hoi, N.P. et al., "Some Biological Effects of Thyronamine", *Med. Pharmacol. exp.* 15: 17-23, 1966.

Buu-Hoi, N.P. et al., "Thyronamine, a New Substance with Long-acting positive Inotropic Effect", *Pharmacology* 2: 281-287, 1969.

Cody et al., "Molecular Structure and Biochemical Activity of 3,5,3'-Triiodothyronamine", *Endocrine Research*, 10: 91-99, 1984.

Cote, P., et al., "Thyronamine, a new inotropic agent: its cardiovascular effects and mechanism of action", *Cardiovascular Res.* 8: 721-730, 1974.

Database CAPLUS on STN, Acc. No. 1971:135556, Fuller et al., *J. of Medicinal Chemistry*, 1971, 14(4), 322-325.

Dratman, M., "On the Mechanism if Action of Thyroxin, an Amino Acid Analog of Tyrosine", *J. theor. Biol.*, 46: 255-270, 1974.

Falkenstein, E., et al., "Multiple Actions of Steriod Hormones-A Focus on Rapid, Nongenomic Effects", *Pharmacol. Rev.* 52:513-555, 2000.

Fingl, E. et al., "General Principles," *The Pharmacological Basis of Therapeutics*, 1975, Goodman, L.S. et al. (eds.), Chapter1, Fifth Edition, 1-46.

Hamilton, M.A., et al., "Safety and Hemodynamic Effects of Intravenous Triiodothyronine in Advanced Congestive Heart Failure", *Am. J. Cardiol.*. 81: 443-447, 1998.

Han, et al., "Synthesis of side chain-modified idothyronines", *Int. J. Peptide Protein Res.*, 30: 652-661, 1987.

Huse, W.D. et al., "Generation of a Large Combinatorial Library of the Immunoglobulin Repertoire in Phage Lambda," *Science*, 1989, 246, 1275-1281.

Köhler, G. et al., "Continuous Cultures of Fused Cells Secreting Antibody of Predefined Specificity," *Nature*, 1975, 256, 495-497.

Köhler, G. et al., "Derivation of Specific Antibody-Producing Tissue Culture and Tumor Lines by Cell Fusion," *Eur. J. Immunol.*, 1976, 6, 511-519.

Kronval, G., "A Surface Component in Group A, C, and G Streptococci with Non-Immune Reactivity for Immunoglobulin G," *J. Immunol.*, 1973, 111(5), 1401-1406.

Meyer, T., et al., "Triiodothyronamine- A Beta-adrenergic Metabolite of Triiodothyronine?", *Horm. metabol. Res.* 15: 602-606, 1983.

Monroe, D., "Liposome Immunoassay: A New Ultrasensitive Analytical Method," *Amer. Clin. Prod. Rev.*, 1986, 5, 34-41.

Nillne, E.A. et al., "Deficiencies in Pro-thyrotropin-releasing Hormone Processing and Abnormalities in Thermoregulation in Cpe$^{fat/}$$_{fat}$ Mice," *J. Biol. Chem.*, 2002, 277(50), 48587-48595.

Östberg, L. et al., "Human x (Mouse x Human) Hybridomas Stably Producing Human Antibodies," *Hybridoma*, 1983, 2(4), 361-367.

Petit, L. et al., "A Synthesis of Thyronamine and Its Lower Homolog", *J. org. Chem.* 26: 3832-3834, 1961.

Queen, C. et al., "A Humanized Antibody that Binds to the Interleukin 2 Receptor," *Proc. Natl. Acad. Sci. USA*, 1989, 86, 10029-10033.

Ribeiro, M.O. et al., "Thyroid hormone-sympathetic interaction and adapative thermogenesis are thyroid hormone receptor isoform-specific," *J. Clin. Invest.*, 2001, 108(1), 97-105.

Rozanov, C.B., et al., "Immunohistochemical Mapping of Brain Triiodothyronine Reveals Prominent Localization in Central Noradrenergic Systems", *Neuroscience*, 74: 897-915, 1996.

Stöhr, R., "Synthese des Thyronamins", *Hoppe-Seyler Z. physiol. Chem.* 201: 142-149, 1931

Sun, Z.-Q., et al., "Effects of thyroid hormone on action potential and repolarizing currents in rat ventricular myocytes", *Am. J. Physiol. Endocrinol. Metab.* 278: E302-E307, 2000.

Thibault, O., "Recherhes sur la nature de la <<thyroxine active>>. Renforcement immediate par la thyroxamine des effets de l'adrénaline sur divers muscles lisses", 1951 *C. R. Soc. Chim. biol.*, 797-800.

Tomita, K., et al., "Synthesis and Biological Activity of Some Triiodinated Analogues of Thyroxine", *J. Biol. Chem.* 219: 595-604, 1956

Walker, J.D., et al., "The novel effects of 3,5,3'-triiodo-L-thyronine on myocyte contractile function and β-adrenergic responsivness in dilated cardiomyopathy", *J. Thorac. Cardiovasc. Surg.* 108: 672-679, 1994.

Ward, E.S. et al., "Binding Activities of a Repertoire of Single Immunoglobulin Variable Domains Secreted from *Escherichia coli*," *Nature*, 1989, 341, 544-546.

Yen, P.M., "Physiological and Molecular Basis of Thyroid Hormone Action", *Physiol. Rev.* 81: 1097-1142, 2001.

Scanlan et al., "3-Iodothyronamine is an endogenous and rapid-acting derivative of thyroid hormone," *Nature Medicine* 10(6):638-642, 2004.

Lindemann et al., "Trace amine-associated receptors from structurally and functionally distinct subfamilies of novel G protein-coupled receptors," *Genomics* 85:372-385, 2005.

Barnes, J.H. et al., "Synthesis of throxine and related substances, XII, Preparation of simple analogs of thyroxine," *Journal of the Chemical Society*, 1953, Database CA [online], Accession No. *1954:24942*, abstract, 1 page.

Barton, D.H.R. et al., "The biosynthesis of Amaryllidaceae alkaloids," *Proc. Chem. Soc.*, 1961, Database CA [online], Accession No. *1961:137639*, abstract, 1 page.

Bhakuni, D.S. et al., "Synthesis of (.+-.)-scoulerine, (.+-.)-coreximine, (.+-.)- tetrahydropalmatine and their monobromo and bidromo derivatives," *Indian Journal of Chemistry, Section B: Organic Chemistry Including Medicinal Chemistry*, 1983, Database CA [online], Accession No. *1983:488435, 22B(1)*, abstract, 1 page.

Bompart, Jaques et al., "Synthesis of new .beta.-blocking analogs of bevantolol," *Annales oPharmaceutiques Francaises*, 1985, Database CA [online], Accession No. *1985:215069 42(5)*, abstract, 1 page.

Chen, Chi-Ming et al., "Synthesis of (.+-.)-annonelliptine and (.+-.)-anomoline," *Journal of Natural Products*, 1995, Database CA [online], Accession No. *1996:52130, 58(11)*, abstract, 1 page.

Davis, Bruce, "crown ether-catalyzed deuterium exchange in the synthesis of benzyl cyanides," *Journal of Labelled Compounds and Radiopharmaceuticals*, 1987, Database CA[online], Accession No. *1987:575570, 24(2)*, abstract, 1 page.

Funke, A. et al., "Preparation of several series of amine derivatives of diphenyl ethers," *Bulletin de la Societe Chimique de France*, 1951, Database [online], Accession No. *1953:25301*, abstract, 1 page.

Horvath, Dragos, "A Virtual Screening Approach Applied to the Search for Trypanothione Reductase Inhibitors," *J. Med. Chem.*, 1997, 40, 2412-2423.

Il'yuchenok, I. Yu. et al., "Radioprotective and pharmacological properties of some phenylethylamine derivatives," 1976, Database CA [online], Accession No. *1977:218, 39(5)*abstract, 1 page.

Kametani, Tetsuji et al., "Syntheses of heterocyclic compounds, CCCLXXXVI, Alternative total syntheses of galanthamine and N-benzylgalanthamine iodide," *Journal of the Chemical Society*, 1971, Database CA [online], Accession No. *1971:406156, 6*, abstract, 1 page.

Kametani, Tetsuji et al., "Studies on the Syntheses of heterocyclic compounds. CCCXV. Modified total synthesis of (=)-galanthamine through phenol oxidation," *Journal of the Chemical Society*, 1969, Database CA [online], Accession No. *1970:21811, section C (18)*, abstract, 1 page.

Kim, Jin Mi et al., "Preparation of 4-amino-1-benzylpiperidines as antimalarials," *WO 01/14331Regents of University of California*, 2001, Database CA [online], *Accession No. 2001:152643*, abstract, 2 pages.

Kukovinets, O.S. et al., "Synthesis of fenoxycarb, a highly active juvenoid and its analog," *Bashikirskii Khimicheskii Zhurnal*, 1995, Database CA [online], *Accession No. 1996:246214, 2(1)*, abstract, 1 page.

Lu, Rong Jian et al., "Detritylation with ytterbium triflate," *Tetrahedron Letters*, 2000, Database CA [online], *Accession No. 2000:303504, 41(16)*, abstract, 1 page.

Slotta, K.H. et al., "Synthesis of thyroxine-like substances from diphenyl ether," *Berichte der Deutschen Chemischen Gesellschaft [Abteilung] B: Abhandlungen*, 1936, Database CA [online], *Accession No. 1936:34165, 65(B)*, abstract, 1 page.

Suzuki, Toshikazu et al., "Metabolism of a new cardiotonic agent, (−)-.alpha.-(3,4-dimethoxyphenethylaminomethyl)-4-hydroxybenzyl alcohol (TA-064), in man. O-Dimethylation and ring hydroxylation," *Drug Metabolism and Disposition*, 1983, Database Ca [online], *Accession No. 1983:515496, 11(4)*, abstract, 1 page.

Buu-Hoi, N.P. et al., "Synthesis and pharmacological properties of 3,5-diiodothyronamine," *Chimica Therapeutica*, 1969, 4(3), 151-156, abstract only, CAPLUS 1969-490981.

* cited by examiner

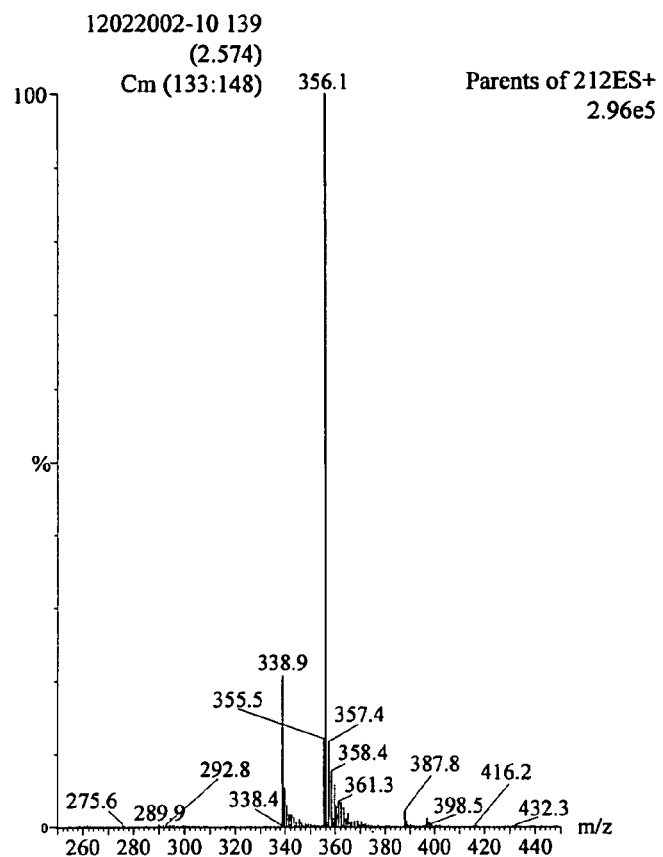
Figure 5C
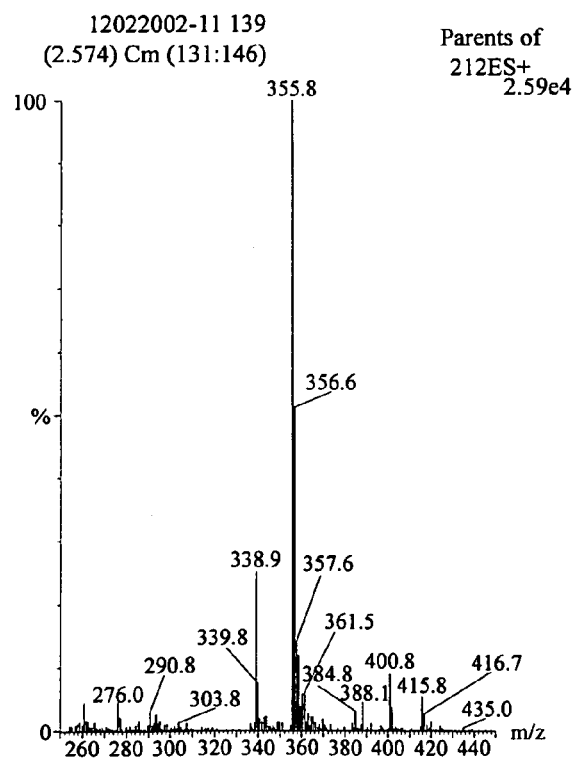

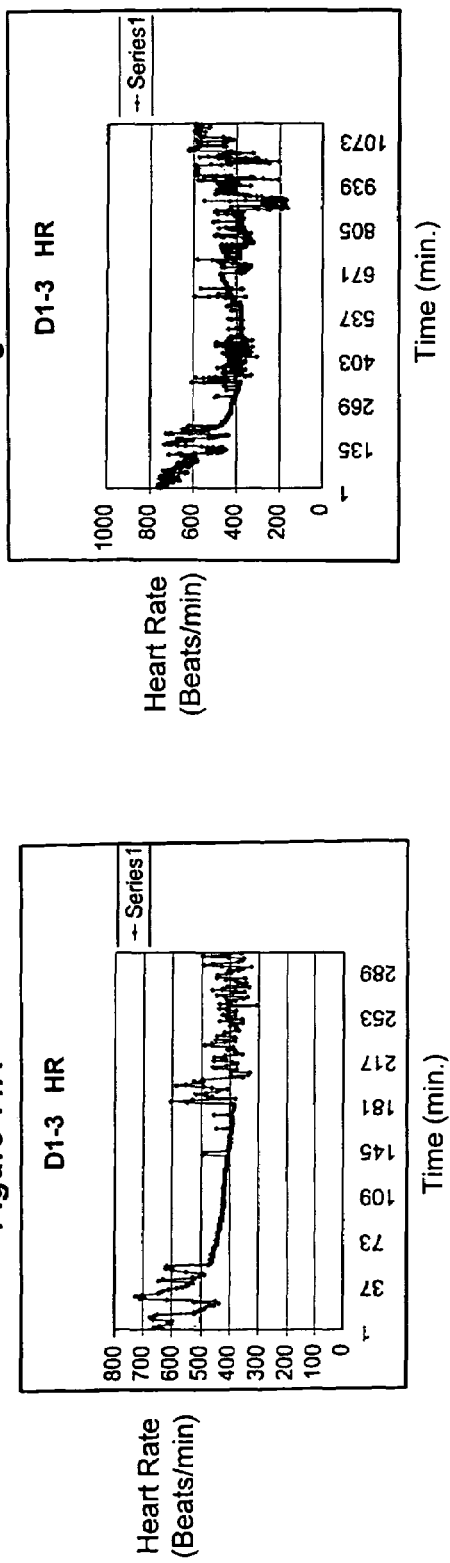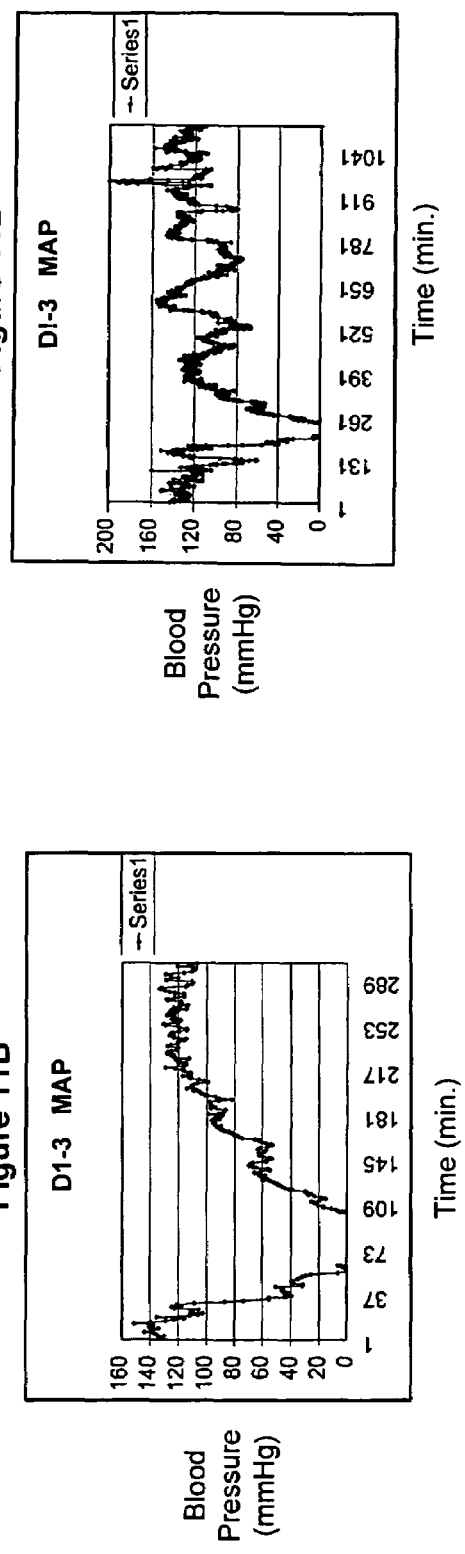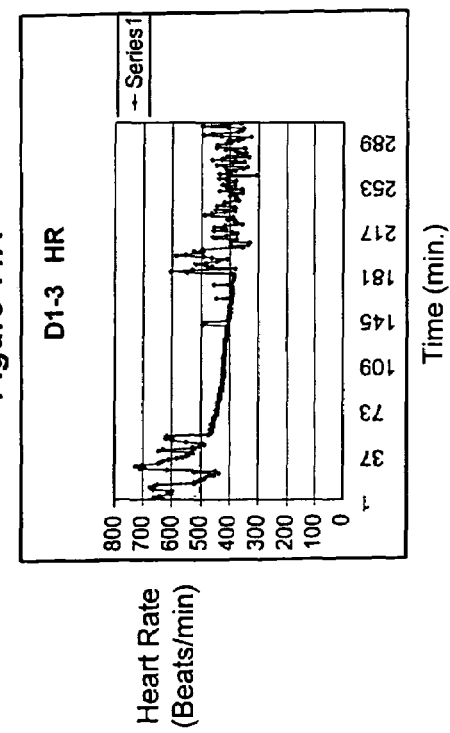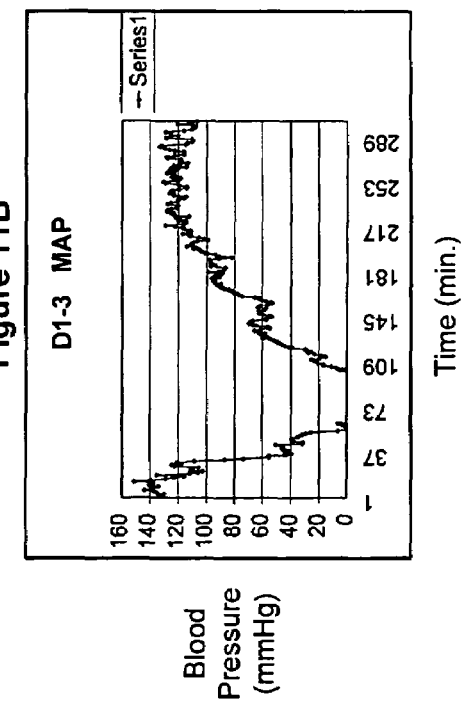

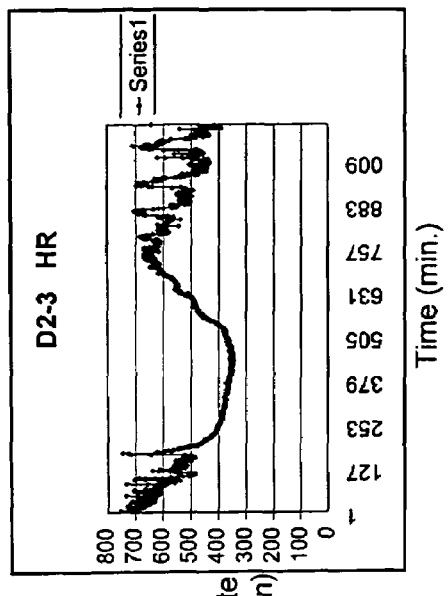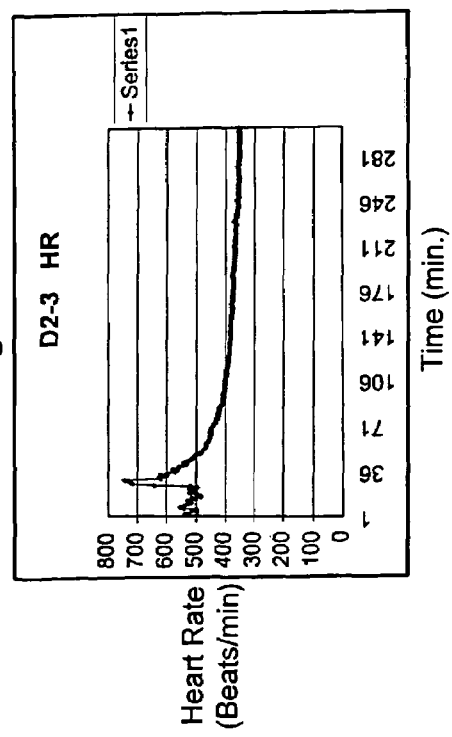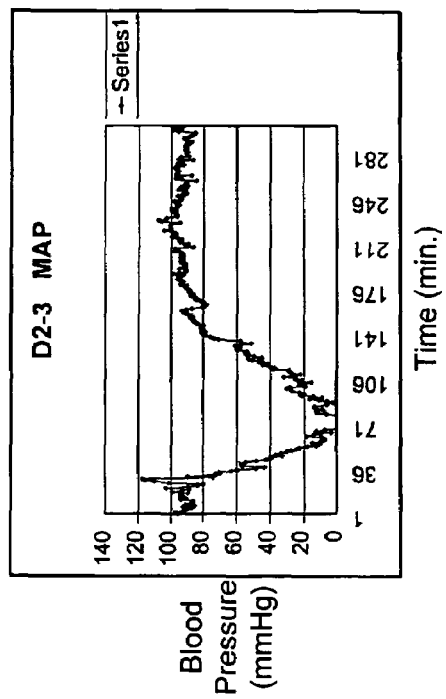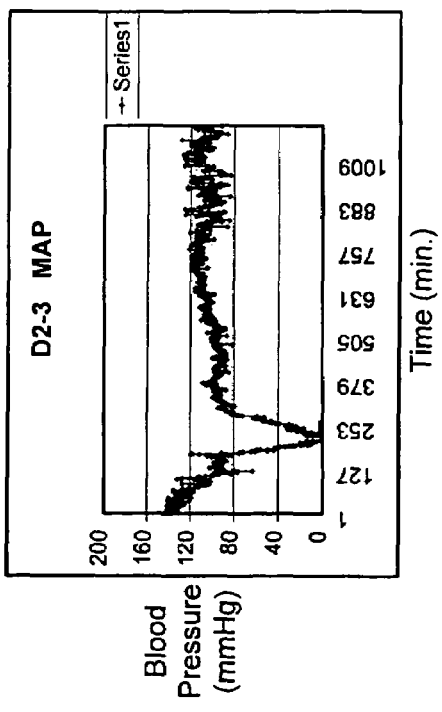

Figure 20    Mass Spectrometry Peak Intensities

| | Peak Intensity, Thousands (95% CI) | S.D. |
|---|---|---|
| Serum T1AM | 452 (379-525) | 134 |
| Serum T0AM | 155 (128-181) | 49 |
| Plasma T1AM | 124 (96-153) | 53 |
| Plasma T0AM | 97 (90-103) | 11 |

THYRONAMINE DERIVATIVES AND ANALOGS AND METHODS OF USE THEREOF

CROSS REFERENCE TO RELATED APPLICATIONS

This application is a continuation-in-part of U.S. application Ser. No. 10/825,881, filed Apr. 16, 2004 (currently pending), which is a continuation-in-part of U.S. application Ser. No. 10/418,399, filed Apr. 18, 2003 (U.S. Pat. No. 6,979,750), the disclosures of which are incorporated herein by reference.

STATEMENT OF GOVERNMENT INTEREST

This invention was made with Government support by Grant Nos. DK52798, DA10703, DA12408, and DA07262-09, awarded by the National Institutes of Health. The Government has certain rights in this invention.

FIELD OF THE INVENTION

This invention generally relates to derivatives and analogs of thyroid hormone. More specifically, the invention relates to thyronamine derivatives and analogs of thyroid hormone, pharmaceutical compositions containing the thyronamine derivatives and analogs, methods of making the thyronamine derivatives and analogs and methods of use thereof.

BACKGROUND OF THE INVENTION

Thyroid hormone is an important regulator of vertebrate development and homeostasis. Yen, P. M., 2001, Physiol. Rev. 81, 1097-1142. Thyroid hormone is critical for normal fetal brain development, and brain disorders such as cretinism can result from a lack of thyroid hormone in the developing fetus. In adults, thyroid hormone exerts effects in almost all tissues, and important processes such as metabolic rate, thermal regulation, lipid inventory, cardiac function, and bone maintenance are affected by thyroid hormone. Individuals with excess blood levels of thyroid hormone (hyperthyroid) generally have elevated metabolic rate and body temperature, decreased serum cholesterol, and increased heart rate compared to those with normal thyroid hormone levels (euthyroid). Conversely, hypothyroidism is characterized by depressed metabolic rate and body temperature, elevated serum cholesterol, and decreased heart rate compared to euthyroid controls.

Thyroxine ($T_4$, FIG. 1) is the predominant form of thyroid hormone that is secreted from the thyroid gland, and $T_4$ is converted to the more physiologically active 3,5,3'-triiodothyronine ($T_3$, FIG. 1) by enzymatic deiodination in peripheral target tissues. Three different deiodinases have been identified to date (D-I, D-II, and D-III). The D-1 and D-II enzymes mediate "outer ring" deiodination such as the conversion of $T_4$ to $T_3$, whereas the D-III enzyme mediates "inner ring" deiodination, exemplified by the conversion of $T_4$ to reverse-$T_3$ ($rT_3$, FIG. 1). To date, no significant biological activity has been ascribed to $rT_3$ even though significant blood levels of this metabolite are found. Moreover, a variety of further deiodinated forms of $T_4$ are known to exist in vivo and the biological significance of these metabolites in unclear.

The majority of known biological activities of thyroid hormone are mediated by binding of $T_3$ to thyroid hormone receptors (TRs). The TRs belong to the nuclear receptor superfamily of hormone-activated transcription factors, and there are two different TR genes, TRα and TRβ. The mRNAs of TRα and TRβ are further processed giving rise to four TR isoforms (TRα$_1$, TRα$_2$, TRβ$_1$, TRβ$_2$) that are co-expressed in ratios that are unique to each tissue. $T_3$ binds to the ligand binding domain (LBD) of nuclear localized TRs, and the activated TR regulates the transcription of hormone responsive genes. In this mode of action, the effects of thyroid hormone are manifested exclusively through positive and negative regulation of hormone-responsive gene transcription.

There are, however, physiological effects of thyroid hormone that are not readily explained by a transcription regulation mode of action. These so-called "non-genomic effects" are characterized by a rapid onset in response to hormone and/or insensitivity to translation inhibitors, such as cyclohexamide. Specific examples of such effects include the rapid contractile response to $T_3$ in cultured cardiac myocytes, the shortening of the action potential with concomitant attenuation of repolarizing currents in ventricular myocytes, and in studies in animals. Falkenstein, E., et al., 2000, Pharmacol. Rev. 52, 513-555; Walker, J. D., et al., 1994, J. Thorac. Cardiovasc. Surg. 108, 672-679; Sun, Z.-Q., et al., 2000, Am. J. Physiol. Endocrinol. Metab. 278, E302-E307; Hamilton, M. A., et al., 1998, Am. J. Cardiol. 81, 443-447; Buu-Hoi, N. P., et al., 1969, Pharmacology 2, 281-287; Boissier, J. R., et al., 1973, Eur. J. Pharmacol. 22, 141-149; Cote, P., et al., 1974, Cardiovascular Res. 8, 721-730. The rapid rate of these effects suggests that they are mediated by receptors other than the nuclear TRs in response to a thyroid hormone. The source and mechanism of these non-genomic effects are not known. Dratman, 1974, J. theor. Biol., 46, 255-270; Han, et al., 1987, Int. J. Peptide Protein Res., 30, 652-661; Rozanov and Dratman, 1996, Neuroscience, 74, 897-915; Tomita and Lardy, J. Biol. Chem. 219: 595-604, 1956. A need exists in the art to understand and regulate/modulate these non-genomic effects related to thyroid hormone. The present invention is directed to these, as well as other important ends.

SUMMARY OF THE INVENTION

The invention is generally related to thyronamine derivatives and analogs of thyroid hormone, pharmaceutical compositions containing the thyronamine derivatives and analogs, methods of making the thyronamine derivatives and analogs and methods of use thereof.

In one embodiment, thyronamine derivatives and analogs are provided of formula:

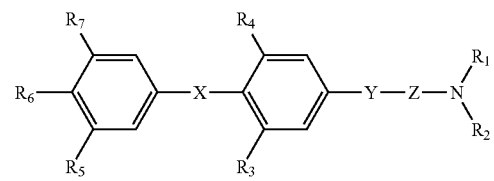

or a stereoisomer, prodrug, pharmaceutically acceptable salt, hydrate, solvate, acid salt hydrate, N-oxide or isomorphic crystalline form thereof;

wherein independently, $R_1$ and $R_2$ are: H, lower alkyl, cyclic alkyl, or benzyl;

Y and Z are: —$[C(R)_2]_n$—, CHOR, O, S, NR, CONH, or NHCO, provided that Y and Z are not both O, both S, both NR, both CONH, both NHCO, or CONH and NHCO;

$R_3$, $R_4$, $R_5$, and $R_7$ are: H, I, Br, Cl, F, $CH_3$, $CF_3$, CN, SR, $OCH_3$, $CH_2CH_3$, or $CH(CH_3)_2$;

$R_6$ is: OR, H, SH, F, $CF_3$, lower alkyl, or $N(R)_2$;

X is: O, S, SO, $SO_2$, NR, $C(R)_2$, -lower alkyl-O—, —O-lower alkyl-, $COCH_2O$, or $OCH_2CO$; and R is H, lower alkyl, aryl optionally substituted with 1-3 substituents selected from the group consisting of lower alkyl, halo, hydroxy, and alkoxy; or benzyl wherein said phenyl portion is optionally substituted with 1-3 substituents selected from the group consisting of lower alkyl, halo, hydroxy, and alkoxy;

n is 1 to 6; and provided that the compound is not thyronamine, 3,5-diiodothyronamine, 3,5,3'-triiodothyronamine, thyroxamine, 3,5,3',5'-tetraiodothyroethanolamine, 3,5,3'-triiodothyroethanolamine, or 3,5-diiodothyroethanolamine.

In certain embodiments, $R_4$ and $R_5$ are H, $CH_3$, $CF_3$, CN, $OCH_3$, $CH_2CH_3$, or $CH(CH_3)_2$, and in a further detailed embodiment, $R_1$ and $R_2$ are H, $R_3$ is I, $R_4$, $R_5$, and $R_7$ are H, $R_6$ is OH, X is O, Y and Z are each $CH_2$. In another detailed embodiment, $R_4$ is: H, $CH_3$, $CF_3$, CN, $OCH_3$, $CH_2CH_3$, or $CH(CH_3)_2$; and $R_5$ is: I, Br, Cl, or F, and in other detailed embodiments, $R_1$ and $R_2$ are H, $R_4$ and $R_7$ are H, $R_3$ and $R_5$ are I, $R_6$ is OH, X is O, Y and Z are each $CH_2$. In another detailed embodiment, $R_1$ and $R_2$ are H, $R_4$ is H, $R_3$, $R_5$, and $R_7$ are I, $R_6$ is OH, X is O, Y and Z are each $CH_2$. In another detailed embodiment, $R_1$ is lower alkyl, $R_6$ is OH or OR, and X is O. In a further detailed embodiment, $R_3$ is a halogen, $R_6$ is H, and X is O. In a further detailed embodiment, X is $R_1$ is H or lower alkyl, and Y is $C(R)_2$.alkoxy. In a further detailed embodiment, $R_1$ and $R_2$ are H or lower alkyl, $R_6$ is H or $CF_3$, and X is alkoxy. In a further detailed embodiment, $R_1$ and $R_2$ are H or lower alkyl, $R_6$ is H, X is O, Y is O, and Z is alkyl. In a further detailed embodiment, Y is —$[C(R)_2]_n$—, where R is aryl and n is 1.

In another embodiment, thyronamine derivatives and analogs are provided of formula II:

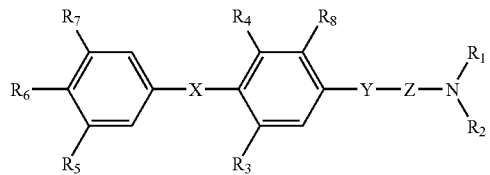

or a stereoisomer, prodrug, pharmaceutically acceptable salt, hydrate, solvate, acid salt hydrate, N-oxide or isomorphic crystalline form thereof;

wherein independently, $R_1$ and $R_2$ are: H, lower alkyl, cyclic alkyl, or benzyl;

Y and Z are: —$[C(R)_2]_n$—, CHOR, O, S, NR, CONH, or NHCO, provided that Y and Z are not both O, both S, both NR, both CONH, both NHCO, or CONH and NHCO;

$R_3$, $R_4$, $R_5$, and $R_7$ are: H, I, Br, Cl, F, $CH_3$, $CF_3$, CN, SR, $OCH_3$, $CH_2CH_3$, or $CH(CH_3)_2$;

$R_6$ is: OR, H, SH, F, $CF_3$, lower alkyl, or $N(R)_2$;

$R_8$ is: OR, R, $CH_2OR$, $CH_2NR_2$, $CH_2N+R_3$, SR, $CH_2SR$;

X is: O, S, SO, $SO_2$, NR, $C(R)_2$, -lower alkyl-O—, —O-lower alkyl-, $COCH_2O$, or $OCH_2CO$;

R is H, lower alkyl, aryl optionally substituted with 1-3 substituents selected from the group consisting of lower alkyl, halo, hydroxy, and alkoxy; or benzyl wherein said phenyl portion is optionally substituted with 1-3 substituents selected from the group consisting of lower alkyl, halo, hydroxy, and alkoxy; and n is 1 to 6; and provided that the compound is not thyronamine, 3,5-diiodothyronamine, 3,5,3'-triiodothyronamine, thyroxamine, 3,5,3',5'-tetraiodothyroethanolamine, 3,5,3'-triiodothyroethanolamine, or 3,5-diiodothyroethanolamine.

In certain embodiments, $R_8$ is H or OCH3, Y is CONH, and Z is alkyl.

In another embodiment, thyronamine derivatives and analogs are provided of formula III:

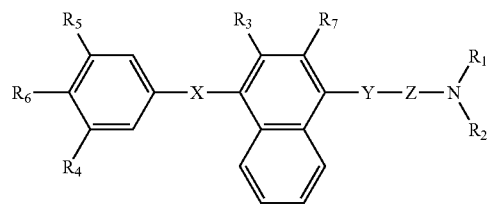

or a stereoisomer, prodrug, pharmaceutically acceptable salt, hydrate, solvate, acid salt hydrate, N-oxide or isomorphic crystalline form therof;

wherein independently, $R_1$ and $R_2$ are: H, lower alkyl, cyclic alkyl, or benzyl;

Y and Z are: —$[C(R)_2]_n$—, CHOR, O, S, NR, CONH, or NHCO, provided that Y and Z are not both O, both S, both NR, both CONH, both NHCO, or CONH and NHCO;

$R_3$, $R_4$, and $R_5$ are: I, Br, Cl, F, H, $CH_3$, $CF_3$, CN, SR, $OCH_3$, $CH_2CH_3$, or $CH(CH_3)_2$;

$R_6$ is: OH, H, SH, F, $CF_3$, lower alkyl, or $N(R)_2$;

$R_7$ is: OR, R, $CH_2OR$, $CH_2NR_2$, $CH_2N+R_3$, SR, or $CH_2SR$;

X is: O, S, SO, $SO_2$, NR, $C(R)_2$, -lower alkyl-O—, —O-lower alkyl-, $COCH_2O$, or $OCH_2CO$;

R is H, lower-alkyl, aryl optionally substituted with 1-3 substituents selected from the group consisting of lower alkyl, halo, hydroxy, and alkoxy; or benzyl wherein said phenyl portion is optionally substituted with 1-3 substituents selected from the group consisting of lower alkyl, halo, hydroxy, and alkoxy; and n is 1 to 6.

In certain embodiments, X is O.

In another embodiment, thyronamine derivatives and analogs are provided of formula IV:

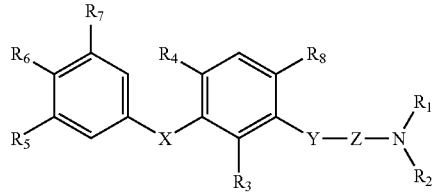

or a stereoisomer, prodrug, pharmaceutically acceptable salt, hydrate, solvate, acid salt hydrate, N-oxide or isomorphic crystalline form therof;

wherein independently, $R_1$ and $R_2$ are: H, lower alkyl, cyclic alkyl, or benzyl;

Y and Z are: —$[C(R)_2]_n$—, CHOR, O, S, NR, CONH, or NHCO, provided that Y and Z are not both O, both S, both NR, both CONH, both NHCO, or CONH and NHCO;

$R_3$, $R_4$, $R_5$, and $R_7$ are: I, Br, Cl, F, H, $CH_3$, $CF_3$, CN, SR, $OCH_3$, $CH_2CH_3$, or $CH(CH_3)_2$;

$R_6$ is: OH, H, SH, F, $CF_3$, lower alkyl, or $N(R)_2$;

$R_8$ is: OR, R, $CH_2OR$, $CH_2NR_2$, $CH_2N^+R_3$, SR, $CH_2SR$

X is: O, S, SO, $SO_2$, NR, $C(R)_2$, -lower alkyl-O—, —O-lower alkyl-, $COCH_2O$, or $OCH_2CO$;

R is H, lower alkyl, aryl optionally substituted with 1-3 substituents selected from the group consisting of lower alkyl, halo, hydroxy, and alkoxy; or benzyl wherein said phenyl portion is optionally substituted with 1-3 substituents selected from the group consisting of lower alkyl, halo, hydroxy, and alkoxy; and n is 1 to 6.

In certain embodiments, $R_1$ and $R_2$ are H or lower alkyl, $R_6$ is H, X is O, Y is O, and Z is alkyl. In a further detailed embodiment, Y is —CHR—, where R is aryl.

In another embodiment, thyronamine derivatives and analogs are provided of formula V:

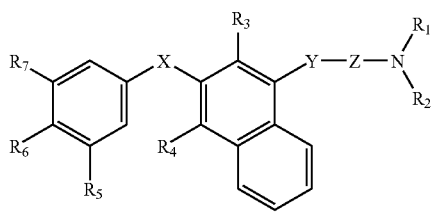

or a stereoisomer, prodrug, pharmaceutically acceptable salt, hydrate, solvate, acid salt hydrate, N-oxide or isomorphic crystalline form thereof;

wherein independently, $R_1$ and $R_2$ are: H, lower alkyl, cyclic alkyl, or benzyl;

Y and Z are: —$[C(R)_2]_n$—, CHOR, O, S, NR, CONH, or NHCO, provided that Y and Z are not both O, both S, both NR, both CONH, both NHCO, or CONH and NHCO;

$R_3$, $R_4$, $R_5$, and $R_7$ are: H, I, Br, Cl, F, $CH_3$, $CF_3$, CN, SR, $OCH_3$, $CH_2CH_3$, or $CH(CH_3)_2$;

$R_6$ is: OR, H, SH, F, $CF_3$, lower alkyl, or $N(R)_2$;

X is: O, S, SO, $SO_2$, NR, $C(R)_2$, -lower alkyl-O—, —O-lower alkyl-, $COCH_2O$, or $OCH_2CO$;

R is H, lower alkyl, aryl optionally substituted with 1-3 substituents selected from the group consisting of lower alkyl, halo, hydroxy, and alkoxy; or benzyl wherein said phenyl portion is optionally substituted with 1-3 substituents selected from the group consisting of lower alkyl, halo, hydroxy, and alkoxy; and n is 1 to 6.

In another embodiment, pharmaceutical compositions are provided comprising at least one pharmaceutically acceptable carrier or excipient and an effective amount of the compound.

In other detailed embodiments, an antibody is provided that specifically binds to the compound.

In a further embodiment, pharmaceutical compositions are provided comprising at least one pharmaceutically acceptable carrier or excipient and an effective amount of the compound.

In a further embodiment, methods of exerting a positive inotropic effect on the heart without affecting the heart rate of a mammalian subject are provided comprising the step of administering to the subject an effective amount of the compounds described herein. In a further embodiment, methods of exerting a negative inotropic effect on the heart without affecting the heart rate of a mammalian subject are provided comprising the step of administering to the subject an effective amount of the compounds described herein.

In a further embodiment, methods of lowering the core body temperature of a mammalian subject are provided comprising the step of administering to the subject an effective amount of the compounds described herein, and further wherein administering the compounds induces torpor or hibernation in the subject.

In another embodiment, methods of treating a mammalian subject during surgery comprising administering to the subject a therapeutically effective amount of the compounds described herein, or a stereoisomer, prodrug, pharmaceutically acceptable salt, hydrate, solvate, acid salt hydrate, N-oxide or isomorphic crystalline form thereof. In a detailed embodiment, the method reduces the core body temperature and induces anesthesia in the subject. In a further detailed embodiment, the method reduces blood loss of the subject.

In another embodiment, methods for alleviating a disease state in a mammal believed to be responsive to treatment with a thyronamine agonist are provided, comprising the step of administering to the mammal a therapeutic amount of the compounds described herein.

In detailed embodiments, the methods provide administering a composition which is an agonist of a G protein coupled receptor, for example, a trace amine receptor.

In another embodiment, methods for alleviating a disease state in a mammal believed to be responsive to treatment with a thyronamine antagonist are provided, comprising the step of administering to the mammal a therapeutic amount of the compounds as described herein.

In detailed embodiments, the methods provide administering a composition which is an antagonist of a G protein coupled receptor, for example, a trace amine receptor.

In a further detailed embodiment, the methods are provided for treating the disease state which is congestive heart failure, or treating the disease state is fever or heatstroke. In a further detailed embodiment, the methods are provided for treating the disease state which is bipolar disorder, depression, schizophrenia, eating disorders, anxiety, seizure, epilepsy, insomnia and sleeping disorders, gastro esophageal reflux disease, diseases involving gastrointestinal motility or asthma. In a detailed embodiment, methods are provided for treating the disease state which is diabetes, hyperglycemia, hypoglycemia, enhance or reduce gut motility, cardiac arrhythmia, stroke, osteoporosis, obesity, atherosclerosis, hypertension, hyperthyroidism or hypothyroidism.

In another embodiment, methods of treating a mammalian subject during open heart surgery believed to be responsive to treatment with a thyronamine antagonist are provided comprising administering a therapeutically effective amount the compounds as described herein.

In another embodiment, methods of treating a mammalian subject during trauma or blood loss believed to be responsive to treatment with a thyronamine antagonist are provided comprising administering a therapeutically effective amount the compounds as described herein.

In another embodiment, an isotopically labeled compound of the compounds described herein are provided. The compounds can be isotopically labeled with $^3$H, $^2$H, or $^{125}$I.

In another embodiment, methods of treating a mammalian subject having a disease state which is alleviated by treatment with a thyronamine agonist are provided comprising the step of administering to the subject a therapeutically effective amount of thyronamine, 3,5-diiodothyronamine, 3,5,3'-triiodothyronamine, thyroxamine, 3,5,3',5'-tetraiodothyroethanolamine, 3,5,3'-triiodothyroethanolamine, or 3,5-diiodothyroethanolamine, or a stereoisomer, prodrug, pharmaceutically acceptable salt, hydrate, solvate, acid salt hydrate, N-oxide or isomorphic crystalline form thereof.

In another embodiment, methods of treating a mammalian subject having a disease state which is alleviated by treatment with a thyronamine antagonist are provided comprising the step of administering a therapeutically effective amount of thyronamine, 3,5-diiodothyronamine, 3,5,3'-triiodothyronamine, thyroxamine, 3,5,3',5'-tetraiodothyroethanolamine, 3,5,3'-triiodothyroethanolamine, or 3,5-diiodothyroethanolamine, or a stereoisomer, prodrug, pharmaceutically acceptable salt, hydrate, solvate, acid salt hydrate, N-oxide or isomorphic crystalline form thereof.

In another embodiment, methods for preparing a protected phenylboronic acid are provided comprising the steps of providing a protected p-bromophenol; and reacting the protected p-bromophenol with alkyl lithium and B(OR)$_3$, and hydrolyzing the product of the reacting step to form a protected phenylboronic acid, where R is methyl, ethyl or propyl. In a detailed embodiment, the protected p-bromophenol is protected with a moiety selected from trimethylsilyl, tert-butyldimethylsilyl and triisopropylsilyl.

In another embodiment, methods for preparing a thyronamine derivative or a stereoisomer, prodrug, pharmaceutically acceptable salt, hydrate, solvate, acid salt hydrate, N-oxide or isomorphic crystalline form thereof are provided comprising the steps of:

contacting, in the presence of copper, an amino-protected tyramine of the formula:

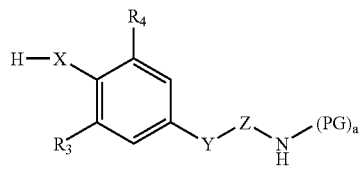

with a hydroxyl- or thiol-protected phenylboronic acid of the formula:

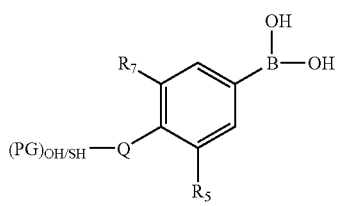

to form the structure of the formula:

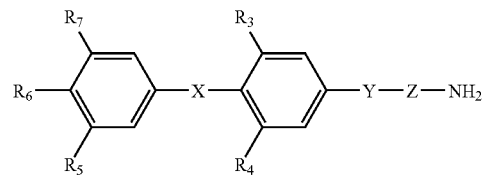

deprotecting the hydroxyl or thiol group; and deprotecting the amino group;

wherein, (PG)$_a$ is an amino protecting group;

(PG)$_{OH/SH}$ is a hydroxyl- or thiol-protecting group;

Q is: O or S;

Y and Z are: —[C(R)$_2$]$_n$—, CHOR, O, S, NR, CONH, or NHCO, provided that Y and Z are not both O, both S, both NR, both CONH, both NHCO, or CONH and NHCO;

R$_3$, R$_4$, R$_5$, and R$_7$ are: H, I, Br, Cl, F, CH$_3$, CF$_3$, CN, SR, OCH$_3$, CH$_2$CH$_3$, or CH(CH$_3$)$_2$;

R$_6$ is: OR, H, SH, F, CF$_3$, lower alkyl, or N(R)$_2$;

X is: O, S, SO, SO$_2$, NR, C(R)$_2$, -lower alkyl-O—, —O-lower alkyl-, COCH$_2$O, or OCH$_2$CO; and R is H, lower alkyl, aryl optionally substituted with 1-3 substituents selected from the group consisting of lower alkyl, halo, hydroxy, and alkoxy; or benzyl wherein said phenyl portion is optionally substituted with 1-3 substituents selected from the group consisting of lower alkyl, halo, hydroxy, and alkoxy;

n is 1 to 6.

In another embodiment, methods for preparing a thyronamine derivative or a stereoisomer, prodrug, pharmaceutically acceptable salt, hydrate, solvate, acid salt hydrate, N-oxide or isomorphic crystalline form thereof are provided comprising the steps of:

contacting, in the presence of copper, an amino-protected tyramine of the formula:

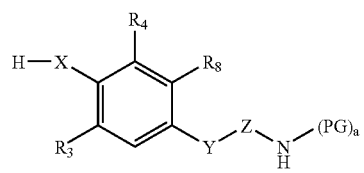

with a hydroxyl- or thiol-protected phenylboronic acid of the formula:

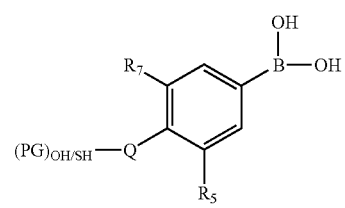

to form the structure of the formula:

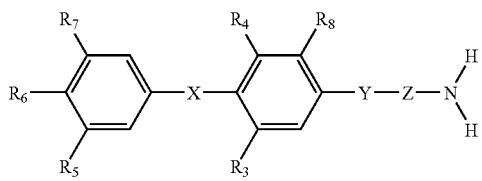

or a stereoisomer, prodrug, pharmaceutically acceptable salt, hydrate, solvate, acid salt hydrate, N-oxide or isomorphic crystalline form thereof;

deprotecting said hydroxyl or thiol group; and deprotecting said amino group;

wherein, $(PG)_a$ is an amino protecting group;

$(PG)_{OH/SH}$ is a hydroxyl- or thiol-protecting group;

Q is: O or S;

Y and Z are: $-[C(R)_2]_n-$, CHOR, O, S, NR, CONH, or NHCO, provided that Y and Z are not both O, both S, both NR, both CONH, both NHCO, or CONH and NHCO;

$R_3$, $R_4$, $R_5$, and $R_7$ are: H, I, Br, Cl, F, $CH_3$, $CF_3$, CN, SR, $OCH_3$, $CH_2CH_3$, or $CH(CH_3)_2$;

$R_6$ is: OR, H, SH, F, $CF_3$, lower alkyl, or $N(R)_2$;

$R_8$ is: OR, R, $CH_2OR$, $CH_2NR_2$, $CH_2N^+R_3$, SR, $CH_2SR$;

X is: O, S, SO, $SO_2$, NR, $C(R)_2$, -lower alkyl-O—, —O-lower alkyl-, $COCH_2O$, or $OCH_2CO$;

R is H, lower alkyl, aryl optionally substituted with 1-3 substituents selected from the group consisting of lower alkyl, halo, hydroxy, and alkoxy; or benzyl wherein said phenyl portion is optionally substituted with 1-3 substituents selected from the group consisting of lower alkyl, halo, hydroxy, and alkoxy; and n is 1 to 6.

In another embodiment, methods for preparing a thyronamine derivative or a stereoisomer, prodrug, pharmaceutically acceptable salt, hydrate, solvate, acid salt hydrate, N-oxide or isomorphic crystalline form thereof are provided comprising the steps of:

contacting, in the presence of copper, an amino-protected tyramine of the formula:

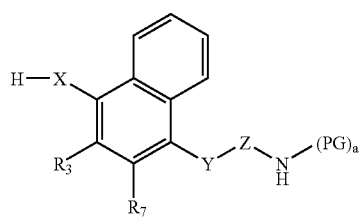

with a hydroxyl- or thiol-protected phenylboronic acid of the formula:

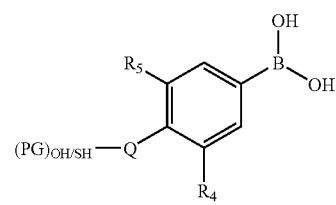

to form the structure of the formula:

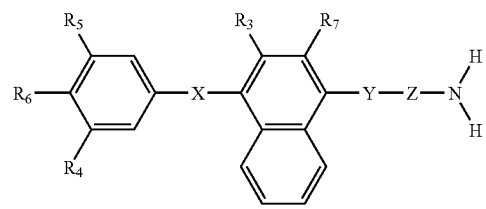

or a stereoisomer, prodrug, pharmaceutically acceptable salt, hydrate, solvate, acid salt hydrate, N-oxide or isomorphic crystalline form thereof;

deprotecting said hydroxyl or thiol group; and deprotecting said amino group;

wherein, $(PG)_a$ is an amino protecting group;

$(PG)_{OH/SH}$ is a hydroxyl- or thiol-protecting group;

Q is: O or S;

Y and Z are: $-[C(R)_2]_n-$, CHOR, O, S, NR, CONH, or NHCO, provided that Y and Z are not both O, both S, both NR, both CONH, both NHCO, or CONH and NHCO;

$R_3$, $R_4$, and $R_5$ are: I, Br, Cl, F, H, $CH_3$, $CF_3$, CN, SR, $OCH_3$, $CH_2CH_3$, or $CH(CH_3)_2$;

$R_6$ is: OH, H, SH, F, $CF_3$, lower alkyl, or $N(R)_2$;

$R_7$ is: OR, R, $CH_2OR$, $CH_2NR_2$, $CH_2N^+R_3$, SR, or $CH_2SR$;

X is: O, S, SO, $SO_2$, NR, $C(R)_2$, -lower alkyl-O—, —O-lower alkyl-, $COCH_2O$, or $OCH_2CO$;

R is H, lower alkyl, aryl optionally substituted with 1-3 substituents selected from the group consisting of lower alkyl, halo, hydroxy, and alkoxy; or benzyl wherein said phenyl portion is optionally substituted with 1-3 substituents selected from the group consisting of lower alkyl, halo, hydroxy, and alkoxy; and n is 1 to 6.

In another embodiment, methods for preparing a thyronamine derivative or a stereoisomer, prodrug, pharmaceutically acceptable salt, hydrate, solvate, acid salt hydrate, N-oxide or isomorphic crystalline form thereof are provided comprising the steps of:

contacting, in the presence of copper, an amino-protected tyramine of the formula:

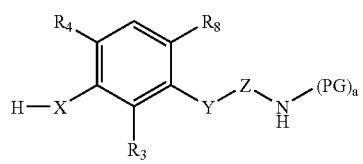

with a hydroxyl- or thiol-protected phenylboronic acid of the formula:

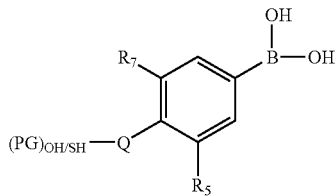

to form the structure of the formula:

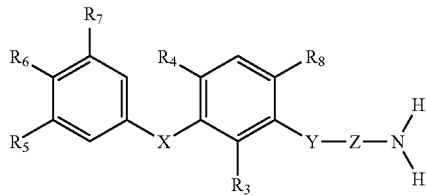

or a stereoisomer, prodrug, pharmaceutically acceptable salt, hydrate, solvate, acid salt hydrate, N-oxide or isomorphic crystalline form thereof;
deprotecting said hydroxyl or thiol group; and
deprotecting said amino group;
wherein,
$(PG)_a$ is an amino protecting group;
$(PG)_{OH/SH}$ is a hydroxyl- or thiol-protecting group;
Q is: O or S;
Y and Z are: —$[C(R)_2]_n$—, CHOR, O, S, NR, CONH, or NHCO, provided that Y and Z are not both O, both S, both NR, both CONH, both NHCO, or CONH and NHCO;
$R_3$, $R_4$, $R_5$, and $R_7$ are: I, Br, Cl, F, H, $CH_3$, $CF_3$, CN, SR, $OCH_3$, $CH_2CH_3$, or $CH(CH_3)_2$;
$R_6$ is: OH, H, SH, F, $CF_3$, lower alkyl, or $N(R)_2$;
$R_8$ is: OR, R, $CH_2OR$, $CH_2NR_2$, $CH_2N+R_3$, SR, $CH_2SR$
X is: O, S, SO, $SO_2$, NR, $C(R)_2$, -lower alkyl-O—, —O-lower alkyl-, $COCH_2O$, or $OCH_2CO$;
R is H, lower alkyl, aryl optionally substituted with 1-3 substituents selected from the group consisting of lower alkyl, halo, hydroxy, and alkoxy; or benzyl wherein said phenyl portion is optionally substituted with 1-3 substituents selected from the group consisting of lower alkyl, halo, hydroxy, and alkoxy; and
n is 1 to 6.

In another embodiment, methods for preparing a thyronamine derivative or a stereoisomer, prodrug, pharmaceutically acceptable salt, hydrate, solvate, acid salt hydrate, N-oxide or isomorphic crystalline form thereof are provided comprising the steps of:

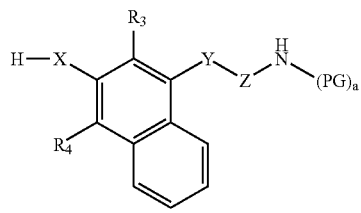

with a hydroxyl- or thiol-protected phenylboronic acid of the formula:

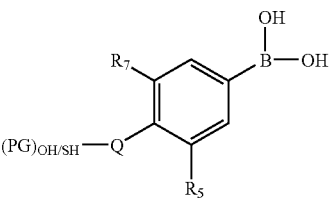

to form the structure of the formula:

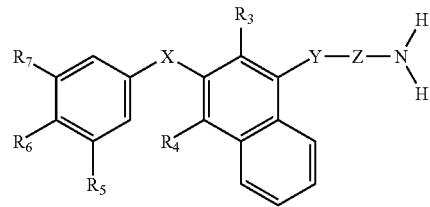

or a stereoisomer, prodrug, pharmaceutically acceptable salt, hydrate, solvate, acid salt hydrate, N-oxide or isomorphic crystalline form thereof;
deprotecting said hydroxyl or thiol group; and
deprotecting said amino group;
wherein,
$(PG)_a$ is an amino protecting group;
$(PGO_{OH/SH}$ is a hydroxyl- or thiol-protecting group;
Q is: O or S;
Y and Z are: —$[C(R)_2]_n$—, CHOR, O, S, NR, CONH, or NHCO, provided that Y and Z are not both O, both S, both NR, both CONH, both NHCO, or CONH and NHCO;
$R_3$, $R_4$, $R_5$, and $R_7$ are: H, I, Br, Cl, F, $CH_3$, $CF_3$, CN, SR, $OCH_3$, $CH_2CH_3$, or $CH(CH_3)_2$;
$R_6$ is: OR, H, SH, F, $CF_3$, lower alkyl, or $N(R)_2$;
X is: O, S, SO, $SO_2$, NR, $C(R)_2$, -lower alkyl-O—, —O-lower alkyl-, $COCH_2O$, or $OCH_2CO$;
R is H, lower alkyl, aryl optionally substituted with 1-3 substituents selected from the group consisting of lower alkyl, halo, hydroxy, and alkoxy; or benzyl wherein said phenyl portion is optionally substituted with 1-3 substituents selected from the group consisting of lower alkyl, halo, hydroxy, and alkoxy; and
n is 1 to 6.

In another embodiment, methods are provided for preparing a thyronamine derivative or a stereoisomer, prodrug, pharmaceutically acceptable salt, hydrate, solvate, acid salt hydrate, N-oxide or isomorphic crystalline form thereof further comprising the step of independently substituting an I, Br, Cl or F at the 3' position, 5' position or both the 3' position and the 5' position. In a detailed embodiment, the method further comprises the step of O-alkylating or S-alkylating the hydroxyl or thiol functionality of the compound. In a detailed embodiment, the method further comprises the step of N-alkylating the amino functionality of the compound.

A method is provided for screening for a bioactive agent capable of treating depression or a mood related disorder comprising: a) combining a thyronamine compound and a candidate bioactive agent; and b) determining the effect of the candidate agent on the bioactivity of the thyronamine compound.

A method is provided of evaluating the effect of a drug for treating depression or a mood related disorder comprising: a) administering the drug to a patient; b) removing a biological sample from the patient; and c) determining the amount or activity of the thyronamine compound in the biological sample. The method further comprises comparing the amount or activity of the thyronamine compound in the biological sample of the patient to an amount or activity of the thyronamine compound in the biological sample of a healthy individual.

A method of diagnosing depression or mood related disorder is provided comprising: determining the levels of a thyronamine compound in a first tissue type or cell of a first individual; and comparing the levels of the thyronamine compound from a second normal tissue type or cell from a second unaffected individual; wherein a difference in the levels of the thyronamine compound indicates that the first individual has depression or mood related disorder. The method further comprises measuring the levels of the thyronamine compound in the first tissue type or cell of the first individual is increased compared to the levels of the thyronamine compound from the second normal tissue type or cell from the second unaffected individual. The tissue type is a whole blood sample, blood plasma sample, or a blood serum sample.

BRIEF DESCRIPTION OF THE DRAWINGS

FIGS. 11A, 11B: Graph of heart rate vs. time (minutes), or blood pressure (mm Hg) vs. time (minutes), following intraperitoneal injection into a mouse of an iodo-thyronamine compound, $T_1$amine, measured over an approximately 4 hour period; FIGS. 11C, 11D: Graph of heart rate vs. time (minutes), or blood pressure (mm Hg) vs. time (minutes), following intraperitoneal injection into a mouse of an iodo-thyronamine compound, $T_1$amine, measured over an approximately 17 hour period.

FIGS. 12A, 12B: Graph of heart rate vs. time (minutes), or blood pressure (mm Hg) vs. time (minutes), following intraperitoneal injection into a mouse of an iodo-thyronamine compound, $T_1$amine, measured over an approximately 4 hour period; FIGS. 12C, 12D: Graph of heart rate vs. time (minutes), or blood pressure (mm Hg) vs. time (minutes), following intraperitoneal injection into a mouse of an iodo-thyronamine compound, $T_1$amine, measured over an approximately 17 hour period.

FIG. 20: Mass spectrometry peak intensities.

DETAILED DESCRIPTION

Figure 1:
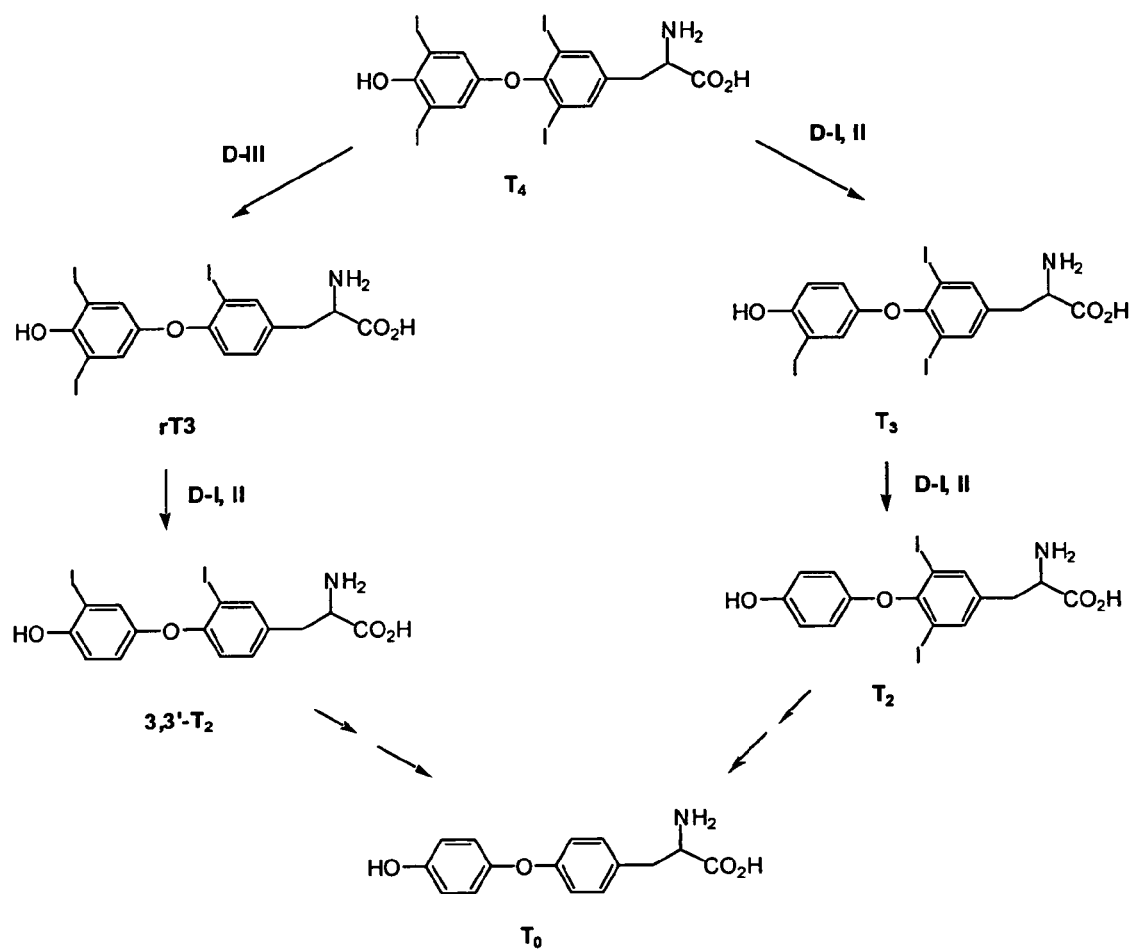
FIG. 1: Iodination state of thyroid hormone metabolites

With respect to thyronamine, "derivative" refers to a compound of the general formula:

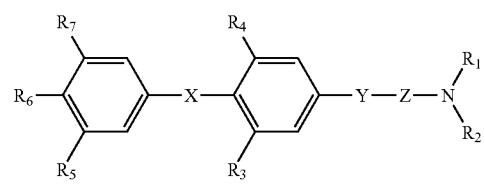

where the variables are as defined herein.

With respect to thyronamine, "analog" or "functional analog" refers to a modified form of the respective thyronamine derivative in which one or more chemically derivatized functional side ($R_1$, $R_2$, $R_3$, $R_4$, $R_5$, $R_6$ or $R_7$) or linking groups (X, Y or Z) has been modified such that the analog retains substantially the same biological activity or improved biological activity as the unmodified thyronamine derivative in vivo and/or in vitro.

"Agonist" or "thyronamine agonist" refers to an endogenous or exogenous compound, substance or entity that has affinity for and stimulates physiologic activity at cell receptors normally stimulated by naturally-occurring substances, thus triggering a biochemical response characteristic of those receptors. As used herein, the term refers to a thyronamine derivative or analog, a suitable homolog, or a portion thereof, capable of promoting at least one of the biological responses normally associated with thyronamine.

For example, treatment with a thyronamine agonist can result in inotropic effects upon cardiac output, lowered body temperature of a mammalian subject, or improvement in symptoms of congestive heart failure.

"Antagonist" or "thyronamine antagonist" refers to an endogenous or exogenous compound, substance or entity that opposes the physiological effects of another compound and, at the receptor level, it is an endogenous or exogenous compound, substance or entity that has affinity for and opposes and/or blocks at least one of the normal physiological responses normal induced by another compound, substance or entity at the cell receptors. As used herein, the term refers to a thyronamine derivative or analog, a suitable homolog, or a portion thereof, which blocks at least one of the normal actions of thyronamine. For example, treatment with certain thyronamine antagonists can increase body temperature in a mammalian subject suffering from hypothermia, or reduce cardiac output in a mammalian subject.

"Receptor" refers to a molecule, a polymeric structure, or polypeptide in or on a cell that specifically recognizes and binds a compound acting as a molecular messenger, for example, neurotransniitter, hormone, lymphokine, lectin, or drug.

"Lower alkyl" refers to an optionally substituted, saturated straight or hydrocarbon having from 1 to about 12 carbon atoms (and all combinations and subcombinations of ranges and specific numbers of carbon atoms therein), with from 1 to about 8 carbon atoms, being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, 3-methylpentyl, 2,2-dimethylbutyl, and 2,3-dimethylbutyl. Specifically included within the definition of "lower alkyl" are those aliphatic hydrocarbon chains that are optionally substituted.

"Alkoxy," refers to the group R—O— where R is a lower alkyl group, as defined above.

"Cyclic alkyl" refers to an optionally substituted, alkyl group having one or more rings in their structures having from about 3 to about 20 carbon atoms (and all combinations and subcombinations of ranges and specific numbers of carbon atoms therein), with from about 3 to about 10 carbon atoms being preferred. Multi-ring structures can be bridged or fused ring structures. Groups include, but are not limited to, cyclopropyl, cyclobutyl, cyclopentyl, cyclohexyl, cyclooctyl, and adamantyl. Specifically included within the definition of "cyclic alkyl" are those aliphatic hydrocarbon chains that are optionally substituted.

"Aryl" refers to an aromatic 5- to 13-membered mono- or bi-carbocyclic ring such as phenyl or naphthyl. Preferably, groups containing aryl moieties are monocyclic having 5 to 7 carbon atoms in the ring. Non-limiting examples include, for example, phenyl, naphthyl, anthracenyl, and phenanthrenyl. "Heteroaryl" means an aromatic 5- to 13-membered carbon containing mono- or bi-cyclic ring having one to five heteroatoms that independently can be nitrogen, oxygen or sulfur. Preferably, groups containing heteroaryl moieties are monocyclic having 5 to 7 members in the ring where one to two of the ring members are selected independently from nitrogen, oxygen or sulfur. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Groups containing aryl or heteroaryl moieties can optionally be substituted as defined below or unsubstituted. Aryl can be, for example, phenyl, or phenyl substituted with halogen, OH, OR, or lower alkyl.

"Aralkyl" refers to the group —R—Ar where Ar is aryl as defined above and R is an alkyl moiety having 1 to 8, preferably 1 to 6, and more preferably 1 to 4 carbon atoms. Examples of aralkyl groups include benzyl, phenethyl, 3-phenylpropyl, and 4-phenyl butyl. "Biaralkyl" refers to the group —R—(—Ar)—Ar where Ar and R are as defined and the alkyl moiety has two aryl groups on a single carbon atom or on two different carbon atoms.

"Optional" or "optionally" means that the subsequently described event or circumstance may or may not occur, and that the description includes instances in which it does not. For example, optionally substituted phenyl indicates either unsubstituted phenyl, or phenyl mono-, di-, or tri-substituted, independently, with OH, COOH, lower alkyl, lower alkoxy, halo, nitro, amino, alkyl amino, dialkylamino, trifluoromethyl and/or cyano.

"Effective amount" refers to an amount of a compound that can be therapeutically effective to inhibit, prevent or treat the symptoms of particular disease, disorder or side effect.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Stereoisomer, prodrug, pharmaceutically acceptable salt, hydrate, solvate, acid salt hydrate, N-oxide or isomorphic crystalline form thereof" refer to derivatives of the disclosed compounds wherein the parent compound is modified by making acid or base salts thereof. Examples of stereoisomer, prodrug, pharmaceutically acceptable salt, hydrate, solvate, acid salt hydrate, N-oxide or isomorphic crystalline form thereof include, but are not limited to, mineral or organic acid salts of basic residues such as amines; alkali or organic salts of acidic residues such as carboxylic acids; and the like. The stereoisomer, prodrug, pharmaceutically acceptable salt, hydrate, solvate, acid salt hydrate, N-oxide or isomorphic crystalline form thereof include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present compositions and methods.

Certain acidic or basic compounds can exist as zwitterions. All forms of the compounds, including free acid, free base and zwitterions, are contemplated to be within the scope of the present compositions and methods. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

"Patient" refers to animals, including mammals, preferably humans.

"Prodrug" refers to compounds specifically designed to maximize the amount of active species that reaches the desired site of reaction which are of themselves typically inactive or minimally active for the activity desired, but through biotransformation are converted into biologically active metabolites.

"Stereoisomers" refers to compounds that have identical chemical constitution, but differ as regards the arrangement of the atoms or groups in space.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

When any variable occurs more than one time in any constituent or in any formula, its definition in each occurrence is independent of its definition at every other occurrence. Combinations of substituents and/or variables are permissible only if such combinations result in stable compounds.

Methods of Treatment

Thyronamine derivatives and analogs are biogenic amines useful for medical treatments and shown to have biological activity by the following physiological and biochemical mechanisms.

(1) Thyronamine derivatives and analogs mediate rapid response ("non-genomic" effects) through activation of their cognate receptors, from the G-protein coupled receptor (GPCR) superfamily. An example of a GPCR is the trace amine receptor (TAR-1).

(2) Thyronamine derivatives and analogs are synthesized from their corresponding amino acids by an enzymatic pathway that involves decarboxylation of the amino acid as the key step that generates the arylethylamine substructure common to this group of signaling molecules.

(3) The non-selective enzyme aromatic amino acid decarboxylase (AAD), which also catalyzes the conversion of histadine to histamine and 5-hydroxytryptophan to serotonin (5-hydroxytryptamine), is known to catalyze the decarboxylation of a wide variety of natural and synthetic aromatic amino acids, requiring an aromatic group linked to an alanine as the key feature of substrate recognition. Thyroid hormones, e.g., $T_3$ and $T_4$, as well as the lower iodination state metabolites, should be substrates for AAD, giving rise to the aryl ethylamine compounds, e.g., thyronamine derivatives and analogs (5) The potency of thyronamine derivatives and analogs has been measured by binding to the rat trace amine receptor (rTAR-1), a G protein coupled receptor heterologously expressed in human embryonic kidney (HEK) cells. Thyronamine derivatives and analogs were found to stimulate cAMP accumulation in rTAR-1 expressing HEK cells in a dose-dependent fashion. The potency index of effective concentration for half-maximal stimulation ($EC_{50}$) of rTAR-1 was calculated from the dose-response curve for each compound. The spectrum of potencies across the thyronamine series demonstrates that the specific number and placement of iodine atoms influences potency in a critical way. 3-iodothyronamine ($T_1AM$) is the most potent rTAR-1 agonist with an $EC_{50}$ of 14 nM, followed by 3,3'-diiodothyronamine (3,3'-$T_2AM$), 3,5-diiodothyronamine ($T_2AM$), and 3,5,3'-triiodothyronamine ($T_3AM$). Thyronamine ($T_0AM$) is the least potent agonist with an $EC_{50}$ of 131 nM.

(6) $T_1AM$, the most potent rTAR-1 agonist, is a naturally-occurring biogenic amine which has been detected in brain extracts of rat, mouse, and guinea pig using a liquid chromatography/mass spectrometry (LC/MS) protocol. On this basis, $T_1AM$, $T_4AM$, $T_3AM$ and $T_0AM$ can be found in brain and other tissues as naturally-occurring biogenic amines.

(7) Intraperitoneal or intracerebral injection of $T_1AM$ into a mouse resulted in a decrease in core body temperature of the animal from approximately 38° C. to approximately 29° C. for a period of approximately 6.5 to 8 hours. This period was followed by a full recovery to a stable core body temperature of 38° C. in the animal. The heart rates of the animals remained constant throughout the treatment period. Blood pressure varied with the drop in body core temperature, but recovered to normal levels within the same time frame as the body core temperature recovery.

Thyronamine derivatives and analogs are effective to lower body core temperature in a mammalian subject. Experiments further demonstrate positive inotropic effects of thyronamine derivatives and analogs on cardiac output in a mammalian subject, including, but not limited to: central and peripheral effects on body temperature and metabolic rate; contraction/relaxation of various tissues and smooth muscle preparations including rodent/guinea pig ileum, vas deferens, uterus (virgin and pregnant); hanging heart assay to explore direct effects of drug(s) on heart function (inotropic and chronotropic effects); cardiac muscle; small and large blood vessels; pancreatic function (e.g. insulin release and blood glucose levels); liver function (glucagon); renal function (water balance); determine thyronamine derivative and analog content (by LC/MS) on a variety of human or other mammalian tissue extracts (e.g. brain, pancreas, liver, kidney, heart).

Because thyronamine derivatives and analogs have certain agonist and antagonist effects, compounds and pharmaceutical compositions containing the compounds as described herein would also have these effects and hence would be useful in certain methods, for example, methods of treatment, methods of exerting a positive inotropic effect, and methods of lowering the core body temperature a mammalian subject. "Core body temperature" in a human subject is approximately 37° C. "Core body temperature" in a mouse is approximately 38° C. Thyronamine derivatives and analogs are biogenic amines that can be found in a variety of tissues. Agonists and antagonists of thyronamine derivatives and analogs can have physiological effects on heart, bone, brain, central nervous system, peripheral nervous system, adipose tissue, liver, pancreas, kidney and pituitary.

The compounds and the pharmaceutical compositions containing them are useful in the treatment of conditions which affect a variety of tissues and organs of a mammalian subject. These compositions act to agonize or antagonize the effects of iodo-thyronamines or thyroid hormones in certain tissues or organs.

Agonists or antagonists of thyronamine derivatives and analogs can be synthesized. Many compounds of the general thyronamine skeleton, i.e. those compounds that contain a two atom linker between the inner phenyl ring and the basic nitrogen (at Y and Z positions) can be agonists. However, compounds of this class that contain a large group such as an aromatic substituent attached to either of the linker atoms (at Y and Z positions) can be antagonists. Alternatively, compounds that contain linkers of more than two atoms connecting the inner aromatic ring to the basic nitrogen can also be antagonists. In particular, compounds containing linkers comprised of between 3 and 7 atoms connecting the inner aromatic ring to a basic nitrogen can be antagonists.

Thyronamine derivatives and analogs lower systemic vascular resistance, increase blood volume, and exert positive inotropic effects upon cardiac function. A "positive inotropic effect" increases the force of heart muscular contraction. The combination of these positive inotropic effects on both blood circulation and the heart results in increased cardiac output. Thyronamine derivatives and analogs have a positive inotropic-effect to increase cardiac output without the chronotropic effect to increase heart rate. Thyronamine derivatives and analogs as described in the present compositions and methods have cardiovascular and surgical applications. Cardiovascular applications include, for example, treatment of congestive heart failure, cardiomyopathy, cardiac arrhythmia, and management of acute stroke. These compositions and methods are useful to treat atherosclerosis or hypertension. Compositions and methods comprising thyronamine derivatives and analogs are effective to increase cardiac output, while reducing or maintaining heart rate, and reducing or maintaining blood pressure in a mammalian subject undergoing treatment.

Approximately 2 out of every 100 people between the ages of 27 and 74 have heart failure. Heart failure becomes more common with advancing age. Congestive heart failure (CHF), is a disorder in which the heart loses its ability to pump blood efficiently. CHF is a condition in which the heart cannot pump out all of the blood that enters it, which leads to an accumulation of blood in the vessels and fluid in the body tissues. CHF is almost always a chronic, long-term condition, although it can sometimes develop suddenly. This condition can affect the right side, the left side, or both sides of the heart. As the heart's pumping action is lost, blood can back up into other areas of the body: the liver, the gastrointestinal tract and extremities (right-sided heart failure), the lungs (left-sided heart failure). The most common causes of heart failure are chronic cardiovascular disease, hypertension, and coronary artery disease. Other structural or functional causes of heart failure include: valvular heart disease, congenital heart disease, dilated cardiomyopathy, lung disease, or heart tumor.

Dilated cardiomyopathy is the most common of the cardiomyopathies, comprising more than 90% of all cases that are referred to heart specialists. Symptoms often develop gradually and usually include symptoms of right heart failure, left heart failure, or both. Dilated cardiomyopathy is a disorder in which the heart muscle is weakened and cannot pump blood efficiently. The wall muscle of the ventricles can be of normal, increased or reduced thickness, but the ventricular diameter is always enlarged. This causes decreased heart function that affects the lungs, liver, and other body systems. Dilated cardiomyopathy represents the end result of more than 50 different diseases. Causes of dilated cardiomyopathy include genetic disorders such as Friedreich's ataxia or myotonic dystrophy, myocarditis (a viral infection of the heart muscle), alcoholism, coronary artery disease, valvular heart disease, and others. In many patients, however, a cause cannot be identified, and their cardiomyopathy is considered "idiopathic." Idiopathic cardiomyopathies are likely to be genetically determined.

Thyronamine derivatives and analogs as described in the present compositions and methods can be administered during surgery and to induce anesthesia. Cardiovascular and surgical applications of these compositions and methods include, but are not limited to, reduction in body core temperature, reduction in heart rate, reduction in blood pressure, control or reduction in bleeding, and wound healing. Therapeutic applications can be particularly relevant to pediatric patients. The present compositions and methods are useful for analgesia (nociception and/or pruritis) or for induction of hibernation in mammalian subjects.

Antagonists of thyronamine derivatives and analogs can have a negative inotropic effect on heart function leading to a decrease in the force of heart muscular contraction. Antagonists of thyronamine derivatives and analogs can raise systemic vascular resistance and decrease blood volume, thus decreasing cardiac output. The compositions and methods of the present invention can be used during open heart surgery. The compositions and methods can also be used in emergency medical situations, to control bleeding, shock, and other complications of traumatic or emergency medical applications.

Thyronamine derivatives and analogs can induce a state of torpor in a mammalian subject. Torpor is a metabolic response exhibited by animals, e.g., mammals or avian species. It describes a temporary physiological state in which an organism's body temperature drops, and its metabolic rate is reduced. An animal is said to be in a state of torpor when it hibernates to avoid the stresses of cold and food shortages or when it estivates to avoid excessive heat or drought. Daily torpor occurs in some animals, for example, birds, rodents, rats and mice.

Compositions and methods comprising thyronamine derivatives and analogs are useful to treat disease related to defects in subcellular calcium homeostasis occurring at the mitochondria. Thyronamine derivatives and analogs play a role in thermoregulation in a mammalian subject. Thyronamine derivatives and analogs activate the TAR1 receptor and influence intracellular and extracellular calcium release. Since mitochondria are organelles that appear to participate in maintaining calcium homeostasis, and because mitochondria are central for thermogenesis to occur in muscle (a thyroid hormone-sensitive response), thyronamine derivatives and analogs can affect calcium homeostasis and thermoregulation in cells. Rapid effects of thyronamine derivatives and analogs on the heart include, but are not limited to $Na^+$ channel activation $Ca^{2+}$ ATPase activation, increased contractile function of isolated cardiac myocytes, and increased β-adrenergic responsiveness of dilated cardiomyopathic (DCM) myocytes. Thyronamine derivatives and analogs can directly couple mitochondrial function to electron transport in a way that opposes thyroid hormone.

Compositions and methods comprising thyronamine derivatives and analogs are useful to treat shock, including but not limited to, haemorrhagic (hypovolemic) shock, cardiogenic shock, neurogenic shock, and septic shock in a mammalian subject and to reduce blood loss in a mammalian subject. Shock is a medical emergency in which the organs and tissues of the body are not receiving an adequate flow of blood. This deprives the organs and tissues of oxygen (carried in the blood) and allows the buildup of waste products. Shock can result in serious damage or even death. The signs of shock (hypovolemic shock) are indicative of low peripheral blood flow and sympatheticoadrenal activity excess. Septic shock results from the damaging consequences of bacteria and toxins which include poor functioning of the heart muscle, widening of the diameter of the blood vessels, a drop in blood pressure, activation of the blood clotting system causing blood clots, followed by a risk of uncontrollable bleeding, damage to the lungs causing acute respiratory distress syndrome, liver failure, kidney failure, and coma. The patient in shock condition appears to be restless, anxious, and fearful. This restlessness can vary to apathy; in this situation the patient seems sleepy. After a while, if untreated or if the blood loss is underestimated, the patient will complain of a chilly sensation and at this time the apathy rapidly progress to coma. The most common and important signs are: changes in blood pressure (arterial and venous blood pressure are decreased), nausea, vomiting, tachycardia, and vasoconstriction (in this case is an effort to compensate the reduced cardiac output). In haemorragic shock the heart can receive 25% of the total cardiac output versus the normal 5-8%. Other signs include pale and cold skin, tachypnea and all the bloods changes as hemodilution, hormonal changes, pH changes, or renal dysfunction. To treat shock in a patient, pharmaceutical compositions comprising thyronamine derivatives and analogs can be administered to lower systemic vascular resistance, increase blood volume, and exert inotropic effects upon cardiac function resulting in an increased cardiac output for the patient, in addition to providing treatment for the patient's underlying condition.

Compositions and methods comprising thyronamine derivatives and analogs are useful to treat neoplasias. Thyronamine derivatives and analogs lower body temperature and decrease metabolic rate and are effective in treating fast-growing neoplasias by limiting their metabolic rate. The method and compositions can be used to treat neoplasia in a subject in need of treatment. Neoplasias include, without limitation, carcinomas, particularly those of the bladder, breast, cervix, colon, head, kidney, lung, neck, ovary, prostate, and stomach; lymphocytic leukemias, particularly acute lymphoblastic leukemia and chronic lymphocytic leukemia; myeloid leukemias, particularly acute monocytic leukemia, acute promyelocytic leukemia, and chronic myelocytic leukemia; malignant lymphomas, particularly Burkitt's lymphoma and Non-Hodgkin's lymphoma; malignant melanomas; myeloproliferative diseases; sarcomas, particularly Ewing's sarcoma, hemangiosarcoma, Kaposi's sarcoma, liposarcoma, peripheral neuroepithelioma, and synovial sarcoma; and mixed types of neoplasias, particularly carcinosarcoma and Hodgkin's disease. The methods and compositions can be used to treat breast cancer, colon cancer, leukemia, lung cancer, malignant melanoma, ovarian cancer, or prostate cancer.

Thyronamine derivatives and analogs as described in the present compositions and methods are useful, e.g., to control uterine contractions and/or bleeding ante-partum or postpartum, and to control blood loss as a result of disease or injury.

Thyronamine derivatives and analogs as described in the present compositions and methods are useful, e.g., as an antipyrogen to treat fever, or to treat heatstroke, hot flashes related to menopause, antihelmenthic drinking (water balance) behavior, male fertility, or female fertility. Fever or heat stroke results in an increase in the core body temperature of the subject.

Thyronamine derivatives and analogs as described in the present compositions and methods are useful, e.g., to treat diseases related to pancreatic function, including insulin and non-insulin related aspects. The present compositions and methods are useful to treat diabetes, diabetic ketoacidosis, hyperglycemia, hypoglycemia, enhance or reduce gut motility, or obesity, and to lower elevated or abnormal levels of cholesterol/LDL.

Thyronamine derivatives and analogs as described in the present compositions and methods are useful, e.g., to treat diseases related to renal failure or hepatic cirrhosis.

The present compositions and methods are useful to treat diabetes or obesity. Thyronamine derivatives and analogs play a role in the development and function of brown and white adipose tissue. Thyronamine derivatives and analogs can regulate factors of brown adipose tissue development to increase adaptive thermogenesis, e.g., to regulate basal oxygen consumption, fat stores, lipogenesis, and lipolysis.

Thyronamine derivatives and analogs as described in the present compositions and methods are useful, e.g., for modulation of thyroid metabolism and to treat diseases related to hyperthyroidism or hypothyroidism. The compositions and methods are useful for treatment of osteoporosis, the risk being increased by hyperthyroidism. The compositions and methods are useful for treatment and/or prevention of cretinism. The compositions and methods are useful to regulate hormone status and for physiological antagonism/agonism at catecholamine receptors, e.g., receptors for dopamine, noradrenaline, adrenaline.

Thyronamine derivatives and analogs as described in the present compositions and methods are useful to treat subclinical thyroid dysfunction as it affects the heart and circulatory system of a mammalian subject. Subclinical hypothyroidism or subclinical hyperthyroidism can be a physiological effect of thyronamine derivatives and analogs whose activity is up regulated or down regulated within the heart or circulatory system of a mammalian subject. Agonists or antagonists of thyronamine derivatives and analogs are useful as therapeutic compositions to treat subclinical hypothyroidism or subclinical hyperthyroidism.

Subclinical hypothyroidism is associated with impaired left ventricular diastolic function at rest, systolic dysfunction on effort, and enhanced risk for atherosclerosis and myocardial infarction. Subclinical hyperthyroidism is associated with increased heart rate, atrial arrhythmias, increased left ventricular mass with marginal concentric remodeling, impaired ventricular relaxation, reduced exercise performance, and increased risk for cardiovascular death. See, e.g., Biondi, et al., *Ann Intern Med.*, 2002, 137: 904-914. Such abnormalities can be reversed by treatment with a therapeutic pharmaceutical composition of an agonist of a thyronamine derivative or analog (to treat subclinical hypothyroidism) or by treatment with a therapeutic pharmaceutical composition of an antagonist of a thyronamine derivative or analog (to treat subclinical hyperthyroidism).

Thyronamine derivatives and analogs can affect normal bone growth and development. In children, hypothyroidism can cause short stature and delayed closure of the epiphyses. Thyronamine derivatives and analogs can affect the expression of various bone markers in serum, reflecting changes in both bone formation and resorption. Both osteoblast and osteoclast activities can be stimulated by thyronamine derivatives and analogs. Indeed, there is enhanced calcification and bone formation coupled to increased bone resorption in hyperthyroid patients. Additionally, the time interval between formation and subsequent mineralization of osteoid is shortened. The net effect on these bone cells is bone resorption and loss of trabecular bone thickness in hyperthyroidism. There also is marked increase in porosity and decreased cortical thickness in cortical bone in hyperthyroid patients. These effects can lead to osteoporosis and increased fractures. Thyronamine derivatives and analogs as described in the present compositions and methods are useful to treat osteoporosis and reverse the effects of bone loss.

Thyronamine derivatives and analogs as described in the present compositions and methods are useful, e.g., to treat psychological or psychophysiological disorders, for example, modulation of feeding behavior, starvation, eating disorders, anxiety, insomnia, migraine, and sleeping disorders. The present compositions and methods are useful to treat, for example, seizure, epilepsy, bipolar disorder, depression, attention deficit/hyperactivity disorder, and schizophrenia.

The present compositions and methods are useful, e.g., to enhance sedation or to treat cognition enhancement; memory enhancement, antiagression, antipsychotic, antispasmodic, antitremor, antidepressive, insomnia, seasonal affective disorder, augmentation or dampening of tricyclic antidepressant action, antiepileptic/antiseizure, mood modifier or enhancer, and psychological dissociative disorder.

The present compositions and methods are useful, e.g., to treat gastro esophageal reflux disease (GERD), anti-diarrheal, and other diseases involving GI motility, for treatment of asthma, use as an antihistamine and for treatment of malignant disease related to, uncontrolled cell growth and division as well as increased vascularization of the tumor.

Detection of Thyronamine Derivatives and Analogs

Thyronamine derivatives and analogs can be detected and quantified by any of a number of means well known to those of skill in the art. These include analytic biochemical methods such as electrophoresis, capillary electrophoresis, high performance liquid chromatography (HPLC), mass spectrometry, thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In one embodiment, thyronamine derivatives and analogs are detected using an immunoassay such as an ELISA assay (see, e.g., Crowther, John R. *ELISA Theory and Practice*. Humana Press: New Jersey, 1995). An "immunoassay" is an assay that utilizes an antibody to specifically bind to an thyronamine derivatives and analogs.

Antibodies to Thyronamine Derivatives and Analogs

Polyclonal antibodies, monoclonal antibodies, chimeric antibodies or humanized antibodies that react specifically to thyronamine derivatives and analogs, e.g., 3-iodo-thyronamine ($T_1AM$) is useful for determining the presence of thyronamine derivatives and analogs in primary cells and immortalized cell lines in vitro, as well as in vivo, in tissues and in biological fluids, for example, by radioimmunoassay and by immunocytochemistry.

Methods of producing polyclonal and monoclonal antibodies that react specifically with thyronamine derivatives and analogs are known to those of skill in the art (see, e.g., Coligan, *Current Protocols in Immunology* (1991); Harlow and Lane, *Antibodies: A Laboratory Manual*, Cold Spring Harbor Laboratory, 1988; Goding, *Monoclonal Antibodies: Principles and Practice* (2d ed. 1986); and Kohler & Milstein, *Nature* 256: 495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246: 1275-1281 (1989); Ward et al., *Nature* 341: 544-546 (1989)). Such antibodies can be used for therapeutic and diagnostic applications, e.g., in the treatment and/or detection of congestive heart failure.

A number of thyronamine derivatives and analogs, e.g., 3-iodothyronamine ($T_1AM$), 3,3'-diiodothyronamine (3,3'-$T_2AM$), 3,5-diiodothyronamine ($T_2AM$), or 3,5,3'-triiodothyronamine ($T_3AM$), can be used to produce antibodies specifically reactive with iodo-thyronamines. Synthetic or naturally occurring thyronamine derivatives and analogs can be used either in pure or impure form. The product is then injected into an animal capable of producing antibodies. Either monoclonal or polyclonal antibodies can be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to thyronamine derivatives and analogs. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies can be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6: 511-519, 1976). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells can be enhanced by various techniques, including injection into the peritoneal cavity of a vertebrate host. Alternatively, one can isolate DNA sequences which encode a monoclonal antibody or a binding fragment thereof by screening a DNA library from human B cells according to the general protocol outlined by Huse et al., *Science* 246: 1275-1281 (1989).

Monoclonal antibodies and polyclonal sera are collected and titered against the immunogen in an immunoassay, for example, a solid phase immunoassay with the immunogen immobilized on a solid support. Typically, polyclonal antisera with a titer of $10^4$ or greater are selected and tested for their cross reactivity against other amines or even other related amines from other organisms, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better.

Once specific antibodies to thyronamine derivatives and analogs are available, iodo-thyronamine can be detected by a variety of immunoassay methods. For a review of immunological and immunoassay procedures, see *Basic and Clinical Immunology* (Stites & Terr eds., 7th ed. 1991). Moreover, the immunoassays as described herein can be performed in any of several configurations, which are reviewed extensively in *Enzyme Immunoassay* (Maggio, ed., 1980); and Harlow & Lane, supra.

Chimeric and Humanized Antibodies

Chimeric and humanized antibodies have the same or similar binding specificity and affinity as a mouse or other nonhuman antibody that provides the starting material for construction of a chimeric or humanized antibody. Some chimeric or humanized antibodies have affinities within a factor of 2-fold, 5-fold or 10-fold that of a mouse. Chimeric antibodies are antibodies whose light and heavy chain genes have been constructed, typically by genetic engineering, from immunoglobulin gene segments belonging to different species. For example, the variable (V) segments of the genes from a mouse monoclonal antibody can be joined to human constant (C) segments, such as $IgG_1$, $IgG_2$, $IgG_3$ and $IgG_4$. A typical chimeric antibody is thus a hybrid protein consisting of the V or antigen-binding domain from a mouse antibody and the C or effector domain from a human antibody.

Humanized antibodies have variable region framework residues substantially from a human antibody (termed an acceptor antibody) and complementarity determining regions substantially from a nonhuman antibody such as a mouse-antibody, (referred to as the donor immunoglobulin). See Queen et al., *Proc. Natl. Acad. Sci. USA* 86:10029-33, 1989, and WO 90/07861, U.S. Pat, Nos. 5,693,762, 5,693, 761, 5,585,089, 5,530,101 and Winter, U.S. Pat. No. 5,225, 539, each of which is herein incorporated by reference in its entirety for all purposes. The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653, incorporated herein by reference. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid: (1) noncovalently binds antigen directly, (2) is adjacent to a CDR region, (3) otherwise interacts with a CDR region (e.g. is within about 6A of a CDR region), or (4) participates in the $V_L$-$V_H$ interface.

Other candidates for substitution are acceptor human framework amino acids that are unusual for a human immunoglobulin at that position. These amino acids can be substituted with amino acids from the equivalent position of the donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

Human antibodies against thyronamine derivatives and analogs can be generated by a variety of techniques. Some human antibodies are selected by competitive binding experiments, or otherwise, to have the same epitope specificity as a particular mouse antibody. Human antibodies can also be screened for a particular epitope specificity by using only a fragment of thyronamine derivative and analog as the immunogen. One technique is the trioma methodology which can utilize an exemplary cell fusion partner, SPAZ-4, for use in this approach have been described by Oestberg et al., *Hybridoma* 2: 361-67, 1983; Oestberg, U.S. Pat. No. 4,634,664; and Engleman et al., U.S. Pat. No. 4,634,666, each of which is incorporated by reference in their entirety for all purposes. In a second technique human antibodies against thyronamine derivatives and analogs can also be produced from non-human transgenic mammals having transgenes encoding at least a segment of the human immunoglobulin locus as discussed. Usually, the endogenous immunoglobulin locus of such transgenic mammals is functionally inactivated. Preferably, the segment of the human immunoglobulin locus includes unrearranged sequences of heavy and light chain components. A further approach for obtaining human anti-thyronamine derivatives and analogs is to screen a DNA library from human B cells according to the general protocol outlined by Huse et al., *Science* 246: 1275-81, 1989, incorporated herein by reference. The protocol described by Huse is rendered more efficient in combination with phage-display technology. See, e.g., Dower et al., WO 91/17271 and McCafferty et al. WO 92/01047, U.S. Pat, Nos. 5,877,218, 5,871,907, 5,858,657, 5,837,242, 5,733,743 and 5,565,332, 5,969,108, 6,172,197 (each of which is incorporated by reference in its entirety for all purposes). Additional methods for selecting and labeling antibodies, or other proteins, that bind to a particular ligand are described by U.S. Pat. Nos. 5,994,519 and 6,180,336, each incorporated herein by reference. The heavy and light chain variable regions of chimeric, humanized, or human antibodies can be linked to at least a portion of a human constant region. The choice of constant region depends, in part, whether antibody-dependent complement and/or cellular mediated toxicity is desired. Chimeric, humanized and human antibodies are typically produced by recombinant expression. Recombinant polynucleotide constructs typically include an expression control sequence operably linked to the coding sequences of antibody chains, including naturally-associated or heterologous promoter regions.

Immunological Binding Assays

Thyronamine derivatives and analogs can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991).

Immunoassays typically use direct or indirect labeling agents to label the complex formed by the antibody and antigen. The labeling agent can itself be one of the moieties comprising the antibody/antigen complex, i.e., a direct labeling agent. Thus, the labeling agent can be a labeled thyronamine derivative and analog or a labeled anti-iodo-thyronamine antibody. Alternatively, the labeling agent can be a third moiety, such as a secondary antibody, that specifically binds to the antibody/iodo-thyronamine complex (a secondary antibody is typically specific to antibodies of the species from which the first antibody is derived). Other proteins capable of specifically binding immunoglobulin constant regions, such as protein A or protein G can also be used as the label agent. These proteins exhibit a strong non-immunogenic reactivity with immunoglobulin constant regions from a variety of species (see, e.g., Kronval et al., *J. Immunol.* 111: 1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non competitive assay formats: Immunoassays for detecting thyronamine derivatives and analogs in samples can be either competitive or noncompetitive. Noncompetitive immunoassays are assays in which the amount of antigen is directly measured. In one preferred "sandwich" assay, for example, anti-iodo-thyronamine antibodies can be bound directly to a solid substrate on which they are immobilized. These immobilized antibodies then capture thyronamine derivatives and analogs present in the test sample. The iodo-thyronamine thus immobilized is then bound by a labeling agent, such as a second iodo-thyronamine antibody bearing a label. Alternatively, the second antibody can lack a label, but it can, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive assay formats: In competitive assays, the amount of thyronamine derivative and analog present in a sample is measured indirectly, e.g., by measuring the amount of added (exogenous) iodo-thyronamine displaced (or competed away) from an anti-iodo-thyronamine antibody by iodo-thyronamines present in a sample. For example, a known amount of labeled iodo-thyronamine is added to a sample and the sample is then contacted with an anti-iodo-thyronamine antibody. The amount of labeled iodo-thyronamine bound to the antibody is inversely proportional to the concentration of iodo-thyronamine present in the sample. In one embodiment, the antibody is immobilized on a solid substrate. The amount of iodo-thyronamine bound to the antibody can be determined either by measuring the amount of iodo-thyronamine present in a iodo-thyronamine/antibody complex, or alternatively by measuring the amount of remaining uncomplexed iodo-thyronamine. The amount of iodo-thyronamine can be detected by providing a labeled iodo-thyronamine molecule.

A hapten inhibition assay is another competitive assay. The hapten is generally conjugated to a carrier protein, for example, KLH or BSA. In this assay the known thyronamine derivative or analog is immobilized on a solid substrate. A known amount of anti-iodo-thyronamine antibody is added to the sample, and the sample is then contacted with the immobilized iodo-thyronamine. The amount of anti-iodo-thyronamine antibody bound to the known immobilized iodo-thyronamine is inversely proportional to the amount of iodo-thyronamines present in the sample. Again, the amount of immobilized antibody can be detected by detecting either the immobilized fraction of antibody or the fraction of the antibody that remains in solution. Detection can be direct where the antibody is labeled or indirect by the subsequent addition of a labeled moiety that specifically binds to the antibody as described above.

Other assay formats: Liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

Reduction of non-specific binding: One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels for detection: The particular label or detectable group used in the assay is not a critical aspect, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied. Thus, a label is any composition detectable by spectroscopic, photochemical, biochemical, immunochemical, electrical, optical or chemical means. Useful labels include magnetic beads (e.g., DYNABEADS™), fluorescent dyes (e.g., fluorescein isothiocyanate, Texas red, rhodamine, and the like), radio-labels (e.g., $^3H$, $^{125}I$, $^{35}S$, $^{14}C$, or 32P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label can be coupled directly or indirectly to the desired component of the assay according to methods well known in the art. As indicated above, a wide variety of labels can be used, with the choice of label depending on sensitivity required, ease of conjugation with the compound, stability requirements, available instrumentation, and disposal provisions. For a review of various labeling or signal producing systems that can be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally simple calorimetric labels can be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Diagnostic Uses for Detection of Disease

Characteristics and Detection of Thyronamine Compounds of the Invention for Use as Diagnostic Reagents. Thyronamine compounds, e.g., $T_0AM$ and $T_1AM$, for use in diagnostic methods to identify depression and other mood related disorders in a mammalian subject, are preferably produced using the methods described above. The methods result in virtually unlimited numbers of thyronamine compounds of the invention of any epitope binding specificity and very high binding affinity to any desired antigen.

Diagnostic methods to identify depression and other mood related disorders in a mammalian subject by detection of thyronamine compounds in the mammalian subject can be accomplished by immunologic assay for thyronamine compounds, HPLC (high pressure liquid chromatography), LC/MS (liquid chromatography-mass spectrometry), mass spectrometric assay for thyronamine compounds, as known in the art and as described herein, or by other diagnostic assays known in the art.

Thyronamine compounds, e.g., $T_0AM$ and $T_1AM$, for use in diagnostic methods to identify mood related disorders, including but not limited to, depression, bipolar disorder, schizophrenia, eating disorders, anxiety, seizure, epilepsy, insomnia and sleeping disorders, gastro esophageal reflux disease, diseases involving gastrointestinal motility or asthma. Thyronamine compounds, e.g., $T_0AM$ and $T_1AM$, for use in diagnostic methods to identify disease state including, but not limited to, diabetes, hyperglycemia, hypoglycemia, cardiac arrhythmia, stroke, osteoporosis, obesity, atherosclerosis, hypertension, hyperthyroidism or hypothyroidism.

Thyronamine compounds of the invention used in the claimed diagnostic methods preferably have a high immunoreactivity, that is, percentages of thyronamine molecules that are correctly folded so that they can specifically bind their target antigen. Such expression usually results in immunoreactivity of at least 80%, 90%, 95% or 99%.

Some methods of the invention employ polyclonal preparations of thyronamine compounds of the invention as diagnostic reagents, and other methods employ monoclonal isolates. The use of polyclonal mixtures has a number of advantages with respect to compositions made of one monoclonal antibody. By binding to multiple sites on a target, polyclonal antibodies or other polypeptides can generate a stronger signal (for diagnostics) than a monoclonal that binds to a single site. Further, a polyclonal preparation can bind to numerous variants of a prototypical target sequence (e.g., allelic variants, species variants, strain variants, drug-induced escape variants) whereas a monoclonal antibody may bind only to the prototypical sequence or a narrower range of variants thereto. However, monoclonal antibodies are advantageous for detecting a single antigen in the presence or potential presence of closely related antigens.

In methods employing polyclonal human antibodies to thyronamine compounds prepared in accordance with the methods described above, the preparation typically contains an assortment of antibodies with different epitope specificities to the intended target antigen. In some methods employing monoclonal antibodies, it is desirable to have two antibodies of different epitope binding specificities. A difference in epitope binding specificities can be determined by a competition assay.

Samples and Target. Although human antibodies can be used as diagnostic reagents for any kind of sample, they are most useful as diagnostic reagents for human samples to detect thyronamine compounds in the sample. Samples can be obtained from any tissue or body fluid of a patient. Preferred sources of samples include, whole blood, plasma, semen, saliva, tears, urine, fecal material, sweat, buccal, skin and hair. Samples can also be obtained from biopsies of internal organs or from cancers. Samples can be obtained from clinical patients for diagnosis or research or can be obtained from undiseased individuals, as controls or for basic research.

The methods can be used for detecting any type of target antigen. Exemplary target antigens including thyronamine compounds, e.g., $T_0AM$ and $T_1AM$. Other target antigens are human proteins whose expression levels or compositions have been correlated with human disease or other phenotype. Examples of such antigens include adhesion proteins, hormones, growth factors, cellular receptors, autoantigens, autoantibodies, and amyloid deposits. Other targets of interest include tumor cell antigens, such as carcinoembryonic antigen. Other antigens of interest are class I and class II MHC antigens.

Formats for Diagnostic Assays. Human antibodies can be used to detect a given target, thyronamine compounds, e.g., $T_0AM$ and $T_1AM$ in a variety, of standard assay formats. Such formats include immunoprecipitation, Western blotting, ELISA, radioimmunoassay, and immunometric assays. See Harlow & Lane, supra; U.S. Pat. Nos. 3,791,932; 3,839,153; 3,850,752; 3,879,262; 4,034,074; 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876, each incorporated herein by reference in their entirety and for all purposes.

Inmunometric or sandwich assays are a preferred format. See U.S. Pat. Nos. 4,376,110, 4,486,530, 5,914,241, and 5,965,375, each incorporated herein by reference in their entirety and for all purposes. Such assays use one antibody or population of antibodies immobilized to a solid phase, and another antibody or population of antibodies in solution.

Typically, the solution antibody or population of antibodies is labelled. If an antibody population is used, the population typically contains antibodies binding to different epitope specificities within the target antigen, e.g., thyronamine compound. Accordingly, the same population can be used for both solid phase and solution antibody. If monoclonal antibodies are used, first and second monoclonal antibodies having different binding specificities are used for the solid and solution phase. Solid phase and solution antibodies can be contacted with target antigen in either order or simultaneously. If the solid phase antibody is contacted first, the assay is referred to as being a forward assay. Conversely, if the solution antibody is contacted first, the assay is referred to as being a reverse assay. If target is contacted with both antibodies simultaneously, the assay is referred to as a simultaneous assay. After contacting the target with antibody, a sample is incubated for a period that usually varies from about 10 min to about 24 hr and is usually about 1 hr. A wash step is then performed to remove components of the sample not specifically bound to the antibody being used as a diagnostic reagent. When solid phase and solution antibodies are bound in separate steps, a wash can be performed after either or both binding steps. After washing, binding is quantified, typically by detecting label linked to the solid phase through binding of labelled solution antibody. Usually for a given pair of antibodies or populations of antibodies and given reaction conditions, a calibration curve is prepared from samples containing known concentrations of target antigen. Concentrations of antigen in samples being tested are then read by interpolation from the calibration curve. Analyte can be measured either from the amount of labelled solution antibody bound at equilibrium or by kinetic measurements of bound labelled solution antibody at a series of time points before equilibrium is reached. The slope of such a curve is a measure of the concentration of target in a sample Suitable supports for use in the above methods include, for example, nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™. (Amersham Pharmacia Biotech, Piscataway N.J., and the like. Immobilization can be by absorption or by covalent attachment. Optionally, antibodies can be joined to a linker molecule, such as biotin for attachment to a surface bound linker, such as avidin.

Pharmaceutical Compositions

Thyronamine derivatives and analogs useful in the present compositions and methods can be administered to a human patient per se, in the form of a stereoisomer, prodrug, pharmaceutically acceptable salt, hydrate, solvate, acid salt hydrate, N-oxide or isomorphic crystalline form thereof, or in the form of a pharmaceutical composition where the compound is mixed with suitable carriers or excipient(s) in a therapeutically effective amount, for example, heart disease or congestive heart failure.

Routes of Administration

The thyronamine derivatives and analogs and pharmaceutical compositions described herein can be administered by a variety of routes. Suitable routes of administration can, for example, include oral, rectal, transmucosal, or intestinal administration; parenteral delivery, including intramuscular, subcutaneous, intramedullary injections, as well as intrathecal, direct intraventricular, intravenous, intraperitoneal, spinal, epidural, intranasal, or intraocular injections. Alternatively, one can administer the compound in a local rather than systemic manner, for example via injection of the compound directly into the subject, often in a depot or sustained release formulation. Furthermore, one can administer the compound in a targeted drug delivery system, for example, in a liposome coated vesicle. The liposomes can be targeted to and taken up selectively by the tissue of choice. In a further embodiment, the thyronamine derivatives and analogs and pharmaceutical compositions described herein are administered orally.

Composition/Formulation

The pharmaceutical compositions described herein can be manufactured in a manner that is itself known, e.g., by means of conventional mixing, dissolving, granulating, dragee-making, levigating, emulsifying, encapsulating, entrapping or lyophilizing processes. Pharmaceutical compositions for use as described herein can be formulated in conventional manner using one or more physiologically acceptable carriers comprising excipients and auxiliaries which facilitate processing of the active compounds into preparations which can be used pharmaceutically. Proper formulation is dependent upon the route of administration chosen. For injection, the agents can be formulated in aqueous solutions, e.g., in physiologically compatible buffers such as Hanks' solution, Ringer's solution, or physiological saline buffer. For transmucosal administration, penetrants appropriate to the barrier to be permeated are used in the formulation. Such penetrants are generally known in the art. For oral administration, the compounds can be formulated readily by combining with pharmaceutically acceptable carriers that are well known in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores.

Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner. For administration by inhalation, the compounds for use are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides. In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

A suitable pharmaceutical carrier for hydrophobic compounds is a cosolvent system comprising benzyl alcohol, a nonpolar surfactant, a water-miscible organic polymer, and an aqueous phase. The cosolvent system can be the VPD co-solvent system. VPD is a solution of 3% (w/v) benzyl alcohol, 8% (w/v) of the nonpolar surfactant polysorbate 80, and 65% (w/v) polyethylene glycol 300, made up to volume in absolute ethanol. The VPD co-solvent system (VPD:5W) consists of VPD diluted 1:1 with a 5% (w/v) dextrose in water solution. This co-solvent system dissolves hydrophobic compounds well, and itself produces low toxicity upon systemic administration. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can substitute for dextrose. Alternatively, other delivery systems for hydrophobic pharmaceutical compounds can be employed. Liposomes and emulsions are well known examples of delivery vehicles or carriers for hydrophobic drugs. Certain organic solvents such as dimethylsulfoxide also can be employed, although usually at the cost of greater toxicity.

Additionally, the compounds can be delivered using a sustained-release system, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few weeks up to over 100 days. The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutically acceptable carriers are determined in part by the particular composition being administered, as well as by the particular method used to administer the composition. Accordingly, there is a wide variety of suitable formulations of pharmaceutical compositions for administering the iodo-thyronamine (see, e.g., *Remington's Pharmaceutical Sciences*, Mack Publishing Co., Easton, Pa. $18_{th}$ ed., 1990, incorporated herein by reference). The pharmaceutical compositions generally comprise a differentially expressed protein, agonist or antagonist in a form suitable for administration to a patient. The pharmaceutical compositions are generally formulated as sterile, substantially isotonic and in full compliance with all Good Manufacturing Practice (GMP) regulations of the U.S. Food and Drug Administration.

Effective Dosages

Pharmaceutical compositions suitable for use include compositions wherein the thyronamine derivatives and analogs are contained in a therapeutically effective amount. Determination of an effective amount is well within the capability of those skilled in the art, especially in light of the detailed disclosure provided herein. For any compound used in the present method, a therapeutically effective dose can be estimated initially from cell culture assays. For example, a dose can be formulated in animal models to achieve a circulating concentration range that includes the $I_{50}$ as determined in cell culture (i.e., the concentration of test compound that is lethal to 50% of a cell culture) or the $I_{100}$ as determined in cell culture (i.e., the concentration of compound that is lethal to 100% of a cell culture). Such information can be used to more accurately determine useful doses in humans. Initial dosages can also be formulated by comparing the effectiveness of the thyronamine derivatives and analogs described herein in cell culture assays with the effectiveness of known heart medications. In this method an initial dosage can be obtained by multiplying the ratio of effective concentrations obtained in cell culture assay for the thyronamine derivatives and analogs and a known heart drug by the effective dosage of the known heart drug. For example, if an thyronamine derivative or analog is twice as effective in cell culture assay than the heart drug (i.e., the $I_{50}$ $T_1$amine is equal to one half times the $I_{50}$ heart drug in the same assay), an initial effective dosage of the thyronamine derivative or analog would be one-half the known dosage for the heart drug. Using these initial guidelines one having ordinary skill in the art could determine an effective dosage in humans. Initial dosages can also be estimated from in vivo data. One having ordinary skill in the art could readily optimize administration to humans based on this data. Dosage amount and interval can be adjusted individually to provide plasma levels of the active compound which are sufficient to maintain therapeutic effect. Usual patient dosages for oral administration range from about 50-2000 mg/kg/day, typically from about 250-1000 mg/kg/day, from about 500-700 mg/kg/day or from about 350-550 mg/kg/day. Therapeutically effective serum levels will be achieved by administering multiple doses each day. In cases of local administration or selective uptake, the effective local concentration of the drug can not be related to plasma concentration. One having skill in the art will be able to optimize therapeutically effective local dosages without undue experimentation. The amount of composition administered will, of course, be dependent on the subject being treated, on the subject's weight, the severity of the affliction, the manner of administration and the judgment of the prescribing physician. The therapy can be repeated intermittently while congestive heart failure is detectable or even when they are not detectable. Moreover, due to its apparent nontoxicity, the therapy can be provided alone or in combination with other drugs, such as for example, anti-inflammatories, antibiotics, corticosteroids, vitamins and the like. Possible synergism between the thyronamine derivatives or analogs described herein and other drugs can occur. In addition, possible synergism between a plurality of thyronamine derivatives or analogs can occur.

The typical daily dose of a pharmaceutical composition of thyronamine derivatives and analogs varies according to individual needs, the condition to be treated and with the route of administration. Suitable doses are in the general range of from 0.001 to 10 mg/kg bodyweight of the recipient per day. Within this general dosage range, doses can be chosen at which the pharmaceutical composition of thyronamine derivatives and analogs has an inotropic effect to increase cardiac output without the chronotropic effect to increase heart rate. In general, but not exclusively, such doses will be in the range of from 0.5 to 10 mg/kg.

In addition, within the general dose range, doses can be chosen at which the compounds pharmaceutical composition of thyronamine derivatives and analogs has an inotropic effect to increase cardiac output without the chronotropic effect to increase heart rate. In general, but not exclusively, such doses will be in the range of from 0.001 to 0.5 mg/kg. It is to be understood that the 2 sub ranges noted above are not mutually exclusive and that the particular activity encountered at a particular dose will depend on the nature of the pharmaceutical composition of thyronamine derivatives and analogs used.

The pharmaceutical composition of thyronamine derivatives and analogs can be in unit dosage form, for example, a tablet or a capsule so that the patient can self-administer a single dose. In general, unit doses contain in the range of from 0.05-100 mg of a compound of the pharmaceutical composition of thyronamine derivatives and analogs. Unit doses contain from 0.05 to 10 mg of the pharmaceutical composition. The active ingredient can be administered from 1 to 6 times a day. Thus daily doses are in general in the range of from 0.05 to 600 mg per day. In an embodiment, daily doses are in the range of from 0.05 to 100 mg per day or from 0.05 to 5 mg per day.

Toxicity

Toxicity and therapeutic efficacy of the thyronamine derivatives and analogs described herein can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds which exhibit high therapeutic indices are chosen. The data obtained from these cell culture assays and animal studies can be used in formulating a dosage range that is not toxic for use in human. The dosage of such compounds lies within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch.1, p.1). One of the advantages, among others, of using the thyronamine derivatives and analogs described herein to treat congestive heart failure is their lack of toxicity. For example, it has been found that repeated intraperitoneal doses of 75 mg/kg produced no ill effects in mice (see Example 5). Since the i.v. serum half-life ($t_{1/2}$) of $T_1$amine is about 2-2.5 hours, repeated daily dosages of the iodo-thyronamine described herein without ill effects is predictable.

Methoda of Preparation

The thyronamine derivatives and analogs can be prepared from the copper mediated coupling of a boronic acid or analog and the appropriate protected phenol as shown in Schemes 1-3. Variations in $R_6$ can be made by utilizing the appropriately protected boronic acid.

Scheme 1: Preparation of Protected Tyramines

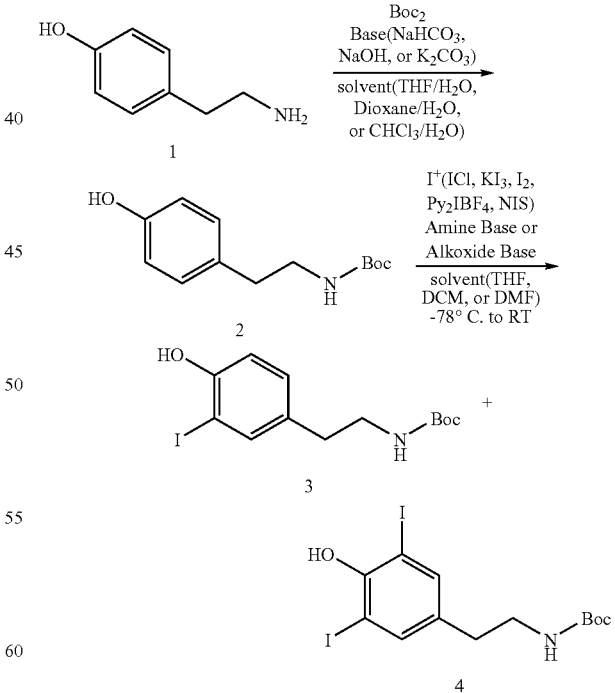

In Scheme 1, the appropriate amine-protected iodine-substituted tyramines 3 and 4 are prepared by first protecting the amino functionality of the tyramine 1 to form the protected tyramine 2 and then substituting one or more of the hydrogens (at the 3-position, 5-position or both) on the phenyl with iodine to form compounds 3 and 4. Other substitutions can also be made in an analogous fashion known to those skilled in the art. The amino functionality of the tyramine is protected using a protecting group in the presence of base, such as $NaHCO_3$, NaOH, or $K_2CO_3$, and solvent, such as $THF/H_2O$, $dioxane/H_2O$ or $CHCl_3/H_2O$. Suitable amine-protecting groups commonly used in the art can be found in Greene and Wuts, *Protective Groups in Organic Synthesis*, 2d ed, John Wiley & Sons, New York, 1991, the disclosure of which is hereby incorporated by reference in its entirety. Suitable protecting groups include but are not limited to, allyloxycarbonyl (Aloc), benzyloxycarbonyl (Cbz), ethoxycarbonyl, 9-fluorenylmethoxycarbonyl (Fmoc), and tert-butoxycarbonyl (t-Boc). The t-Boc is a preferred protecting group. The hydrogens on the phenyl group at 3-position, 5-position or both are substituted with iodine by employing electrophilic iodine reagents, for example, iodine monochloride (ICl), a solution of potassium iodide and iodine ($KI_3$), iodine ($I_2$), bispyridinium iodine tetrafluoroborate ($Py_2IBF_4$), N-iodosuccinimide (NIS) and the like, in the presence of base, such as amine base or alkoxide base. These conditions form a mixture of the appropriate amine-protected iodine-substituted tyramines 3 and 4 which can be separated by column chromatography.

Scheme 2: Preparation of Boronic Acid

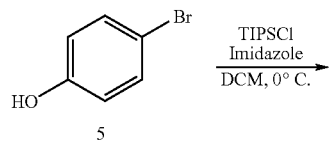

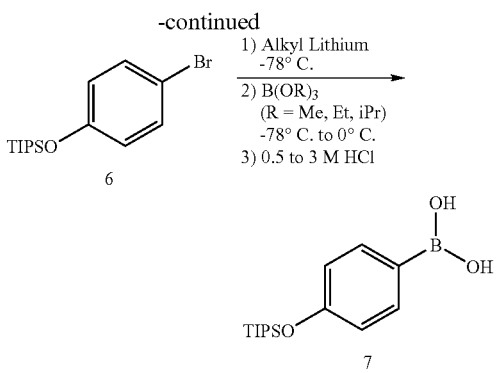

In Scheme 2, the appropriate phenylboronic acid 7 is prepared from the commercially available p-bromophenol 5 starting material. Phenol 5 is first protected with a hydroxyl protecting group, such as triisopropylsilyl chloride (TIPS), to form compound 6, which is subsequently reacted with alkyl lithium, $B(OR)_3$ (where R is methyl, ethyl, or isopropyl), then hydrolyzed to form compound 7. Suitable hydroxyl-protecting groups commonly used in the art can be found in Greene and Wuts, *Protective Groups in Organic Synthesis*, 2d ed, John Wiley & Sons, New York, 1991, the disclosure of which is hereby incorporated by reference in its entirety. Suitable protecting groups include but are not limited to triethylsilyl (TES), tert-butyldimethylsilyl (TBDMS), and triisopropylsilyl (TIPS). TIPSO is a preferred protecting group.

Scheme 3: Synthesis of Thyronamines

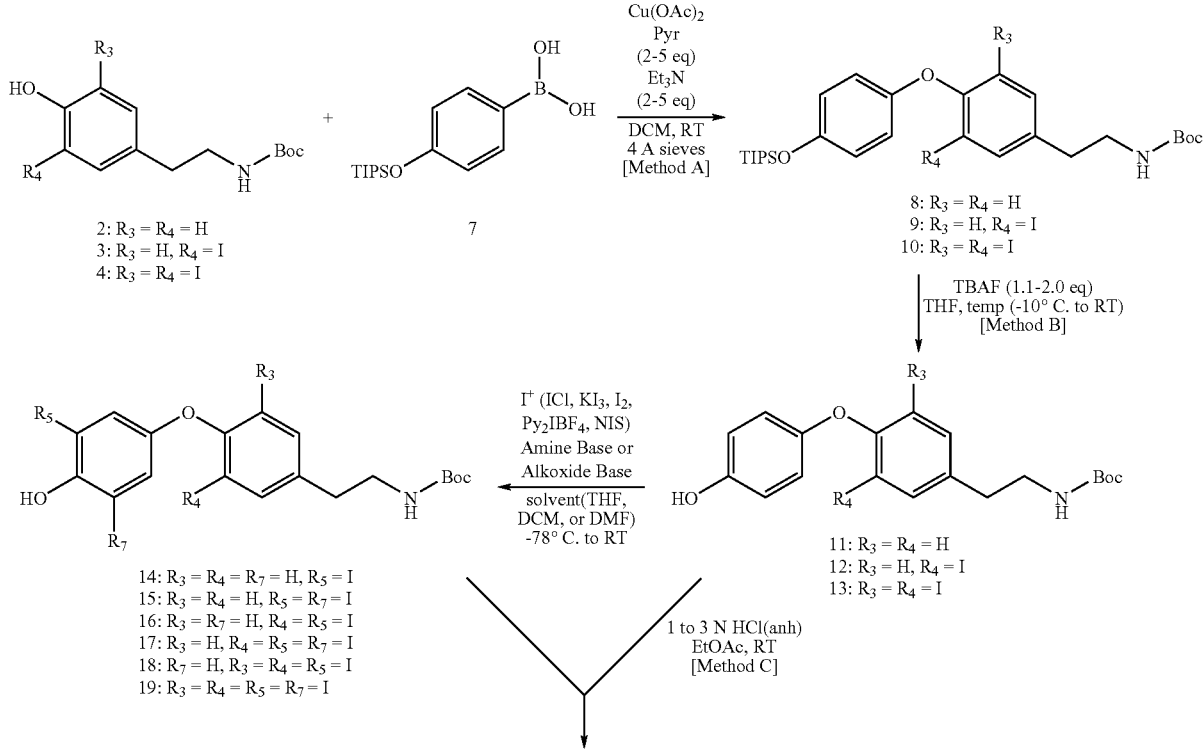

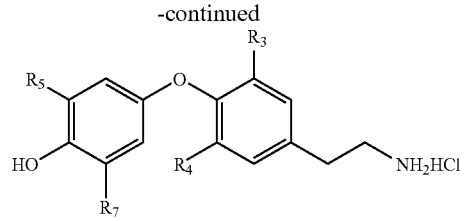

22: $R_3 = R_4 = R_5 = R_7 = H$
23: $R_3 = R_5 = R_7 = H, R_4 = I$
24: $R_5 = R_7 = H, R_3 = R_4 = I$
25: $R_3 = R_4 = R_7 = H, R_5 = H$
26: $R_3 = R_4 = H, R_5 = R_7 = I$
27: $R_3 = R_7 = H, R_4 = R_5 = I$
28: $R_3 = H, R_4 = R_5 = R_7 = I$
29: $R_7 = H, R_3 = R_4 = R_5 = I$
30: $R_3 = R_4 = R_5 = R_7 = I$ where

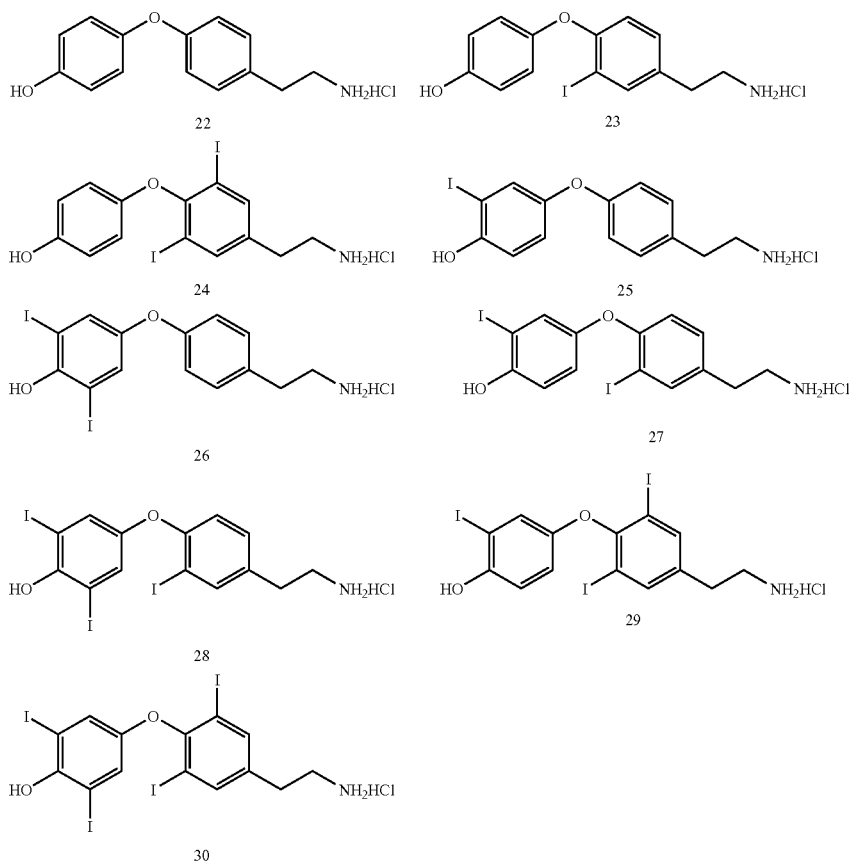

In Scheme 3, compound 7 prepared in Scheme 2 and the amine-protected iodine-substituted tyramine (compound 3 or 4) prepared in Scheme 1 are coupled in the presence of copper to give the thyronamine core. In subsequent steps, the hydroxyl-protecting group and the amino-protecting group are removed. Alternatively, Iodo substitutions can be made at the 3' position, 5'-position or both the 3'- and 5'-positions prior to amine deprotection. Other substitutions at the 3,3',5 and 5' positions, such as fluoro, methy, ethyl and nitrile, can be made by using electrophilic bromide and chloride or by using an appropriately substituted boronic acid of type 7 or protected amine of type 2.

Compounds with other changes at the X position, such as $CH_2$, S, and NH, can also be made. In particular, halogenation followed by formylation of phenol 2 and subsequent treatment with the alkyl lithium of 6 will give compounds of the general formula X is equal to $CH_2$ after catalytic hydrogenation. Nucleophilic addition of the appropriate thiophenol to compound 6 will give compounds of the general formula where X is S. Additionally, a palldium-mediated coupling can be used to synthesis compounds of the general formula where X is NH.

Description of Scheme 4

Compounds of the general formula where $R_6$ is H and X is O can be prepared by reacting the protected thyronamine 2 with phenyl boronic acid to give 20, as shown in Scheme 4. The coupling reaction utilizes a copper(II) salt and suitable amine bases such as pyridine and triethylamine.

Anhydrous polar aprotic solvents are typically used, such as DCM. Temperatures can range from 0° C. to 50° C. The amine protecting group is then removed using standard deprotection conditions.

Scheme 4: Synthesis of Phenyl Derivative

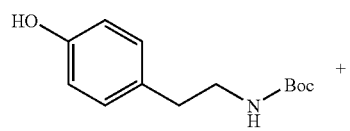

2

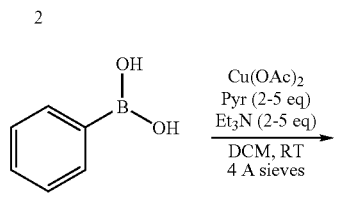

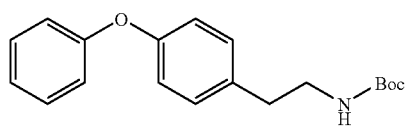

20

1 to 3 N HCl(anh)
EtOAc, RT

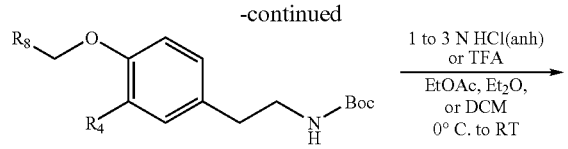

21: $R_4$ = H, $R_8$ = Ph
33: $R_4$ = I, $R_8$ = Ph
34: $R_4$ = H, $R_8$ = PhCH$_2$
35: $R_4$ = H, $R_8$ = p-F—Ph
36: $R_4$ = H, $R_8$ = m-CH$_3$O—Ph
37: $R_4$ = H, $R_8$ = p-CF$_3$—Ph
38: $R_4$ = H, $R_8$ = (m-CH$_3$)—Ph

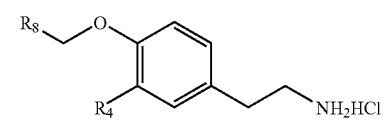

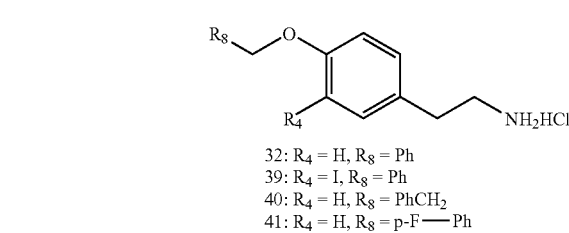

32: $R_4$ = H, $R_8$ = Ph
39: $R_4$ = I, $R_8$ = Ph
40: $R_4$ = H, $R_8$ = PhCH$_2$
41: $R_4$ = H, $R_8$ = p-F—Ph
42: $R_4$ = H, $R_8$ = m-CH$_3$O—Ph
43: $R_4$ = H, $R_8$ = p-CF$_3$—Ph
44: $R_4$ = H, $R_8$ = (m-CH$_3$)—Ph where

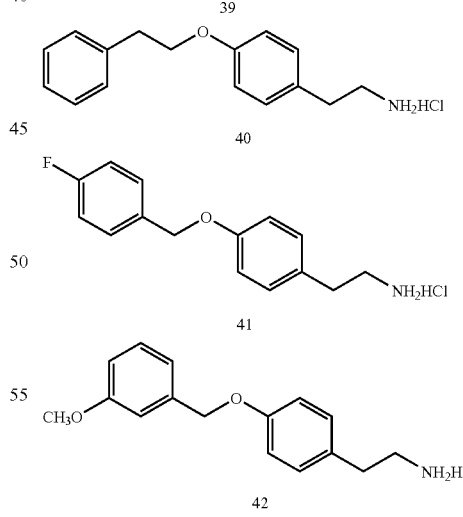

31

Description of Scheme 5

Compounds of the general formula where $R_6$ is H and X is CH$_2$O or CH$_2$CH$_2$O can be prepared by reacting the protected tyramine 2 with benzyl and alkyl halides, as shown in Scheme 5. The amine protecting group of the alkylated products can subsequently be deprotected using standard deprotection conditions. The alkylations can be done in a variety of polar aprotic solvents including, but not limited to, dimethylformamide (DMF), tetrahydrofuran (TIF), acetone, diethyl ether, and dimethyl sulfoxide (DMSO). Temperatures can range from 0° C. to reflux. Typically, DMF at ambient temperature is sufficient.

Scheme 5: Synthesis of O-Alkylated Tyramine Derivatives

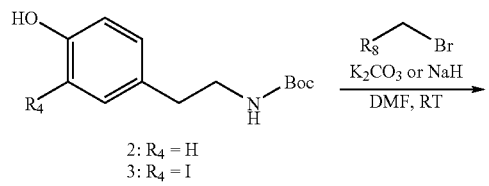

2: $R_4$ = H
3: $R_4$ = I

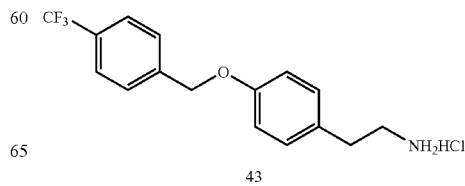

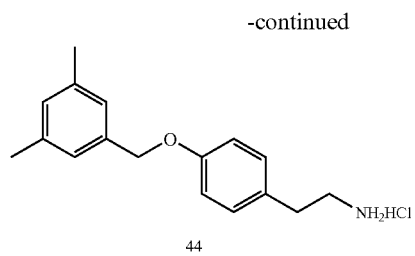

44

Scheme 6: Synthesis of N-Alkylated Derivatives

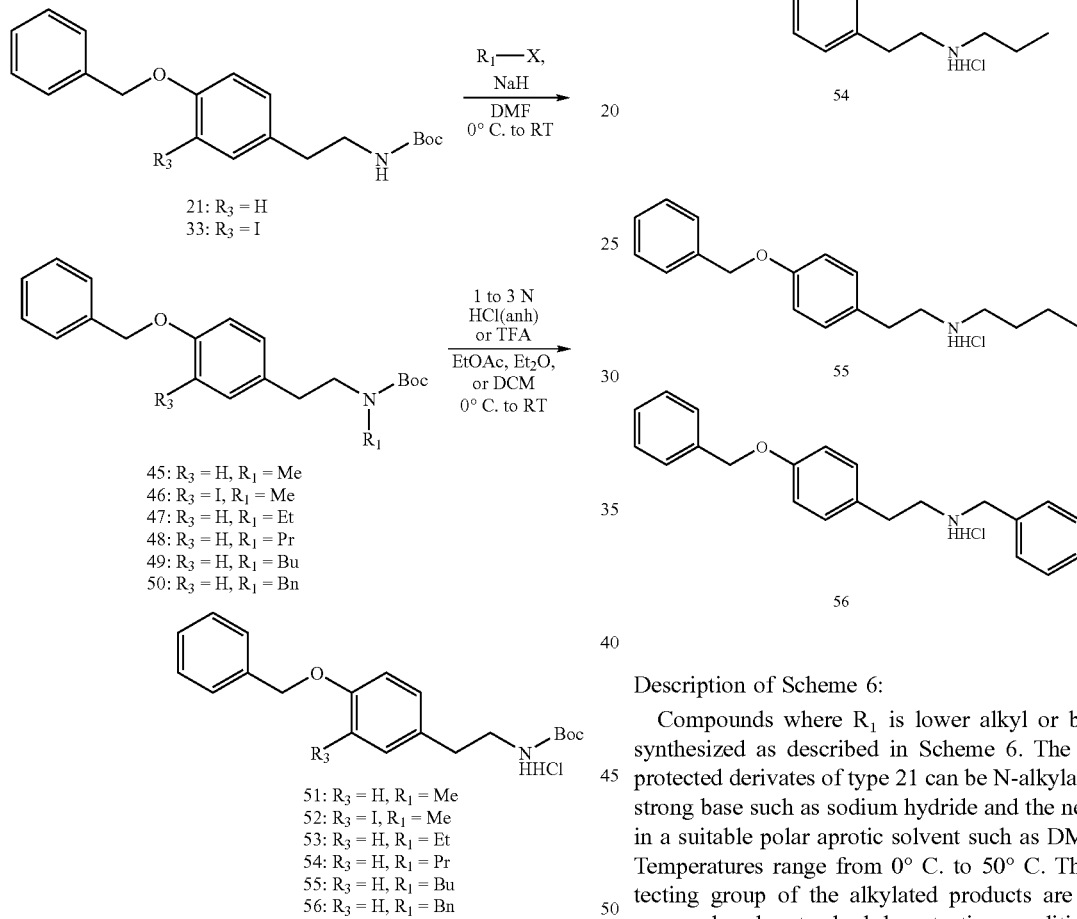

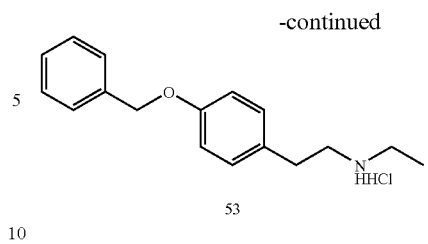

53

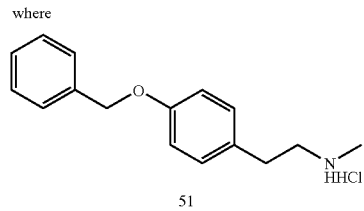

54

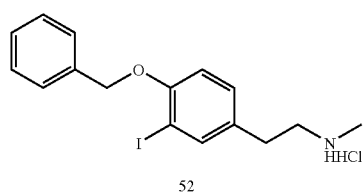

55

56

Description of Scheme 6:

Compounds where $R_1$ is lower alkyl or benzyl can be synthesized as described in Scheme 6. The appropriately protected derivates of type 21 can be N-alkylated utilizing a strong base such as sodium hydride and the necessary alkyl in a suitable polar aprotic solvent such as DMF or DMSO. Temperatures range from 0° C. to 50° C. The amine protecting group of the alkylated products are subsequently removed under standard deprotection conditions.

Description of Scheme 7:

Compounds of the general formula I, where $R_1$ is lower alkyl, $R_6$ is either OH or OR, and X is O can be prepared using the procedure outlined in scheme 7. A previously prepared protected thyronamine intermediate 9 yields a mixture of N-alkylated and O-alkylated products (57 and 58 respectively) in the presence of sodium hydride and methyl iodide at ambient temperatures. Selective N-alkylation can be achieved using potassium hexamethyldisilazide (KH-MDS) and methyl triflate. The phenol protecting group was removed using standard deprotection conditions to give 59. The amine protecting group of 59 and 58 was removed using standard deprotection conditions to give 60 and 61 which were isolated as the hydrochloride salt.

Scheme 7: Synthesis of Alkylated Thyronamines

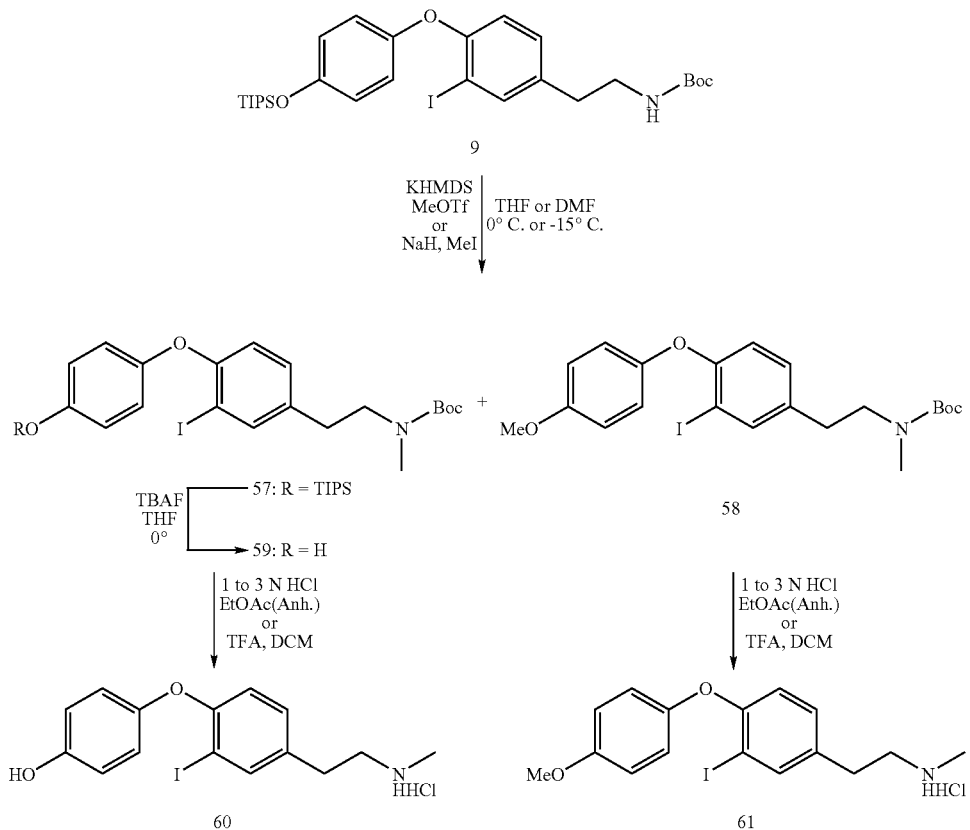

Description of Scheme 8:

Compounds of the general formula I, where $R_6$ is H, $R_3$ is a halogen, and X is O can be prepared by the procedure outlined in scheme 8. The appropriately protected halogenated tyramine 3 was reacted with phenyl boronic acid in the presence of a copper(II) salt and an appropriate amine base such as pyridine and triethylamine. Anhydrous polar aprotic solvents are typically used, such as DCM. Temperatures can range from 0° C. to 50° C. The amine protecting group was then removed using standard deprotection conditions.

Scheme 8: Synthesis of Iodinated Phenyl Derivative

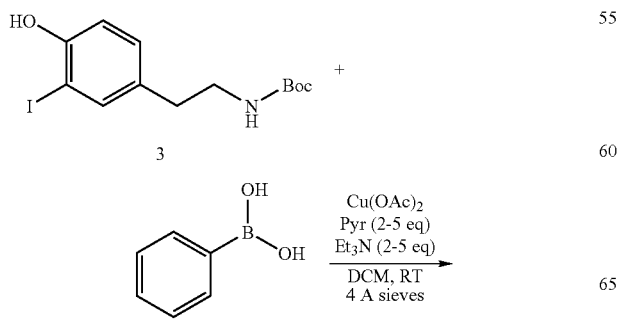

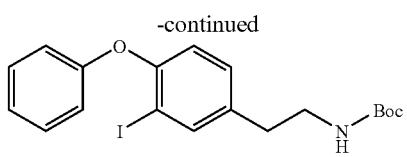

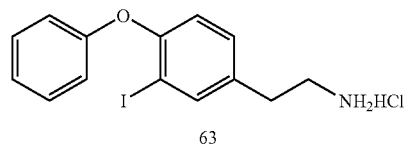

Description of Scheme 9:

Compounds of the general formula I, where X is extended alkoxy can be prepared by the procedure outlined in scheme 9. The appropriately protected tyramine derivative was reacted with the requisite alkyl halide or benzyl halide to give O-alkylated products 64-68. The amine protecting group was then removed using standard deprotection conditions. The alkylations can be done in a variety of polar aprotic solvents including, but not limited to, dimethylformamide (DMF), tetrahydrofuran (THF), acetone, diethyl ether, and dimethyl sulfoxide (DMSO). Temperatures can range from 0° C. to reflux. Typically, DMF at ambient temperature is sufficient.

Scheme 9: Synthesis of O-Alkylated Tyramine Derivatives

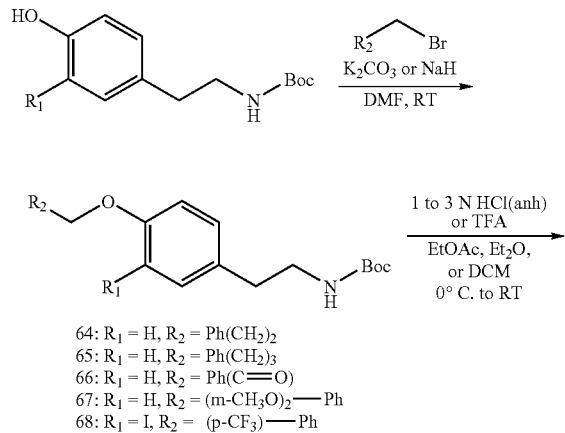

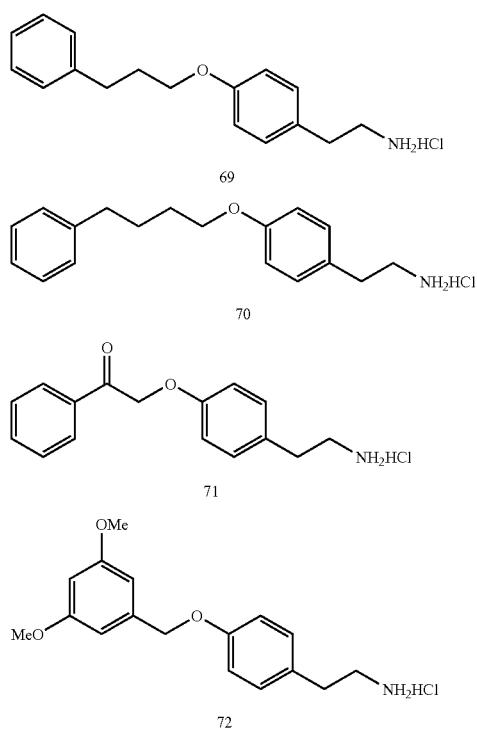

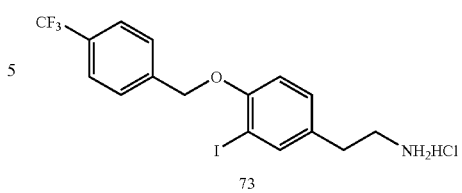

Description of Scheme 10:

Compounds of the general formula I, where $R_6$ is either H or $CF_3$, X is $OCH_2$, and $R_1$ and $R_2$ are either H or lower alkyl can be prepared by the procedure outlined in scheme 10. The requisite free amine can be dimethylated by refluxing with formic acid and formaldehyde. These are standard Eschweiler-Clarke conditions. Appropriately protected amines can be N-alkylated utilizing a strong base such as sodium hydride or potassium hexamethyldisilazide (KHMDS) and the requisite alkyl halide or benzyl halide. The amine protecting group is removed using standard deprotection conditions.

Scheme 10: Synthesis of N-Alkylated Derivatives

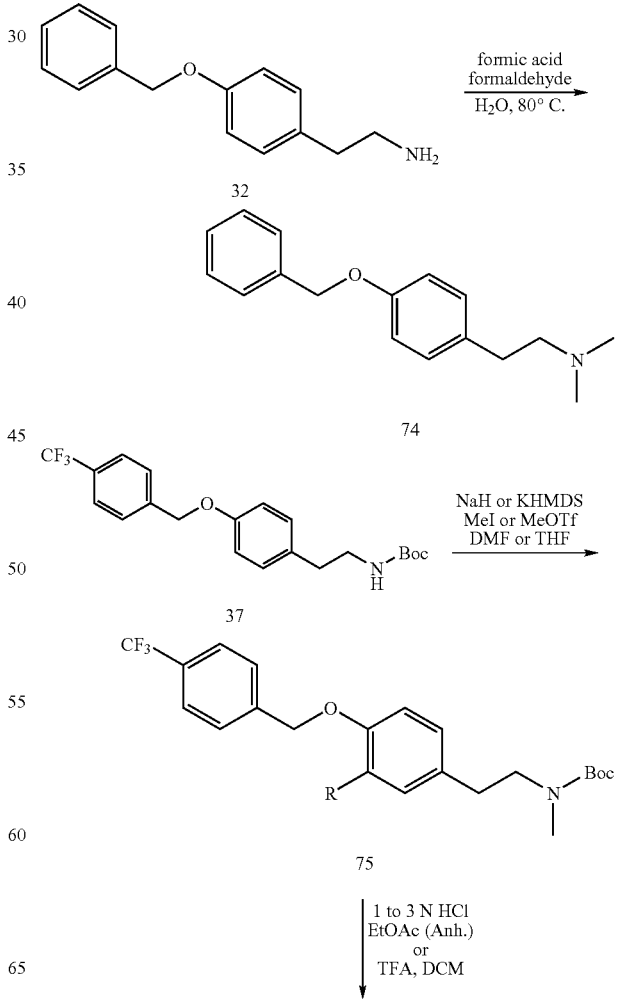

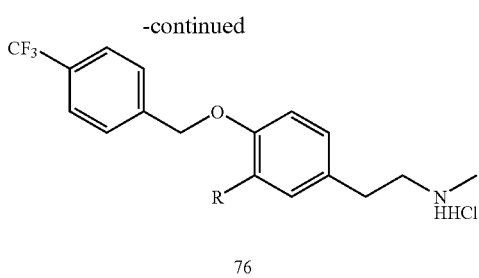

76

Description of Scheme 11:

Compounds of the general formula I, where Y is C(R)$_2$ and R$_1$ is H or lower alkyl or benzyl can be prepared by the procedure outlined in scheme 11. The hydroxyl of commercially available 76 was protected using a suitable protecting group such as tert-butyldimethylsilyl (TBS) to give 77.

Dialkylated products are prepared by treating 77 with an appropriate alkyl lithium base, such a lithium diisopropyl amine (LDA), and the requisite alkyl halide. Typical solvents used include, but are not limited to, tetrahydrofuran (THF) and diethyl ether. The nitrile is then reduced to the amine using a strong reducing agent such as lithium aluminum hydride (LiAlH$_4$) in refluxing tetrahydrofuran (THF) or diethyl ether. The resulting amine is then protected using a suitable protecting group to give compounds of type 79. The phenol protecting group is removed using standard deprotection conditions. The alcohol is reacted with the appropriate boronic acid in the presence of copper(II) salts and suitable amine bases to give the biaryl ethers of type 81. The amine protecting group is removed using standard deprotection conditions. The amine products, such as 82, are isolated as the hydrochloride salt. Reductive amination of the amine with the appropriate aldehyde in the presence of sodium cyanoborohydride yields the N-alkylated product 83.

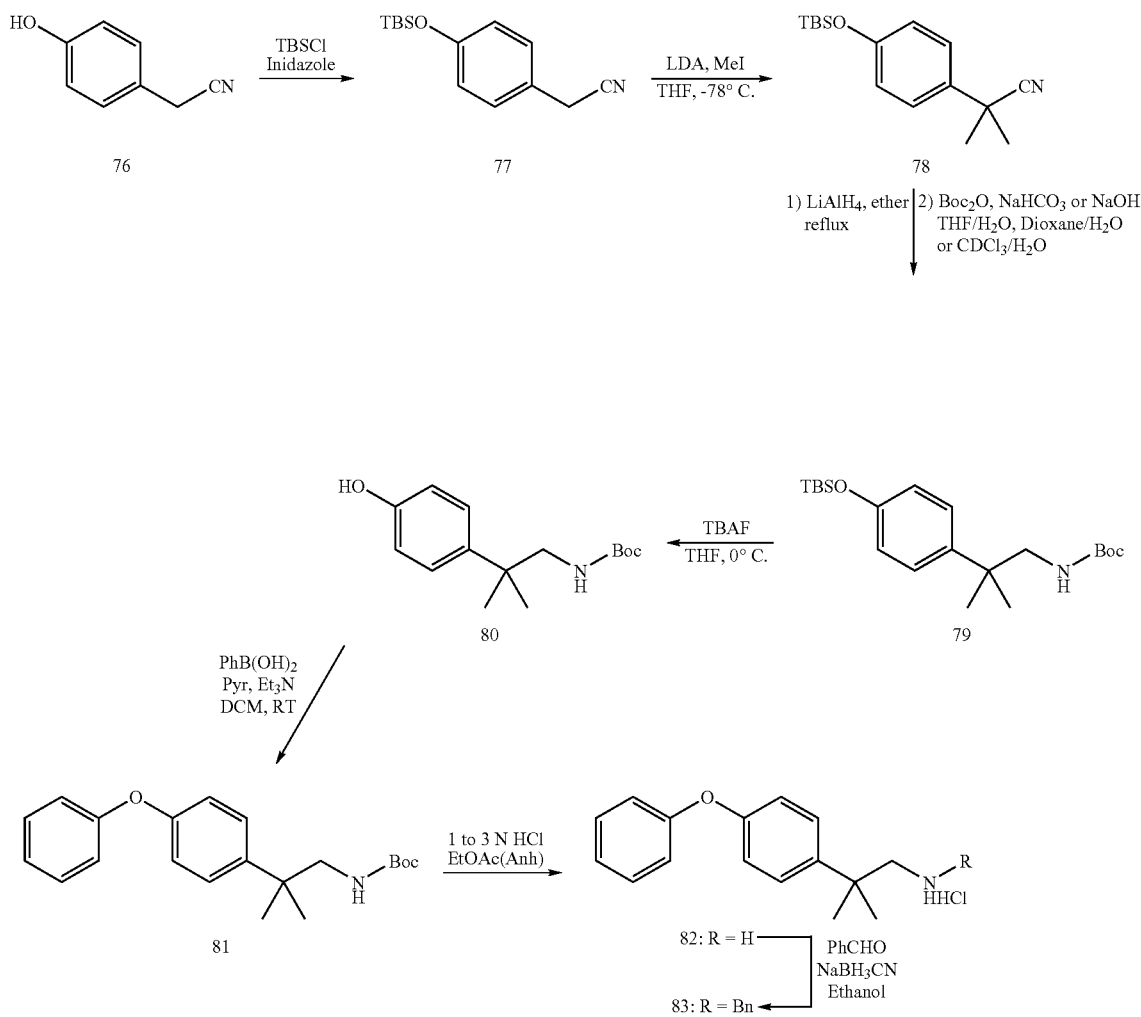

where

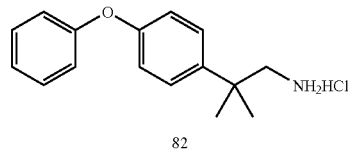

82

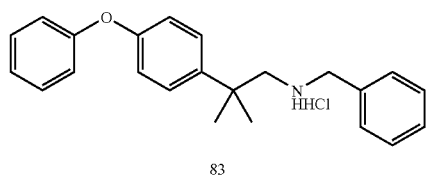

83

Description of Scheme 12:

Compounds of the general formulas I or IV, where $R_6$ is H, X is O, Y is O, $R_1$ and $R_2$ are H or lower alkyl, and Z is an extended alkyl chain can be prepared by the general procedure outlined in scheme 12. The amine of 3-bromopropanolamine hydrobromide 85 was protected with a suitable protecting group. The appropriately substituted phenol was treated with a strong base, such as sodium hydride, and then alkylated with the protected amine 86. Treatment of 89 or 90 can be N-alkylated with an alkyl halide and an appropriate strong base. The amine protecting group was removed using standard deprotection conditions. The dimethylated derivative of 91 was synthesized by heating the free amine in aqueous formic acid and formaldehyde solution under Eschweiler-Clarke reaction conditions. The product was isolated as the hydrochloride salt.

Scheme 12: Synthesis of Arylpropanolamines

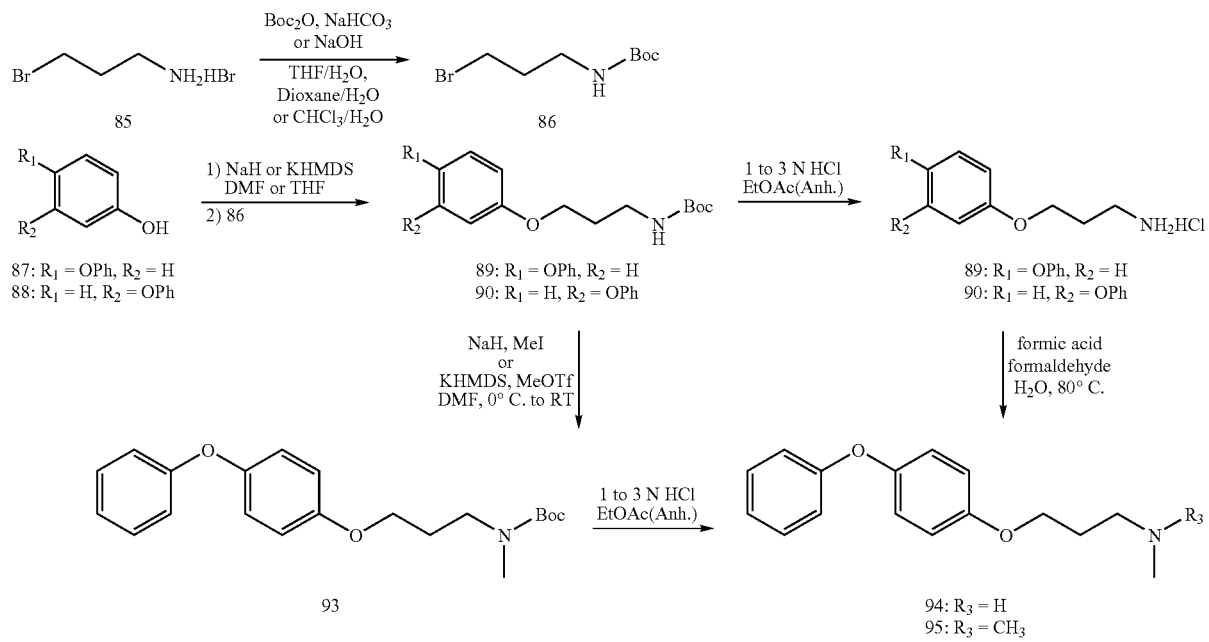

where

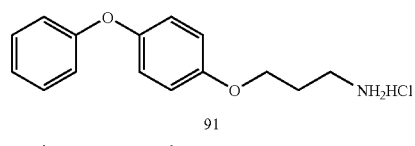

91

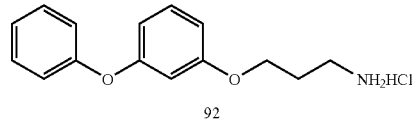

92

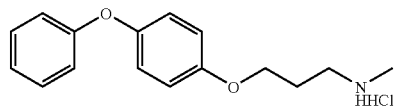

94

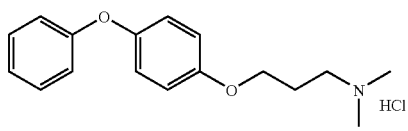

95

Description of Scheme 13:

Compounds of the general formula II, where Y is CONH, Z is extended alkyl, and $R_8$ is either H or $OCH_3$ can be prepared by the procedure outlined in scheme 13. Commercially available aryl diol 96 was reacted with the requisite boronic acid in the presence of a copper(II) salt and an appropriate amine base to give compounds of type 97. The remaining phenol was alkylated in the presence of a strong base and the appropriate alkyl halide. The ester was hydrolyzed using standard saponification conditions. The requisite carboxylic acid was coupled to the appropriate mono protected diamine to give compounds of the type 101-108. Conditions for carboxylic acid activation include, but are not limited to, sulfonyl chloride ($SOCl_2$) and catalytic dimethylformamide (DMF), O-benzatriazol-1-yl-N,N,N,N'-tetramethyluronium hexafluorophosphate (HBTU) and dimethylamino pyridine (DMAP). The amine protecting group was removed using standard deprotection conditions. Refluxing the amine in the presence of formic acid and formaldehyde afforded the dimethylated derivatives.

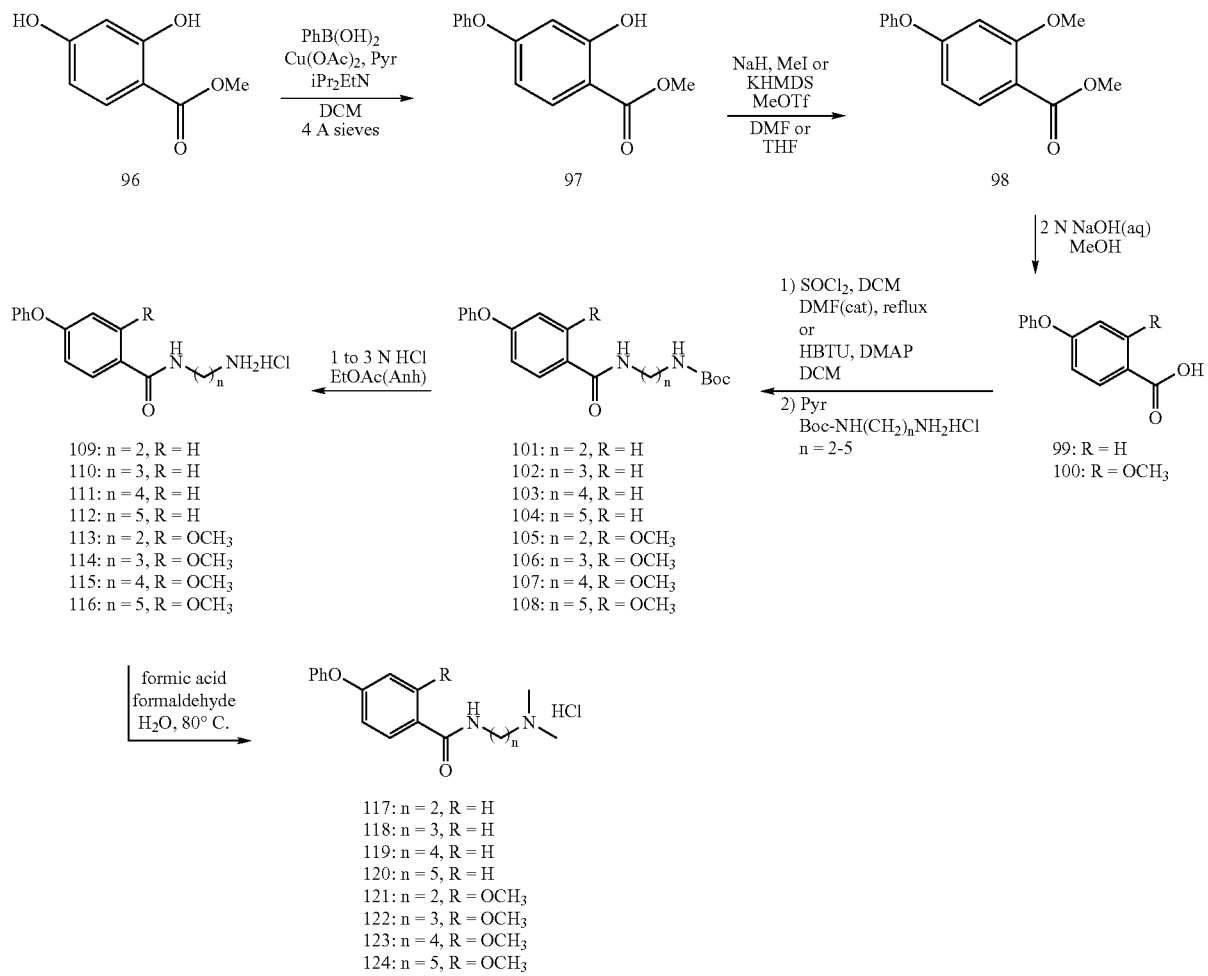

-continued
where compounds 109 through 124 are:
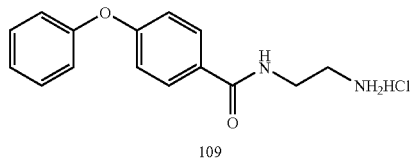
109
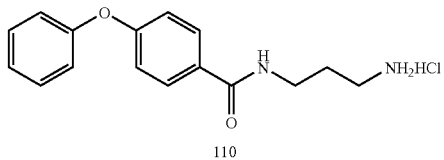
110
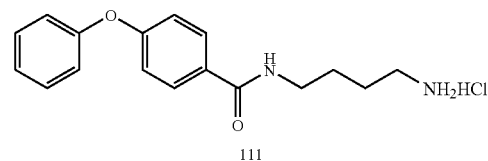
111
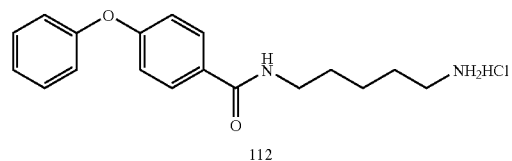
112
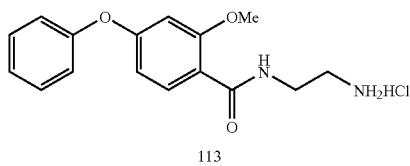
113
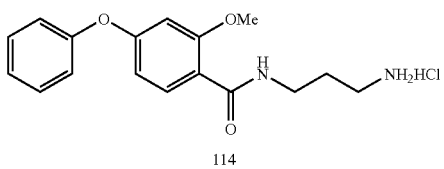
114
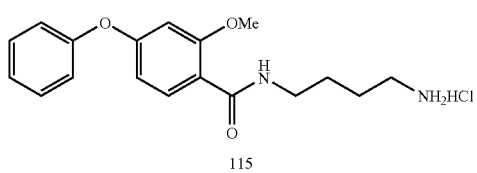
115
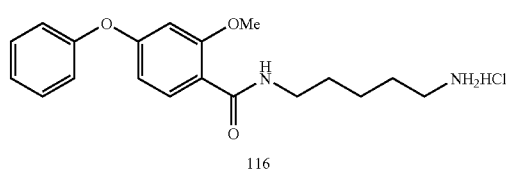
116
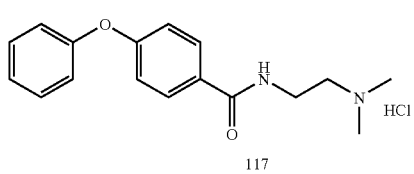
117
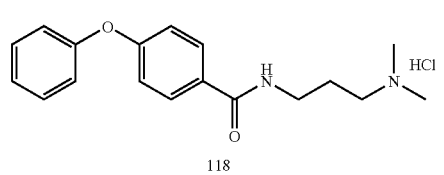
118
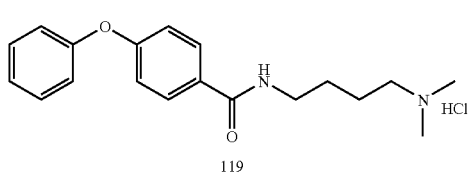
119
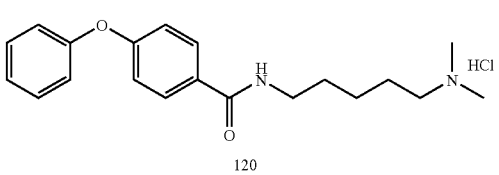
120
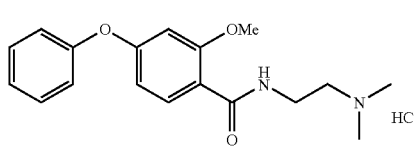
121
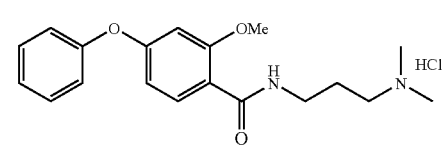
122
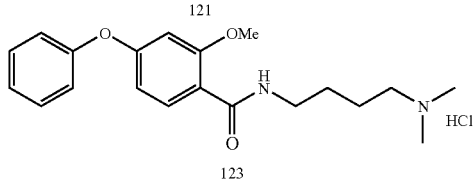
123
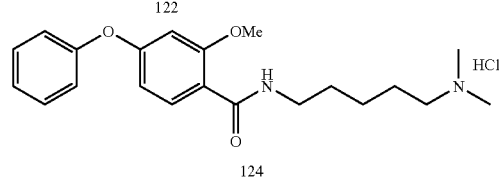
124

Description of Scheme 14:

Compound with the general formula I or IV, where Y is CHAr are prepared by the procedure outlined in scheme 14. Commercially available aldehydes were treated with the appropriate aryl lithium reagent, such as phenyl lithium, to give a dibenzyl alcohol. The alcohol can be chlorinated using standard chlorination conditions, such as sulfonyl chloride. The chloride was reacted in the presence of titanium tetrachloride (TiCl$_4$) and trimethylsilylcyanide (TMSCN) to afford the dibenzyl nitrile intermediate. Reduction of the nitrile with a strong reducing agent, such as lithium aluminum hydrided (LiAlH$_4$) gives the amine products which were isolated as the hydrochloride salt.

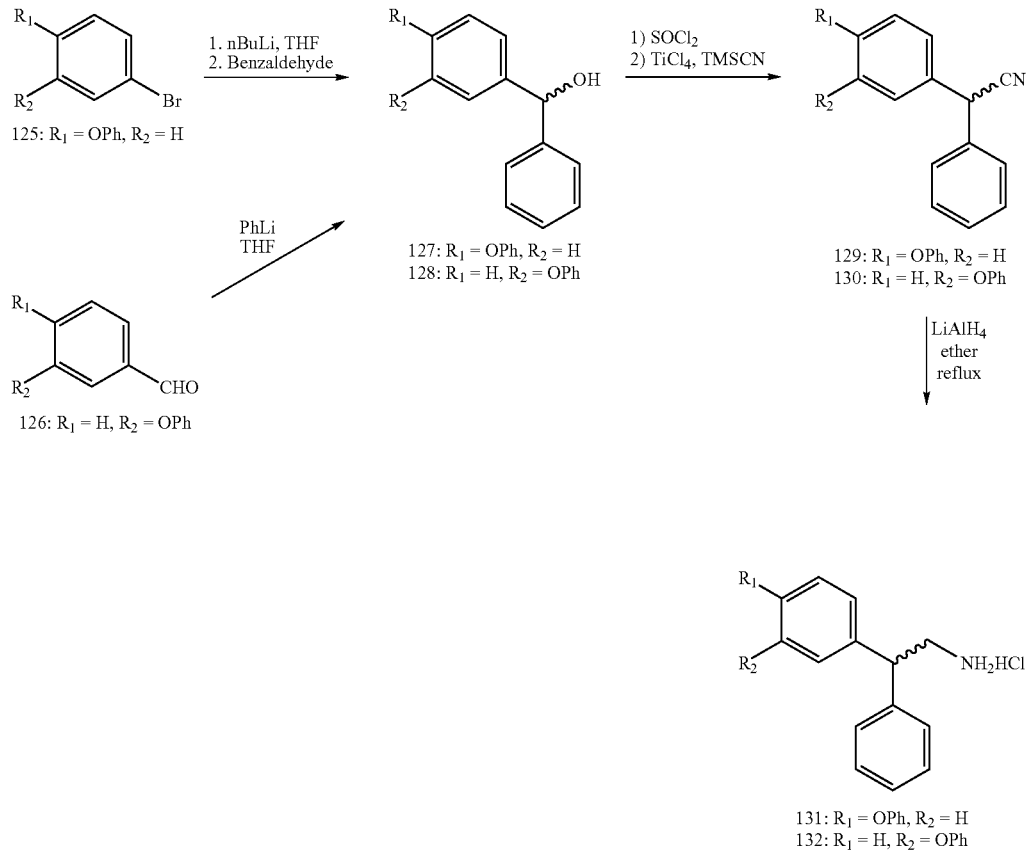

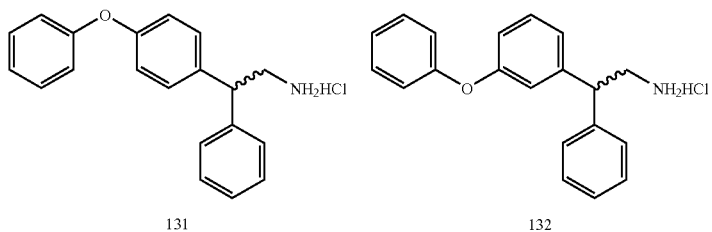

where compounds 131 and 132 are:

Description of Scheme 15:

Compounds with general formula III, where X=O can be made by the procedure outlined in scheme 15. Commercially available napthol 133 was stirred with a boronic acid in the presence of a copper(II) salt with an appropriate amine base to give the biaryl ether 134. The aldehyde was reduced to the alcohol using suitable reducing agents, including, but not limited to, sodium borohydride (NaBH$_4$) in ethanol or sodium triacetoxy borohydride (NaBH(OAc)$_3$). Chlorination of the alcohol using standard chlorination procedures, followed by treatment with trimethylsilylcyanide (TMSCN) in the presence of titanium tetrachloride (TiCl$_4$) yields napthyl cyanides of type 136. Reduction of the nitrile in the presence of a strong reducing agent, such as lithium aluminum hydride (LiAlH$_4$), gives the amine which is isolated as the hydrochloride salt.

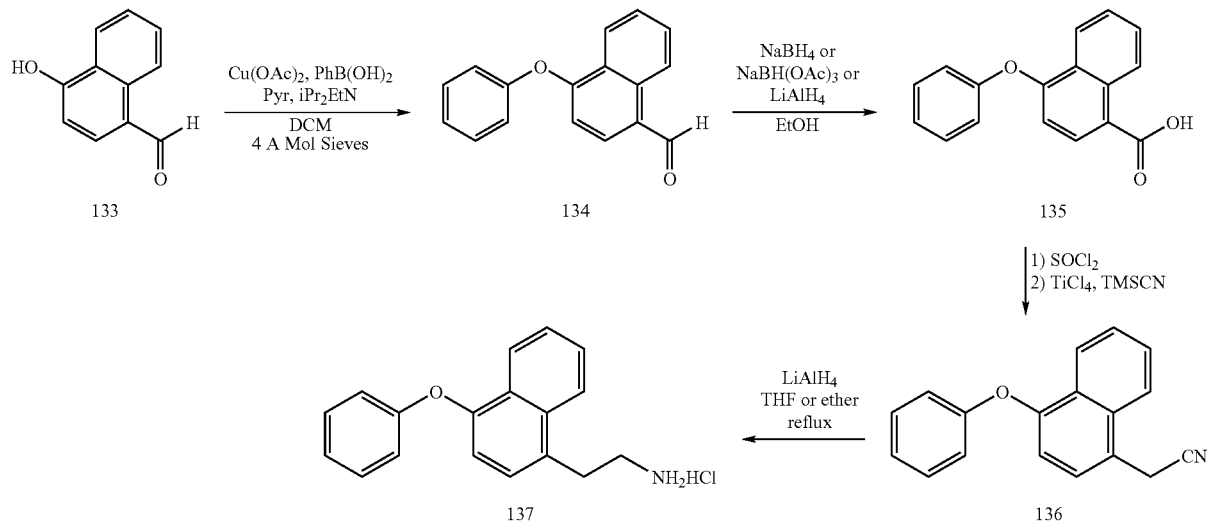

Scheme 15: Synthesis of Arylnapthethylamines

Proposed compounds of the general formula V, where X is O and Y is CHAr may be prepared by the procedure outlined in scheme 16. Readily available bromo napthol, 138, is coupled with an appropriate boronic acid in the presence of a copper(II) salt and amine bases. The resulting product, 139, is then formylated under standard conditions and the aldehyde is subsequently alkylated with an appropriate alkyl lithium or aryl Grignard reagent. Chlorination of alcohols of type 141 followed by displacement with cyanide would give the resulting nitrile, 142. Reduction of the nitrile with a strong reducing agent gives 143, which would be isolated as the hydrochloride salt. Further alkylation of the amine would be achieved by protecting the amine with an appropriate protecting group, such as the tert-butyl carbamate, followed by alkylation with a strong base and the requisite alkyl halide. The amine protecting group would then be removed using standard deprotection conditions.

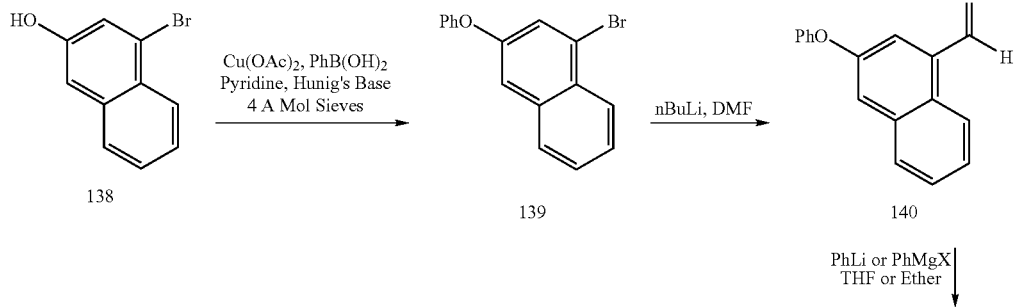

Scheme 16: Synthesis of Substituted Napthethylamine Derivatives

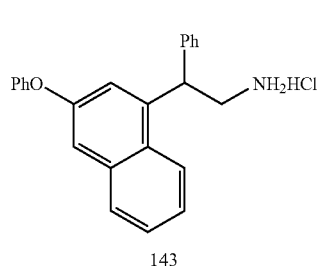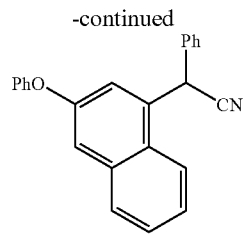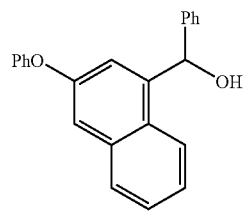

143                                   142                                   141

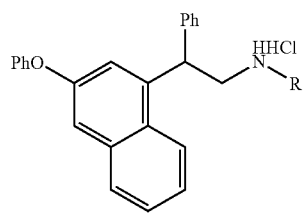

144

Thyronamines isotopically labeled with deuterium can be prepared by utilizing the precursor outlined in scheme 17. Commercially available 4-hydroxy benzylnitrile, 145, could be reduced with lithium aluminum deuteride to give labeled tyramine, 146. The amine is then protected using a suitable protecting such as tert-butyl carbamate. The precursor 146 could then be utilized in the synthesis of thyronamines as outlined in scheme 3.

Scheme 17: Synthesis of [$^2$H,$^2$H]-N-t-Boc-Tyramine

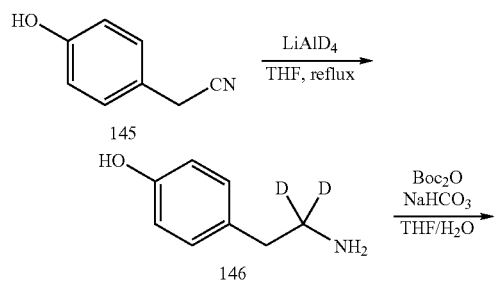

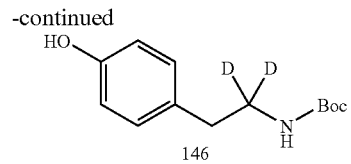

146

Thyronamines isotopically labeled with tritium could be prepared by the procedure outlined in scheme 18. Readily available phenol 149 is coupled with the requisite boronic acid, 148, in the presence of a copper(II) salt and an appropriate amine base. The ester is reduced to the aldehyde using standard reducing conditions to give 151. Reductive amination in the presence of an ammonium salt with an appropriate tritiated reducing agent, such as sodium cyanoborotrituride, gives the labeled product which is immediately protected with a suitable amine protecting group. Simultaneous removal of the phenol and amine protecting groups under standard deprotection conditions gave the labeled Thyronamine, 153.

Scheme 18: Synthesis of [$^3$H]-3-Iodothyronamine

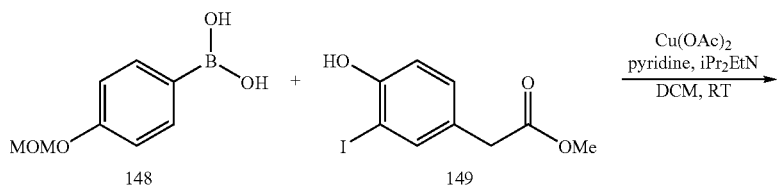

148                                   149

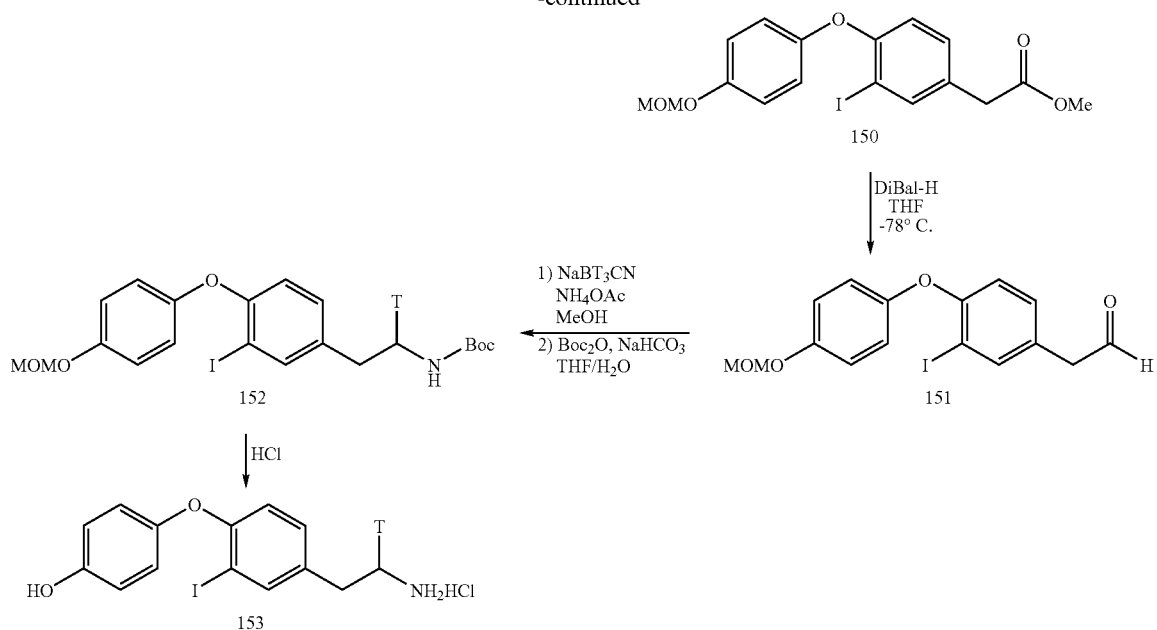

Thyronamines isotopically labeled with $^{125}$Iodine can be prepared by the procedure outlined in scheme 19. Monoiodinated tyramine 3 is coupled with the requisite boronic acid, 148, in the presence of a copper(II) salt and an appropriate amine base. The iodine is refluxed in the presence of a palladium catalyst and an appropriate tin reagent to give the stanylated product 155. Tin-iodine is achieved utilizing sodium $^{125}$iodide and chloramine-T. Simultaneous removal of the phenol and amine protecting groups gives 156 which is isolated as the hydrochloride salt.

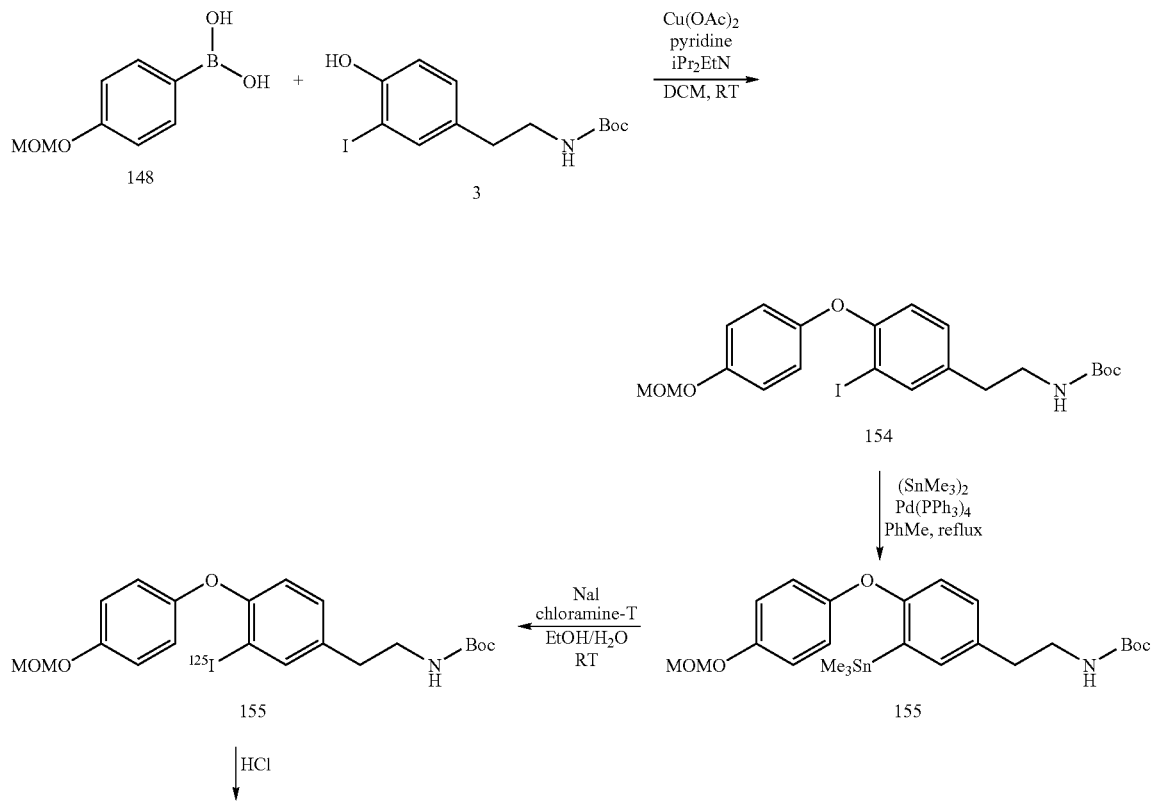

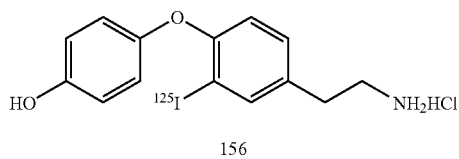

156

In connection with the preparation of thyronamine derivatives and analogs, the methods can offer improved yields, purity, ease of preparation and/or isolation of intermediates and final product, and more industrially useful reaction conditions and workability over prior art methods of preparation. The present methods are particularly useful for the preparation of thyronamine derivatives and analogs on a large scale, including commercial scale, for example, from multi-kilogram to ton quantities or more of thyronamine derivative or analog. Specifically, isolation and/or purification steps of intermediates to the thyronamine derivatives and analogs can be advantageously substantially or completely avoided using the present methods. The present methods can be particularly advantageous in that the thyronamine derivatives and analogs can be obtained in substantially pure form. The term "substantially pure form", as used herein, means that the thyronamine derivative or analog prepared using the present processes can preferably be substantially devoid of organic impurities. The term "organic impurities", as used herein, refers to organic materials, compounds, etc., other than the desired product, that can be typically associated with synthetic organic chemical transformations including, for example, unreacted starting reagents, unreacted intermediate compounds, and the like. In preferred form, the present processes can provide thyronamine compounds that are at least about 75% pure, as measured by standard analytical techniques such as, for example, HPLC. Preferably, the thyronamine derivatives and analogs prepared using the present methods can be at least about 80% pure, with a purity of at least about 85% being more preferred. Even more preferably, the thyronamine derivatives and analogs prepared using the present methods can be at least about 90% pure, with a purity of at least about 95% being more preferred. In particularly preferred embodiments, the thyronamine derivatives and analogs prepared using the present methods can be more than about 95% pure, with a purity of about 99.8% being even more preferred, and with a purity of about 100% being especially preferred.

Alternatively, if a salt of the thyronamine derivative or analog is desired, a suitable acid can be added followed by cooling and seeding of the resultant solution to provide the crystalline salt. Preferably, the acid chosen will be able to form the salt without affecting the integrity of the target compound. Thus, mild acids, such as sulfonic acids, are preferred. In particular, methane sulfonic acid, benzenesulfonic acid, toluenesulfonic acid, hydroxyethanesulfonic acid, camphorsulfonic acid, and other sulfonic acids can prepare suitable crystalline salts. A particularly preferred acid is methane sulfonic acid. It will be appreciated, however, that numerous other salts are possible, when an anhydrous form of the acid is available. For example, mineral acids, such as hydrochloric, hydrobromic, phosphoric, sulfuric, or nitric acid can prepare suitable crystalline salts. Other organic acids, such as fumaric, succinic, oxalic, citric, and the like, can prepare suitable crystalline salts provided that they are sufficiently acidic to protonate the basic moiety of the thyronamine compound.

Under appropriate conditions, however, other solvents can be used to prepare crystalline salts of thyronamine compound, such as ester solvents, including, but not limited to ethyl acetate, propyl acetate, isopropyl acetate, isobutyl acetate, ethyl propionate, propyl propionate, isopropyl propionate; ether solvents, including, but not limited to t-butyl methyl ether, tetrahydrofuran, ethyl ether, isopropyl ether, butyl ether; and aromatic solvents, including, but not limited to toluene and anisole. Other solvents will be readily understood to those of ordinary skill in the art. Filtration and washing of the product, preferably with additional crystallization solvent, affords the thyronamine compound.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present compositions and methods.

Certain acidic or basic compounds can exist as zwitterions. All forms of the compounds, including free acid, free base and zwitterions, are contemplated to be within the scope of the present compositions and methods. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

The reactions of the synthetic methods described and claimed herein can be carried out in suitable solvents which can be readily selected by one skilled in the art of organic synthesis. Generally, suitable solvents are solvents which are substantially non-reactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction, suitable solvents for a particular work-up following the reaction can be selected. Suitable solvents, as used herein can include, by way of example and without limitation, chlorinated solvents, hydrocarbon solvents, aromatic solvents, ether solvents, protic solvents, polar aprotic solvents, and mixtures thereof.

Suitable halogenated solvents include, but are not limited to carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1- trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable hydrocarbon solvents include, but are not limited to alkane or aromatic solvents such as cyclohexane, pentane, hexane, toluene, cycloheptane, methylcyclohexane, heptane, ethylbenzene, m-, o-, or p-xylene, octane, indane, nonane, benzene, ethylbenzene, and m-, o-, or p-xylene.

Suitable ether solvents include, but are not limited to dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol diisopropyl ether, anisole, or t-butyl methyl ether.

Suitable protic solvents include, but are not limited to water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, and glycerol.

Suitable aprotic solvents include, but are not limited to dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (ACN), dimethylsulfoxide (DMSO), propionitrile, ethyl formate, methyl acetate, hexachloroacetone, acetone, ethyl methyl ketone, ethyl acetate, isopropyl acetate, t-butyl acetate, sulfolane, N,N-dimethylpropionamide, nitromethane, nitrobenzene, and hexamethylphosphoramide.

The compositions and methods are further described in the following examples. All of the examples are actual examples. These examples are for illustrative purposes only, and are not to be construed as limiting the appended claims.

EXAMPLES

General: All reactions were conducted under inert argon passed through a Drierite drying tube in flame dried glassware unless otherwise noted. Anhydrous tetrahydrofuran (THF) was dried in a sodium benzophenone ketyl radical still. All other anhydrous solvents and reagents were purchased from Aldrich, Sigma-Aldrich, Fluka, or Acros and were used without any further purification unless otherwise stated. $^1$H and $^{13}$C NMR spectra were taken on a Varian 400 (400 MHz and 100 MHz respectively). Data reported are calibrated to internal TMS (0.0 ppm) for all solvents unless otherwise noted and are reported as follows: chemical shift, multiplicity (app=apparant, par obsc=partially obscured, ovrlp=overlapping, brd=broad, s=singlet, d=doublet, t=triplet, q=quartet, m=multiplet), coupling constant, and integration. High resolution mass spectra were obtained from the departmental mass spectrometry facility. Thin-layer chromatography (TLC) was performed on 0.25 mm Merck precoated silica gel plates and silica gel chromatography was performed using Silica Gel 60 Geduran (EM Science).

Example 1

Preparation of N-t-Boc-tyramine (2)

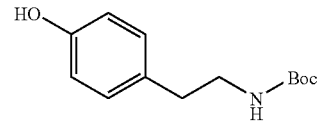

A solution of NaHCO$_3$ (10.7 g, 127 mmol) in water (250 ml) was added to a solution of tyramine (1) (15.8 g, 115 mmol) suspended in THF (500 ml) and vigorously stirred. After 24 hours the mixture was diluted with excess ether and the aqueous was extracted with ether (2×). The combined organic layers were sequentially washed with 0.5 M HCl, water, and brine then dried over MgSO$_4$. Concentration gave a crude yellow oil which was purified by flash SiO$_2$ chromatography (dry loaded, eluted with hexanes/ethyl acetate (3:1)) to give 2 as a white solid (24.7 g, 91% yield): $^1$H-NMR (400 MHz, chloroform-d) δ 6.99 (d, J=8.4 Hz, 2H), 6.78 (d, J=8.4 Hz, 2H), 4.67 (brd s, 1H), 4.47 (brd s, 1H), 3.32 (brd q, J=6.4 Hz, 2H), 2.69 (t, J=6.8. Hz, 2H), 1.44 (s, 9H); $^{13}$C-NMR (100 MHz, chloroform-d) δ 156.3, 154.8, 130.2, 129.7, 115.5, 79.7, 42.0, 35.2, 28.4; HRMS (EI+) for C$_{13}$H$_{19}$NO$_3$ calcd. 237.1365 found 237.1367.

Example 2

Preparation of N-t-Boc-3-iodotyramine (3) and N-t-Boc-3,5-diiodotyramine (4)

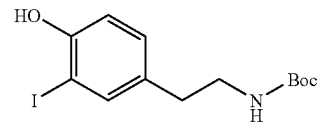

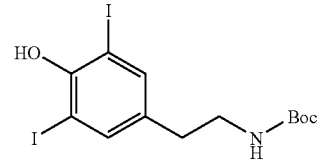

The N-t-Boc-tyramine 2 (15.0 g, 63.3 mmol) was dissolved in DCM (250 ml) and DMF (60 ml). The resulting solution was cooled to −40° C. and sodium methoxide (6.84 g, 127 mmol) was added in one portion. Iodine monochloride (100 ml, 100 mmol) was added to the reaction dropwise and the mixture was stirred keeping the temperature below −30° C. for 30 minutes. The reaction mixture was diluted with ether and washed with 0.5 M HCl. The aqueous was extracted with ether and then the combined organic layers were sequentially washed with 0.1 M Na$_2$S$_2$O$_3$ (2×), water, and brine, then dried over MgSO$_4$. The crude product was purified via SiO$_2$ flash chromatography (dry loaded, eluted with DCM/ethyl acetate (100:1) to (50:1) to (10:1)) to give products 3 and 4 as slightly yellow solids (3: 4.29 g, 19% yield; 4: 9.28 g, 30% yield). For compound 3: $^1$H-NMR (400 MHz, chloroform-d) δ 7.49 (s, 1H), 7.05 (d, J=7.6 Hz, 1H), 6.91 (d, J=8.0 Hz, 1H), 5.62 (brd s, 1 H), 4.56 (brd s, 1H), 3.31 (brd q, J=5.6 Hz, 2H), 2.69 (brd t, J=6.8 Hz, 2H), 1.44 (s, 9H); $^{13}$C-NMR (100 MHz, chloroform-d) δ 155.9, 153.6, 138.3, 133.0, 130.0, 115.0, 85.5, 79.4, 41.8, 34.8, 28.4; HRMS (EI+) for $C_{13}H_{18}INO_3$ calcd. 363.0331 found 363.0336. For compound 4: $^1$H-NMR (400 MHz, chloroform-d) δ 7.51 (s, 2H), 5.74 (s, 1H), 4.58 (brd s, 1H), 3.30 (app q, J=6.2 Hz, 2H), 2.67 (t, J=6.4 Hz, 2H), 1.40 (s, 9H); $^{13}$C-NMR (100 MHz, chloroform-d) δ 155.8, 152.2, 139.4, 135.1, 82.3, 79.5, 41.6, 34.2, 28.4; HRMS (EI+) for $C_{13}H17I_2NO_3$ [M-$C_4H_9$+H] calcd. 432.8672 found 432.8663.

Example 3

Preparation of 1-bromo-4-(triisopropyl)silyloxy-benzene (6)

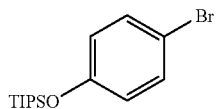

6

To a stirred solution of p-bromophenol (5) (4.0 g, 23.1 mmol) in DCM (40 ml) was added triisopropylsilyl chloride (5 ml, 23.4 mmol). The reaction mixture was cooled to 0° C. and imidazole (3.94 g, 57.9 mmol) was added and the mixture was stirred at 0° C. for 30 minutes then allowed to warm to ambient temperature over 12 hours. The reaction mixture was diluted with ether and sequentially washed with 0.5 M HCl (2×), sat. aq. NaHCO$_3$, water and brine then dried over MgSO$_4$. The crude product was purified by bulb to bulb distillation (boiling point: 149-150° C. at 2.0 mmHg) to give 6 as a clear oil (6.23 g, 82% yield): $^1$H-NMR (400 MHz, chloroform-d) δ 7.30 (d, J=8.8 Hz, 2H), 6.75 (d, J=8.8 Hz, 2H), 1.24 (septet, J=7.2 Hz, 3H), 1.09 (d, J=7.2 Hz, 18H); $^{13}$C-NMR (100 MHz, chloroform-d) δ 155.2, 132.2, 121.7, 113.2, 17.8, 12.6; FTIR (thin film) 2945, 2892, 2867, 1586, 1487, 1274, 909, 883, 828, 732 cm$^{-1}$; HRMS (EI+) for $C_{15}H_{25}BrOSi$ calcd. 328.0858 found 328.0844.

Example 4

Preparation of 4-(triisopropyl)silyloxyphenyl Boronic Acid (7)

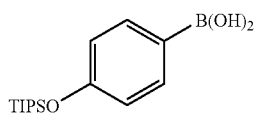

7

To a stirring solution of 4-(triisopropyl)silyloxy-1-bromobenzene (6) (540 mg, 1.64 mmol) in THF (15 ml) at −78° C. was added n-butyl lithium (0.9 ml, 2.18 M in hexanes, 1.96 mmol) dropwise. The reaction mixture was stirred for 30 minutes then triisopropyl borate (0.5 ml, 2.17 mmol) was added in one portion. The reaction was stirred at −78° C. for 1 hour, allowed to warm to ambient temperature over 4 hours, quenched with 3 N HCl (5 ml) and stirred for 30 minutes at 0° C. The aqueous layer was extracted with ethyl acetate (3×) and the combined organic layers were dried over MgSO$_4$. Purification by flash SiO$_2$ chromatography (loaded with DCM, eluted with hexanes/ethyl acetate (10:1) to (3:1) to (1:1)) gave 7 as a white solid (328 mg, 68% yield): $^1$H-NMR (400 MHz, chloroform-d) δ 8.10 (d, J=8.4 Hz, 2H), 6.98 (d, J=8.4 Hz, 2H), 1.30 (septet, J=7.6 Hz, 3H), 1.13 (d, J=7.6 Hz, 18H); $^{13}$C-NMR (100 MHz, chloroform-d) δ 160.1, 137.4, 119.6, 17.9, 12.7.

Method A: General Procedure for Copper Mediated Coupling

The boronic acid (11.3 mmol) and the phenol (5.52 mmol) were dissolved in DCM (60 ml) at ambient temperature in a flask flushed with dry air. A large excess of 4 Å powdered molecular sieves were added and the mixture was allowed to stir for 10 minutes with a drying tube attached. Copper(II) acetate (5.60 mmol), triethylamine (27.3 mmol), and pyridine (27.2 mmol) were added in succession and the reaction was stirred at ambient temperature overnight. The reaction mixture was diluted with ether and filtered through celite and the filtrate was sequentially washed with 0.5 M HCl (1×), water (1×), and brine (1×) then dried over MgSO$_4$. The crude product was purified via flash SiO$_2$ chromatography as described below.

Example 5

Preparation of N-t-Boc-4'-triisopropylsilyloxy-thyronamine (8)

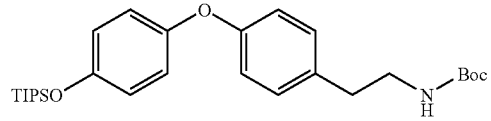

8

Refer to Method A for the general procedure. The crude product was purified via flash SiO$_2$ chromatography (loaded with DCM, eluted with hexanes/ethyl acetate (10:1) to (5:1)) to give 8 as a slightly yellow oil (122 mg, 40% yield): $^1$H-NMR (400 MHz, chloroform-d) δ 7.10 (d, J=8.0 Hz, 2H), 6.90-6.83(m, 6H), 4.59 (brd s, 1H), 3.35 (brd q, J=6.0 Hz, 2H), 2.74 (brd t, J=7.0 Hz, 2H), 1.43 (s, 9H), 1.27 (septet, J=7.6 Hz, 3H), 1.10 (d, J=7.2 Hz, 18H); HRMS (EI+) for $C_{28}H_{43}NO_4Si$ calcd. 485.2961 found 485.2958.

Example 6

Preparation of N-t-Boc-4'-triisopopylsilyloxy-3-iodothyronamine (9)

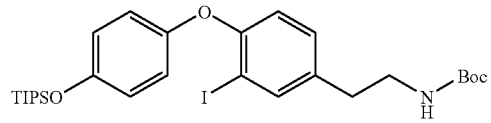

9

Refer to Method A for the general procedure. The crude product was purified via flash SiO$_2$ chromatography (dry loaded, eluted with hexanes/ethyl acetate (10:1)) to give 9 as a slightly yellow oil (923 mg, 36% yield). $^1$H-NMR (400 MHz, chlorofom-d) δ 7.65 (d, J=1.6 Hz, 1H), 7.05 (app d, J=8.0 Hz, 1H), 6.86 (s, 4H), 6.68 (d, J=8.8 Hz, 1H), 4.57 (brd s, 1H), 3.33 (brd q, J=6.5 Hz, 2H), 2.72 (t, J=6.8 Hz, 2H), 1.44 (s, 9H), 1.25 (septet, J=7.2 Hz, 3H), 1.10 (d, J=7.2 Hz, 18H); $^{13}$C-NMR (100 MHz, chlorofom-d) δ 156.1, 155.7, 152.3, 150.1, 139.7, 135.3, 129.8, 120.7, 120.1, 117.5, 87.6, 79.2, 41.6, 34.8, 28.3, 17.8, 12.5; FTIR (thin film) 3360, 2944, 2867, 1704, 1502, 1479, 1366, 1232, 1194, 1171, 910, 883, 734 cm$^{-1}$; HRMS (EI+) for $C_{28}H_{42}INO_4Si$ calcd. 611.1928 found 611.1917.

Example 7

Preparation of N-t-Boc-4'-triisopropylsilyloxy-3,5-diiodothyronamine (10).

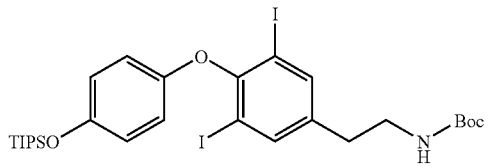

10

Refer to method A for the general procedure. The crude product was purified by flash SiO$_2$ chromatography (dry loaded, eluted with hexanes/ethyl acetate (10:1) to (8:1)) to give 10 as a slightly yellow oil (1.28 g, 51% yield (based on recovered starting material)): $^1$H-NMR (400 MHz, chloroform-d) δ 7.67 (s, 2H), 6.79 (d, J=9.2 Hz, 2H), 6.63 (d, J=9.2 Hz, 2H), 4.79 (brd s, 1H), 3.33 (brd q, J=6.7 Hz, 2H), 2.72 (brd t, J=6.8 Hz, 2H), 1.45 (s, 9H), 1.23 (septet, J=7.6 Hz, 3H), 1.08 (d, J=7.2 Hz, 18H); $^{13}$C-NMR (100 MHz, chloroform-d) δ 155.6, 152.7, 150.8, 150.4, 140.3, 139.6, 120.4, 116.1, 91.1, 79.2, 41.4, 34.5, 28.3, 17.8, 12.4; FTIR (thin film) 3446, 2944, 2867, 1705, 1500, 1438, 1241, 1187, 908, 734 cm$^{-1}$; HRMS (EI+) for $C_{28}H_{41}I_2NO_4Si$ calcd. 737.0894 found 737.0888.

Method B: General Procedure for Silyl Deprotection

To a stirred solution of protected phenol (1.0 mmol) in THF (10 ml) was added TBAF (1.5 ml, 1.5 mmol, 1 M solution in THF) dropwise. The reaction mixture was stirred for 10-30 minutes until complete by TLC analysis, then diluted with ethyl acetate. The reaction mixture was washed with 0.5 M HCl and the aqueous was extracted with ethyl acetate. The combined organic layers were sequentially washed with water and brine then dried over MgSO$_4$. The crude product was purified by flash SiO$_2$ chromatography as described below.

Example 8

Preparation of N-t-Boc-thyronamine (11)

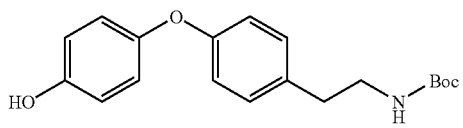

11

Refer to Method B for the general procedure. The crude product was purified via flash SiO$_2$ chromatography (loaded with DCM, eluted with hexanes/ethyl acetate (10:1) to (3:1)) to give 11 as a clear oil (42.4 mg, 86% yield): $^1$H-NMR (400 MHz, methanol-d$_4$) δ 7.11 (d, J=8.0 Hz, 2H), 6.83-6.73 (m, 6H), 4.85 (s,1H), 3.21 (brd t, J=7.4 Hz, 2H), 2.69 (t, J=7.0 Hz, 2H), 1.40 (s, 9H); HRMS (EI+) for $C_{19}H_{23}NO_4$ calcd. 329.1627 found 329.1615.

Example 9

Preparation of N-t-Boc-3-iodothyronamine (12)

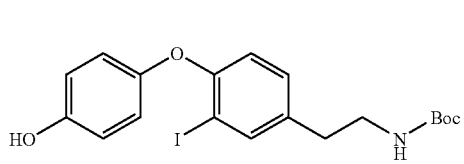

12

Refer to Method B for the general procedure. The crude was purified via flash SiO$_2$ chromatography (loaded with DCM, eluted with hexanes/ethyl acetate (5:1) to (3:1)) to give 12 as a clear oil (54.3 mg, 85% yield): $^1$H-NMR (400 MHz, chloroform-d) δ 7.64 (d, J=2.0 Hz, 1H), 7.01 (app dd, J=8.4, 2.0 Hz, 1H), 6.87 (app dt, J=9.2, 2.8 Hz, 2H), 6.82 (app dt, J=9.2, 2.8 Hz, 2H), 6.67 (d, J=8.4 Hz, 1H), 6.20 (brd s, 1H), 4.65 (brd s, 1H), 3.33 (brd q, J=6.5 Hz, 2H), 2.71 (brd t, J=7.0 Hz, 2H), 1.45 (s, 9H); $^{13}$C-NMR (100 MHz, chloroform-d) δ 156.2, 156.1, 152.5, 149.8, 139.7, 135.2, 129.8, 120.4, 117.6, 116.3, 87.8, 79.7, 41.8, 34.9, 28.4; HRMS (EI+) for $C_{19}H_{22}INO_4$ [M+H-C$_4$H$_9$] calcd. 398.9968 found 398.9950.

Example 10

Preparation of N-t-Boc-3,5-diiodothyronamine (13)

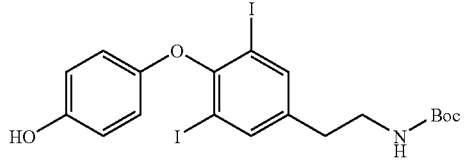

13

Refer to Method B for the general procedure. The crude product was purified by flash SiO$_2$ chromatography (dry loaded, eluted with hexanes/ethyl acetate (10:1) to (5:1)) to give 13 as a yellow oil (221 mg, 72% yield): $^1$H-NMR (400 MHz, methanol-d$_4$) δ 7.74 (s, 2H), 6.67(d, J=9.2 Hz, 2H), 6.54 (d, J=9.2 Hz, 2H), 4.84 (brd s, 1H), 3.25 (t, J=6.8 Hz, 2H), 2.69 (t, J=6.8 Hz, 2H), 1.41 (s, 9H); $^{13}$C-NMR (100 MHz, methanol-d$_4$) δ 158.4, 154.2, 153.3, 151.1, 141.9, 141.7, 117.3, 116.8, 91.9, 80.0, 42.4, 35.4, 28.8; HRMS (EI+) for $C_{19}H_{21}I_2NO_4$ [M+H]$^+$ calcd. 581.9638 found 581.9626.

Example 11

Preparation of N-t-Boc-3'-iodothyronamine (14) and N-t-Boc-3',5'-diiodothyronamine (15)

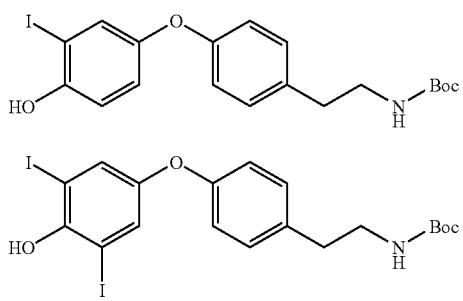

Iodine monochloride (0.24 ml, 0.24 mmol, 1 M solution in DCM) was added dropwise to a stirred solution of N-t-Boc-O-(4-hydroxy)phenyl tyramine 11 (52.1 mg, 0.16 mmol) and butyl amine (0.08 ml, 0.81 mmol) in DCM (1.0 ml) and DMF (0.25 ml) at −40° C. The reaction was kept below −35° C. for one hour, then allowed to warm to ambient temperature overnight. The crude reaction mixture was diluted with ethyl acetate and sequentially washed with 0.1 M $Na_2S_2O_3$ (1×), 0.5 M HCl (1×), water, and brine then dried over $MgSO_4$. The crude products were separated via flash $SiO_2$ chromatography (loaded with DCM, eluted with DCM/ethyl acetate (100:1) to (50:1)) to give 14 and 15 as slighty yellow oils (14: 17.3 mg, 24% yield; 15: 39.1 mg, 43% yield). For compound 14: $^1$H-NMR (400 MHz, chloroform-d) δ 7.33 (d, J=1.6 Hz, 1H), 7.12 (d, J=8.0 Hz, 2H), 6.96-6.94 (m, 2H), 6.87 (d, J=8.4 Hz, 2H), 5.47 (s, 1H), 4.57 (brd s, 1H), 3.36 (app brd q, J=6.0 Hz, 2H), 2.76 (t, J=6.8 Hz, 2H), 1.44 (s, 9H); HRMS (EI+) for $C_{19}H_{22}INO_4$ calcd. 455.0594 found 455.0610. For compound 15: $^1$H-NMR (400 MHz, chloroform-d) δ 7.37 (s, 2H), 7.15 (d, J=8.4 Hz, 2H), 6.88 (d, J=8.4 Hz, 2H), 5.63 (brd s, 1H), 4.57 (brd s, 1H), 3.37 (brd q, J=6.4 Hz, 2H), 2.77 (t, J=6.8 Hz, 2H), 1.44 (s, 9H); $^{13}$C-NMR (100 MHz, chloroform-d) δ 155.8, 155.7, 151.1, 150.1, 134.2, 130.2, 129.7, 118.3, 81.3, 41.8, 35.4, 28.4; HRMS (EI+) for $C_{19}H_{21}I_2NO_4$ [M-$C_4H_9$+H] calcd. 524.8934 found 524.8940.

Example 12

Preparation of N-t-Boc-3,3'-diiodothyronamine (16)

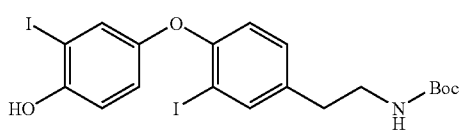

Iodine (41.8 mg, 0.16 mmol) was added to a saturated potassium iodide solution (0.1 ml) and the resulting solution was added dropwise to a stirred solution of phenol 12 (41.9 mg, 0.092 mmol) in an ethyl amine solution (1 ml, 1 M in THF) at −40° C. After 30 minutes the reaction mixture was warmed to 0° C. and stirred for an additional hour. The reaction mixture was diluted with ethyl acetate and sequentially washed with 3 M HCl, 0.1 M $Na_2S_2O_3$, and brine then dried over $MgSO_4$. The crude product was purified by flash $SiO_2$ chromatography (loaded with DCM, eluted with DCM/ethyl acetate (100:1)) to give 16 as a slightly yellow oil (18.2 mg, 34% yield): $^1$H-NMR (400 MHz, chloroform-d) δ 7.67 (d, J=2.0 Hz, 1H), 7.29 (d, J=2.8, 1H), 7.09 (d, J=8.4 Hz, 1H), 6.96 (d, J=8.8 Hz, 1H), 6.91 (dd, J=8.8, 2.8 Hz, 1H), 6.73 (d, J=8.4 Hz, 1H), 5.37 (s, 1H), 4.57 (brd s, 1H), 3.34 (brd q, J=6.4 Hz, 2H), 2.74 (t, J=7.0 Hz, 2H), 1.45 (s, 9H); $^{13}$C-NMR (100 MHz, chloroform-d) δ 155.8, 155.5, 151.5, 150.4, 139.9, 136.2, 130.1, 128.2, 120.8, 118.2, 115.3, 88.1, 85.1, 79.5, 41.7, 35.0, 28.4; HRMS (EI+) for $C_{19}H_{21}I_2NO_4$ [M-$C_4H_9$+H] calcd. 524.8934 found 524.9560.

Example 13

Preparation of N-t-Boc-3,3',5'-triiodothyronamine (17)

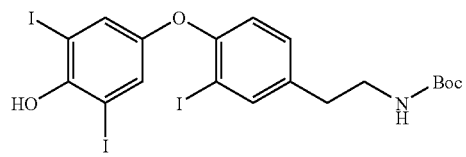

Iodine monochloride (0.16 ml, 0.16 mmol, 1 M solution in DCM) was added dropwise to a stirred solution of phenol 12 (34.1 mg, 0.075 mmol) and butyl amine (0.04 ml, 0.40 mmol) in DMF (0.5 ml) and DCM (2 ml) at 0° C. The reaction stirred at 0° C. until complete by TLC analysis (20 min), then diluted with ethyl acetate and sequentially washed with 0.5 M HCl, 0.1 M $Na_2S_2O_3$, water, and brine then dried over $MgSO_4$. The crude product was purified via flash $SiO_2$ (loaded with DCM, eluted with hexanes/ethyl acetate (5:1) to (2:1)) to give 17 as a slightly yellow oil (41.4 mg, 78% yield): $^1$H-NMR (400 MHz, chloroform-d) δ 7.68 (d, J=1.6 Hz, 1H), 7.33 (s, 2H), 7.12 (dd, J=8.4, 1.6 Hz, 1H), 6.76 (d, J=8.4 Hz, 1H), 5.61 (brd s, 1H), 4.58 (brd s, 1H), 3.35 (q, J=6.4 Hz, 2H), 2.75 (t, J=7.0 Hz, 2H), 1.45 (s, 9H); HRMS (EI+) for $C_{19}H_{20}I_3NO_4$ calcd. 706.8527 found 706.8529.

Example 14

Preparation of N-t-Boc-3,3',5-triiodothyronamine (18)

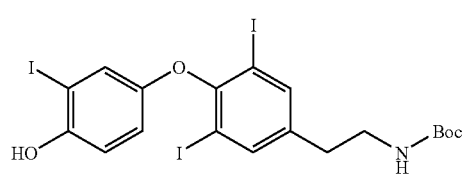

Iodine (17.0 mg, 0.067 mmol) was added to a saturated potassium iodide solution (0.07 ml) and the resulting solution was added dropwise to a stirred solution of phenol 13 (32.1 mg, 0.055 mmol) in THF (1 ml) and butyl amine (0.5 ml) at −40° C. After 30 minutes the reaction mixture was warmed to 0° C. and stirred for an additional hour. The reaction mixture was diluted with ethyl acetate and sequentially washed with 3 M HCl, 0.1 M Na$_2$S$_2$O$_3$, and brine then dried over MgSO$_4$. The crude product was purified by flash SiO$_2$ chromatography (loaded with DCM, eluted with DCM/ethyl acetate (100:1)) to give 18 as a slightly yellow oil (10.3 mg, 26% yield): $^1$H-NMR (400 MHz, chloroform-d) δ 7.76 (s, 2H), 7.01 (d, J=2.8 Hz, 1H), 6.72 (d, J=9.2 Hz, 1H), 6.57 (dd, J=8.8, 2.8 Hz, 1H), 4.86 (s, 1H), 3.27 (obsc brd t, J 6.0 Hz, 2 H), 2.71 (t, J=6.8 Hz, 2H), 1.41 (s, 9H).

Example 15

Preparation of N-t-Boc-3,3',5,5'-tetraioodothyronamine (19)

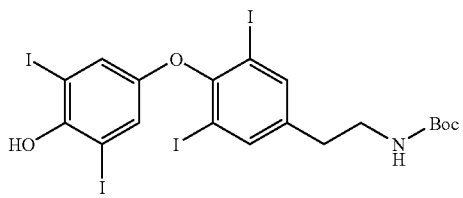

Iodine monochloride (0.11 ml, 0.11 mmol, 1 M solution in DCM) was added dropwise to a stirred solution of phenol 13 (27.7 mg, 0.048 mmol) and butyl amine (0.5 ml, 2.53 mmol) in THF (1 ml) at −45° C. After 30 minutes the reaction was partitioned between 0.5 M HCl and ethyl acetate. The organic phase was sequentially washed with 0.1 M Na$_2$S$_2$O$_3$ and brine then dried over MgSO$_4$. The crude product was purified by flash SiO$_2$ chromatography (dry loaded, eluted with hexanes/ethyl acetate (5:1)) to give 19 as a slightly yellow oil (18.4 mg, 46% yield). $^1$H-NMR (400 MHz, methanol-d$_4$) δ 7.78 (s, 2H), 7.08 (s, 2H), 3.30 (brd s, 2H), 2.73 (t, J=7.0 Hz,2H), 1.42 (s, 9H).

Method C: General Procedure for t-Boc Deprotection

The protected amine (31.2 mg, 0.054 mmol) was dissolved in a 1 N HCl or 3 N HCl solution in ethyl acetate (2 ml, anhydrous) and the reaction mixture was stirred at ambient temperature for 5-15 hours. A white precipitate was noted after 1.5 hours. Additional HCl was added as needed (2 ml) and the reaction mixture was stirred over night. The reaction was completed as described below.

Example 16

Preparation of Thyronamine Hydrochloride (22)

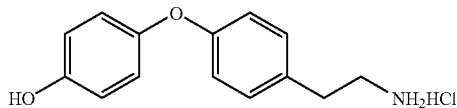

Refer to Method C for the general procedure. The crude reaction mixture was concentrated in vacuo and dried under high vacuum pressure to give 22 as a slightly tan solid (32.9 mg, 100% yield): $^1$H-NMR (400 MHz, dimethylsulfoxide-d$_6$) δ 9.37 (s, 1H), 7.90 (brd s, 3H), 7.20 (d, J=8.4 Hz, 1H), 6.86 (ovrlp d, J=8.8 Hz, 1H), 6.85 (ovrlp d, J=8.4 Hz, 1H), 6.78 (d, J=8.8 Hz, 1H), 2.99 (app brd q, J=8.0 Hz, 2H), 2.81 (t, J=8.2 Hz, 2H); HRMS (EI+) for C$_{14}$H$_{15}$NO$_2$ calcd. 229.1103 found 229.1107.

Example 17

Preparation of 3-iodothyronamine Hydrochloride (23)

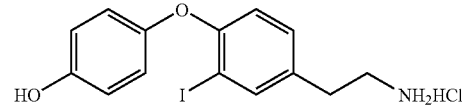

Refer to Method C for the general procedure. The crude precipitate was filtered to give 23 as a white solid (816 mg, 93% yield): $^1$H-NMR (400 MHz, DMSO-d$_6$) δ 9.44 (s, 1H), 8.12 (brd s, 3H), 7.76 (s, 1H), 7.20 (d, J=8.0 Hz, 1H), 6.79 (s, 4H), 6.68 (d, J=8.4 Hz, 1H), 2.98 (app brd q, J=7.2 Hz, 2H), 2.84 (t, J=7.4 Hz, 2H); HRMS (EI+) for C$_{14}$H$_{14}$INO$_2$ [M-NH$_3$] calcd. 337.9804 found 337.9812.

Example 18

Preparation of 3,5-diiodothyronamine Hydrochloride (24)

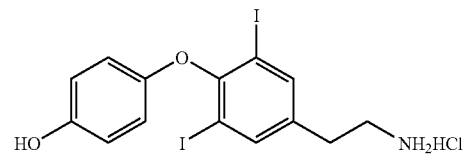

Refer to Method C for the general procedure. The crude reaction mixture was concentrated in vacuo and dried under high vacuum pressure to give 24 as a white solid (26.7 mg, 96% yield): $^1$H-NMR (400 MHz, D$_2$O) δ 7.97 (s, 2H), 6.89 (d, J=6.8 Hz, 2H), 6.79 (d, J=7.2 Hz, 2H), 3.29 (app t, J=6.4 Hz, 2H), 3.01 (app t, J=6.4 Hz, 2H); HRMS (EI+) for C$_{14}$H$_{13}$I$_2$NO$_2$ calcd. 480.9036 found 480.9050.

Example 19

Preparation of 3'-iodothyronamine Hydrochloride (25)

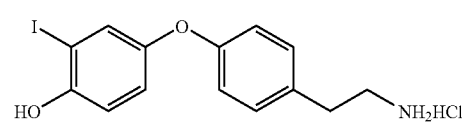

Refer to Method C for the general procedure. The crude reaction mixture was concentrated in vacuo and dried under high vacuum pressure to give 25 as a white solid (12.7 mg, 98% yield): $^1$H-NMR (400 MHz, DMSO-d$_6$) δ 10.24 (s, 1H), 7.86 (s, 3H), 7.30 (d, J=2.4 Hz, 1H), 7.23 (d, J=8.4 Hz, 2H), 6.96-6.86 (m, 4H), 3.01 (brd s, 2H), 2.83 (app t, J=7.6 Hz, 2H); HRMS (EI+) for $C_{14}H_{14}INO_2$ [M-NH$_3$] calcd. 337.9804 found 337.9809.

Example 20

Preparation of 3',5'-diiodothyronamine Hydrochloride (26)

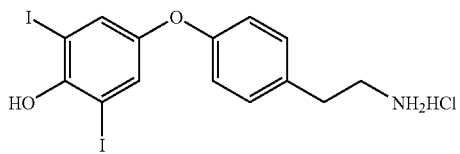

26

Refer to Method C for the general procedure. The crude reaction mixture was diluted with ether and the precipitated product was collected via vacuum filtration to give 26 as a white solid (32.3 mg, 88% yield): $^1$H-NMR (400 MHz, DMSO-d$_6$) δ 9.41 (s, 1H), 7.95 (s, 3H), 7.39 (s, 2H), 7.27 (d, J=8.4 Hz, 2H), 6.96 (d, J=8.4 Hz, 2H), 3.02 (brd s, 2H), 2.86 (app brd t, J=8.0 Hz, 2H); HRMS (EI+) for $C_{14}H_{13}I_2NO_2$ [M-NH$_3$] calcd. 463.8770 found 463.8748.

Example 21

Preparation of 3,3'-diiodothyronamine Hydrochloride (27)

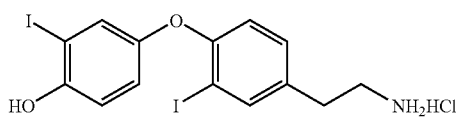

27

Refer to Method C for the general procedure. The crude reaction mixture was concentrated in vacuo and dried under high vacuum pressure to give 27 as a white solid (14.6 mg, 100% yield): $^1$H-NMR (400 MHz, DMSO-d$_6$) δ 10.27 (s, 1H), 7.96 (brd s, 3H), 7.79 (d, J=1.6 Hz, 1H), 7.25 (ovrlp dd, J=8.4, 2.0 Hz, 1H), 7.23 (ovrlp d, J=2.8 Hz, 1H), 6.92 (ovrlp d, J=8.8 Hz, 1H), 6.87 (ovrlp dd, J=8.8, 2.8 Hz, 1H), 6.81 (d, J=8.0 Hz, 1H), 3.03 (app brd s, 2H), 2.84 (brd t, J=7.6 Hz, 2H).

Example 22

Preparation of 3,3',5'-triiodothyronamine Hydrochloride (28)

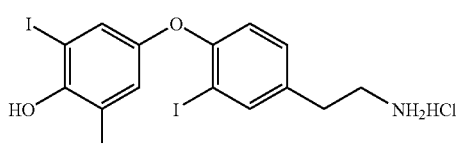

28

Refer to Method C for the general procedure. The crude reaction mixture was diluted with ether and the white precipitate was collected by vacuum filtration to give 28 as a white solid (27.1 mg, 85% yield). $^1$H-NMR (400 MHz, DMSO-d$_6$) δ 9.39 (s, 1H), 7.92 (brd s, 3H), 7.81 (d, J=2.0 Hz, 1H), 7.29 (ovrlp dd, J=8.0, 2.0 Hz, 1H), 7.29 (ovrlp s, 2H), 6.95 (d, J=8.4 Hz, 1H), 3.05 (brd s, 2H), 2.85 (t, J=7.6 Hz, 2H).

Example 23

Preparation of 3,3',5-triiodothyronamine Hydrochloride (29)

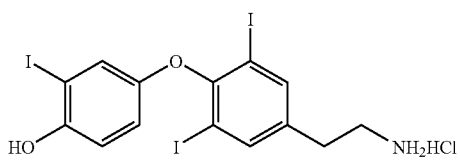

29

Refer to Method C for the general procedure. The crude reaction was concentrated in vacuo and dried under high vacuum pressure to give 29 as a tan solid (9.6 mg, 100% yield): $^1$H-NMR (400 MHz, DMSO-d$_6$) δ 10.00 (s, 1H), 7.86 (ovrlp s, 2H), 7.80 (ovrlp brd s,3H), 6.98 (d, J=2.8 Hz, 1H), 6.83 (d, J=9.2 Hz, 1H), 6.65 (dd, J=8.8, 3.2 Hz, 1H), 3.11 (t, J=7.2 Hz, 2H), 2.84 (t, J=7.2 Hz, 2H).

Example 24

Preparation of 3,3',5,5'-tetraiodothyronamine Hydrochloride (30)

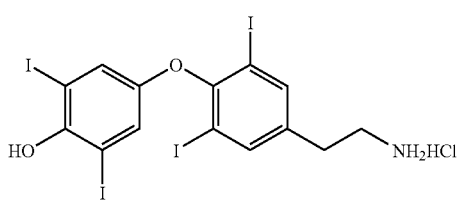

30

Refer to Method C for the general procedure. The crude reaction was concentrated in vacuo and dried under high vacuum pressure to give 30 as a tan solid (13.8 mg, 100% yield): $^1$H-NMR (400 MHz, DMSO-d$_6$) δ 9.25 (s, 1H), 7.87 (s, 2H), 7.11 (s, 2H), 3.12 (app brd s, 2H), 2.85 (t, J=7.2 Hz, 2H).

Example 25

Preparation of N-t-Boc-O-phenyl Tyramine (20)

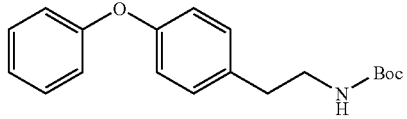

20

Refer to Method A for the general procedure. The crude product was purified via flash SiO$_2$ chromatography (dry loaded, eluted with hexanes/ethyl acetate (10:1) to (5:1)) to give 20 as a white crystalline solid (50.5 mg, 73% yield): $^1$H-NMR (400 MHz, chlorofom-d) δ 7.32 (app t, J=7.6 Hz, 2H), 7.14 (d, J=8.4 Hz, 2H), 7.08 (t, J=7.6 Hz, 1H), 6.99 (d, J=7.6 Hz, 2H), 6.94 (app d, J=8.4 Hz, 2H), 4.57 (brd s, 1H), 3.36 (brd q, J=6.0 Hz, 2H), 2.77 (t, J=7.0 Hz, 2H), 1.44 (s, 9H); $^{13}$C-NMR (100 MHz, chlorofom-d) δ 157.4, 155.8, 133.8, 130.0, 129.7, 123.1, 119.0, 118.7, 79.2, 41.8, 35.5, 28.4; HRMS (EI+) for C$_{19}$H$_{23}$NO$_3$ 313.1678 found 313.1686.

Example 26

Preparation of O-phenyl-tyramine Hydrochloride (31)

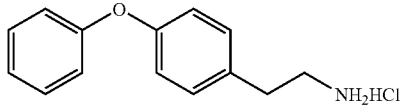

31

Refer to Method C for the general procedure. The crude reaction was concentrated in vacuo and dried under high vacuum pressure to give 31 as a tan solid (18.3 mg, 100% yield): $^1$H-NMR (400 MHz, DMSO-d$_6$) δ 8.17 (brd s, 3H), 7.38 (app t, J=7.6 Hz, 2H), 7.28 (d, J=8.4 Hz, 2H), 7.13 (t, J=7.4 Hz, 1H), 7.02-6.94 (m, 4H), 3.02 (app brd t, J=8.0 Hz, 2H), 2.90 (app t, J=8.4 Hz, 2H); HRMS (EI+) for C$_{14}$H$_{15}$NO calcd. 213.1154 found 213.1158.

Method D: General Procedure for O-alkylation of N-t-Boc Tyramine

The requisite alkyl halide (20.2 mmol) and potassium carbonate (3.50 g, 25.3 mmol) were added to a stirred solution of N-t-Boc tyramine (4.02 g, 17.0 mmol) in DMF (25 ml) at ambient temperature. The reaction mixture was vigorously stirred at ambient temperature for 4 to 48 hours, then diluted with ether and washed with 0.5 M HCl. The aqueous was extracted with ether and the combined organic layers were sequentially washed with water (2×) and brine then dried over MgSO$_4$. Concentration gave the crude O-alkylated product which was purified as described below.

Example 27

Preparation of N-t-Boc-O-benzyl-tyramine (21)

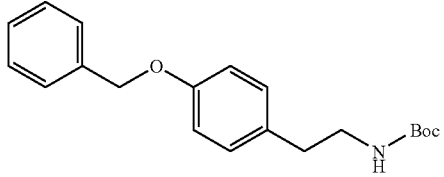

21

Refer to Method D for the general procedure. The crude product was purified via flash SiO$_2$ (loaded with DCM, eluted with hexanes/ethyl acetate (10:1) to (5:1)) to give 21 as a flaky white solid (3.24 g, 58% yield): $^1$H-NMR (400 MHz, chloroform-d) δ 7.42-7.27 (m, 5H), 7.08 (d, J=8.4 Hz, 2H), 6.90 (d, J=8.4 Hz, 2H), 5.02 (s, 2H), 4.60 (brd s, 1H), 3.32 (app brd q, J=6.0 Hz, 2H), 2.71 (app brd t, J=6.6 Hz, 2H), 1.43 (s, 9H); $^{13}$C-NMR (100 MHz, chloroform-d) δ 157.3, 155.8, 137.0, 131.2, 129.6, 128.5, 127.8, 127.3, 114.8, 79.0, 69.9, 41.8, 35.2, 28.3; HRMS (EI+) for C$_{20}$H$_{25}$NO$_3$ calcd. 327.1834 found 327.1819.

Example 28

Preparation of N-t-Boc-O-benzyl-3-iodotyramine (33)

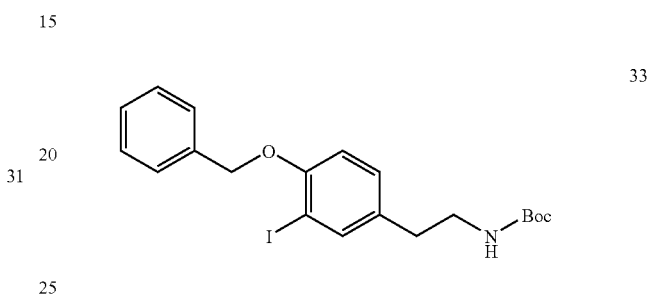

33

Benzyl bromide (0.07 ml, 0.59 mmol) and K$_2$CO$_3$ (89 mg, 0.64 mmol) were added to a stirred solution of phenol 2 (104 mg, 0.28 mmol) in DMF (2 ml). The mixture was vigorously stirred for 3 hours until the reaction was complete by TLC analysis. The reaction mixture was partitioned between ether and 0.5 M HCl. The organic layer was sequentially washed with water (2×) and brine then dried over MgSO$_4$. Concentration resulted in a yellow oil which was purified via flash SiO$_2$ chromatography (dry loaded, eluted with hexanes/ethyl acetate (10:1) to (5:1)) to give 33 as a clear oil (98.8 mg, 78% yield). $^1$H-NMR (400 MHz, DMSO-d$_6$) δ 7.63 (d, J=2.0 Hz, 1H), 7.49 (d, J=7.6 Hz, 2H), 7.39 (t, J=7.6 Hz, 2H), 7.32 (app t, J=7.4 Hz, 1H), 7.08 (app dd, J=7.2, 2.0 Hz, 1H), 6.78 (d, J=8.4 Hz, 1H), 5.13 (s, 2H), 4.52 (brd s, 1H),3.31 (app q, J=6.8 Hz, 2H), 2.69 (app t, J=7.0 Hz, 2H), 1.44 (s, 9H); HRMS (EI+) for C$_{20}$H$_{24}$INO$_3$ calcd. 453.0801 found 453.0806.

Example 29

Preparation of N-t-Boc-O-(2-phenyl)ethyl Tyramine (34)

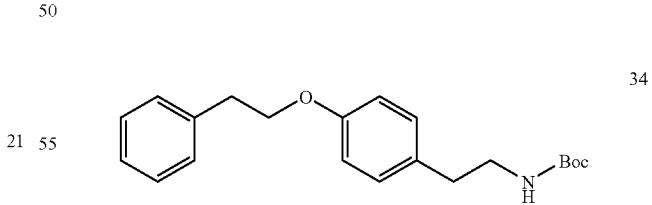

34

Refer to Method D for the general procedure. The crude product was purified via flash SiO$_2$ chromatography (dry loaded, eluted with hexanes/ethyl acetate (5:1)) to give 34 as a clear oil (38.6 mg, 49% yield based on recovered starting material): $^1$H-NMR (400 MHz, chloroform-d) δ 7.38-7.22 (m, 5H), 7.08 (d, J=8.0 Hz, 2H), 6.83 (d, J=8.4 Hz, 2H), 4.52 (brd s, 1H), 4.15 (t, J=7.2 Hz, 2H), 3.33 (app brd q, J=6.0 Hz, 2H), 3.09(t, J=7.0 Hz, 2H), 2.72 (t, J=6.8 Hz, 2H), 1.43 (s, 9H); $^{13}$C-NMR (100 MHz, chloroform-d) δ 157.4, 155.8, 138.2, 131.0, 129.7, 129.0, 128.4, 126.4, 114.6, 79.1, 68.7, 41.9, 35.8, 35.2, 28.4; HRMS (EI+) for $C_{21}H_{27}NO_3$ calcd. 341.1991 found 341.1990.

Example 30

Preparation of N-t-Boc-O-(p-fluoro)benzyl Tyramine (35)

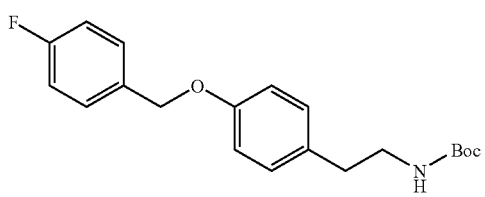

35

Refer to Method D for the general procedure. The crude product was purified via flash SiO$_2$ chromatography (loaded with DCM, eluted with hexanes/ethyl acetate (10:1) to (5:1)) to give 35 as a white solid (653 mg, 86% yield): $^1$H-NMR (400 MHz, chloroform-d) δ 7.40 (app dd, J=8.4, 5.2 Hz, 2H), 7.10 (ovrlp d, J=8.4 Hz, 2H), 7.06 (ovrlp app t, J=8.8 Hz, 2H), 6.90 (app d, J=8.8 Hz, 2H), 5.00 (s, 2H), 4.52 (brd s, 1H), 3.34 (app brd q, J=6.4 Hz, 2H), 2.73 (t, J=7.0 Hz, 2H), 1.43 (s, 9H); $^{13}$C-NMR (100 MHz, chloroform-d) δ 162.7 ($J_{CF}$=245 Hz), 157.5, 156.1, 133.0, 131.7, 130.0, 129.5 ($J_{CF}$=8.2 Hz), 115.7 ($J_{CF}$=21.4 Hz), 115.1, 79.4, 69.6, 42.1, 35:5, 28.6.

Example 31

Preparation of N-t-Boc-O-(m-methoxy)benzyl Tyramine (36)

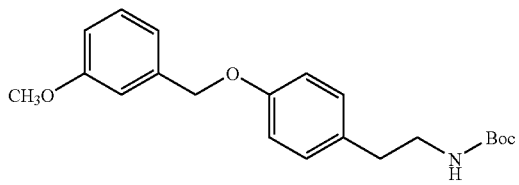

36

Refer to Method D for the general procedure. The crude product was purified via flash SiO$_2$ chromatography (loaded with DCM, eluted with hexanes/ethyl acetate (10:1) to (5:1)) to give 36 as a white solid (577 mg, 74% yield): $^1$H-NMR (400 MHz, chloroform-d) δ 7.29 (t, J=8.0 Hz, 1H), 7.09(d, J=8.4 Hz, 2H), 6.99(app d, J=8.4 Hz, 2H), 6.91 (d, J=8.4 Hz, 2H), 6.85 (app dd, J=8.4, 2.4 Hz, 1H), 5.02 (s, 2H), 4.54 (brd s, 1H), 3.81 (s, 3H), 3.33 (brd q, J=6.0 Hz, 2H), 2.73 (t, J=6.8 Hz, 2H), 1.43 (s, 9H).

Example 32

Preparation of N-t-Boc-O-(p-trifluoromethyl)benzyl Tyramine (37)

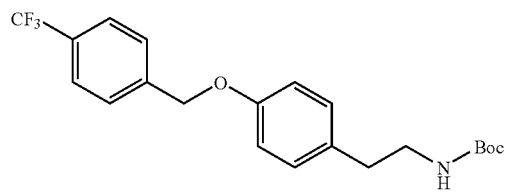

37

Refer to Method D for the general procedure. The crude product was purified via flash SiO$_2$ chromatography (loaded with DCM, eluted with hexanes/ethyl acetate (10:1) to (5:1)) to give 37 as a white solid (740 mg, 87% yield): $^1$H-NMR (400 MHz, chloroform-d) δ 7.63 (d, J=8.4 Hz, 2H), 7.54 (d, J=8.0 Hz, 2H), 7.11 (d, J=8.0 Hz, 2H), 6.90 (d, J=8.8 Hz, 2H), 5.10 (s, 2H), 4.53 (brd s, 1H), 3.34 (brd q, J=6.4 Hz, 2H), 2.74 (t, J=7.0 Hz, 2H), 1.43 (s, 9H).

Example 33

Preparation of N-t-Boc-O-(m,m-dimethyl)benzyl Tyramine (38)

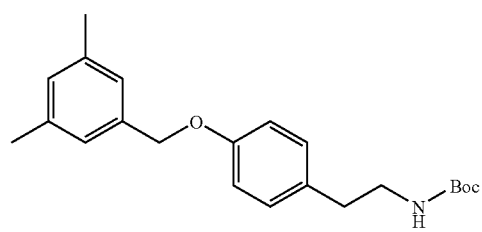

38

Refer to Method D for the general procedure. The crude product was purified via flash SiO$_2$ chromatography (loaded with DCM, eluted with hexanes/ethyl acetate (20:1) to (10:1)) to give 38 as a white solid (74.7 mg, 40% yield): $^1$H-NMR (400 MHz, chloroform-d) δ 7.10 (d, J=8.8 Hz, 2H), 7.04 (s, 2H), 6.96 (s, 1H), 6.92 (d, J=8.8 Hz, 2H), 4.97 (s, 2H), 4.53 (brd s, 1H), 3.33 (app brd q, J=5.6 Hz, 2H), 2.73 (t, J=6.8 Hz, 2H), 1.43 (s, 9H).

Example 34

Preparation of O-benzyl-tyramine hydrochloride (32)

32

Refer to Method C for the general procedure. The crude reaction mixture was diluted with ether and the white precipitate was collected by vacuum filtration to give 32 as a white solid (156 mg, 97% yield): $^1$H-NMR (400 MHz, DMSO-d$_6$) δ 8.03 (s, 3H), 7.46-7.30(m, 5H), 7.17 (app d, J=8.8 Hz, 2H), 6.97 (app d, J=8.4 Hz, 2H), 5.08 (s, 2H), 2.97 (app t, J=7.5 Hz, 2H), 2.81 (app t, J=7.5 Hz, 2H); HRMS (EI+) for C$_{15}$H$_{17}$NO calcd. 227.1310 found 227.1316.

Example 35

Preparation of O-benzyl-3-iodotyramine Hydrochloride (39)

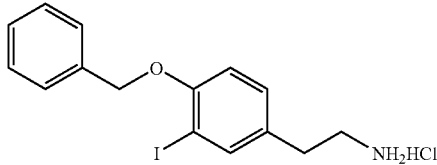

39

Refer to Method C for the general procedure. The crude reaction mixture was diluted with ether and the white precipitate was collected by vacuum filtration to give 36 as a white solid (18.6 mg, 88% yield): $^1$H-NMR (400 MHz, DMSO-d$_6$) δ 7.90 (brd s, 3H), 7.69 (d, J=2.0 Hz, 1H), 7.48 (d, J=7.2 Hz, 2H), 7.40 (t, J=7.4 Hz, 2H), 7.32 (app t, J=7.2 Hz, 1H), 7.23 (dd, J=8.4, 2.0 Hz, 1H), 7.03 (d, J=8.8 Hz, 1H), 5.17 (s, 2H), 2.99 (brd s, 2H), 2.78 (t, J=7.8 Hz, 2H).

Example 36

Preparation of O-(2-phenyl)ethyl Tyramine Hydrochloride (40)

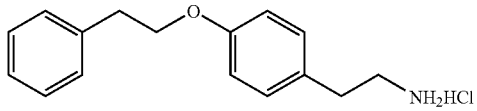

40

Refer to Method C for the general procedure. The crude reaction mixture was diluted with ether and the precipitate was collected by vacuum filtration to give 40 as a white solid (22.4 mg, 93% yield): 1H-NMR (400 MHz, DMSO-d$_6$) δ 7.86 (brd s, 3H), 7.16-7.23 (m, 5H), 7.12 (d, J=8.4 Hz, 2H), 6.86 (d. J=8.0 Hz, 2H), 4.13 (t, J=6.8 Hz, 2H), 2.98 (ovrlp t, J=7.0 Hz, 2H), 2.40 (ovrlp app t, J=8.0 Hz, 2H), 2.75 (app t, J=8.0 Hz, 2H).

Example 37

Preparation of O-(p-fluoro)benzyl Tyramine Hydrochloride (41)

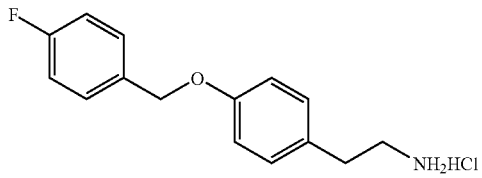

41

Refer to Method C for the general procedure. The crude reaction mixture was diluted with ether and the precipitate was collected by vacuum filtration to give 41 as a white solid (50.4 mg, 90% yield): $^1$H-NMR (400 MHz, DMSO-d$_6$) δ 7.93 (brd s, 3H), 7.45 (app dd, J=8.4, 5.6 Hz, 2H), 7.22 (ovrlp app t, J=8.8 Hz, 2H), 7.18 (d, J=8.8 Hz, 2H), 6.97 (d, J=8.8 Hz, 2H), 5.07 (s, 2H), 2.98 (app t, J=7.8 Hz, 2H), 2.80 (app t, J=8.0 Hz, 2H).

Example 38

Preparation of O-(m-methoxy)benzyl Tyramine Hydrochloride (42)

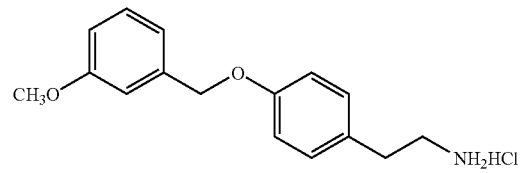

42

Refer to Method C for the general procedure. The crude reaction mixture was diluted with ether and the precipitate was collected by vacuum filtration to give 42 as a white solid (67.0 mg, 97% yield): $^1$H-NMR (400 MHz, DMSO-d6) δ 7.87 (brd s, 3H), 7.30 (t, J=8.0 Hz, 1H), 7.17 (d, J=8.4 Hz, 2H), 6.94-7.20 (m, 4H), 6.88 (app d, J=7.2 Hz, 1H), 5.06 (s, 2H), 3.75 (s, 3H), 2.98 (brd s, 2H), 2.79 (app t, J=7.8 Hz, 2H).

Example 39

Preparation of O-(p-trifluoromethyl)benzyl Tyramine Hydrochloride (43)

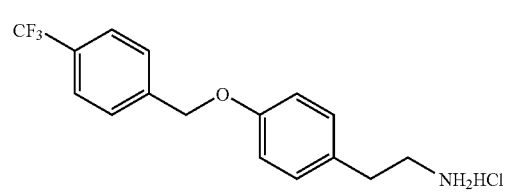

43

Refer to Method C for the general procedure. The crude reaction mixture was diluted with ether and the precipitate was collected by vacuum filtration to give 43 as a white solid (37.3 mg, 84% yield): $^1$H-NMR (400 MHz, DMSO-d6) δ 7.90 (s, 3H), 7.77 (d, J=8.4 Hz, 2H), 7.66 (d, J=8.0 Hz, 2H), 7.19 (d, J=8.8 Hz, 2H), 6.99 (d, J=8.4 Hz, 2H), 5.22 (s, 2H), 2.99 (app t, J=8.0 Hz, 2H), 2.80 (app t, J=7.8 Hz, 2H).

Example 40

Preparation of O-(m,m-dimethyl)benzyl Tyramine Hydrochloride (44)

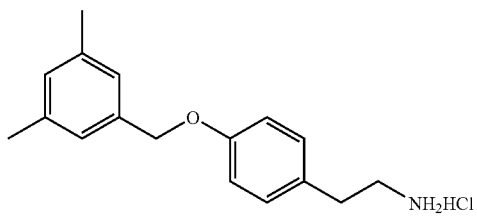

44

Refer to Method C for the general procedure. The crude reaction mixture was diluted with ether and the precipitate was collected by vacuum filtration to give 44 as a white solid (28.6 mg, 86% yield): $^1$H-NMR (400 MHz, chloroform-d) δ 7.97 (brd s, 3H), 7.17 (d, J=8.4 Hz, 2H), 7.03 (s, 2H), 6.96 (ovrlp d, J=8.4 Hz, 2H), 6.95 (ovrlp s, 1H), 4.99 (s, 2H), 2.97 (brd s, 2H), 2.81 (app t, J=8.0 Hz, 2H), 2.27 (s, 6H).

Method E: General Procedure for N-Alkylated Derivatives

A solution of the requisite protected amine (3.0 mmol) in DMF (5 ml) was added dropwise to a slurry of sodium hydride (150 mg, 3.75 mmol, 60% dispersion in oil) in DMF (10 ml) at 0° C. The reaction was stirred until evolution of hydrogen ceased (10 to 60 min). The desired alkyl halide (7.30 mmol) was then added at 0° C. over 5 minutes and the stirring was continued for an additional 45 minutes. The reaction mixture was allowed to warm to ambient temperature over 2 hours, after which excess sodium hydride was quenched with either methanol (5 ml) or 0.5 m HCl. The mixture was then diluted with ether and sequentially washed with water (3×), brine, then dried over MgSO$_4$. Concentration gave the crude N-alkylated product which was purified as described below.

Example 41

Preparation of N-t-Boc-N-methyl-O-benzyl-tyramine (45)

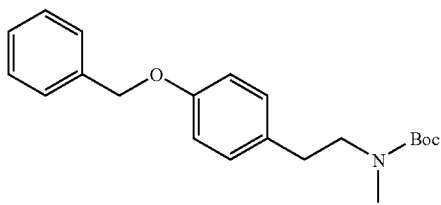

45

Refer to Method E for the general procedure. The crude N-methylated product was purified by flash SiO$_2$ chromatography (loaded with DCM, eluted with hexanes/ethyl acetate (20:1) to (5:1)) to give 45 as a clear oil (0.86 mg, 84% yield): $^1$H-NMR (400 MHz, chloroform-d) δ 7.43-7.31 (m, 5H), 1.07 (brd s, 2H), 6.90 (d, J=8.4 Hz, 2H), 5.04 (s, 2H), 3.37 (brd s, 2H) 2.81 (brd s, 2H) 2.74 (brd s, 3H) 1.40 (s, 9H); HRMS (EI+) for C$_{21}$H$_{27}$NO$_3$ calcd. 341.1991 found 341.1983.

Example 42

Preparation of N-t-Boc-N-methyl-O-benzyl-3-iodotyramine (46)

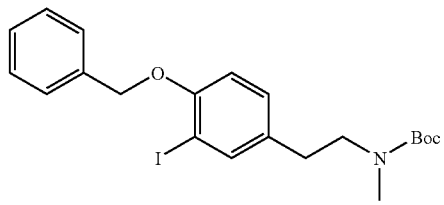

46

Refer to Method E for the general procedure. The crude N-methylated product was purified by flash SiO$_2$ chromatography (loaded with DCM, eluted with hexanes/ethyl acetate (10:1) to (5:1)) to give 46 as a clear oil (0.86 mg, 84% yield): $^1$H-NMR (400 MHz, DMSO-d$_6$) δ 7.62 (d, J=2.0 Hz, 1H), 7.48 (d, J=7.2 Hz, 2H), 7.40 (t, J=7.6 Hz, 2H), 7.32 (app t, J=7.2 Hz, 1H), 7.13 (brd d, J=7.2 Hz, 1H), 6.99 (d, J=8.4 Hz, 1H), 5.16 (s, 2H), 3.32 (obsc brd s, 2H), 2.73 (s, 3H), 2.66 (t, J=7.0 Hz, 2H), 1.36 (brd s, 3H), 1.25 (brd s, 6 H)[Note: signals at 1.36 and 1.25 ppm are rotamers of the t-Boc group].

Example 43

Preparation of N-t-Boc-N-ethyl-O-benzyl-tyramine (47)

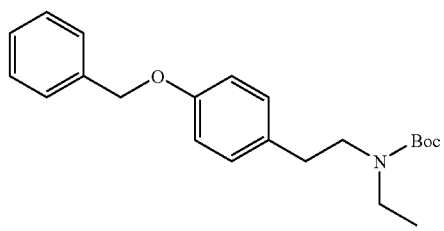

47

Refer to Method E for the general procedure. The crude ethylated product was purified via flash SiO$_2$ chromatography (loaded with DCM, eluted with hexanes/ethyl acetate (100:1) to (10:1)) to give 47 as a slightly yellow oil (123 mg, 80% yield): $^1$H-NMR (400 MHz, chloroform-d) δ 7.43-7.26 (m, 5H), 7.09 (brd s, 2H), 6.89 (d, J=8.4 Hz, 2H), 5.02 (s, 2H), 3.33 (brd s, 2H), 3.19 (brd s, 2H), 2.75 (brd s, 2H), 1.45 (s, 9H), 1.06 (brd t, J=6.2 Hz, 3H).

Example 44

Preparation of N-t-Boc-N-propyl-O-benzyl Tyramine (48)

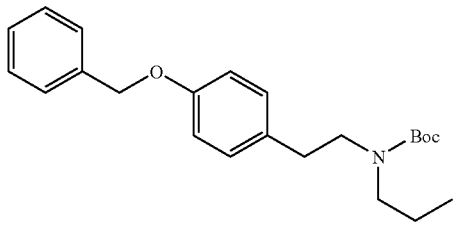

48

Refer to Method E for the general procedure. The crude propylated product was purified via flash SiO$_2$ chromatography (loaded with DCM, eluted with hexanes/ethyl acetate (100:1) to (10:1)) to give 48 as a slightly yellow oil (145 mg, 82% yield): $^1$H-NMR (400 MHz, chloroform-d) δ 7.42-7.20 (m, 5H), 7.09 (brd s, 2H), 6.89 (d, J=8.8 Hz, 2H), 5.02 (s, 2H), 3.32 (brd s, 2H), 3.11 (app brd s, 2H), 2.75 (brd s, 2H), 1.48 (ovlrp brd s, 2H), 1.44 (s, 9H), 0.85 (t, J=7.2 Hz, 3H).

Example 45

Preparation of N-t-Boc-N-butyl-O-benzyl Tyramine (49)

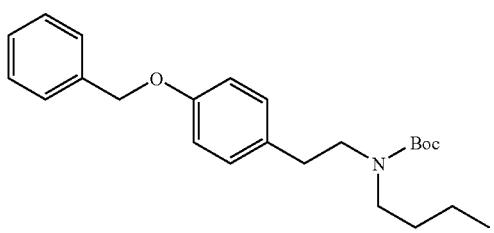

49

Refer to Method E for the general procedure. The crude butylated product was purified via flash SiO$_2$ chromatography (loaded with DCM, eluted with hexanes/ethyl acetate (100:1) to (10:1)) to give 49 as a slightly yellow oil (126 mg, 75% yield): $^1$H-NMR (400 MHz, chloroform-d) δ 7.44-7.30 (m, 5H), 7.09 (brd s, 2H), 6.90 (d, J=8.4 Hz, 2H), 5.04 (s, 2H), 3.32 (brd s, 2H), 3.13 (brd s, 2H), 2.75 (brd s, 2H), 1.45 (s, 11H), 1.27 (sextet, J=7.3 Hz, 2H), 0.90 (t, J=7.4 Hz, 3H).

Example 46

Preparation of N-t-Boc-N-benzyl Tyramine (50)

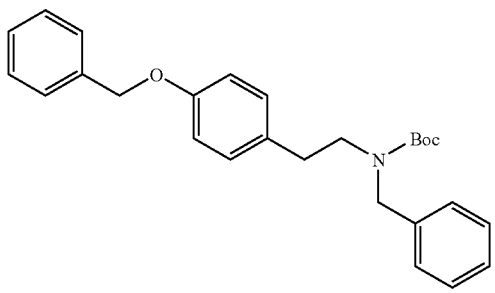

50

Refer to Method E for the general procedure. The crude benzylated product was purified via flash SiO$_2$ chromatorgraphy (loaded with DCM, eluted with hexanes/ethyl acetate (100:1) to (10:1) to give 50 as a slightly yellow oil (167 mg, 80% yield): $^1$H-NMR (400 MHz, 1H), 7.02 (brd s, 1H), 6.88 (d, J=6.4 Hz, 2H), 5.04 (s, 2H), 4.38 (brd s, 1H), 4.31 (brd s, 1H), 3.39 (brd s, 1H), 3.29 (brd s, 1H), 2.75 (brd s, 1H), 2.69 (brd s, 1H), 1.47 (brd s, 9H).

Example 47

Preparation of N-methyl-O-benzyl-tyramine Hydrochloride (51)

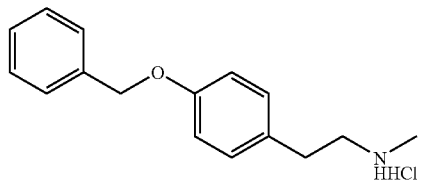

51

Refer to Method C for the general procedure. The crude reaction mixture was concentrated in vacuo to give 51 which was dried under high vacuum (118 mg, 89% yield). $^1$H-NMR (400 MHz, DMSO-d$_6$) δ 8.90 (brd s, 1H), 7.45-7.32 (m, 5H), 7.18 (d, J=8.4 Hz, 2H), 6.75 (d, J=8.4 Hz, 2H), 5.08 (s, 2H), 3.33 (s, 1H), 3.05 (brd s, 2H) 2.86 (t, J=8.8 Hz, 2H) 2.54 (s, 3H).

Example 48

Preparation of N-methyl-O-benzyl-3-iodotyramine Hydrochloride (52)

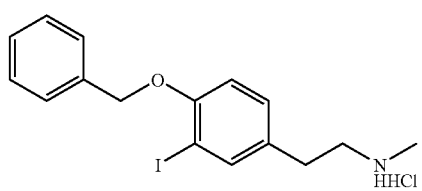

52

Refer to Method C for the general procedure. The crude reaction mixture was diluted with ether and the white precipitate was collected by vacuum filtration to give 52 as a white solid (35.9 mg, 91% yield): $^1$H-NMR (400 MHz, DMSO-d$_6$) δ 8.64 (brd s, 2H), 7.71 (d, J=2.0 Hz, 1H), 7.49 (d, J=7.2 Hz, 2H), 7.41 (app t, J=7.3 Hz, 2H), 7.33 (app t, J=7.4 Hz, 1H), 7.24 (dd, J=8.2, 2.2 Hz, 1H), 7.05 (d, J=8.4 Hz, 1H), 5.18 (s, 2H), 3.10(brd s, 2H), 2.83 (app t, J=7.8 Hz, 2H), 2.55 (brd s, 3H).

Example 49

Preparation of N-ethyl-O-benzyl Tyramine Hydrochloride (53)

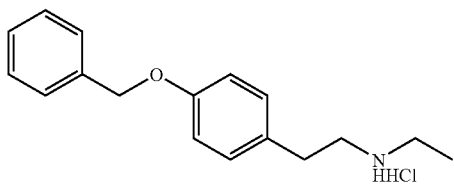

Refer to Method C for the general procedure. The crude reaction mixture was diluted with ether and the white precipitate was collected by vacuum filtration to give 53 as a white solid (38.9 mg, 92% yield): $^1$H-NMR (400 MHz, DMSO-$d_6$) δ 8.70 (brd s, 2H), 7.45-7.30 (m, 5H), 7.18 (d, J=8.4 Hz, 2H), 6.97 (d, J=8.4 Hz, 2H), 5.09 (s, 2H), 3.08 (app t, J=7.6 Hz, 2H), 2.95 (q, J=7.2 Hz, 2H), 2.85 (app t, J=8.2 Hz, 2H), 1.19 (t, J=7.2 Hz, 3H).

Example 50

Preparation of N-propyl-O-benzyl Tyramine Hydrochloride (54)

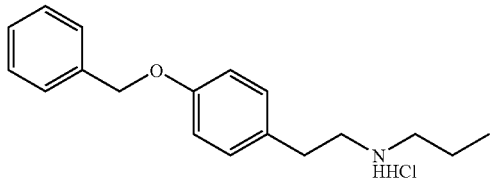

Refer to Method C for the general procedure. The crude reaction mixture was diluted with ether and the white precipitate was collected by vacuum filtration to give 54 as a white solid (35.9 mg, 88% yield): $^1$H-NMR (400 MHz, DMSO-$d_6$) δ 8.72 (brd s, 2H), 7.45-7.30 (m, 5H), 7.17 (d, J=8.4 Hz, 2H), 6.98 (d, J=8.8 Hz, 2H), 5.09 (s, 2H), 308 (app t, J=8.2 Hz, 2H), 2.89-2.84 (m, 4H), 1.62 (sextet, J=7.5 Hz, 2H), 0.91 (t, J=7.6 Hz, 3H).

Example 51

Preparation of N-butyl-O-benzyl Tyramine Hydrochloride (55)

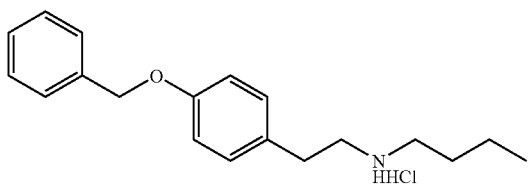

Refer to Method C for the general procedure. The crude reaction mixture was diluted with ether and the white precipitate was collected by vacuum filtration to give 55 as a white solid (32.1 mg, 91% yield): $^1$H-NMR (400 MHz, DMSO-$d_6$) δ 8.71 (brd s, 2H), 7.45-7.30 (m, 5H), 7.17 (d, J=8.8 Hz, 2H), 6.98 (d, J=8.8 Hz, 2H), 5.09 (s, 2H), 3.08 (app t, J=8.2 Hz, 2H), 2.92-2.84 (m, 4H), 1.58 (quintet, J=7.7 Hz, 2H), 1.33 (sextet, J=7.4 Hz, 2H), 0.89 (t, J=7.2 Hz, 3H).

Example 52

Preparation of N-benzyl-O-benzyl Tyramine Hydrochloride (56)

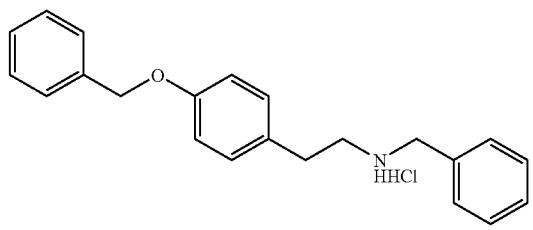

Refer to Method C for the general procedure. The crude reaction mixture was diluted with ether and the white precipitate was collected by vacuum filtration to give 56 as a white solid (66.2 mg, 85% yield): $^1$H-NMR (400 MHz, DMSO-$d_6$) δ 9.21 (brd s, 2H), 7.56-7.30 (m, 10H), 7.16 (d, J=8.4 Hz, 2H), 6.97 (d, J=8.4 Hz, 2H), 5.08 (s, 2H), 4.16 (brd s, 2H), 3.09 (brd s, 2H), 2.91 (app t, J=8.2, 2H).

General: All reactions were conducted under inert argon passed through a Drierite drying tube in flame dried glassware unless otherwise noted. Anhydrous tetrahydrofuran (THF) was dried in a sodium benzophenone ketyl radical still. All other anhydrous solvents and reagents were purchased from Aldrich, Sigma-Aldrich, Fluka, or Acros and were used without any further purification unless otherwise stated. $^1$H and $^{13}$C NMR spectra were taken on a Varian 400 (400 MHz and 100 MHz respectively). Data reported are calibrated to internal TMS (0.0 ppm) for all solvents unless otherwise noted and are reported as follows: chemical shift, multiplicity (app=apparrant, par obsc =partially obscured, ovrlp=overlapping, brd=broad, s=singlet, d=doublet, t=triplet, q=quartet, m=multiplet), coupling constant, and integration. High resolution mass spectra were obtained from the departmental mass spectrometry facility. Thin-layer chromatography (TLC) was performed on 0.25 mm Merck precoated silica gel plates and silica gel chromatography was performed using Silica Gel 60 Geduran (EM Science).

Example 52

Preparation of N-t-Boc-N-Methyl-4'-triisopropylsilyloxy-3-iodo-thyronamine (57) and N-t-Boc-N-methyl-4'-methoxy-3-iodo-thyronamine (58)

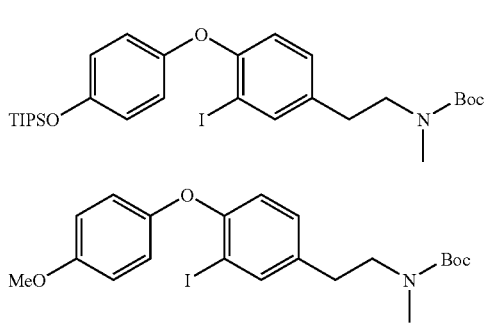

In a flame dried flask, sodium hydride (13.7 mg, 0.57 mmol) was suspended in DMF (2 ml) and cooled to 0° C. in an ice bath. A solution of N-t-Boc4'-triisopropyl-silyloxy-3-iodothyronamine (9) (229 mg, 0.37 mmol) in DMF (0.5 ml) was added dropwise. The reaction was stirred for 30 minutes at 0° then iodomethane (0.03 ml, 0.48 mmol) was added and the reaction was allowed to warm to RT over 2 hours. Additional sodium hydride (4.54 mg, 0.19 mmol) and iodomethane (0.03 ml, 0.48 mmol) were added and the reaction was stirred overnight. The reaction mixture was diluted with ether and quenched with 0.5 M HCl. The aqueous was extracted with ether (1×) and the combined organic layers were sequentially washed with water (2×) and brine then dried over $MgSO_4$. The crude oil was purified via flash $SiO_2$ chromatography (loaded with DCM, eluted with hexanes/ethyl acetate (10:1) to (5:1)) to give 57 (21.7 mg, 9% yield) and 58 (129 mg, 72% yield) as a clear oils. For compound 57: $^1$H-NMR (400 MHz, chloroform-d) δ 7.66 (s, 1H), 7.04 (brd s, 1H), 6.84 (s, 4H), 6.67 (d, J=8.4 Hz, 1H), 3.40 (t, J=7.2 Hz, 2H), 2.83 (brd s, 3H), 2.73 (brd s, 2H), 1.42 (brd s, 9H), 1.29-1.20 (m, 3H), 1.10 (d, J=18H). For compound 58: $^1$H-NMR (400 MHz, chloroform-d) δ 7.66 (s, 1H), 7.04 (brd s, 1H), 6.89 (app dt, J=9.2, 3.0 Hz, 2H), 6.84 (app dt, J=9.2, 3.0 Hz, 2H), 6.69 (d, J=8.4 Hz, 1H), 3.79 (s, 3H), 3.40 (brd t, J=7.2 Hz, 2H), 2.83 (brd s, 3H), 2.73 (brd s, 2H), 1.42 (brd s, 9H).

Example 53

Preparation of N-Methyl-3-iodothyronamine Hydrochloride (60)

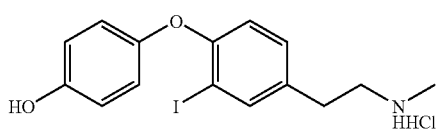

Refer to Method B for general silyl deprotection procedure. The crude silyl deprotected product was was used without further purification. Refer to method C for the general t-Boc deprotection procedure. The filtered precipitate gave 60 as a white solid (7.7 mg, 76% yield): $^1$H-NMR (400 MHz, DMSO-$d_6$) δ 9.39 (s, 1H), 8.57 (brd s, 2H), 7.78 (d, J=2.4 Hz, 1H), 7.21 (dd, J=8.8, 2.4 Hz, 1H), 6.82 (app dt, J=9.2, 2.8 Hz, 2H), 6.78 (app dt, J=9.2, 2.8 Hz, 2H), 6.71 (d, J=8.2 Hz, 1H), 3.12 (app brd d, J=6.0 Hz, 2H), 2.86 (app brd t, J=7.8 Hz, 2H), 2.56 (brd s, 3H).

Example 60

Preparation of N-Methyl-4'-methoxy-3-iodothyronamine Hydrochloride (61)

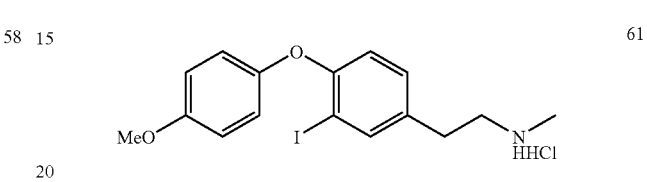

Refer to Method C for the general procedure. The filtered precipitate gave 61 as a white solid (34.9 mg, 89% yield): $^1$H-NMR (400 MHz, DMSO-$d_6$) δ 8,82 (brd s, 2H), 7.80 (d, J=2.0 Hz), 7.25 (dd, J=8.4, 2.0 Hz, 1H), 6.95. (app dt, J=9.2, 2.6 Hz, 2H) 6.91 (app dt, J=9.2, 2.6 Hz, 2H), 6.78 (d, J=8.4 Hz, 1H), 3.74 (s, 3H), 3.16-3.08 (brd m, 2H), 2.89 (app t, J=7,8 Hz, 2H), 2.57-2.53 (brd m, 3H).

Example 54

Preparation of N-t-Boc-3-Iodo4-Phenoxy Tyramine (62)

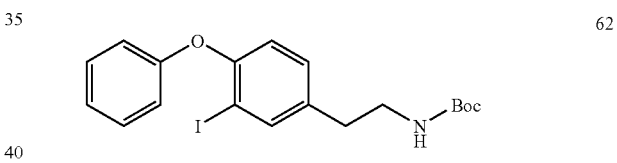

Refer to Method A for the general procedure. The crude oil was purified via flash $SiO_2$ (loaded with DCM, eluted with hexanes/ethyl acetate (10:1) to (8:1) to (5:1)) to give 62 as a clear oil which solidified upon sitting (483 mg, 66% yield): $^1$H-NMR (400 MHz, chloroform-d) δ 7.66 (d, J=1.6 Hz, 1H), 7.30 (app t, J=7.4 Hz, 2H), 7.08 (app t, J=7.4 Hz, 2H), 6.92 (app d, J=8.4 Hz, 2H), 6.80 (d, J=8.4 Hz, 1H), 4.57 (brd s, 1H), 3.32 (q, J=6.5 Hz, 2H), 2.72 (t, J=7.0, 2H), 1.42 (s, 9H).

Example 55

Preparation of 3-Iodo-4-Phenoxy Tyramine Hydrochloride (63)

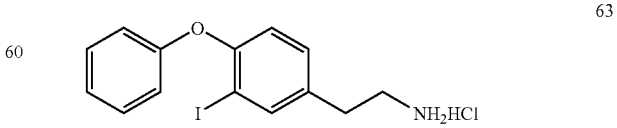

Refer to Method C for the general procedure. The precipitate was collected by filtration to give 63 as a white solid (250 mg, 88% yield): $^1$H-NMR (400 MHz, DMSO-$d_6$) δ

7.92 (brd s, 3H), 7.80 (d, J=2.0 Hz, 1H), 7.33 (app t, J=8.0 Hz, 2H), 7.27 (dd, J=8.2, 2.2 Hz, 1H), 7.08 (t, J=7.4 Hz, 1H), 6.91 (d, J=8.8 Hz, 1H), 6.87 (app d, J=8.6 Hz, 2H), 3.07-2.97 (m, 2H), 2.83 (app t, J=7.8 Hz, 2H).

Example 56

Preparation of N-t-Boc-4-(3'-Phenyl)propyloxy Tyramine (64)

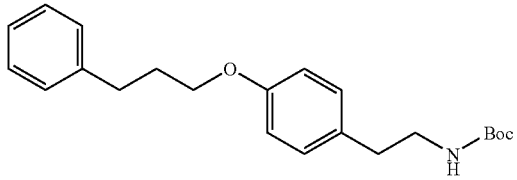

64

Refer to Method D for the general procedure. The crude product was purified via flash SiO$_2$ (eluted with hexane/ethyl acetate (5:1)) to give 64 as a white solid (260 mg, 73% yield). $^1$H-NMR (400 MHz, chloroform-d) δ 7.31-7.20 (m, 5H), 7.09 (d, J=8.8 Hz, 2H), 6.83 (d, J=8.8 Hz, 2H), 4.51 (brd s, 1H), 3.95 (t, J=6.0 Hz, 2H), 3.34 (app brd d, J=5.2 Hz, 2H), 2.81 (t, J=7.6 Hz, 2H), 2.73 (app brd t, J=6.8 Hz, 2H), 2.12 (ovrlp t, J=6.4 Hz, 2H), 1.44 (s, 9H).

Example 57

Preparation of N-t-Boc-4-(4'-Phenyl)butyloxy Tyramine (65)

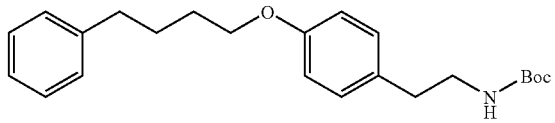

65

Refer to Method D for the general procedure. The crude product was purified via flash SiO$_2$ (eluted with hexane/ethyl acetate (5:1)) to give 65 as a white solid (178 mg, 48% yield). $^1$H-NMR (400 MHz, chloroform-d) δ 7.30-7.17 (m, 5H), 7.08 (d, J=8.4 Hz, 2H), 6.82 (d, J=8.8 Hz, 2H), 4.51 (brd s, 1H), 3.95 (t, J=6.0 Hz, 2H), 3.33 (app brd d, J=6.0 Hz, 2H), 2.74-2.63 (m, 4H), 1.83-1.80 (m, 4H), 1.43 (s, 9H).

Example 58

Preparation of N-t-Boc-4-Benzoylmethoxy Tyramine (66)

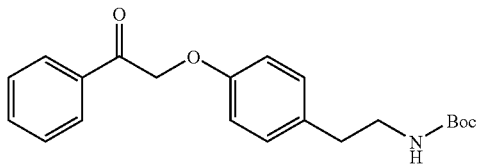

66

Refer to Method D for the general procedure. The crude product was purified via flash SiO$_2$ (eluted with hexane/ethyl acetate (3:1)) to give 66 as a white solid (385 mg, 98% yield). $^1$H-NMR (400 MHz, chloroform-d) δ 8.01 (d, J=7.2 Hz, 2H), 7.62 (t, J=7.2 Hz, 1H), 7.50 (t, J=7.2 Hz, 2H), 7.10 (d, J=8.4 Hz, 2H), 6.88 (d, J=8.4 Hz, 2H), 5.26 (s, 2H), 4.51 (brd s, 1H), 3.33 (app brd d, J=6.0 Hz, 2H), 2.73 (app brd t, J=7.2 Hz, 2H), 1.43 (s, 9H).

Example 59

Preparation of N-t-Boc-4-(m,m-dimethoxy)benzyloxy Tyramine (67)

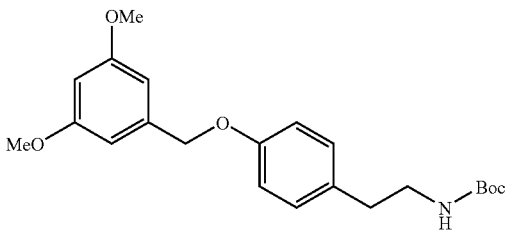

67

Refer to method D for the general procedure. The crude product was purified by flash SiO$_2$ chromatography(loaded with DCM, eluted with hexanes/ethyl acetate (10:1) to (5:1) to (3:1)) to give 67 as a white crystaline solid (568 mg, 65% yield): $^1$H-NMR (400 MHz, chloroform-d) δ 7.09 (d, J=8.4 Hz, 2H), 6.90 (d, J=8.8 Hz, 2H), 6.58 (d, J=2.0 Hz, 2H), 6.40 (d, J=2.0 Hz, 1H), 4.98 (s, 2H), 4.56 (brd s, 1H), 3.79 (s, 6H), 3.32 (brd s, 2H), 2.72 (app t, J=7.0, 2H), 1.43 (s, 9H); $^{13}$C-NMR (100 MHz, chloroform-d) δ 160.9, 157.3, 155.8, 139.5, 131.3, 129.7, 114.9, 105.1, 99.8, 79.1, 69.9, 55.3, 41.8, 35.2, 28.4.

Example 60

Preparation of N-t-Boc-3-Iodo-4-(p-trifluoromethyl)benzyloxy Tyramine (68)

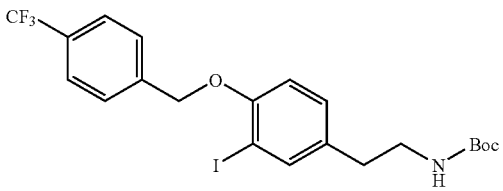

68

Refer to Method D for the general procedure. The crude product was purified by flash SiO2 (loaded with DCM, eluted with hexanes/ethyl acetate (10:1) to (5:1)) to give 68 as a yellow solid (464 mg, 64% yield): $^1$H-NMR (400 MHz, chloroform-d) δ 7.63 (ovrlp d, J=8.8 Hz, 2H), 7.62 (ovrlp s, 1H), 7.59 (d, J=8.8 Hz, 2H), 7.08 (d, J=7.6 Hz, 1H), 6.74 (d, J=8.4 Hz, 1H), 5.14 (s, 2H), 4.50 (brd s, 1H), 3.30 (q, J=6.4 Hz, 2H), 2.68 (t, J=7.0 Hz, 2H), 1.41 (s, 9H).

Example 61

Preparaion of 4-(3'-Phenyl)propyloxy Tyramine Hydrochloride (69)

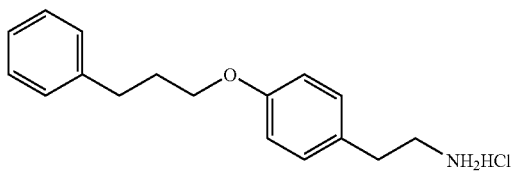

69

Refer to Method C for the general procedure. The crude reaction mixture was concentrated in vacuo and dried under high vacuum pressure to give 69 as a white solid (80 mg, 98% yield). $^1$H-NMR (400 MHz, DMSO-$d_6$) δ 8.06 (brd s, 2H), 7.33-7.15 (m, 8H), 6.88 (d, J=8.0 Hz, 2H), 3.94 (brd t, J=6.0 Hz, 2H), 2.97 (app brd t, J=8.4 Hz, 2H), 2.81 (app brd t, J=8.4 Hz, 2H), 2.73 (app brd t, J=6.0 Hz, 2H), 2.02-1.99 (m, 2H).

Example 62

Preparation of 4-(3'-Phenyl)butyloxy Tyramine Hydrochloride (70)

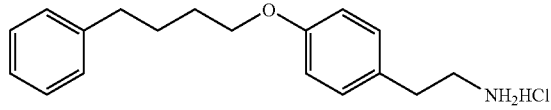

70

Refer to Method C for the general procedure. The crude reaction mixture was concentrated in vacuo and dried under high vacuum pressure to give 70 as a white solid (95 mg, 99% yield). $^1$H-NMR (400 MHz, DMSO-$d_6$) δ 8.01 (brd s, 2H), 7.28-7.14 (m, 8H), 6.87 (d, J=8.0 Hz, 2H), 3.94 (brd t, J=6.0 Hz, 2H), 2.94 (app brd t, J=8.4 Hz, 2H), 2.81 (app brd t, J=8.4 Hz, 2H), 2.62 (app brd t, J=6.0 Hz, 2H), 1.73-1.62 (m, 4H).

Example 63

Peparation of 4-Benzoylmethoxy Tyramine Hydrochloride (71)

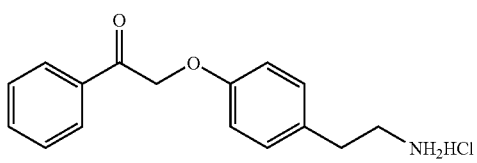

71

Refer to Method C for the general procedure. The crude reaction mixture was concentrated in vacuo and dried under high vacuum pressure to give 71 as a white solid (45 mg, 99% yield). $^1$H-NMR (400 MHz, DMSO-$d_6$) δ 8.02 (app brd d, J=7.6 Hz, 2H), 7.70 (t, J=7.6 Hz, 1H), 7.58 (t, J=7.6 Hz, 2H), 7.16 (d, J=8.8 Hz, 2H), 6.93 (d, J=8.8 Hz, 2H), 5.55 (s, 2H), 2.98 (app brd t, J=8.0 Hz, 2H), 2.81 (app brd t, J=6.0 Hz, 2H).

Example 64

Preparation of 4-(m,m-Dimethoxy)benzyloxy Tyramine Hydrochloride (72)

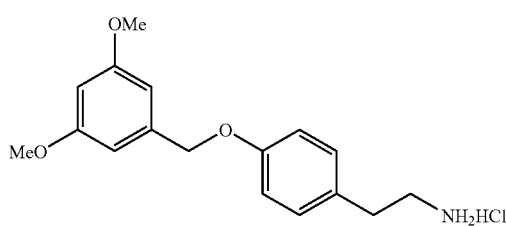

72

Refer to method C for the general procedure. The precipitate was filtered to give 72 as a white solid (136 mg, 97% yield): $^1$H-NMR (400 MHz, DMSO-$d_6$) δ 7.89 (brd s, 3H), 7.17 (d, J=8.4 Hz, 2H), 6.96 (d, J=8.8 Hz, 2H), 6.58 (d, J=1.6 Hz, 2H), 6.44 (d, J=1.6 Hz, 1H), 5.02 (s, 2H), 3.73 (s, 6H), 2.98 (app t, J=7.8 Hz, 2H), 2.79 (app t, J=7.8 Hz, 2H).

Example 65

Preparation of 4-(p-Trifluoromethyl)benzyloxy Tyramine Hydrochloride (73)

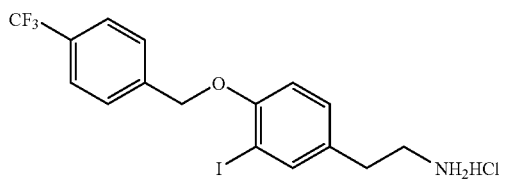

73

Refer to Method C for the general procedure. The precipitate was filtered to give 73 as a white solid (94.9 mg, 93% yield): $^1$H-NMR (400 MHz, DMSO-$d_6$) δ 7.94 (brd s, 3H), 7.75 (d, J=8.0 Hz, 2H), 7.68 (ovrlp d, J=1.6 Hz, 1H), 7.67 (ovrlp d, J=8.8 Hz, 2H), 7.21 (dd, J=8.4, 2.0 Hz, 1H), 6.99 (d, J=8.4 Hz, 1H), 5.26 (s, 2H), 2.96 (app t, J=7.8 Hz, 2H), 2.78 (app t, J=7.8 Hz, 2H).

Method F: General Procedure for Dimethylation of Amines.

The hydrochloride salt of the amine (0.22 mmol) was dissolved in water, treated with potassium carbonate (>0.22 mmol) and extracted with dichloromethane. The organic layer was dried over magnesium sulfate, filtered and concentrated under reduced pressure to give the free amine. A solution of free amine (0.22 mmol), formic acid (>1.10 mmol, 88% in water solution), and formaldehyde (>1.10 mmol, 37% in water solution) was stirred at 80° C. for ~20 hrs. After cooling to room temperature, the reaction was diluted with water, adjusted to pH ~10 with potassium carbonate, and extracted with dichloromethane. The organic layer was washed with brine, dried over magnesium sulfate, and concentrated under reduced pressure to give the crude product. The crude mixture was treated with 3 N anhydrous HCl/ethyl acetate (1 mL), exposed to diethyl ether, and filtered to give the hydrochloride salts. If the hydrochloride salts did not precipitate the diethyl ether/ethyl acetate solution was concentrated under reduced pressure and rinse with diethyl ether to give the hydrochloride salts.

Example 66

Preparation of N,N-Dimethyl-4-benzyloxy Tyramine Hydrochloride (74)

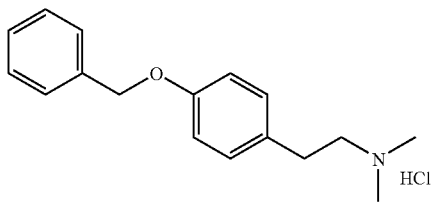

74

Refer to Method F for the general procedure. The precipitate was filtered to give 74 as a white solid (84.6 mg, 60% yield): $^1$H-NMR (400 MHz, DMSO-$d_6$) δ 10.46 (brd s, 1H), 7.42-7.26 (m, 5H), 7.15 (app d, J=8.4 Hz, 2H), 6.94 (app d, J=8.8 Hz, 2H), 3.21-3.13 (m, 2H), 2.93-2.86 (m, 2H), 2.73 (d, J=4.0 Hz, 6H).

Example 67

Preparation of N-t-Boc-N-methyl-4-(p-trifluoromethyl)benzyloxy Tyramine (75)

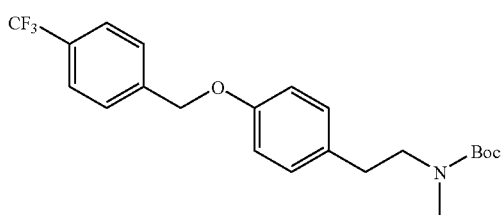

75

Refer to Method E for the general procedure. The crude N-methylated product was purified via flsh $SiO_2$ (loaded and eluted with hexanes/ethyl acetate (10:1)) to give 75 (330 mg, 79% yield): $^1$H-NMR (400 MHz, chloroform-d) δ 7.63 (d, J=8.4 Hz, 2H), 7.54 (d, J=8.0 Hz, 2H), 7.10 (brd s, 2H), 6.88 (d, J=8.0 Hz, 2H), 5.10 (s, 2H), 3.38 (brd s, 2H), 2.81 (brd s, 3H), 2.74 (brd s, 2H), 1.40 (brd s, 9H).

Example 68

Preparation of N-Methyl-4-(p-trifluoromethyl)benzyloxy Tyramine Hydrochloride (76)

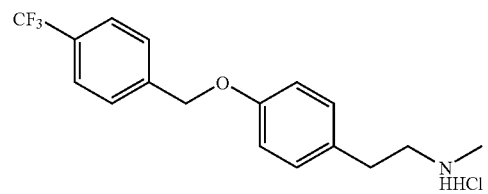

76

Refer to Method C for the general procedure. The precipitate was filtered to give 76 as a white solid (93.4 mg, 88% yield): $^1$H-NMR (400 MHz, chloroform-d) δ 8.77 (brd s, 2H), 7.76 (d, J=8.4 Hz, 2H), 7.66 (d, J=7.6 Hz, 2H), 7.19 (d, J=8.8 Hz, 2H), 6.99 (d, J=8.8 Hz, 2H), 5.22 (s, 2H), 3.08 (brd s, 2H), 2.86 (app brd t, J=8.0, 2H), 2.55 (ovrlp brd s, 3H).

Example 69

Preparation of 4-t-Butyldimethylsilyloxy Benzyl Cyanide (78)

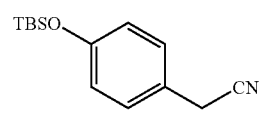

78

To a stirred solution of 4-hydroxybenzyl cyanide 77 (2.0 g, 15.0 mmol) in DMF (10 ml) was added t-butyldimethylsilyl chloride (2.5 g, 16.5 mmol). The reaction mixture was cooled to 0° C. and imidazole (2.3 g, 33.0 mmol) was added and then the mixture was allowed to warm to ambient temperature. After stirring for 3 hours, the reaction mixture was diluted with ether and washed with 0.5 M HCl, sat. aq. $NaHCO_3$, water, and brine, then dried over $MgSO_4$. The crude product was purified via flash $SiO_2$ (eluted with hexane/ethyl acetate (8:1)) to give 78 as a clear oil (3.6 g, 98% yield). $^1$H-NMR (400 MHz, chloroform-d) δ 7.87 (d, J=8.5 Hz, 2H), 6.86 (d, J=8.5 Hz, 2H), 3.54 (s, 2H), 0.98 (s, 9H), 0.23 (s, 6H).

Example 70

Preparation of 2-(p-t-Butyldimethylsilyloxy)phenyl-2-cyano-propane (79)

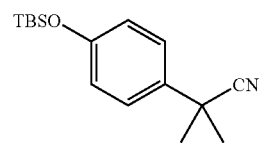

79

To a solution of 78 (1.2 g, 5.0 mmol) in THF (10 ml) at −78° C. was added LDA (2.75 ml, 2.0 M in heptane, THF, and ethylbenzene, 5.5 mmol) dropwise. Iodomethane (0.37 ml, 6.0 mmol) was added to the reaction dropwise and the mixture was stirred at −78° C. for 30 minutes then allowed to warm to ambient temperature over 4 hours. The resulting solution was cooled to −78° C. again and LDA (2.75 ml, 2.0 M in heptane, THF, and ethylbenzene, 5.5 mmol) was added dropwise. Iodomethane (0.37 ml, 6.0 mmol) was added to the reaction dropwise and the mixture was stirred at −78° C. for 30 minutes then allowed to warm to ambient temperature over 16 hours. The reaction mixture was diluted with ether and washed with 0.5 M HCl. The aqueous was extracted with ether and then combined organic layers were sequentially washed with water, and brine, then dried over MgSO$_4$. The crude product was purified via flash SiO$_2$ (eluted with hexane/ethyl acetate (20:1)) to give 79 as a slightly yellow oil (1.3 g, 91% yield). $^1$H-NMR (400 MHz, chloroform-d) δ 7.31 (d, J=8.3 Hz, 2H), 6.83 (d, J=8.3 Hz, 2H), 1.69 (s, 6H), 0.98 (s, 9H), 0.20 (s, 6H).

Example 71

Preparation of N-t-Boc-4-t-Butyldimethylsilyloxy-β,β-dimethyl Tyramine (80)

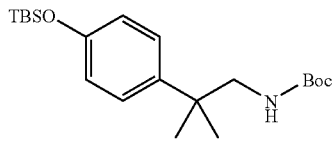

To a solution of 79 (1.0 g, 3.6 mmol) in THF (15 ml) at 0° C. was added lithium aluminum hydride (207 mg, 5.5 mmol) and the mixture was stirred at 0° C. for 15 minutes then refluxed 2 hours. The resulting solution was cooled to 0° C. and quenched with 2 M NaOH and stirred for 15 minutes at 0° C. The crude mixture was filtered through celite and the filtrate was washed with brine, dried over MgSO$_4$, and concentrate to dryness. The crude mixture was dissolved in THF (10 ml). The resulting mixture was added a solution of NaHCO$_3$ (337 mg, 4.0 mmol) in water (5 ml) and di-t-butyldicarbonate (865 mg, 4.0 mmol) and stirred for 15 hours. The reaction mixture was diluted with ether and washed with 0.5 M HCl. The aqueous was extracted with ether and then combined organic layers were sequentially washed with water, and brine, then dried over MgSO$_4$. The crude product was purified via flash SiO$_2$ (eluted with hexane/ethyl acetate (30: 1)) to give 80 as a slightly yellow solid (627 mg, 46% yield). $^1$H-NMR (400 MHz, chloroform-d) δ 7.33 (d, J=8.4 Hz, 2H), 6.85 (d, J=8.4 Hz, 2H), 3.28 (s, 2H), 1.69 (s, 6H), 1.41 (s, 9H), 0.98 (s, 9H), 0.20 (s, 6H).

Example 72

Preparation of N-t-Boc-β,β-dimethyl Tyramine (81)

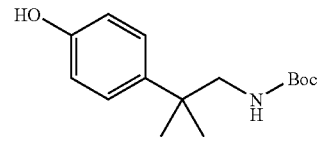

Refer to Method B for the general procedure. The crude product was purified via flash SiO$_2$ (eluted with hexane/ethyl acetate (10:1)) to give 81 as a white solid (110 mg, 98% yield). $^1$H-NMR (400 MHz, chloroform-d) δ 6.97 (d, J=8.4 Hz, 2H), 6.77 (d, J=8.4 Hz, 2H), 3.25 (s, 2H), 1.71 (s, 6H), 1.44 (s, 9H).

Example 73

Preparation of N-t-Boc-4-Phenoxy-β,β-dimethyl Tyramine (82)

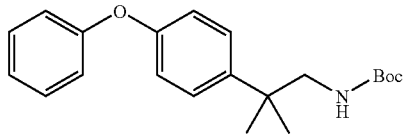

Refer to Method A for the general procedure. The crude product was purified via flash SiO$_2$ (eluted with hexane/ethyl acetate (4:1)) to give 82 as a slightly yellow solid (63 mg, 46% yield). $^1$H-NMR (400 MHz, chloroform-d) δ 7.32 (app t, J=8.2 Hz, 2H), 7.19 (d, J=8.4 Hz, 2H), 7.10 (app t, J=8.2 Hz, 1H), 6.97 (d, J=8.2 Hz, 2H), 6.89 (app d, J=8.2 Hz, 2H), 4.60 (brd s, 1H), 3.27 (s, 2H), 1.70 (s, 6H), 1.34 (s, 9H).

Example 74

Preparation of 4-Phenoxy-β,β-dimethyl Tyramine Hydrochloride (83)

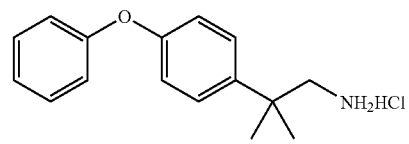

Refer to Method C for the general procedure. The crude reaction mixture was concentrated in vacuo and dried under high vacuum pressure to give 83 as a white solid (46 mg, 92% yield). $^1$H-NMR (400 MHz, DMSO-d$_6$) δ 7.72 (brd s, 3H), 7.44-7.37 (m, 4H), 7.14 (t, J=7.6 Hz, 1H), 7.02-6.99 (m, 4H), 3.32 (s, 2H), 1.35 (s, 6H).

Example 75

Preparation of N-Benzyl-4-phenoxy-β,β-dimethyl Tyramine Hydrochloride (84)

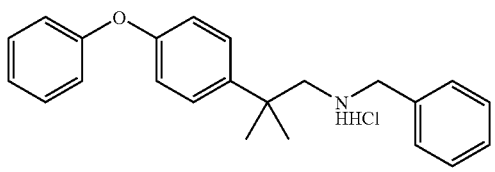

84

Sodium cyanoborohydride (10 mg, 0.17 mmol) was added to a solution of 83 (30 mg, 0.11 mmol) and benzaldehyde (12 μl, 0.12 mmol) in MeOH (2 ml). After 1 hour stirring, the reaction mixture was diluted with ether and washed with water. The aqueous was extracted with ether and then combined organic layers were washed with water, and brine, then dried over MgSO$_4$. The crude product was purified via flash SiO$_2$ (eluted with hexane/ethyl acetate (10:1)) to give the protected amine as a white solid. The protected amine was dissolved in 3 N HCl solution in ethylacetate (2 ml) and the reaction mixture was stirred at ambient temperature for 15 hours. The crude reaction mixture was concentrated in vacuo and dried under high vacuum pressure to give 84 as a white solid (25 mg, 61% yield). $^1$H-NMR (400 MHz, DMSO-d$_6$) δ 8.83 (brd s, 2H), 7.52-7.32 (m, 10H), 7.15 (d, J=7.6 Hz, 1H), 7.02-6.95 (m, 3H), 4.09 (s, 2H), 3.34 (s, 2H), 1.35 (s, 6H).

Method G: General Procedure for Protection of Amines with Boc$_2$O

To a stirred solution of the amine hydrochloride or hydrobromide (4.57 mmol) in tetrahydrofuran (33 mL) was added an aqueous solution of sodium bicarbonate (9.14 mmol in 10 mL of water) followed by dropwise addition of a solution of di-tert-butyl dicarbonate (4.57 mmol) in tetrahydrofuran (5 mL). After stirring at room temperature overnight, the reaction was quenched with water and extracted with diethyl ether. The organic layer was washed with brine, dried over magnesium sulfate, filtered, and concentrated under reduced pressure to give the crude product. The product was purified as described below.

Example 76

Preparation of N-t-Boc-3-bromo-propylamine (86)

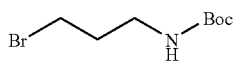

86

Refer to Method G for the general procedure. The crude product was purified via flash SiO$_2$ chromatography (ethyl acetate/hexanes (10%/90%) to (15%/85%)) to give 86 as a white solid (0.85 g, 78% yield). $^1$H-NMR (400 MHz, chloroform-d) δ 4.65 (s, 1H), 3.44 (t, J=6.6 Hz, 2H), 3.28 (q, J=6.4 Hz, 2H), 2.05 (m, 2H), 1.46 (s, 9H).

Method H: General Procedure for the Alkylation of Phenols.

To a suspension of sodium hydride (5.36 mmol) in DMF (30 mL) was added a solution of phenol (3.58 mmol) in DMF (5 mL). The reaction was stirred under argon at 0° C. for 15 minutes before adding a solution of alkyl halide (3.58 mmol) in DMF (5 mL). After stirring under argon at room temperature for 2 hrs, the reaction was quenched with water and extracted with diethyl ether. The organic layer was washed with brine, dried over magnesium sulfate, filtered, and concentrated under reduced pressure to give the crude product. The product was purified as described below.

Example 77

Preparation of N-tBoc-3-(4-phenoxyphenoxy)propylamine (89)

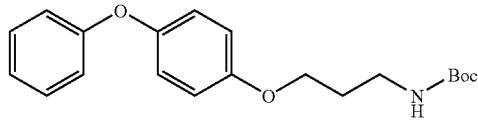

89

Refer to Method H for the general procedure. The crude product was purified via flash SiO$_2$ chromatography (ethyl acetate/hexanes (5%/95%) to (15%/85%)) to give 89 (1.02 g, 83% yield): $^1$H-NMR (400 MHz, chloroform-d) δ 7.29 (app t, J=8.0 Hz, 2H), 7.04 (t, J=7.6 Hz, 1H), 6.95 (m, 4H), 6.87 (app d, J=9.2 Hz, 2H), 4.76 (brd s, 1H), 4.01 (t, J=6.4 Hz, 2H), 3.34 (brd q, J=6.0 Hz, 2H), 1.98 (t, J=6.2 Hz, 2H), 1.45 (s, 9H)

Example 78

Preparation of N-tBoc-3-(3-phenoxyphenoxy)propylamine (90)

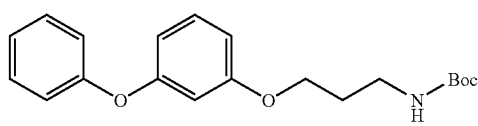

90

Refer to Method H for the general procedure. The crude product was purified via flash SiO$_2$ chromatography (ethyl acetate/hexanes (5%/95%) to (15%/85%)) to give 90 (2.55 g, 91% yield): $^1$H-NMR (400 MHz, chloroform-d) δ 7.34 (t, J=7.8 Hz, 2H), 7.21 (t, J=8.2 Hz, 1H), 7.11 (t, J=6.8 Hz, 1H), 7.02 (d, J=8.4 Hz, 2H), 6.62 (d, J=8.0 Hz, 1H), 6.58 (d, J=8.0 Hz, 1H), 6.55 (s, 1H), 4.73 (brd s, 1H), 3.98 (t, J=6.0 Hz, 2H), 3.30 (brd q, J=6.8 Hz, 2H), 1.95 (t, J=6.2 Hz, 2H), 1.43 (s, 9H).

Example 79

Preparation of 3-(4-phenoxyphenol)-propylamine Hydrochloride (91)

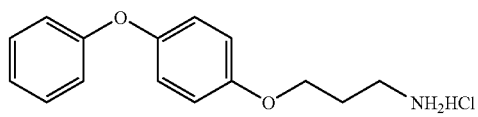

91

Refer to Method C for the general procedure. The precipitate was filtered to give 91 as a white solid (0.12 g, 53% yield): ¹H-NMR (400 MHz, methanol-$d_4$) δ 7.29 (t, J=8.0 Hz, 2H), 7.04 (t, J=7.4 Hz, 1H), 6.96 (s, 4H), 6.89 (d, J=7.6 Hz, 2H), 4.11 (t, J=5.8 Hz, 2H), 3.16 (t, J=7.2 Hz, 2H), 2.14 (m, 2H).

Example 80

Preparation of 3-(3-phenoxyphenol)-propylamine Hydrochloride (92)

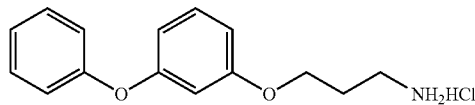

Refer to Method C for the general procedure. The precipitate was filtered to give 92 as a white solid (0.76 g, 75% yield): ¹H-NMR (400 MHz, methanol-$d_4$) δ 7.35 (t, J=8.2 Hz, 2H), 7.24 (t, J=8.4 Hz, 1H), 7.12 (t, J=7.4 Hz, 1H), 6.98 (d, J=7.6 Hz, 2H), 6.70 (app d, J=7.6 Hz, 1H), 6.57 (app s, 1H), 6.56 (app s, 1H), 4.08 (t, J=5.8 Hz, 2H), 3.13 (t, J=7.2 Hz, 2H), 2.12 (m, 2H).

Example 81

Preparation of N-t-Boc-N-Methyl-3-(4-phenoxyphenol)-propylamine (93)

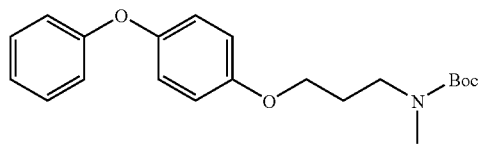

Refer to Method E for the general procedure. The crude product was purified via flash $SiO_2$ chromatography (ethyl acetate/hexanes (5%/95%) to (15%/85%)) to give 93 (0.21 g, 62% yield): ¹H-NMR (400 MHz, chloroform-d) δ 7.29 (t, J=8.0 Hz, 2H), 7.04 (t, J=6.8 Hz, 1H), 6.96 (d, J=9.2 Hz, 2H), 6.93 (d, J=8.4 Hz, 2H), 6.86 (d, J=8.8 Hz, 2H), 3.96 (t, J=6.2 Hz, 2H), 3.41 (t, J=7.0 Hz, 2H), 2.88 (s, 3H), 2.00 (brd t, J=3.0 Hz, 2H), 1.44 (s, 9H).

Example 82

Preparation of N-methyl-3-(4-phenoxyphenol)-propylamine Hydrochloride (94)

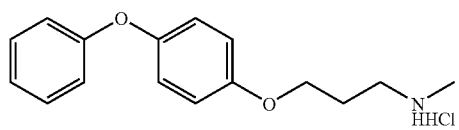

Refer to Method C for general procedure. The precipitate was filtered to gove 94 as a white solid (0.94 g, 90% yield): ¹H-NMR (400 MHz, methanol-$d_4$) δ 7.29 (t, J=8.0 Hz, 2H), 7.04 (t, J=7.4 Hz, 1H), 6.96 (s, 4H), 6.90 (app t, J=7.4 Hz, 2H), 4.11 (t, J=5.8 Hz, 2H), 3.23 (t, J=7.2 Hz, 2H), 2.74 (s, 3H), 2.17 (m, 2H).

Example 83

Preparation of N,N-dimethyl-3-(4-phenoxyphenol)-propylamine Hydrochloride (95)

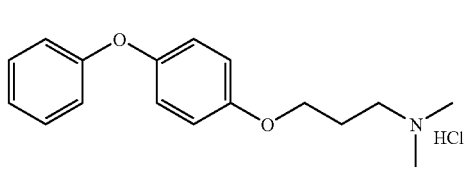

Refer to Method F for general procedure. The precipitate was filtered to give 95 as a white solid (0.17 g, 76% yield): ¹H-NMR (400 MHz, methanol-$d_4$) δ 7.30 (t, J=8.0 Hz, 2H), 7.04 (t, J=7.4 Hz, 1H), 6.96 (s, 4H), 6.89 (d, J=8.0 Hz, 2H), 4.10 (d, J=5.8 Hz, 2H), 3.32 (m, 2H), 2.92 (s, 6H), 2.21 (m, 2H).

Method I: General Procedure for the Regioselective Evan's Coupling

To a solution of phenol (1.19 mmol), phenyl boronic acid (1.78 mmol), copper (II) acetate (1.19 mmol) and dried 4 A molecular sieves (1 g) in DCM (12 mL) was added pyridine (0.48 mL) and diisopropylethylamine (77 mL). The mixture was stirred under an anhydrous air atmosphere at room temperature until the dark green solution turned black (~2 days), the reaction was filtered through celite and silica gel, rinsed with ethyl acetate, washed with water and acidified to pH ~4-5. The organic layer was washed with brine, dried over magnesium sulfate, filtered, and concentrated under reduced pressure to give the crude product. The product was purified as described below.

Example 84

Preparation of Methyl-2-hydroxy-4-phenoxybenzoate (97)

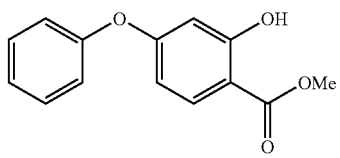

Refer to Method I for the general procedure. The crude product was purified via flash $SiO_2$ chromatography (loaded with DCM, eluted with ethyl acetate/hexanes (0%/100%) to (2%/98%)) to give 97 as a colorless oil (0.29 g, 59% yield):. ¹H-NMR (400 MHz, chloroform-d) δ10.91 (s, 1H), 7.78 (d, J=8.7 Hz, 1H), 7.39 (t, J=7.8 Hz, 2H), 7.21 (t, J=7 Hz, 1H), 7.08 (d, J=8.3 Hz, 2H), 6.51 (dd, J=8.8, 2.4 Hz, 1H), 6.45 (d, J=2.4 Hz, 1H), 3.93 (s, 3H).

Example 85

Preparation of Methyl-2-methoxy-4-phenoxybenzoate (98)

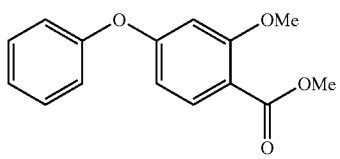

Refer to Method G for the general procedure. The crude product was purified via flash SiO$_2$ chromatography (ethyl acetate/hexanes (5%/95%) to (10%/90%)) to give 98 (0.19 g, 93% yield): $^1$H-NMR (400 MHz, chloroform-d) δ 7.81 (d, J=8.8 Hz, 1H), 7.39 (t, J=8.0 Hz, 2H), 7.19 (t, J=7.3 Hz, 1H), 7.07 (d, J=7.8 Hz, 2H), 6.62 (d, J=2.4 Hz, 1H), 6.49 (dd, J=8.8, 2.4 Hz, 1H), 3.87 (s, 1H), 3.85 (s, 1H).

Example 86

Preparation of 2-methoxy-4-phenoxybenzoic Acid (100)

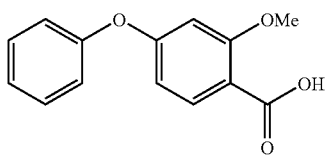

To a solution of methyl-2-methoxy4-phenoxybenzoate 98 (0.18 g, 0.691 mmol) in methanol (1.38 mL) was added a 2 N aqueous sodium hydroxide solution (1.72 mL, 3.45 mmol). The reaction was refluxed for 3 hrs. After cooling to room temperature, the methanol was evaporated and the reaction was acidified to pH ~3 with 3 N HCl. The reaction was extracted with ethyl acetate and washed with brine. The organic layer was dried over magnesium sulfate, filtered, and concentrated under reduced pressure. The crude product was purified via flash SiO$_2$ chromatography (ethyl acetate/hexanes (50%/50%)) to give 109b (0.169 g, 93% yield): $^1$H-NM (400 MHz, chloroform-d) δ 8.12 (d, J=8.8 Hz, 1H), 7.43 (t, J=8.0 Hz, 2H), 7.24 (m, J=8.0, 8.0 Hz, 1H), 7.09 (d, J=7.3 Hz, 2H), 6.67 (d, J=2.4 Hz, 1H), 6.6 (dd, J=8.8, 2.4 Hz, 1H), 4.01 (s, 3H).

Method J: General Procedure for the Formation of Acid Chlorides

To a solution of thionyl chloride (0.97 mmol) and carboxylic acid (0.64 mmol) in DCM (3 mL) was added a drop of DMF. After refluxing for 2 hrs, the reaction was concentrated under reduced pressure to give the crude acid chloride.

Method K: General Procedure for the Formation of Amides via Acid Chlorides

To a solution of amine hydrochloride (0.71 mmol) in pyridine (2 mL) was added a solution of acid chloride (0.64 mmol) in DCM (3 mL). After stirring under argon at room temperature for 2 hrs, the reaction was quenched with water and extracted with diethyl ether. The organic layer was washed with brine, dried over magnesium sulfate, filtered and concentrated under reduced pressure to give the crude product. The product was purified as described below.

Method L: General Procedure for the Formation of Amides via Standard Coupling Conditions

To a solution of the requisite carboxylic acid (1.95 mmol) and HBTU (2.14 mmol) in DCM (20 mL) was added dimethylaminopyridine (0.001 mmol). The solution was stirred under argon at 0° C. for 30 minutes before adding the amine hydrochloride (2.14 mmol) and diisopropylethylamine (0.68 mL). The reaction was slowly warmed to room temperature and stirred under argon for 2 hrs. The reaction was diluted with ethyl acetate (40 mL), washed with 5% aqueous HCl (2×35 mL), saturated aqueous sodium bicarbonate (35 mL), and brine (35 mL). The organic layer was dried over magnesium sulfate, filtered, and concentrated under reduced pressure to give the crude product. The product was purified as described below.

Example 87

Preparation of N-t-Boc-2-(4-Phenoxybenzamido)-ethylamine (101)

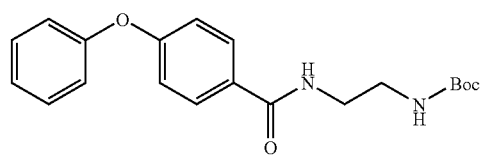

Refer to Method J and K for the general procedures. The crude product was purified via flash SiO$_2$ chromatography (ethyl acetate/hexanes (10%/90%) to (50%/50%)) to give 101 (0.30 g, 90% yield): $^1$H-NMR (400 MHz, chloroform-d) δ 7.75 (d, J=8.8 Hz, 2H), 7.34 (t, J=8.0 Hz, 2H), 7.12 (t, J=7.4, 1H), 6.98 (d, J=7.6 Hz, 2H), 6.92 (d, J=8.8 Hz, 2H), 3.37 (t, J=6.0, 2H), 3.20 (t, J=6.0 Hz, 2H), 1.35 (s, 3H).

Example 88

Preparation of N-t-Boc-3-(4-phenoxybenzamido)-propylamine (102)

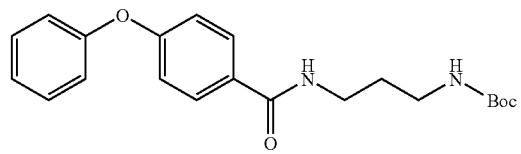

Refer to Method L for the general procedures. The crude product was purified via flash SiO$_2$ chromatography (ethyl acetate/hexanes (10%/90%) to (50%/50%)) to give 102 (0.61 g, 64% yield): $^1$H-NMR (400 MHz, chloroform-d) δ 7.83 (d, J=8.0 Hz, 2H), 7.37 (t, J=7.8 Hz, 2H), 7.17 (t, J=6.8, 1H), 7.05 (d, J=8.0 Hz, 2H), 7.01 (d, J=8.8 Hz, 2H), 4.87 (brd s, 1H), 3.50 (q, J=6.1 Hz, 2H), 3.25 (q, J=5.2 Hz, 2H), 1.72 (m, 2H), 1.55 (s, 9H).

Example 89

Preparation of
N-t-Boc-4-(4-phenoxybenzamido)-butylamine (103)

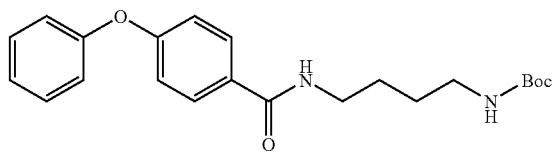

Refer to Method J and K for the general procedures. The crude product was purified via flash SiO$_2$ chromatography (ethyl acetate/hexanes (20%/90%) to (50%/50%)) to give 103 (0.35 g, 71% yield): $^1$H-NMR (400 MHz, chloroform-d) δ 7.77 (d, J=8.4 Hz, 2H), 7.37 (t, J=8.0 Hz, 2H), 7.17 (t, J=7.4, 1H), 7.04 (d, J=7.6 Hz, 2H), 7.00 (d, J=8.8 Hz, 2H), 6.42 (brd s, 1H), 4.63 (brd s, 1H), 3.48 (q, J=6.2 Hz, 2H), 3.17 (app q, J=6.4 Hz, 2H), 1.64 (m, 4H), 1.44 (s, 9H).

Example 90

Preparation of
N-t-Boc-5-(4-phenoxybenzamido)-pentylamine (104)

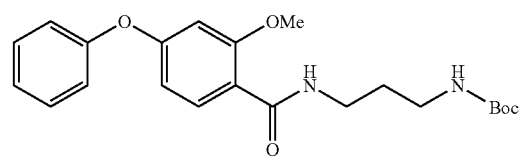

Refer to Method L for the general procedures. The crude product was purified via flash SiO$_2$ chromatography (ethyl acetate/hexanes (25%/90%) to (50%/50%)) to give 104 (0.78 g, 77% yield): $^1$H-NMR (400 MHz, chloroform-d) δ 7.74 (d, J=8.8 Hz, 2H), 7.37 (t, J=8.0 Hz, 2H), 7.17 (t, J=7.6, 1H), 7.04 (d, J=8.0 Hz, 2H), 7.00 (d, J=8.8 Hz, 2H), 6.14 (brd s, 1H), 4.57 (brd s, 1H), 3.45 (q, J=6.5 Hz, 2H), 3.13 (app q, J=6.4 Hz, 2H), 1.63 (m, 2H), 1.52 (m, 4H), 1.44 (s, 9H).

Example 91

Preparation of N-t-Boc-2-(2-methoxy-4-phenoxy-benzamido)-ethylamine (105)

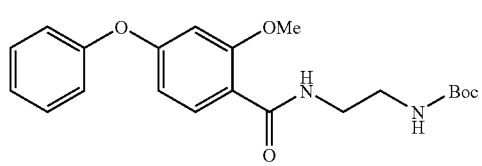

Refer to Method J and K for the general procedures. The crude product was purified via flash SiO$_2$ chromatography (ethyl acetate/hexanes (25%/90%) to (50%/50%)) to give 105 (0.25 g, 82% yield): $^1$H-NMR (400 MHz, chloroform-d) δ 8.15 (d, J=8.3 Hz, 1H), 8.03 (brd s, 1H), 7.39 (t, J=7.3 Hz, 2H), 7.18 (t, J=7.3 Hz, 1H), 7.06 (d, J=7.8 Hz, 2H), 6.63 (d, J=1.9 Hz, 1H), 6.59 (dd, J=8.6, 2.2 Hz, 1H), 4.98 (brd s, 1H), 3.92 (s, 3H), 3.57 (q, J=5.9 Hz, 2H), 3.37 (brd q, J=5.9 Hz, 2H), 1.43 (s, 9H).

Example 92

Preparation of N-t-Boc-3-(2-methoxy-4-phenoxy-benzamido)-propylamine (106)

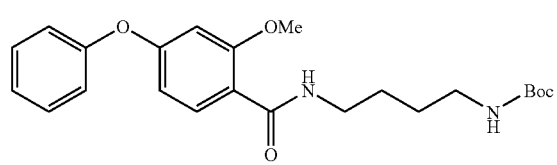

Refer to Method J and K for the general procedures. The crude product was purified via flash SiO$_2$ chromatography (ethyl acetate/hexanes (25%/90%) to (50%/50%)) to give 106 (0.33 g, 86% yield): $^1$H-NMR (400 MHz, chloroform-d) δ 8.15 (d, J=8.3 Hz, 1H), 8.07 (s, 1H), 7.38 (t, J=8.1 Hz, 2H), 7.18 (t, J=7.3 Hz, 1H), 7.06 (d, J=7.3 Hz, 2H), 6.64 (d, J=1.9 Hz, 1H), 6.59 (dd, J=8.6, 2.2 Hz, 1H), 5.04 (s, 1H), 3.93 (s, 3H), 3.51 (q, J=6.2 Hz, 2H), 3.21 (q, J=5.5 Hz, 2H), 1.73 (m, J=12.6, 6.2, 6.1 Hz, 2H), 1.45 (s, 9H).

Example 93

Preparation of N-t-Boc-4-(2-methoxy-4-phenoxy-benzamido)-butylamine (107)

Refer to Method J and K for the general procedures. The crude product was purified via flash SiO$_2$ chromatography (ethyl acetate/hexanes (25%/90%) to (50%/50%)) to give 107 (0.34 g, 83% yield): $^1$H-NMR (400 MHz, chloroform-d) δ 8.15 (d, J=8.8 Hz, 1H), 7.77 (s, 1H), 7.38 (t, J=8.0 Hz, 2H), 7.18 (t, J=7.6 Hz, 1H), 7.06 (d, J=7.3 Hz, 3H), 6.63 (d, J=2.4 Hz, 2H), 6.60 (dd, J=8.8, 2.4 Hz, 2H), 4.59 (s, 1H), 3.91 (s, 8H), 3.47 (q, J=6.5 Hz, 2H), 3.17 (q, J=5.9 Hz, 2H), 1.63 (m, 4H), 1.44 (s, 9H).

Example 94

Preparation of N-t-Boc-5-(2-methoxy-4-phenoxy-benzamido)-pentylamine (108)

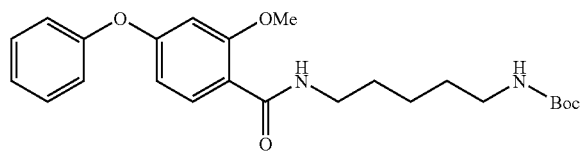
108

Refer to Method J and K for general procedures. The crude product was purified via flash SiO$_2$ chromatography (ethyl acetate/hexanes (25%/90%) to (50%/50%)) to give 108 (0.35 g, 93% yield): $^1$H-NMR (400 MHz, chloroform-d) δ 8.16 (d, J=8.8 Hz, 1H), 7.75 (brd s, 1H), 7.38 (t, J=8.1 Hz, 2H), 7.18 (t, J=7.3 Hz, 1H), 7.06 (d, J=7.8 Hz, 2H), 6.63 (d, J=2.0 Hz, 1H), 6.60 (dd, J=8.6, 2.2 Hz, 1H), 4.58 (brd s, 1H), 3.91 (s, 3H), 3.46 (dd, J=6.8, 5.9 Hz, 2H), 3.13 (q, J=6.2 Hz, 2H), 1.59 (m, 4H), 1.44 (s, 9H), 1.41 (m, 2H).

Example 95

Preparation of 2-(4-phenoxybenzamido)-ethylamine Hydrochloride (109)

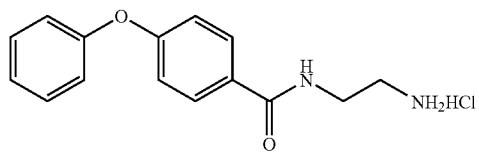
109

Refer to Method C for the general procedures. The precipitate was filtered to give 109 as a white solid (0.25 g, ~100% yield): $^1$H-NMR (400 MHz, methanol-d$_4$) δ 7.88 (d, J=8.8 Hz, 2H), 7.41 (t, J=7.8 Hz, 2H), 7.20 (t, J=7.4 Hz, 1H), 7.05 (d, J=8.0 Hz, 2H), 7.01 (d, J=8.8 Hz, 2H), 3.66 (t, J=5.8 Hz, 2H), 3.17 (t, J=6.0 Hz, 2H); $^{13}$C-NMR (400MHz, methanol-d$_4$) δ 170.5, 162.5, 157.2, 131.2, 130.6, 129.1, 125.6, 121.0, 118.4, 41.4, 38.8.

Example 96

Preparation of 3-(4-phenoxybenzamido)-Propylamine Hydrochloride (110)

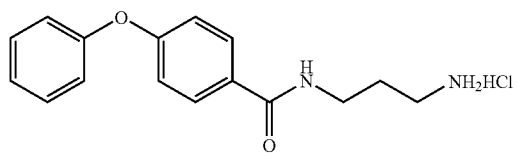
110

Refer to Method C for general the procedures. The precipitate was filtered to give 110 as a white solid (0.23 g, 96% yield): $^1$H-NMR (400 MHz, methanol-d$_4$) δ 7.84 (d, J=8.8 Hz, 2H), 7.41 (t, J=8.1 Hz, 2H), 7.20 (t, J=7.3 Hz, 1H), 7.06 (d, J=7.8 Hz, 2H), 7.01 (d, J=8.8 Hz, 2H), 3.49 (t, J=6.6 Hz, 2H), 2.98 (t, J=7.3 Hz, 2H), 1.94 (quintet, J=7.0 Hz, 2H).

Example 97

Preparation of 4-(4-phenoxybenzamido)-butylamine Hydrochloride (111)

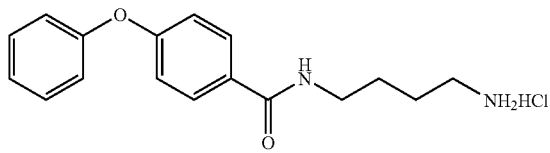
111

Refer to Method C for the general procedures. The precipitate was filtered to give 111 as a white solid (0.21 g, 97% yield): $^1$H-NMR (400 MHz, methanol-d$_4$) δ 7.82 (d, J=9.3 Hz, 2H), 7.41 (t, J=8.1 Hz, 2H), 7.20 (t, J=7.3 Hz, 1H), 7.05 (d, J=8.8 Hz, 2H), 7.00 (d, J=8.8 Hz, 2H), 3.42 (t, J=6.6 Hz, 2H), 2.98 (t, J=7.1 Hz, 2H), 1.71 (m, 4H).

Example 98

-Preparation of 5-(4-phenoxybenzamido)-pentylamine Hydrochloride (112)

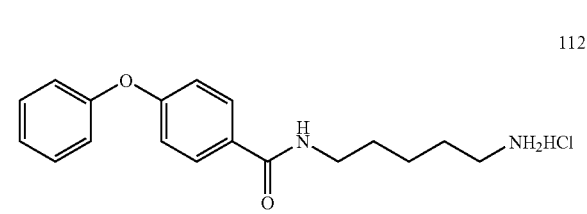
112

Refer to Method C for the general procedures. The precipitate was filtered to give 112 as a white solid (0.13 g, 98% yield): $^1$H-NMR (400 MHz, methanol-d$_4$) δ 7.81 (d, J=8.8 Hz, 2H), 7.41 (t, J=8.1 Hz, 2H), 7.20 (t, J=7.6 Hz, 1H), 7.05 (d, J=8.8 Hz, 2H), 7.00 (d, J=9.3 Hz, 2H), 3.39 (t, J=6.8 Hz, 2H), 2.93 (t, J=7.8 Hz, 2H), 1.69 (m, 4H), 1.46 (m, 2H).

Example 99

Preparation of 2-(2-methoxy-4-phenoxybenzamido)-ethylamine Hydrochloride (113)

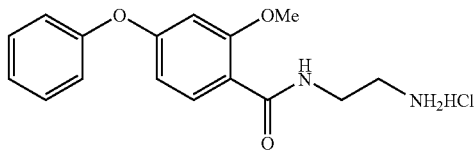
113

Refer to Method C for the general procedures. The precipitate was filtered to give 113 as a white solid (0.09 g, 98% yield): $^1$H-NMR (400 MHz, methanol-d$_4$) δ 7.97 (d, J=8.8 Hz, 1H), 7.42 (t, J=7.6 Hz, 2H), 7.22 (t, J=7.3 Hz, 1H), 7.08 (d, J=8.8 Hz, 2H), 6.76 (d, J=2.4 Hz, 1H), 6.56 (dd, J=8.8, 2.4 Hz, 1H), 3.93 (s, 3H), 3.69 (t, J=5.9 Hz, 2H), 3.17 (t, J=5.9 Hz, 2H); $^{13}$C-NMR (400 MHz, methanol-d$_4$) δ 168.8, 163.9, 161.0, 156.9, 134.3, 131.2, 125.8, 121.2, 116.5, 110.4, 102.6, 56.7, 41.3, 38.7.

Example 100

Preparation of 3-(2-methoxy-4-phenoxybenzamido)-propylamine Hydrochloride (114)

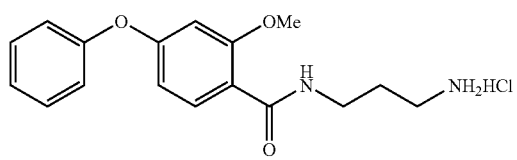

114

Refer to Method C for the general procedures. The precipitate was filtered to give 114 as a white solid (0.24 g, 98% yield): $^1$H-NMR (400 MHz, methanol-d$_4$) δ 7.90 (d, J=8.8 Hz, 1H), 7.41 (t, J=8.1 Hz, 2H), 7.20 (t, J=7.3 Hz, 1H), 7.07 (d, J=7.3 Hz, 2H), 6.75 (d, J=2.4 Hz, 1H), 6.55 (dd, J=8.6, 2.2 Hz, 1H), 3.91 (s, 3H), 3.52 (t, J=6.6 Hz, 2H), 2.98 (t, J=7.1 Hz, 2H), 1.95 (m, 2H); 13C-NMR (400 MHz, methanol-d$_4$) δ 167.4, 162.4, 159.6, 155.8, 132.7, 130.0, 124.5, 119.9, 115.8, 109.3, 101.5, 55.5, 37.0, 35.9, 27.8.

Example 101

Preparation of 4-(2-methoxy-4-phenoxybenzamido)-butylaniine Hydrochloride (115)

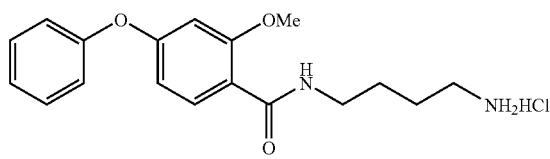

115

Refer to Method C for the general procedures. The precipitate was filtered to give 115 as a white solid (0.24 g, 98% yield): $^1$H-NMR (400 MHz, methanol-d$_4$) δ 7.89 (d, J=8.8 Hz, 1H), 7.41 (t, J=8.6 Hz, 2H), 7.20 (t, J=7.6 Hz, 1H), 7.07 (d, J=8.8 Hz, 2H), 6.75 (d, J=2.0 Hz, 1H), 6.55 (dd, J=8.8, 2.4 Hz, 1H), 3.91 (s, 3H), 3.45 (t, J=6.6 Hz, 2H), 2.99 (t, J=6.8 Hz, 2H), 1.72 (m, 4H); $^{13}$C-NMR (400 MHz, methanol-d$_4$) δ 167.8, 163.4, 160.7, 133.81, 131.2, 125.7, 121.0, 117.5, 110.5, 102.7, 56.7, 40.4, 39.8, 27.6, 25.9.

Example 102

Preparation of 5-(2-methoxy-4-phenoxybenzamido)-pentylamine Hydrochloride (116)

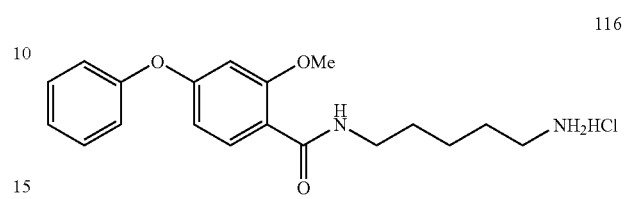

116

Refer to Method C for the general procedures. The precipitate was filtered to give 116 as a white solid (0.28 g, 58% yield): $^1$H-NMR (400 MHz, methanol-d$_4$) δ 7.88 (d, J=8.8 Hz, 1H), 7.41 (t, J=8.1 Hz, 2H), 7.20 (t, J=7.3 Hz, 1H), 7.07 (d, J=8.8 Hz, 2H), 6.75 (d, J=2.0 Hz, 1H), 6.55 (dd, J=8.6, 2.2 Hz, 1H), 3.90 (s, 3H), 3.42 (t, J=7.1 Hz, 2H), 2.94 (t, J=7.6 Hz, 2H), 1.69 (m, 4H), 1.47 (m, 2H); $^{13}$C-NMR (400 MHz, methanol-d$_4$) δ 163.3, 160.7, 157.1, 133.8, 131.2, 125.6, 121.0, 120.4, 117.6, 110.5, 102.8, 56.7, 40.65, 40.26, 30.1, 28.2, 24.76.

Example 103

Preparation of N,N-dimethyl 2-(4-phenoxybenzamido)-ethylamine Hydrochloride (117)

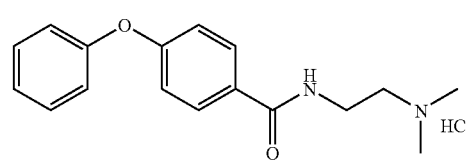

117

Refer to Method F for the general procedures. The precipitate was filtered to give 117 as a white solid (0.09 g, 98% yield): $^1$H-NMR (400 MHz, methanol-d$_4$) δ 7.87 (d, J=8.8 Hz, 2H), 7.42 (t, J=7.8 Hz, 2H), 7.21 (t, J=7.6 Hz, 1H), 7.05 (d, J=8.8 Hz, 2H), 7.02 (d, J=9.2 Hz, 2H), 3.74 (t, J=5.8 Hz, 2H), 3.37 (t, J=5.8 Hz, 2H), 2.98 (s, 6H).

Example 104

Preparation of N,N-dimethyl 3-(4-phenoxybenzamido)-propylamine Hydrochloride (118)

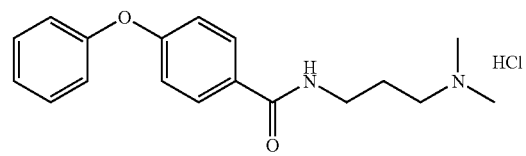

118

Refer to Method F for the general procedures. The precipitate was filtered to give 118 as a white solid (0.12 g, 76% yield): $^1$H-NMR (400 MHz, methanol-$d_4$) δ 7.86 (d, J=8.8 Hz, 2H), 7.41 (t, J=8.1 Hz, 2H), 7.20 (t, J=7.6 Hz, 1H), 7.05 (d, J=7.8 Hz, 2H), 7.01 (d, J=8.8 Hz, 2H), 3.48 (t, J=6.6 Hz, 2H), 3.19 (t, J=7.6 Hz, 2H), 2.91 (s, 6H), 2.03 (m, 2H).

Example 105

Preparation of N,N-dimethyl 4-(4-phenoxybenzamido)-butylamine Hydrochloride (119)

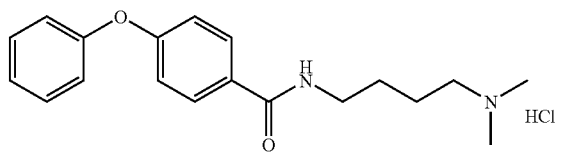

119

Refer to Method F for the general procedures. The precipitate was filtered to give 119 as a white solid (0.16 g, 11% yield): $^1$H-NMR (400 MHz, methanol-$d_4$) δ 7.82 (d, J=8.8 Hz, 2H), 7.41 (t, J=7.8 Hz, 2H), 7.20 (t, J=7.4 Hz, 1H), 7.06 (d, J=7.6 Hz, 2H), 7.00 (d, J=8.8 Hz, 2H), 3.43 (t, J=6.8 Hz, 2H), 3.19 (t, J=8.0 Hz, 2H), 2.89 (s, 6H), 1.77 (m, 2H), 1.69 (m, 2H).

Example 106

Preparation of N,N-dimethyl 5-(4-phenoxybenzamido)-pentylamine Hydrochloride (120)

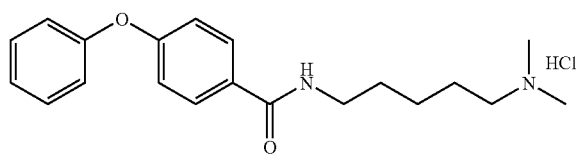

120

Refer to Method F for the general procedures. The precipitate was filtered to give 120 as a white solid (0.09 g, 31% yield): $^1$H-NMR (400 MHz, methanol-$d_4$) δ 7.82 (d, J=8.8 Hz, 2H), 7.41 (t, J=8.0 Hz, 2H), 7.20 (t, J=7.6 Hz, 1H), 7.04 (d, J=8.4 Hz, 2H), 7.00 (d, J=8.8 Hz, 2H), 3.40 (t, J=6.0 Hz, 2H), 3.13 (t, J=7.8 Hz, 2H), 2.88 (s, 6H), 1.78 (m, 2H), 1.69 (m, 2H), 1.46 (m, 2H).

Example 107

Preparation of N,N-dimethyl 2-(2-methoxy-4-phenoxybenzamido)-ethylamine Hydrochloride (121)

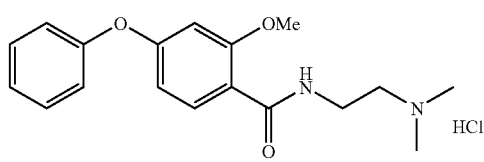

121

Refer to Method F for the general procedures. The precipitate was filtered to give 121 as a white solid (0.09 g, 41% yield): $^1$H-NMR (400 MHz, methanol-$d_4$) δ 7.98 (d, J=8.8 Hz, 1H), 7.43 (t, J=8.1 Hz, 2H), 7.22 (t, J=7.3 Hz, 1H), 7.08 (d, J=7.3 Hz, 2H), 6.76 (d, J=2.4 Hz, 1H), 6.56 (dd, J=8.8, 2.4 Hz, 1H), 3.93 (s, 3H), 3.80 (t, J=5.9 Hz, 2H), 3.38 (t, J=5.9 Hz, 2H), 2.98 (s, 6H); $^{13}$C-NMR (400 MHz, methanol-$d_4$) δ 168.8, 164.0, 161.0, 156.9, 134.3, 131.21, 125.8, 121.2, 116.3, 110.4, 102.6, 59.2, 56.7, 44.0, 36.4.

Example 108

Preparation of N,N-dimethyl 3-(2-methoxy-4-phenoxybenzamido)-propylamine Hydrochloride (122)

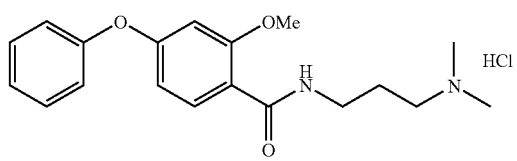

122

Refer to Method F for the general procedures. The precipitate was filtered to give 122 as a white solid (0.23 g, 75% yield): $^1$H-NMR (400 MHz, methanol-$d_4$) δ 7.92 (d, J=8.6 Hz, 1H), 7.42 (m, 2H), 7.21 (t, J=7.6 Hz, 1H), 7.07 (d, J=7.8 Hz, 2H), 6.76 (d, J=2.4 Hz, 1H), 6.56 (dd, J=8.6, 2.2 Hz, 1H), 3.92 (s, 3H), 3.52 (t, J=6.6 Hz, 2H), 3.18 (t, J=7.3 Hz, 2H), 2.91 (s, 6H), 2.04 (m, 2H); $^{13}$C-NMR (400 MHz, methanol-$d_4$) δ 168.6, 163.6, 160.8, 157.0, 134.0, 131.1, 125.7, 121.1, 116.9, 110.5, 102.6, 56.7, 43.5, 37.1, 26.3, 20.5.

Example 109

Preparation of N,N-dimethyl 4-(2-methoxy-4-phenoxybenzamido)-butylamine Hydrochloride (123)

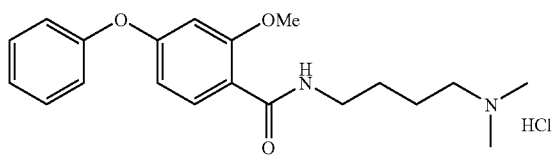

123

Refer to Method F for the general procedures. The precipitate was filtered to give 123 as a white solid (0.25 g, 59% yield): $^1$H-NMR (400 MHz, methanol-$d_4$) δ 7.88 (d, J=8.8 Hz, 1H), 7.42 (t, J=9.0 Hz, 2H), 7.21 (t, J=7.3 Hz, 1H), 7.07 (d, J=7.3 Hz, 2H), 6.75 (d, J=2.0 Hz, 1H), 6.55 (dd, J=8.8, 2.4 Hz, 1H), 3.91 (s, 3H), 3.46 (t, J=6.6 Hz, 2H), 3.19 (t, J=8.1 Hz, 2H), 2.89 (s, 6H), 1.79 (m, 2H), 1.69 (m, 2H); $^{13}$C-NMR (400 MHz, methanol-$d_4$) δ 166.8, 162.2, 159.5, 155.9, 132.5, 130.0, 124.5, 120.0, 116.3, 109.3, 101.5, 57.4, 55.4, 42.2, 38.4, 26.4, 21.8.

Example 110

Preparation of N,N-dimethyl 5-(2-methoxy-4-phenoxybenzamido)-pentylamine Hydrochloride (124)

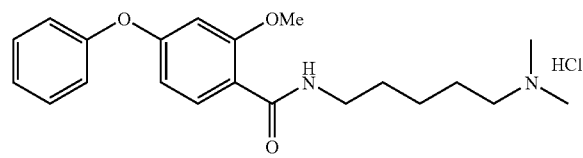

124

Refer to Method F for the general procedures. The precipitate was filtered to give 124 as a white solid (0.26 g, 56% yield): $^1$H-NMR (400 MHz, methanol-$d_4$) δ 7.88 (d, J=8.8 Hz, 1H), 7.42 (t, J=7.6 Hz, 2H), 7.20 (t, J=7.6 Hz, 1H), 7.07 (d, J=8.8 Hz, 2H), 6.75 (d, J=2.0 Hz, 1H), 6.55 (dd, J=8.8, 2.4 Hz, 1H), 3.90 (s, 3H), 3.43 (t, J=7.1 Hz, 2H), 3.13 (t, J=8.3 Hz, 2H), 2.88 (s, 6H), 1.79 (m, 2H), 1.69 (m, 2H), 1.46 (m, 2H); $^{13}$C-NMR (400 MHz, methanol-$d_4$) δ 166.6, 162.1, 159.4, 155.9, 150.2, 132.5, 130.0, 124.4, 120.0, 109.3, 101.5, 57.7, 55.5, 42.21, 38.9, 28.8, 24.0, 23.4.

Example 111

Preparation of 4-phenoxyphenyl-phenylmethanol (127)

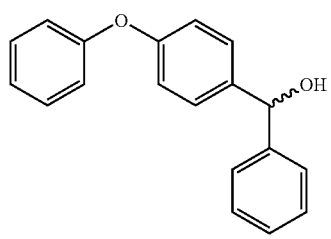

127

To a stirred solution of 4-bromodiphenyl ether (2.0 g, 8.03 mmol) in TBF (15 mL) at −78° C. was added n-butyllithium (3.85 mL, 2.6 M solution in hexanes). The reaction was stirred under argon for 2 hrs before a solution of benzaldehyde (0.85 g, 8.03 mmol) in THF at −78° C. was added. After stirring at −78° C. for 2 hrs, the reaction was quenched with water and extracted with ether. The organic layer was washed with brine, dried over magnesium sulfate, filtered, and concentrated under reduced pressure to give the crude product. The crude mixture was purified via flash SiO$_2$ chromatography (ethyl acetate/hexanes (10%/90%) to (15%/85%)) to give 127 (2.22 g, 97% yield): $^1$H-NMR (400 MHz, chloroform-d) δ 7.28-7.40 (m, 9H), 7.10 (t, J=7.6, 1H), 6.94-7.01 (m, 4H), 5.84 (d, J=3.6 Hz, 1H), 2.17 (d, J=3.6 Hz, 1H).

Example 112

Preparation of 3-phenoxyphenyl-phenylmethanol (128)

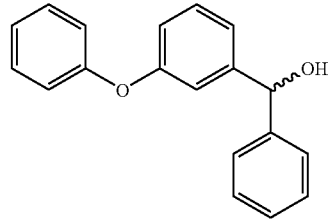

128

To a stirred solution of 3-phenoxybenzaldehyde (2 g, 10.09 mmol) in THF (15 mL) at −78° C. was added phenyllithium (6.73 mL, 1.8M solution in cyclohexane-ether) dropwise. After stirring under argon at −78° C. for 4 hrs, the reaction was quenched with water and extracted with diethyl ether. The organic layer was washed with brine, dried with magnesium sulfate, filtered, and concentrated under reduced pressure to give the crude product. The crude mixture was purified via flash SiO$_2$ chromatography (ethyl acetate/hexanes (10%/90%) to (20%/80%)) to give 128 (2.79 g, 86% yield): $^1$H-NMR (400 MHz, chloroform-d) δ 6.87-7.38 (m, 10H), 7.09 (m, 1H), 6.99 (app d, J=7.3 Hz, 1H), 6.88 (m, J=8.6, 2.2 Hz, 1H), 5.81 (s, 4H).

Method M: General Procedure for the Preparation of Dibenzylic Nitriles

A solution of thionyl chloride (10.80 mmol) and dibenzylic alcohol (7.20 mmol) in DCM (2 mL) was stirred at room temperature for 2 hrs. The reaction was concentrated under reduced pressure to give the dibenzylic chloride. To a solution of the dibenzylic chloride (7.20 mmol) in DCM (33.12 mL) was added trimethylsilyl cyanide (7.20 mmol) and titanium tetrachloride (7.20 mL). After stirring under argon at room temperature for 2 hrs, the reaction was quenched with methanol (13.90 mL) and water (41.62 mL) and diluted with dichloromethane (104 mL). The organic layer was washed with saturated, aqueous sodium bicarbonate (68.25 mL) and water (68.25 mL), dried over magnesium sulfate, filtered and concentrated under reduced pressure to give the crude product. The product was purified as described below.

Example 113

Preparation of 2-(4-phenoxyphenyl)-2-phenylacetonitrile (129)

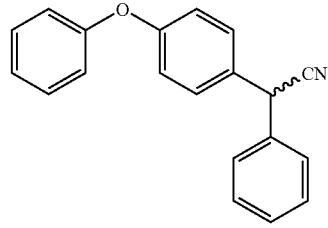

129

Refer to Method M for the general procedure. The crude mixture was purified via flash SiO$_2$ chromatography (ethyl acetate/hexanes 5%/95%) to (10%/90%)) to give 129 (0.49 g, 90% yield): $^1$H-NMR (400 MHz, chloroform-d) δ 7.25-7.40 (m, 9H), 7.13 (t, J=7.4, 1H), 6.99 (m, 4H), 5.12 (s, 1H).

Example 114

Preparation of 2-(3-phenoxyphenyl)-2-phenylacetonitrile (130)

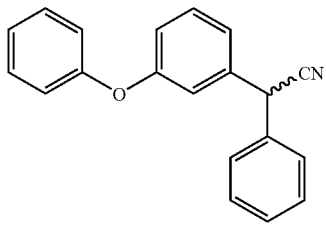

Refer to Method M for the general procedure. The crude mixture of 130 (2.45 g, 98% yield) was used without further purification: $^1$H-NMR (400 MHz, chloroform-d) δ 7.27-7.42 (m, 10H), 7.13 (app t, J=6.4 Hz, 1H), 7.01 (app d, J=8.8 Hz, 1H), 6.90 (m, 1H), 6.08 (s, 1H).

Method N: General Procedure for Reduction of Nitriles to Amines

To a suspension of lithium aluminum hydride (26.7 mmol) in THF (56 mL) at 0° C., was added a solution of nitrile (6.66 mmol) in THF (10 mL). After refluxing under argon for 24 hrs, the reaction was quenched sequentially with water (1.014 mL), 10% aqueous sodium hydroxide (2.028 mL) and water (3.043 mL). The reaction was filtered to remove the precipitated aluminum salts. The filtrate was washed with water and brine and extracted with ethyl acetate. The organic layer was dried over magnesium sulfate, filtered, and concentrated under reduced pressure to give the crude product. The crude mixture was treated with 3 N HCl in anhydrous ethyl acetate (5-10 mL), exposed to diethyl ether, and filtered to give the hydrochloride salts. If the hydrochloride salts did not precipitate the diethyl ether/ethyl acetate solution was concentrated under reduced pressure and rinse with diethyl ether to give the hydrochloride salts.

Example 115

Preparation of 2-(4-phenoxyphenyl)-2-phenylethanamine Hydrochloride (131)

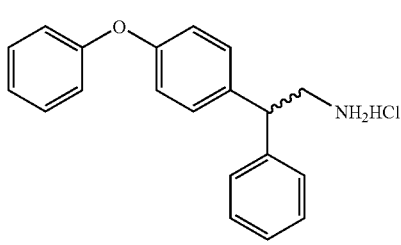

Refer to Method N for the general procedure. The precipitate was filtered to give 131 as a white solid (0.24 g, 47% yield): $^1$H-NMR (400 MHz, methanol-d$_4$) δ 7.22-7.35 (m, 9H), 7.04 (t, J=7.6 Hz, 1H), 6.89-6.92 (m, 4H), 4.22 (t, J=8.0 Hz, 1H), 3.56 (d, J=8.0 Hz, 1H).

Example 116

Preparation of 2-(3-phenoxyphenyl)-2-phenylethanamine Hydrochloride (132)

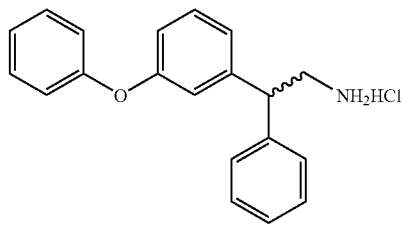

Refer to Method N for the general procedure. The precipitate was filtered to give 132 as a white solid (2.79 g, 26% yield): $^1$H-NMR (400 MHz, methanol-d$_4$) δ 7.34 (m, 10H), 7.12 (app t, J=7.3 Hz, 1H), 6.98 (m, 1H), 6.86 (dd, J=8.1, 2.7 Hz, 1H), 4.26 (t, J=8.1 Hz, 1H), 3.62 (d, J=8.3 Hz, 2H).

Example 117

Preparation of 4-phenoxynaphthaldehyde (134)

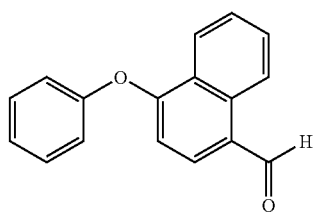

Refer to Method A for the general procedure. The crude product was purified via flash SiO$_2$ chromatography (loaded with DCM, eluted with ethyl acetate/hexanes (0%/100%) to (5%/95%)) to give 134 (0.72 g, 39% yield): $^1$H-NMR (400 MHz, chloroform-d) δ 10.15 (s, 1H), 9.24 (d, J=8.3 Hz, 1H), 8.34 (d, J=9.3 Hz, 1H), 7.69 (m, 3H), 7.63 (t, J=6.8 Hz, 1H), 7.39 (app t, J=8.1 Hz, 2H), 7.18 (t, J=7.3 Hz, 1H), 7.06 (d, J=8.8 Hz, 1H), 6.66 (s, 1H).

Example 118

Preparation of 4-phenoxynaphthalenylmethanol (135)

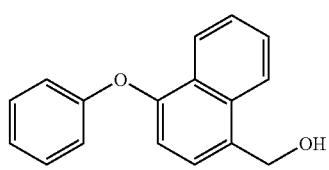

To a solution of 134 (0.28 g, 1.12 mmol) in ethanol (20 mL) was added sodium borohydride (0.042 g, 1.12 mmol). After stirring at room temperature for 15 min, the reaction was quenched with water and extracted with ethyl ether. The organic layer was washed with brine, dried over magnesium sulfate, filtered, and concentrated under reduced pressure to give the crude product. The crude mixture was purified via flash $SiO_2$ chromatography (ethyl acetate/hexanes (25%/75%) to give 135 (0.28 g, 95% yield): $^1$H-NMR (400 MHz, chloroform-d) δ 8.29 (d, J=8.3 Hz, 1H), 8.17 (d, J=8.3 Hz, 1H), 7.61 (m, 1H), 7.53 (m, 1H), 7.41 (d, J=7.8 Hz, 1H), 7.35 (t, J=7.8 Hz, 2H), 7.13 (t, J=7.3 Hz, 1H), 7.05 (dd, J=8.6, 1.2 Hz, 2H), 6.88 (d, J=7.8 Hz, 1H), 5.12 (s, 2H).

Example 119

Preparation of 4-phenoxynaphthalenylacetonitrile (136)

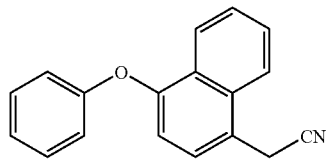

136

Refer to Method M for the general procedure. The crude mixture was purified via flash $SiO_2$ chromatography (loaded with DCM, eluted with ethyl acetate/hexanes (10%/90%)) to give 136 (0.21 g, 54% yield): $^1$H-NMR (400 MHz, chloroform-d) (8.36 (d, J=7.8 Hz, 1H), 7.67 (app t, J=7.1 Hz, 1H), 7.59 (app t, J=8.1 Hz, 1H), 7.47 (d, J=7.8 Hz, 1H), 7.38 (app t, J=8.1 Hz, 2H), 7.16 (t, J=7.6 Hz, 1H), 7.07 (d, J=7.8 Hz, 2H), 6.87 (d, J=7.8 Hz, 1H), 4.11 (s, 2H).

Example 120

Preparation of 4-phenoxynaphthalenethylamine (137)

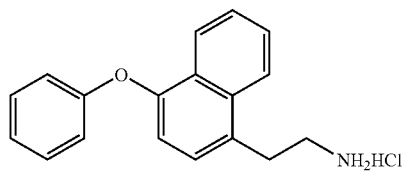

137

Refer to Method N for the general procedure. The precipitate was filtered to give 137 as a white solid (0.13 g, 54% yield): $^1$H-NMR (400 MHz, methanol-$d_4$) δ 8.24 (d, J=8.8 Hz, 1H), 8.12 (d, J=8.8 Hz, 1H), 7.66 (app t, J=7.6 Hz, 1H), 7.55 (app t, J=7.6 Hz, 1H), 7.36 (m, 3H), 7.13 (app t, J=7.3 Hz, 1H), 7.02 (d, J=7.3 Hz, 2H), 6.88 (d, J=7.8 Hz, 1H), 3.43 (t, J=7.6 Hz, 1H), 3.27 (t, J=7.3 Hz, 2H).

Example 121

Thyronamine Derivatives and Analogs Mediate Rapid Physiologic Action Via Trace Amine Receptors The biological activity of thyroid hormones are generally mediated by the nuclear thyroid hormone receptors (TRs). However, certain physiological actions of thyroid hormone occur rapidly (in a matter of seconds), and therefore cannot be accounted for transcriptional regulation by TRs.

Biogenic amines such as dopamine, norepinephrine, and seratonin mediate rapid responses through activation of their cognate receptors, which belong to the 7-transmembrane containing G-protein coupled receptor (GPCR) superfamily. These biogenic amines are synthesized from their corresponding amino acids by an enzymatic sequence that involves decarboxylation of the amino acid as the key step that generates the arylethylamine substructure common to this group of signaling molecules. For example, the decarboxylation reaction that provides dopamine from L-DOPA (FIG. 2) is catalyzed by the non-selective enzyme aromatic amino acid decarboxylase (AAD), which also catalyzes the conversion of histadine to histamine and 5-hydroxytryptophan to seratonin. In fact, AAD is known to catalyze the decarboxylation of a wide variety of natural and synthetic aromatic amino acids, apparently requiring an aromatic group linked to an alanine amino acid as the key feature of substrate recognition.

Figure 2:
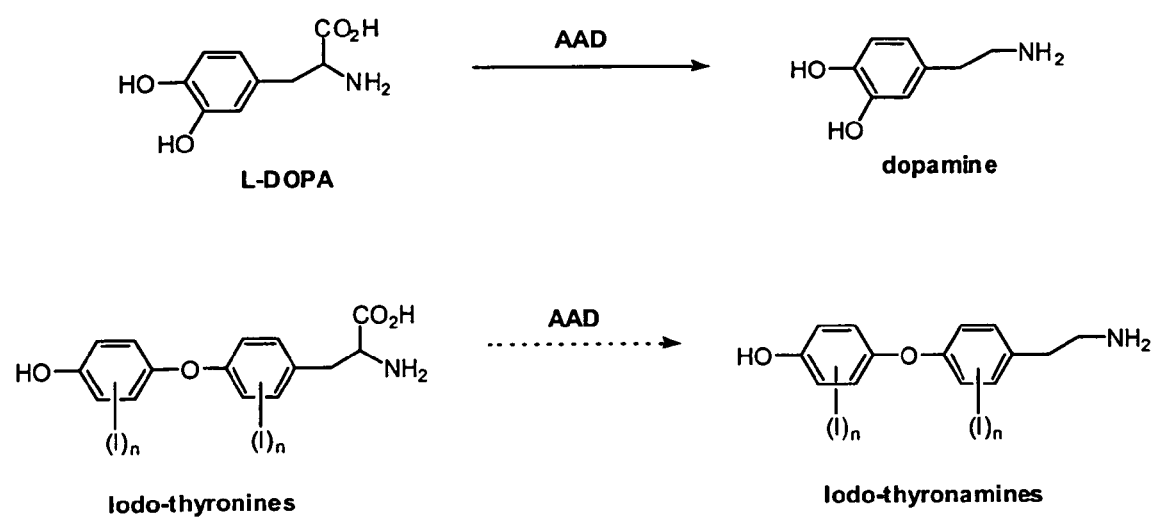
FIG. 2: Parallel pathways of amino acid decarboxylase to produce dopamine and iodo-thyronamine.
Figure 3:
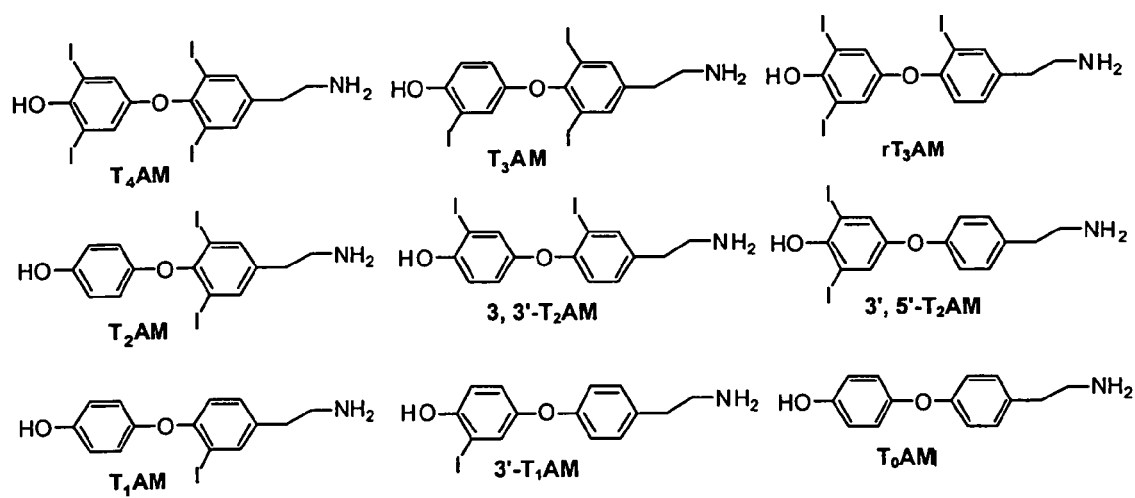
FIG. 3: Thyronamine synthetic products

Thyroid hormones, i.e. $T_3$ and $T_4$ as well as the lower iodination state metabolites (FIG. 1), can be substrates for AAD, giving rise to the aryl ethylamine compounds hereafter referred to as thyronamine derivatives and analogs or as iodo-thyronamines (FIG. 2). On the basis of the structural similarity between the iodo-thyronamines and dopamine, one or more of these iodo-thyronamines activating a cognate iodo-thyronamine GPCR can constitute a new signaling pathway to mediate rapid effects of thyroid hormone. In an embodiment, chemical synthesis of a panel of thyronamines is shown in FIG. 3, the members of which correspond to every possible iodination state between thyroxamine ($T_4AM$) and thyronamine ($T_0AM$). From this panel, $T_4AM$, $T_3AM$, and $T_0AM$ have been described previously. See, for example, Thibault, O., 1951 *C. R. Soc. Chim. biol.*, 797-800; Meyer, T., 1983, *Horm. metabol. Res.* 15: 602-606; Buu-Hoi, 1966, *Med. Pharmacol. exp.* 15: 17-23. The other six iodo-thyronamines in the panel have not been described previously. The synthesis of iodo-thyronamines, $T_1AM$, $T_2AM$, 3'-$T_1AM$, 3,3'-$T_2AM$, 3,5'-$T_2AM$, and $rT_3AM$ have not been previously synthesized or described in the literature.

A physiological role for iodo-thyronamine can be reasoned as follows: (1) Thyroid hormones are aromatic amino acids ultimately derived from tyrosine; (2) Thyroid hormones are chemically and biosynthetically similar to L-DOPA and 5hydroxytryptophan, the biosynthetic precursors of the neurotransmitters dopamine, norepinephrine, and serotonin (5-hydroxytryptamine), respectively; (3) The AAD-catalyzed decarboxylation of L-DOPA gives rise to the neurotransmitter dopamine as shown in FIG. 2. Since AAD is a non-selective enzyme that will promote the efficient decarboxylation of a wide variety of aromatic amino acids, the thyroid hormones ($T_4$, $T_3$) and their deiodinated metabolites (shown in FIG. 1), are effective substrates for AAD resulting in iodo-thyronamine products (FIG. 2); (4) These iodo-thyronamines would be ligands for membrane bound receptors, for example, G-protein coupled receptors (GPCRs), and iodo-thyronamine induced activation of these receptors could be responsible for the rapid signaling effects of thyroid hormone.

The cloning and characterization of a rat receptor (subsequently from mice and human also) that is activated by several biogenic trace amines has been reported. See, e.g., Bunzow, et al., 2001, *Mol. Pharmacol.* 60: 1181-1188; Borowsky, et al., 2001, *Proc. Natl. Acad. Sci.* 98: 8966-8971. This receptor is designated as trace amine receptor (TAR),a 7-transmembrane G protein coupled receptor (GPCR) and a homolog of catecholamine and 5-hydroxytryptophan receptors. Multiple subtypes exist: 15 rat TARs and 5 human TARs. TARs are expressed in tissues including, but not limited to brain, heart, pancreas, kdney, stomach, small intestine, skeletal mucle, prostate, liver, and spleen.

In an embodiment, metabolites of thyroid hormone, for example, thyronamines and iodo-thyronamines, bind to rTAR. Using a cAMP assay, thyroid hormone metabolites, e.g., 3-iodothyronamine, bind to the TAR receptor with high affinity (in the same range as the natural ligands). Thyroid hormone metabolites, e.g., 3-iodothyronamine, are also present in the crude extract of rat and mouse brain. Finally, the rapid action of the thyroid hormone metabolite, e.g., 3-iodothyronamine, was demonstrated in a physiological heart model system (13-19 day old chick embryo). For example, 3-iodothyronamine, or more stable and potent synthetic analogs, can be useful for treating cardiovascular disorders such as congestive heart failure. Additionally, these compounds could also have many other uses as therapeutics for diseases related to thyroid hormone status.

Example 122

Thyronamine Derivatives and Analogs Mediate Rapid Physiologic Action Via Trace Amine Receptors The biological activity of thyroid hormones are generally mediated by the nuclear thyroid hormone receptors (TRs). However, certain physiological actions of thyroid hormone occur rapidly (in a matter of seconds),and therefore cannot be accounted for transcriptional regulation by TRs.

Biogenic amines such as dopamine, norepinephrine, and seratonin mediate rapid responses through activation of their cognate receptors, which belong to the 7-transmembrane containing G-protein coupled receptor (GPCR) superfamily. These biogenic amines are synthesized from their corresponding amino acids by an enzymatic sequence that involves decarboxylation of the amino acid as the key step that generates the arylethylamine substructure common to this group of signaling molecules. For example, the decarboxylation reaction that provides dopamine from L-DOPA (FIG. 2) is catalyzed by the non-selective enzyme aromatic amino acid decarboxylase (AAD), which also catalyzes the conversion of histadine to histamine and 5-hydroxytryptophan to seratonin. In fact, AAD is known to catalyze the decarboxylation of a wide variety of natural and synthetic aromatic amino acids, apparently requiring an aromatic group linked to an alanine amino acid as the key feature of substrate recognition.

Thyroid hormones, i.e. $T_3$ and $T_4$ as well as the lower iodination state metabolites (FIG. 1), can be substrates for AAD, giving rise to the aryl ethylamine compounds hereafter referred to as thyronamine derivatives and analogs or as iodo-thyronamines (FIG. 2). On the basis of the structural similarity between the iodo-thyronamines and dopamine, one or more of these iodo-thyronamines activating a cognate iodo-thyronamine GPCR can constitute a new signaling pathway to mediate rapid effects of thyroid hormone. In an embodiment, chemical synthesis of a panel of thyronamines is shown in FIG. 3, the members of which correspond to every possible iodination state between thyroxamine ($T_4AM$) and thyronamine ($T_0AM$). From this panel, $T_4AM$, $T_3AM$, and $T_0AM$ have been described previously. See, for example, Thibault, O., 1951 *C. R. Soc. Chim. biol.,* 797-800; Meyer, T., 1983, *Horm. metabol. Res.* 15: 602-606; Buu-Hoi, 1966, *Med. Pharmacol. exp.* 15: 17-23; Stohr, R., 1931, *Hoppe-Seyler Z. physiol. Chem.* 201, 142; Petit and Buu-Hoi, 1961, *J. org. Chem.* 26, 3832; Cody et al., 1984, *Endocrine Research,* 10, 91-99. The other six iodo-thyronamines in the panel have not been described previously. The synthesis of iodo-thyronamines, $T_1AM$, $T_2AM$, 3'-$T_1AM$, 3,3'-$T_2AM$, 3,5'-$T_2AM$, and $rT_3AM$ have not been previously synthesized or described in the literature.

A physiological role for iodo-thyronamines can be reasoned as follows: (1) Thyroid hormones are aromatic amino acids ultimately derived from tyrosine; (2) Thyroid hormones are chemically and biosynthetically similar to L-DOPA and 5hydroxytryptophan, the biosynthetic precursors of the neurotransmitters dopamine, norepinephrine, and serotonin (5-hydroxytryptamine), respectively; (3) The AAD-catalyzed decarboxylation of L-DOPA gives rise to the neurotransmitter dopamine as shown in FIG. 2. Since AAD is a non-selective enzyme that will promote the efficient decarboxylation of a wide variety of aromatic amino acids, the thyroid hormones ($T_4$, $T_3$) and their deiodinated metabolites (shown in FIG. 1), are effective substrates for AAD resulting in iodo-thyronamine products (FIG. 2); (4) These iodo-thyronamines would be ligands for membrane bound receptors, for example, G-protein coupled receptors (GPCRs), and iodo-thyronamine induced activation of these receptors could be responsible for the rapid signaling effects of thyroid hormone.

The cloning and characterization of a rat receptor (subsequently from mice and human also) that is activated by several biogenic trace amines has been reported. See, e.g., Bunzow, et al., 2001, *Mol. Pharmacol.* 60: 1181-1188; Borowsky, et al., 2001, *Proc. Natl. Acad. Sci.* 98: 8966-8971. This receptor is designated as trace amine receptor (TAR), a 7-transmembrane G protein coupled receptor (GPCR) and a homolog of catecholamine and 5-hydroxytryptophan receptors. Multiple subtypes exist: 15 rat TARs and 5 human TARs. TARs are expressed in tissues including, but not limited to brain, heart, pancreas, kidney, stomach, small intestine, skeletal muscle, prostate, liver, and spleen.

In an embodiment, metabolites of thyroid hormone, for example, thyronamines and iodo-thyronamines, bind to rTAR. Using a cAMP assay, thyroid hormone metabolites, e.g., 3-iodothyronamine, bind to the TAR receptor with high affinity (in the same range as the natural ligands). Thyroid hormone metabolites, e.g., 3-iodothyronamine, are also present in the crude extract of rat and mouse brain. Finally, the rapid action of the thyroid hormone metabolite, e.g., 3-iodothyronamine, was demonstrated in a physiological heart model system (13-19 day old chick embryo). For example, 3-iodothyronamine, or more stable and potent synthetic analogs, can be useful for treating cardiovascular disorders such as congestive heart failure. Additionally, these compounds could also have many other uses as therapeutics for diseases related to thyroid hormone status.

Example 123

Functional Role for Thyronamine Derivatives and Analogs As Signaling Molecules in an In Vitro Rat Trace Amine Receptor (TAR) Assay

A G-protein coupled receptor (GPCR) called the trace amine receptor (TAR-1) belongs to the subfamily of receptors for biogenic amines. TAR-1 is homologous to receptors for dopamine, norephinephrine, and serotonin (5-hydroxytryptamine), but these biogenic amines are not potent agonists of TAR-1. Instead, TAR-1 has been found to respond to endogenous trace amines such as p-tyramine, 3-methoxy-p-tyramine, and phenethylamine, as well as a variety of synthetic phenethylamine derivatives. TAR-1 couples to $G\alpha_s$ in response to these agonists resulting in cAMP accumulation in cells expressing TAR-1. See, e.g., Bunzow, et al., 2001, *Mol. Pharmacol.* 60: 1181-1188; Borowsky, et al., 2001, *Proc. Natl. Acad. Sci.* 98: 8966-8971.

Figure 4:
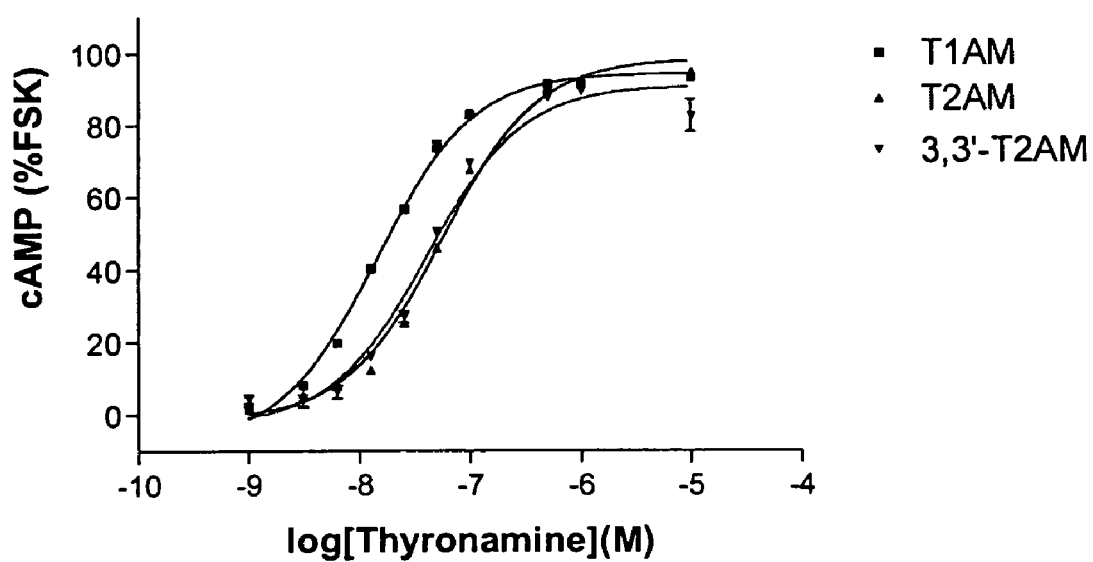
FIG. 4: Dose-response for thyronamines on the trace amine receptor (rTAR-1).

Given the chemical similarity between iodo-thyronamines and biogenic amines, and because TAR-1 belongs to the biogenic amine GPCR subfamily whose endogenous agonist remains to be established, TAR-1 is an ideal candidate receptor for iodo-thyronamines. To test this, the synthetic iodo-thyronamines were assayed for their ability to stimulate cAMP accumulation in human embryonic kidney (HEK) cells stably expressing rTAR-1, as well as cells transfected with an empty vector. None of the compounds tested had any effect on cAMP accumulation in the cells that received empty vector. However, several of the iodo-thyronamines were found to stimulate cAMP accumulation in the rTAR-1 expressing cells in a dose-dependent fashion (FIG. 4). To address the issue of receptor selectivity, all of the iodo-thyronamines were tested for their ability to activate the dopamine receptors and the β-adrenergic receptors. As with rTAR-1, HEK cells stably expressing either $D_1R$ or $\beta_2AR$ (both $G\alpha_s$ coupled) were treated with the panel of iodo-thyronamines and no ligand stimulation of cAMP accumulation was found (data not shown), demonstrating that the iodo-thyronamines are not promiscuous agonists of catecholamine receptors.

The potency index of effective concentration for half-maximal stimulation ($EC_{50}$) of rTAR-1 was calculated from the dose-response curve for each compound (Table 1). The spectrum of potencies across the thyronamine series demonstrates that the specific number and placement of iodine atoms influences potency in a critical way. 3-iodothyronamine ($T_1AM$) is the most potent rTAR-1 agonist with an $EC_{50}$ of 14 nM, and thyronamine ($T_0AM$) is the least potent agonist with an $EC_{50}$ of 131 nM. Thus, addition of a single iodine atom to the 3-position of $T_0AM$ results in an approximate 10-fold increase in agonist potency for rTAR-1. All other combinations of iodines on the thyronamine skeleton result in decreased potency. $T_4AM$ and $rT_3AM$ showed no ability to stimulate cAMP accumulation in this assay further demonstrating that potent iodo-thyronamine activation of rTAR-1 follows specific requirements regarding number and regiochemical positioning of iodines within the thyronamine carbon skeleton.

We also tested the panel of iodo-thyronamines for activation of the mouse TAR-1 and found that $T_1AM$ was again the most potent agonist in the collection (Table 1). The $EC_{50}$ value for $T_1AM$ activation of mTAR-1 is 112 nM, and the only other iodo-thyronamine with an $EC_{50}$ value less than 1 µM against mTAR-1 is $T_2AM$. The observed potency for $T_1AM$ compares favorably to the potency of other biogenic amines activating their cognate GPCRs. For example, in similar cell-culture based assays, $EC_{50}$ values ranging from 2 to 275 nM have been reported for dopamine activation of dopamine receptors. The differences in potency of $T_1AM$ as well as the rank order potency of the other thyronamines in the series are manifestations of each species specific TAR-1 polypeptide sequence which should inform future molecular structure-activity studies.

TABLE 1

Rank Order Potencies of Iodo-Thyronamine Activation of rTAR-1

| Compound Name | Rat TAR $EC_{50}$ (nM) |
|---|---|
| 3-iodothyronamine ($T_1AM$) | 14 |
| 3,3'-diodothyronamine (3,3'-$T_2AM$) | 41 |
| 3,5-diodothyronamine ($T_2AM$) | 56 |
| 3,5,3'-tri-iodothyronamine ($T_3AM$) | 87 |
| thyronamine ($T_0AM$) | 131 |
| 3,3',5'-triodothyronamine ($rT_3AM$) | >1000 |
| thyroxamine ($T_4AM$) | >1000 |

A further panel of thyronamines analogs were tested for activation of the mouse TAR-1. Potent agonists were found in the collection. Compounds 53, 54, 55, 56, 74, 82, 83, 94, 95, 109, 110, 111, 112, 113, 114, 115, 117, 118, 119, 120, 121, 122, 123, and 124, had an $EC_{50}$ of 1000 or greater. Compounds 91 and 92 had an $EC_{50}$ of 500 to 1000. Compounds 31, 32, 39, 40, 41, 42, 43, 44, 51, 52, 69, 70, 71, 131, 132, and 137 had an $EC_{50}$ of 500 or less.

cAMP Assay. HEK293 cells were harvested in Krebs-Ringer-HEPES buffer (KRH) and preincubated in KRH with 200 µM 3-isobutyl-methylxanthine. For drug treatments cells were incubated in KRH with 100 µM 3-isobutyl-1-methylxanthine with the test compound (or 10 µM forskolin) for 1 hour at 37° C. The cells were then boiled for 20 minutes after adding an equal volume of 0.5 mM sodium acetate buffer, centrifuged to remove cell debris, and the resulting extract was analyzed for cAMP content using competitive binding of [$^3$H]cAMP to a cAMP binding protein (Diagnostic Products Corp., Los Angeles, Calif.). Data were normalized according to protein content as determined using the Bradford reagent (Bio-Rad). Concentration-response curves were plotted and $EC_{50}$ values calculated with Prism software (GraphPad, San Diego, Calif.).

Example 124

Identification of 3-Iodo-Thyronamine, $T_1AM$, in Rat, Mouse, and Guinea Pig Brain

To investigate whether 3-iodothyronamine, $T_1AM$, the most potent iodo-thyronamine found to activate TAR-1, was a naturally occurring metabolite, liquid chromatography/mass spectrometry (LC/MS) was performed on rat brain. Rat whole brain homogenates were prepared in 0.1 M perchloric acid (PCA), conditions that are standard for the extraction of biogenic amines such as dopamine. The crude extracts were analyzed by liquid chromatography/mass spectrometry (LC/MS) using an elution and detection protocol that was optimized with the synthetic $T_1AM$ standard. The mass spectrometer for these studies was a triple quadrapole MS/MS instrument that is ideal for single ion monitoring in complex biological mixtures. Nevertheless, no $T_1AM$ was detected in crude PCA brain homogenates using this method.

Figure 5A:
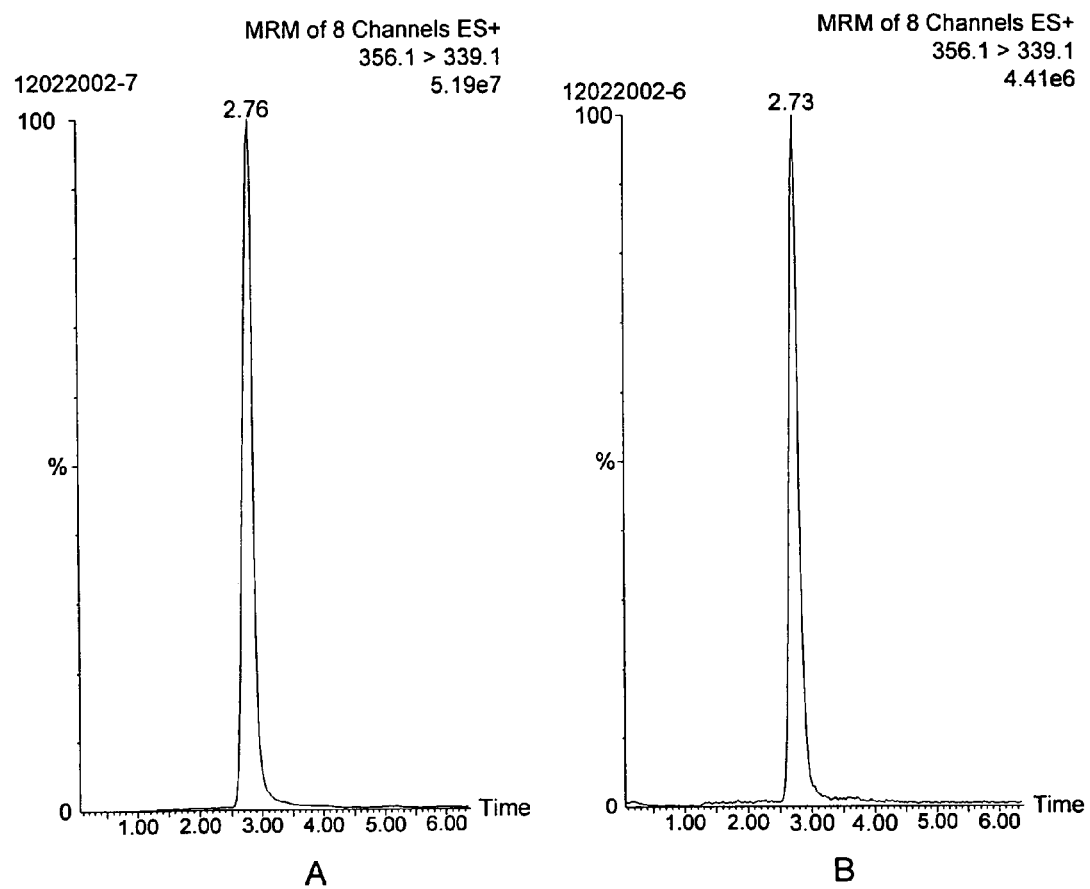
FIG. 5A: Liquid chromatography; 5B, 5C: mass spectrometry (LC/MS) on rat brain.
Figure 5B:
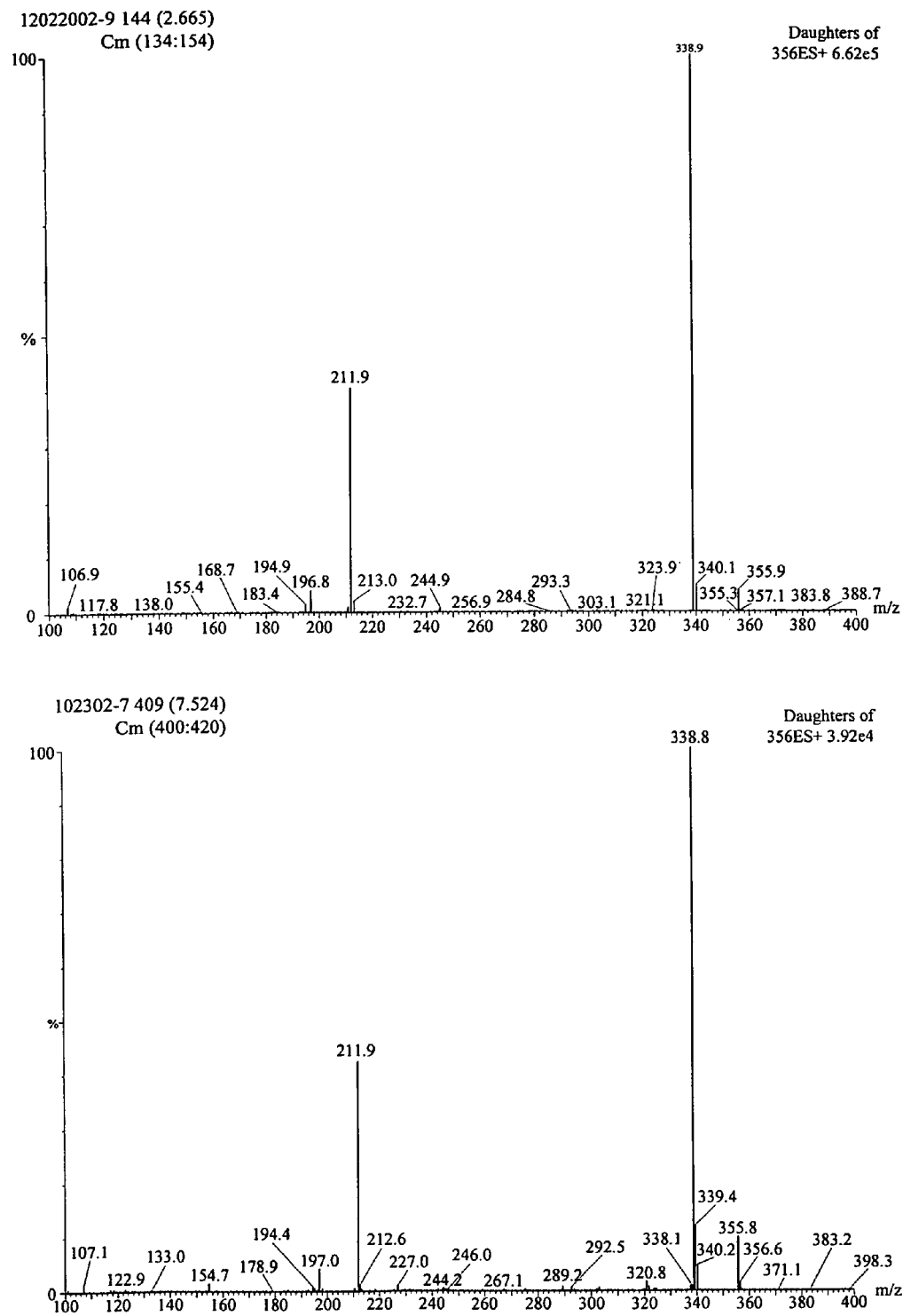

The detection limit of this system is about 50 fmol, leading one to conclude that $T_1AM$ is present in whole brain extracts below this limit. Accordingly, an alternative extraction procedure was developed: (i) adjusting the pH of PCA homogenate to pH 12, (ii) extracting the free-base biogenic amines with ethyl acetate, (iii) concentrating the ethyl acetate fraction to dryness, and (iv) dissolving the concentrated residue in 1/100 the initial volume of 0.1 M PCA. Analysis of this concentrated and partially purified brain extract unambiguously revealed the presence of $T_1AM$ (FIG. 5). The endogenous $T_1AM$ identified from the brain extract was found to be chemically identical to the synthetic $T_1AM$ standard in terms of HPLC column retention time, parent ion mass (356) and first daughter ion mass (339) corresponding to loss of ammonia (FIG. 5B). A second daughter ion common to both synthetic and biological samples of 212 m/e, corresponding to loss of iodide from the first daughter ion, confirms the presence of iodine in both samples. Moreover, the Q1 and Q3 mass spectra of both the synthetic and biologically derived $T_1AM$ were identical (FIG. 5B,C), providing further confirmation that $T_1AM$ is biogenic amine. $T_1AM$ in rat brain is approximately 600 fmol per rat brain or approximately 200 fmol per gram of rat brain. $T_1AM$ level is approximately 3 to 20% of $T_4$ level in rat brain. In addition to rat brain, $T_1AM$ in brain extracts from mouse and guinea pig has been detected using this protocol (data not shown).

These data verify that $T_1AM$ is a naturally occurring biogenic amine. Since $T_1AM$ contains an iodine atom attached to the elements of a thyronine carbon skeleton, and since thyroid hormone is the only organically bound source of iodine in vertebrates, there is little doubt that $T_1AM$ is an endogenous metabolite of thyroid hormone. The dual action of amino acid decarboxylase (AAD) and deiodinases on $T_4$ represents the simplest pathway of metabolic reactions that produce $T_1AM$ from thyroid hormone.

Figure 6A:
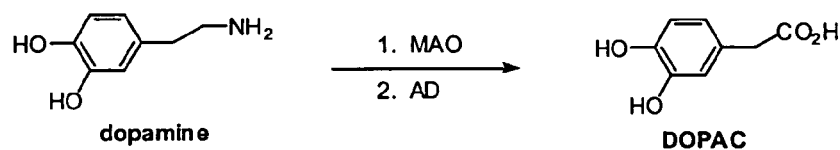
FIGS. 6A, 6B: Metabolites of dopamine and $T_1$amine from sequential action of monoamine oxidase and aldehyde dehydrogenase.
Figure 6B:
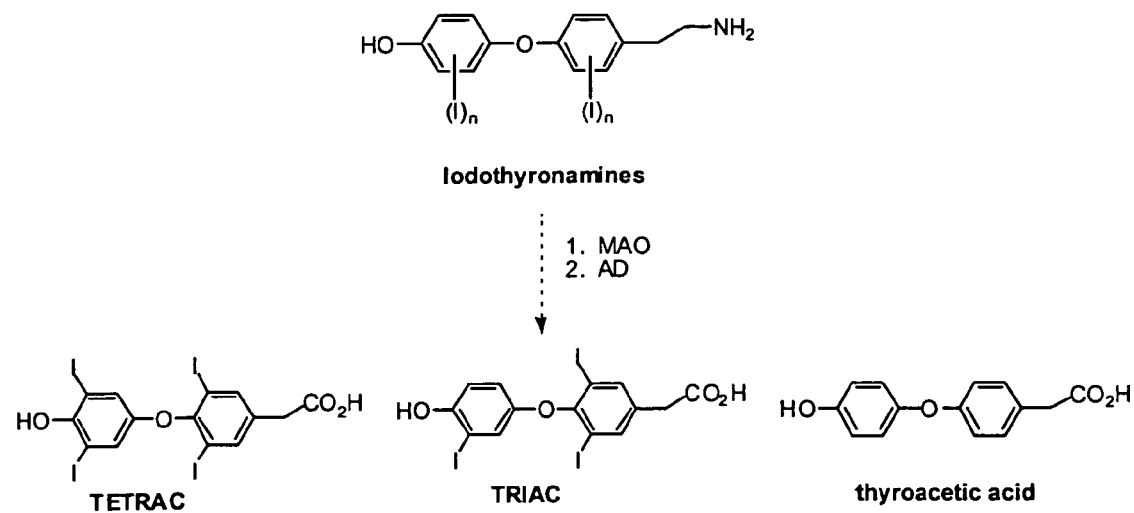

Like dopamine, $T_1AM$ is a biogenic amine that contains the phenethylamine substructure and should be a substrate for the non-selective amine-degrading enzyme, monoamine oxidase (MAO). One of the primary metabolites of dopamine is DOPAC (FIG. 6A), which arises from the sequential action of MAO and aldehyde dehydrogenase on dopamine. It is interesting to note that similar aryl acetic acid metabolites of thyroid hormone have been known for some time, including the compounds TETRAC, TRIAC, and thyroacetic acid (FIG. 6B), and a definitive account of the enzymatic processing that gives rise to these metabolites has not been reported. On the basis of the demonstration that $T_1AM$ is naturally occurring, it is reasonable to postulate that other thyronamines with different iodine content such as $T_4AM$, $T_3AM$, and $T_0AM$ are also present endogenously. This provides a concise metabolic route for the formation of the aryl acetic acid metabolites of thyroid hormone; the corresponding thyronamines are processed in the same way as dopamine by the non-selective action of MAO and aldehyde dehydrogenase.

Example 125

Figure 7:
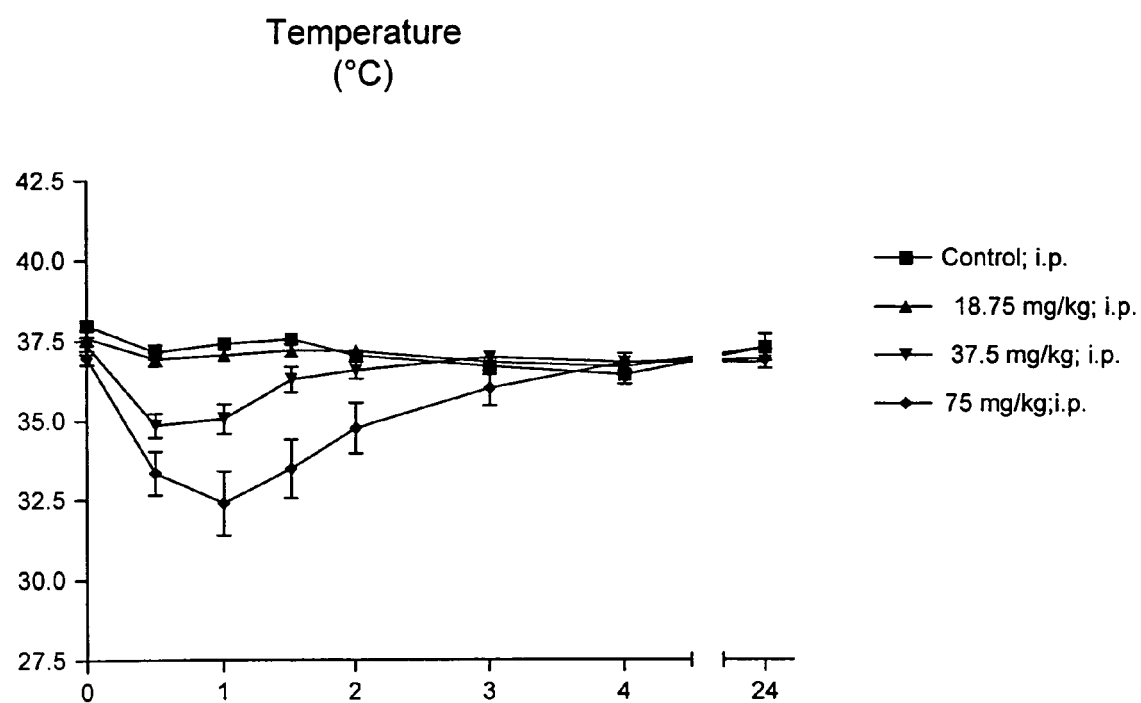
FIG. 7: Graph of core body temperature (° C.) vs. time (hours) following intraperitoneal injection into mice (n=8) of an iodo-thyronamine compound, $T_1$amine.

Function of 3-Iodo-Thyronamine, $T_1AM$, on Core Body Temperature of Mice Injected Intraperitoneally or Intracerebrally Eight week old male C57 Black 6J (C57Bl/6J) mice were injected intraperitoneally (i.p.) with the indicated dose of 3-iodothyronamine ($T_1AM$) dissolved in 60% DMSO and normal saline (pH 7.4). Mice were injected intraperitoneally with a dose of $T_1AM$ at 18.75, 37.5, or 75 mg/kg body weight. Core body temperature was measured as rectal temperature every 30 minutes for the first 2 hours and then again at 3, 4, and 24 hours post injection. The core body temperature response (with standard error) to each dose reflects the response of 7-8 mice in a room maintained at 24° C. See FIG. 7.

Figure 8:
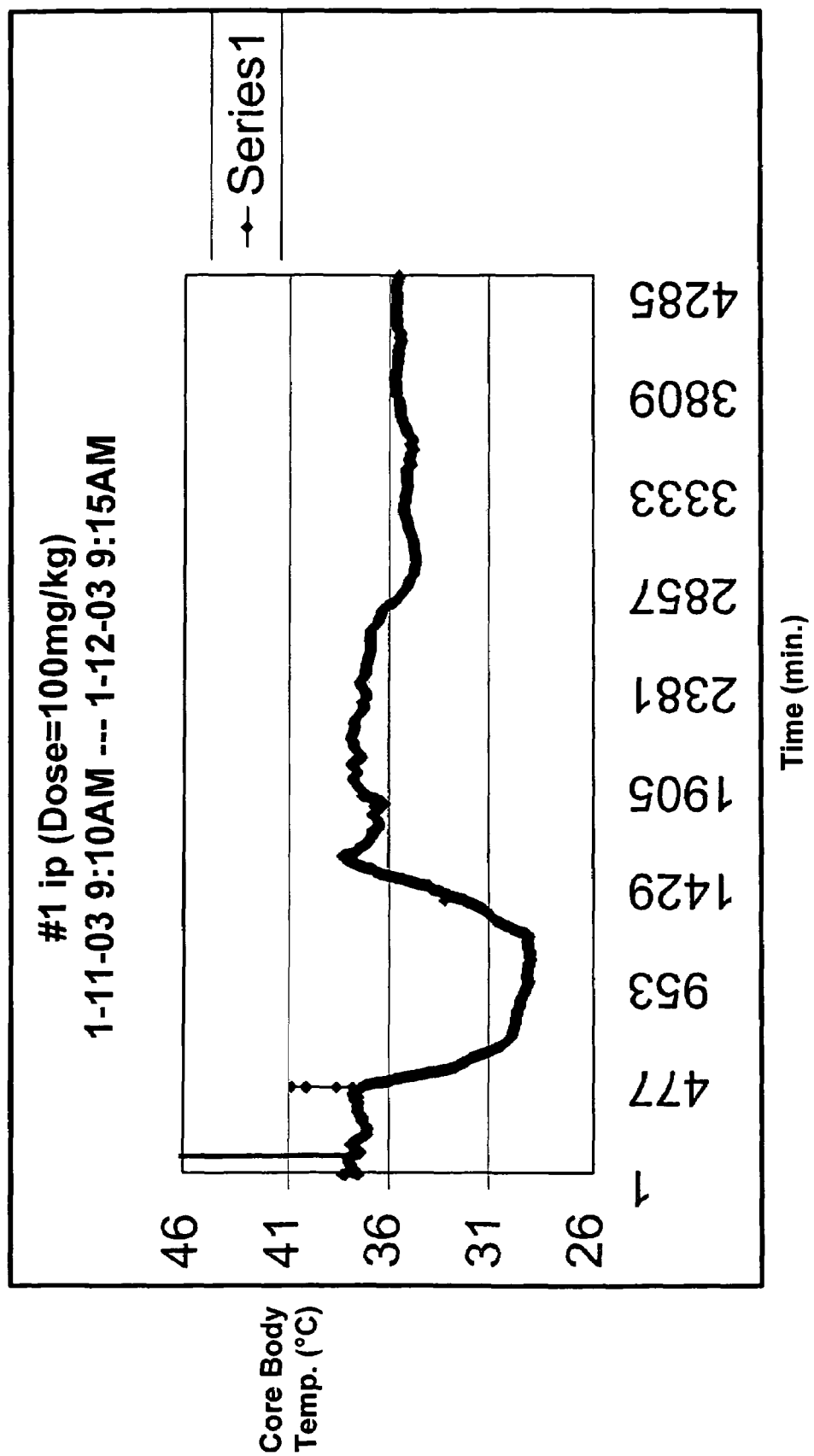
FIG. 8: Graph of core body temperature (° C.) vs. time (hours) following intraperitoneal injection into a mouse of an iodo-thyronamine compound, $T_1$amine.

Core body temperature response was measured in an adult male C57Bl/6J mouse injected intraperitoneally with a dose of $T_1AM$ at 100 mg/kg $T_1AM$. The mouse was implanted with a telemetry-emitting temperature sensing probe for more accurate measurement of core body temperature. See FIG. 8.

Figure 9:
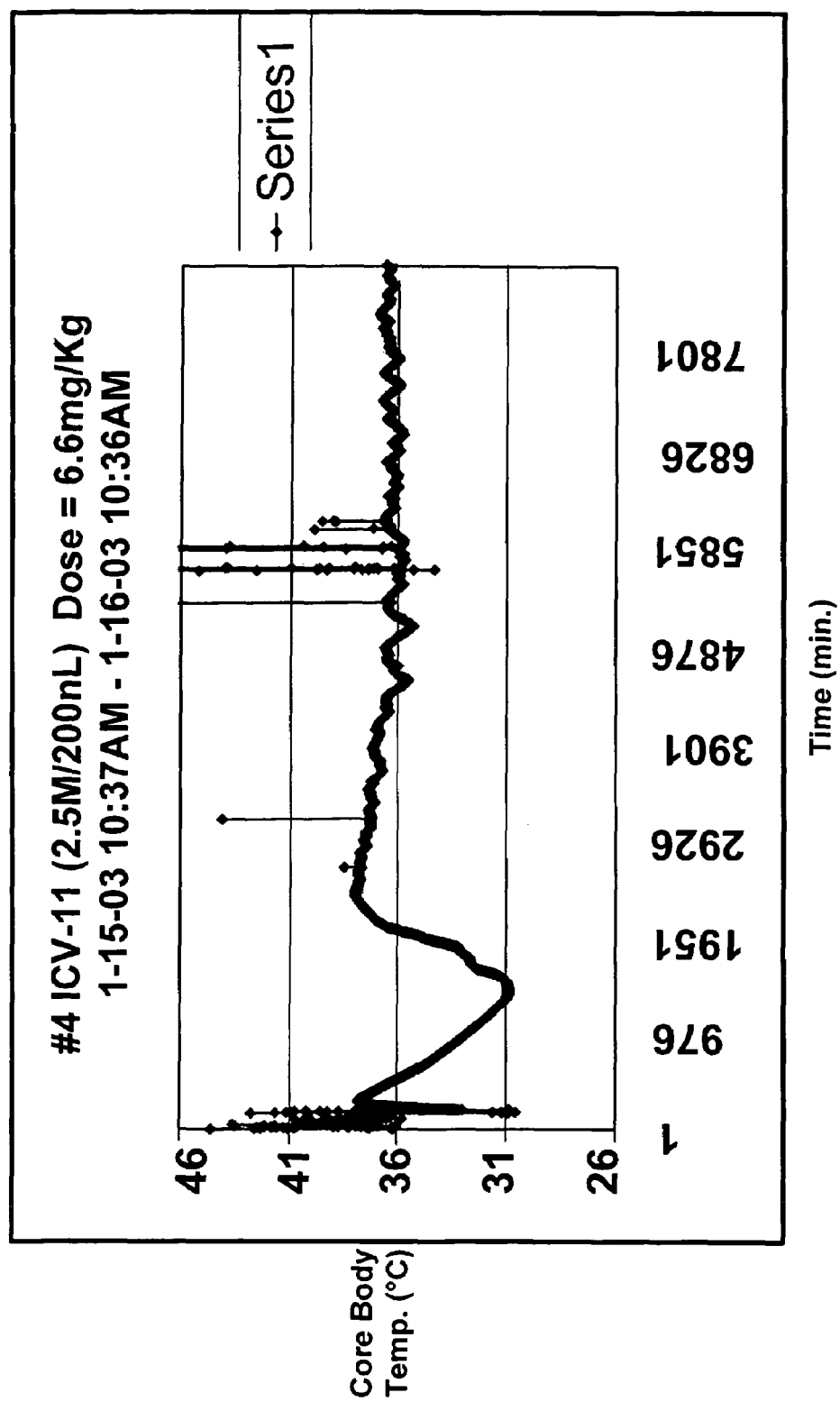
FIG. 9: Graph of core body temperature (° C.) vs. time (hours) following intracerebroventricular injection into a mouse of an iodo-thyronamine compound, $T_1$amine.
Figure 10C:
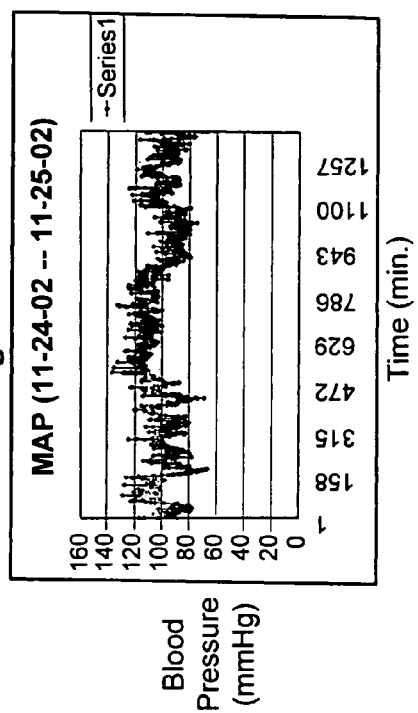
FIGS. 10C, 10D: Graph of heart rate vs. time (minutes), or blood pressure (mm Hg) vs. time (minutes), in a mouse in the absence of treatment with an iodo-thyronamine compound.
Figure 10D:
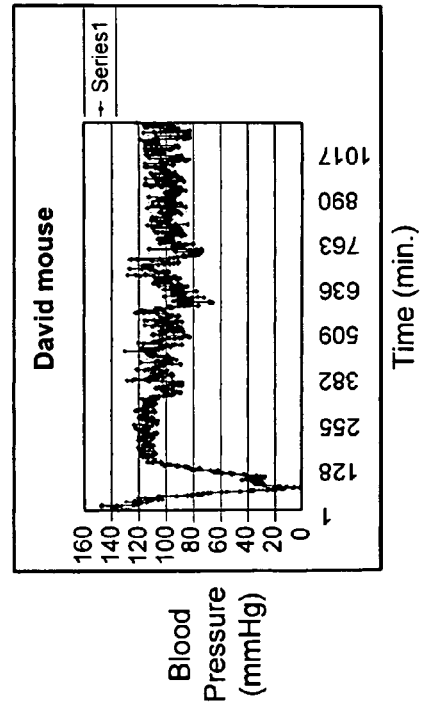
Figure 10A:
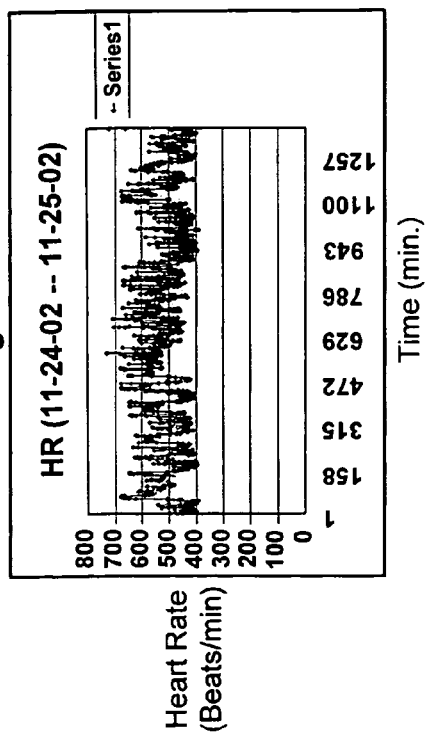
FIGS. 10A, 10B: Graph of heart rate vs. time (minutes), or blood pressure (mm Hg) vs. time (minutes), following intraperitoneal injection into a mouse of an iodo-thyronamine compound, $T_1$amine.
Figure 10B:
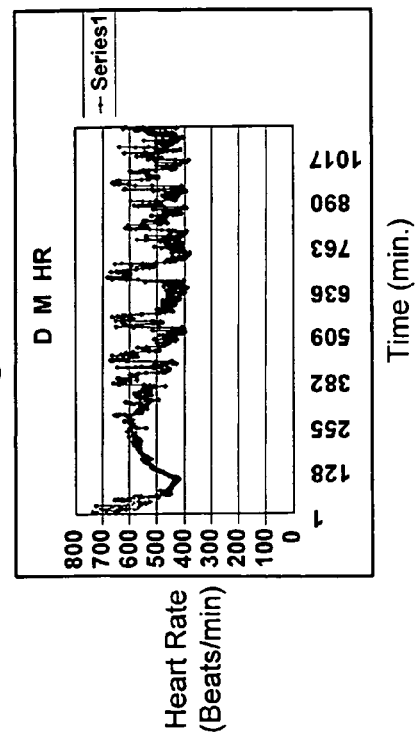
Figure 13C:
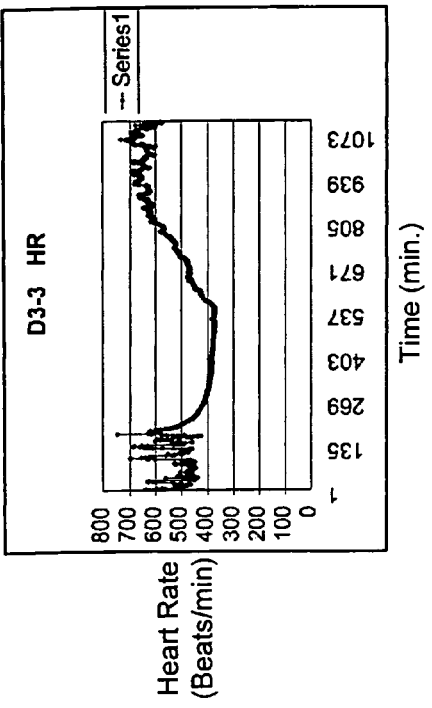
FIGS. 13C, 13D: Graph of heart rate vs. time (minutes), or blood pressure (mm Hg) vs. time (minutes), following intraperitoneal injection into a mouse of an iodo-thyronamine compound, $T_1$amine, measured over an approximately 17 hour period.
Figure 13D:
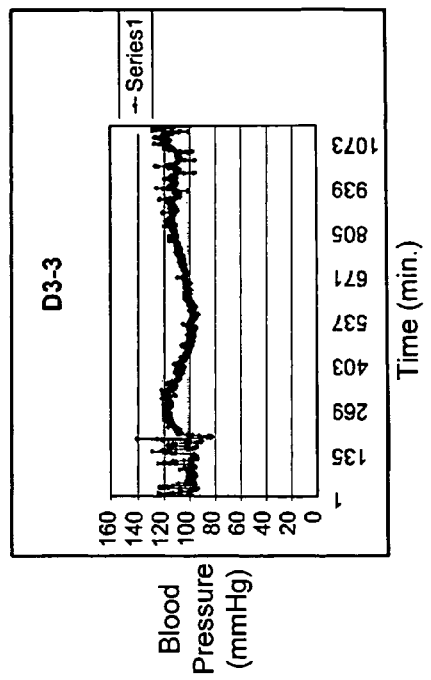
Figure 13A:
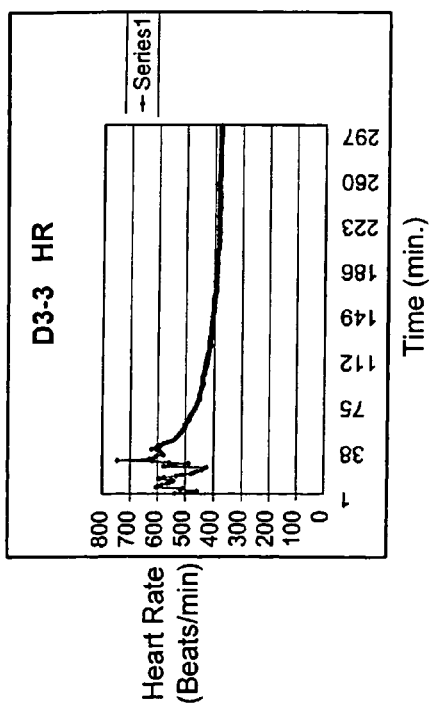
FIGS. 13A, 13B: Graph of heart rate vs. time (minutes), or blood pressure (mm Hg) vs. time (minutes), following intraperitoneal injection into a mouse of an iodo-thyronamine compound, $T_1$amine, measured over an approximately 4 hour period.
Figure 13B:
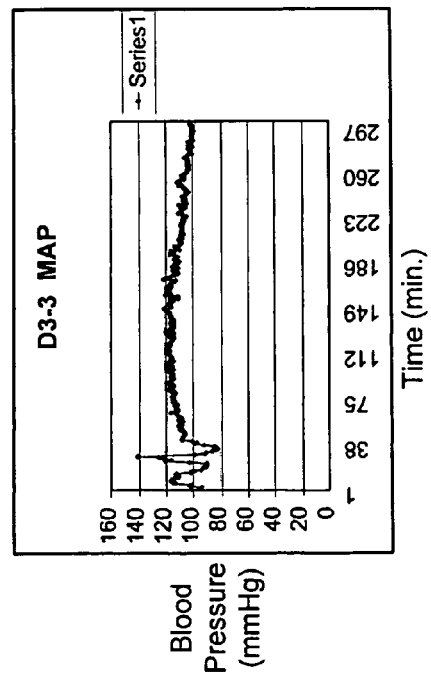

Thermal response was measured in an adult male C57Bl/6J mouse to a unilateral intracerebroventricular injection of $T_1AM$ dissolved in 60% DMSO/40% normal saline at a dose of 6.6 mg/kg body weight. The mouse was instrumented with a telemetry-emitting temperature sensing probe. See FIG. 9.

Heart rate and blood pressure responses were measured in an adult male C57Bl/6J mouse injected intraperitoneally with $T_1AM$ in 60% DMSO/40% normal saline at a dose of approximately 75-80 mg/kg body weight in two replicate experiments. See FIGS. 10 and 11.

Heart rate and blood pressure responses were measured in two drug naive adult male C57Bl/6J mouse following intraperitoneal injection of $T_1AM$ at a dose of approximately 75 mg/kg body weight. See FIGS. 12 and 13.

In each experiment, intraperitoneal or intracerebral injection of $T_1AM$ resulted in a decrease in core body temperature of the animal from approximately 38° C. to approximately 29° C. for a period of approximately 6.5 to 8 hours. This period was followed by a full recovery to a stable core body temperature of approximately 38° C. Heart rate of the animals remained constant throughout the treatment period. Blood pressure of the animals varied with the drop in body core temperature, but returned to normal levels within the same time frame as the body core temperature recovery.

Example 126

Effect of $T_0$ Amine or 3-Iodo-Thyronamine, $T_1AM$, on Blood Glucose Levels of Mice Injected Intraperitoneally An experiment demonstrated that compositions of the present invention, e.g., $T_1AM$ and $T_0AM$, increase blood glucose levels in mice in a dose-dependent manner significantly above controls when administered intraperitoneally (i.p.) to the mice.

Figure 14:
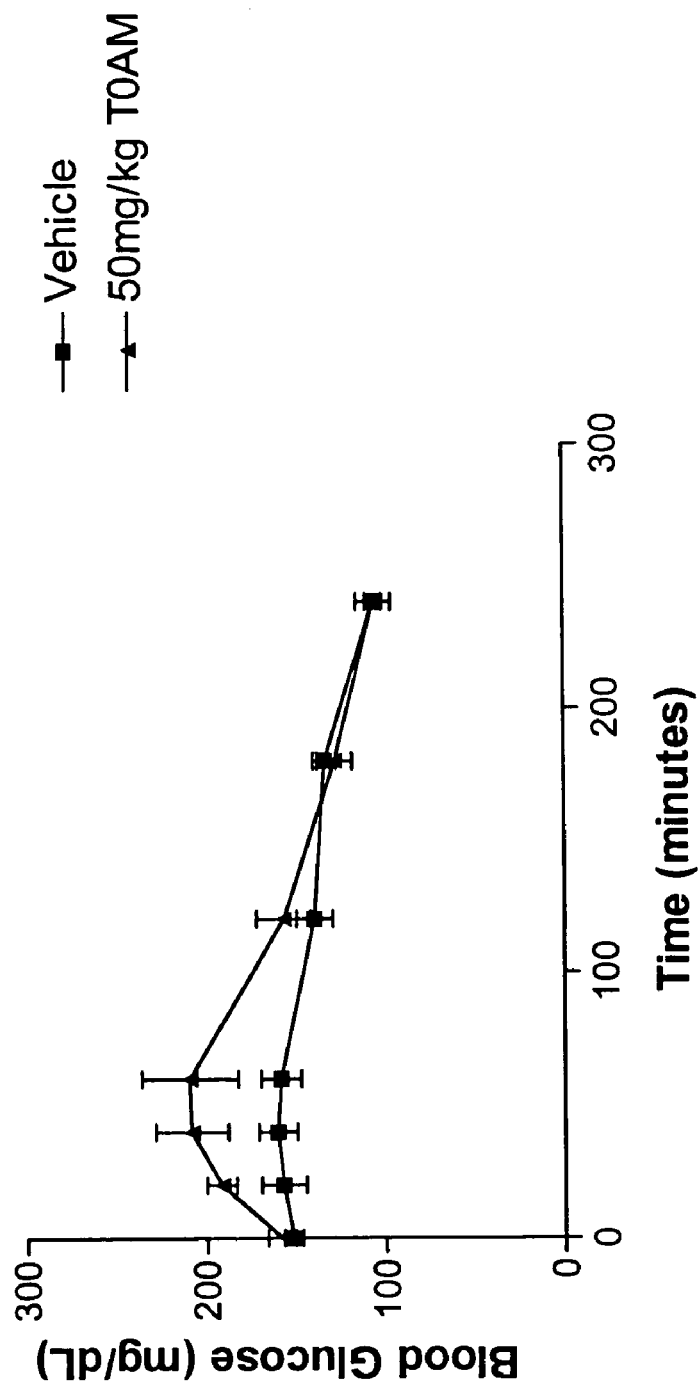
FIG. 14: The effects of $T_0$AM on blood glucose levels at room temperature (21° C.-22° C.).
Figure 15:
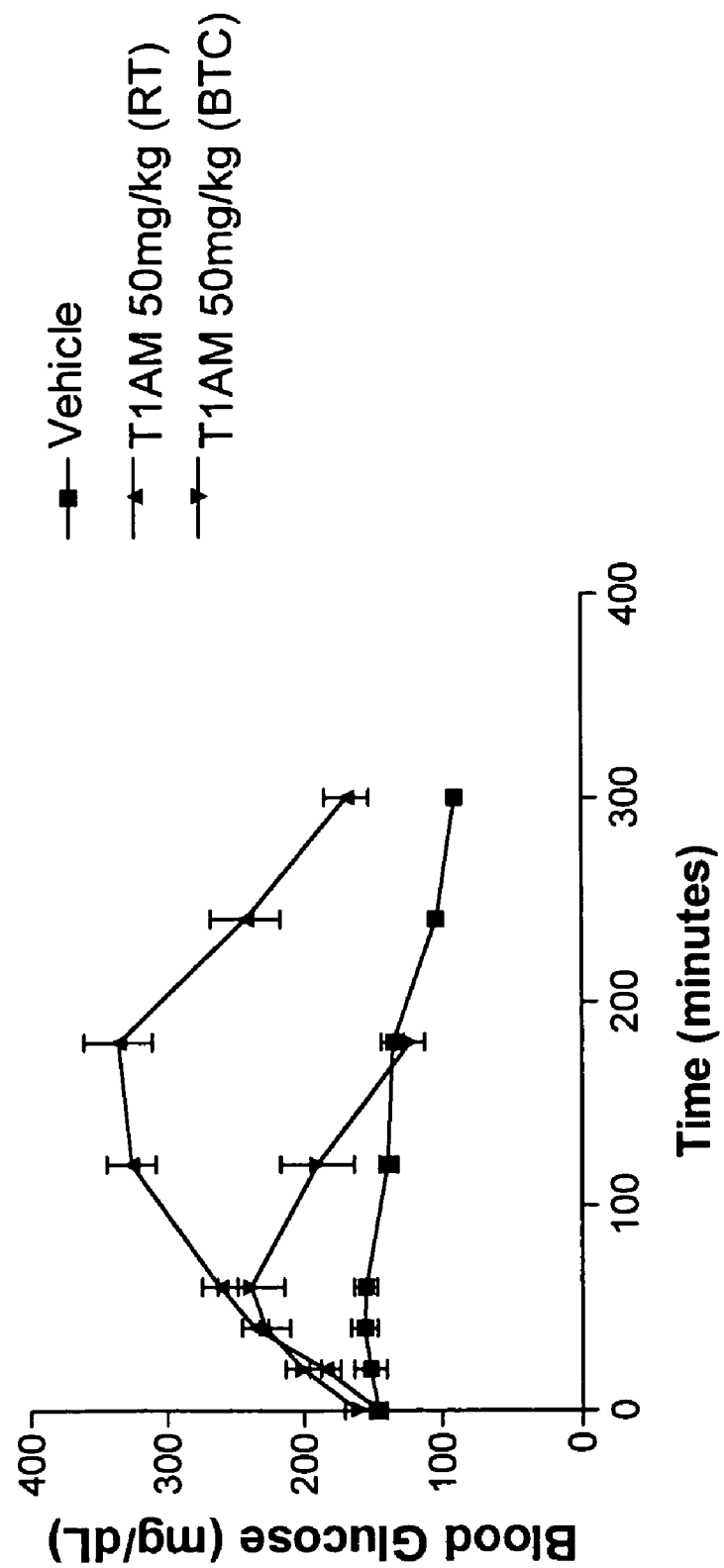
FIG. 15: The effect of $T_1$AM on mouse blood glucose levels at room temperature (RT; ambient temperature 21° C.-22° C.) and when body temperature is held constant near 37° C. (BTC; ambient temperature −31° C.).

When individual male and female inbred C57BL/6J mice were injected i.p. with either $T_0AM$ or $T_1AM$ a significant increase in blood sugar levels was detected as measured by a diabetic glucometer. FIG. 14 shows the effects of 50 mg/kg $T_0AM$ on blood glucose levels of mice housed at room temperature (21° C.-22° C.). The elevation in blood sugar occurs simultaneous with a significant decrease in the mouse's core body temperature. FIG. 15 shows the effects of 50 mg/kg $T_1AM$ on mouse blood glucose levels of mice at room temperature (RT; ambient temperature 21° C.-22° C.) or when body temperature is held constant near 37° C. (BTC; ambient temperature −31° C.). If body temperature is held constant using a heat lamp and pad, hyperglycemia produced by $T_1AM$ is still significant, but the effect is smaller in magnitude. The ability of $T_0AM$ to dose-dependently increase blood glucose levels in animals whose core body temperature is maintained at 37° C. by external heating devices is currently being evaluated.

The compositions of the present invention, thyronamines and analogs thereof, which are derivatives of thyroid hormone, the major homeostatic regulator of metabolism, can rapidly but transiently increase blood glucose levels. This provides insight into how blood sugar levels are normally regulated. The rapid and dramatic effect of these compounds on blood glucose suggests that they can be involved in conditions of blood sugar dysregulation such as diabetes, hyperglycemia, or hypoglycemia, as well as diseases of the thyroid gland (hypo and hyperthyroidism). Pharmaceutical compositions that contain thyronamine antagonists can be useful to regulate conditions related to blood sugar dysregulation, such as diabetes, hyperglycemia, or hypoglycemia, by controlling levels of blood sugar in a diabetic subject in need of treatment. Pharmaceutical compositions that contain thyronamine antagonists and agonists can be useful to regulate conditions related to diseases of the thyroid gland (hypo and hyperthyroidism).

The ability to manipulate $T_0AM$ and $T_1AM$ levels both in vivo and in vitro (by the administration of these molecules to animals or cell cultures; by developing and administering trace amine receptor antagonists to animals or cell cultures; and/or the manipulation of the biosynthetic pathways involved in the synthesis, storage, and degradation of these molecules) allows development of working models designed to evaluate the involvement of these and related molecules in normal and pathological states involving sugar homeostasis.

Example 127

Radioligand Binding Assay

In order to establish a complete dose response curve and $ED_{50}$ and to look at more doses of compositions of the present invention, especially lower doses, a radioligand binding assay can be useful to accurately measure theses parameters. This type of analysis can also be repeated in several species (e.g. mice, rats, guinea pigs, sheep, and primates). A number of normal and diseased human tissues (including blood) can be evaluated for the presence and abundance of $T_1AM$ and $T_0AM$. If detectable in human blood then it will be important to determine whether there is any correlation between abundance and disease states. Of course it will be important to seek a better understanding of the molecular and cellular mechanisms by which $T_1/T_0AM$ rapidly and transiently increase blood glucose levels. For these types of studies the establishment of a radioligand binding assay would be an invaluable addition to the sole functional assay we currently employ. Radiolabelled thyronamines or analogs thereof can be synthesized as shown for $^3H$ labeling (Scheme 17), $^2H$ labeling (Scheme 18) or $^{125}I$ labeling (Scheme 19). See above. These radiolabeled ($^3H$, $^2H$, or $^{125}I$) thyronamine ligands can be valuable reagents for identifying binding sites in vivo, following where these molecules go once injected into the animal, and where they traffic to at the cellular level.

Example 128

$T_1AM$ Levels Correlation to Depression and Mood

One of the most consistent clinical findings in individuals with severe hypothyroidism is depression. Furthermore, it has been well documented that the administration of thyroid hormone (TH) in the form of T3 can significantly hasten the responsiveness of depressed individuals undergoing tricyclic antidepressant therapy. The underlying mechanism of this potentiation remains to be elucidated. Other physiological manifestations of depression that may also have a TH component include thermoregulatory disturbances, decreased metabolic rate, decreased cardiorespiratory fitness, inactivity, and hyperglycemia. Recently we discovered 3-iodothyronamine ($T_1AM$), a novel endogenous metabolite of TH (Scanlan et al., *Nature Medicine* 10:638, 2004) that is a potent agonist of rodent and human G protein-coupled trace amine associated receptors (Lindemann et al., *Genomics* 85:372, 2005). Within minutes of being injected with $T_1AM$ mice respond with a reduction in their metabolic rate, body temperature, locomotor activity, and heart rate while blood glucose becomes elevated. $T_1AM$ can also rapidly reduce cardiac output in an ex vivo rat heart preparation Given the similarity between this collection of responses to $T_1AM$ in rodents and the manifestations of human depression we set out to test two hypothesis: 1) $T_1AM$ is present in humans and 2) the more $T_1AM$ there is in blood the more negative the individual's mood will be.

To establish the presence of $T_1AM$ and $T_0AM$ in human plasma and serum mass spectrometry coupled with high performance liquid chromatography was used in conjunction with chemically synthesized standards of $T_1AM$ and $T_0AM$.

Human blood was collected between the hours of 07:00 AM and 08:00 AM from (see data slides) 17 consenting, healthy, racially diverse, male and female volunteers between the ages of 24 and 30 years of age who had fasted overnight for at least 8 hours. None of the volunteers were diabetic or anemic. Prior to having their blood drawn each volunteer completed a demographic survey and the POMS mood assessment survey. All patient information was kept confidential and all processing of samples and analysis of the data was conducted by individuals blind as to which volunteer's sample was being evaluated.

Blood was collected in tubes designed for either the collection of plasma or serum. In the case of plasma, blood was drawn into a purple-top vacutainer tube and immediately placed on ice. To obtain plasma the whole blood was centrifuged at 2500 g for 10 minutes at 4° C. to pellet the red and white blood cells. The plasma harvested from each volunteer was aliquoted into 1 ml volumes and frozen at −80° C. until analyzed. Immediately prior to extraction the plasma (0.25-2.00 ml) was quickly thawed and placed on ice for extraction according to the method published by Scanlan et al. (*Nature Medicine* 10:638, 2004). In some instances 12N HCl was used in the initial protein precipitation step to improve recovery of the $T_1AM$ and $T_0AM$. Serum was obtained from whole blood collected in red-top vacutainer tubes that were rocked on a nutator for 20 minutes at room temperature. The serum was then harvested from the clot immediately after subjecting the tube to centrifugation at 2500 g for 10 minutes at 4° C. The serum collected from each volunteer was then separately aliquoted into 1 ml volumes and frozen at −80° C. until analyzed at which time 1-2 ml would be quickly thawed and placed on ice for extraction according to the method published by Scanlan et al. (*Nature Medicine* 10:638, 2004). In some cases 12N HCl was used in the initial protein precipitation step in an effort to improve the recovery of the $T_1AM$ and $T_0AM$.

Following complete evaporation each crude extract was resuspended in 25 microliters of 0.1N perchloric acid. Ten microliters of this solution was then fractionated by HPLC as described in Scanlan et al. (2004) with the resulting fractions subjected to analysis by mass spectrometry with channels set as described by Scanlan et al. (2004).

Confirmation that T₁AM and T₀AM are present in human plasma and serum was based on the retention time, mass of the parent ions, and their fragmentation spectra as reported by Scanlan et al. (2004).

Both T₀AM and T₁AM were detected using LC/MS (liquid chromatography-mass spectrometry) in unspiked plasma and serum from 17 volunteers. Statistical analysis demonstrated that plasma T₁AM peak intensities significantly positively correlated with the depression-dejection mood factor of POMS, as well as the total mood disturbance score.

Figure 16:
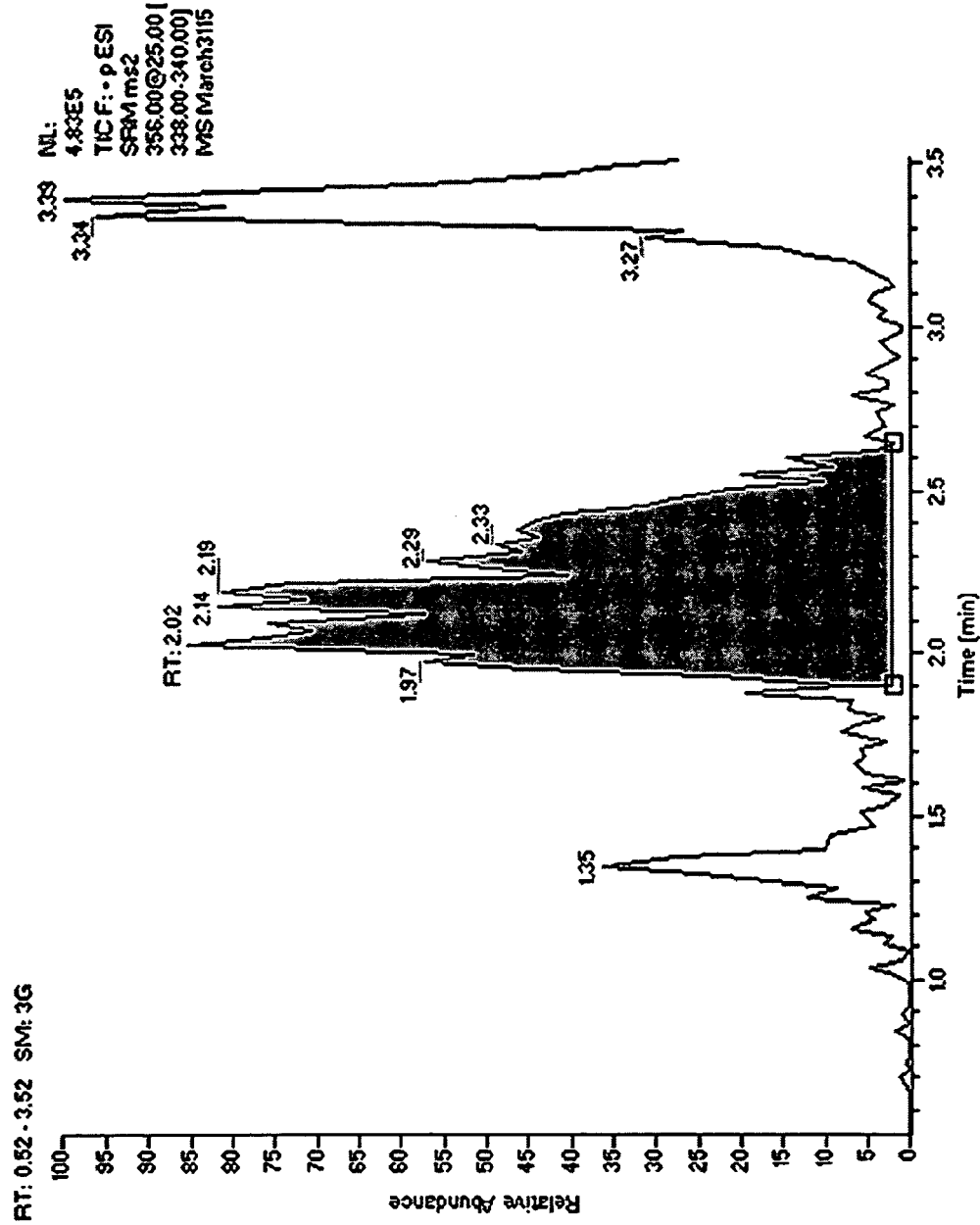
FIG. 16: HPLC trace of serum $T_1$AM in a human sample.

FIG. 16 shows an HPLC chromatogram of an extract of human serum showing a high intensity, broad peak with a retention time characteristic of T₁AM. (2.0-2.4 min).

Figure 17:
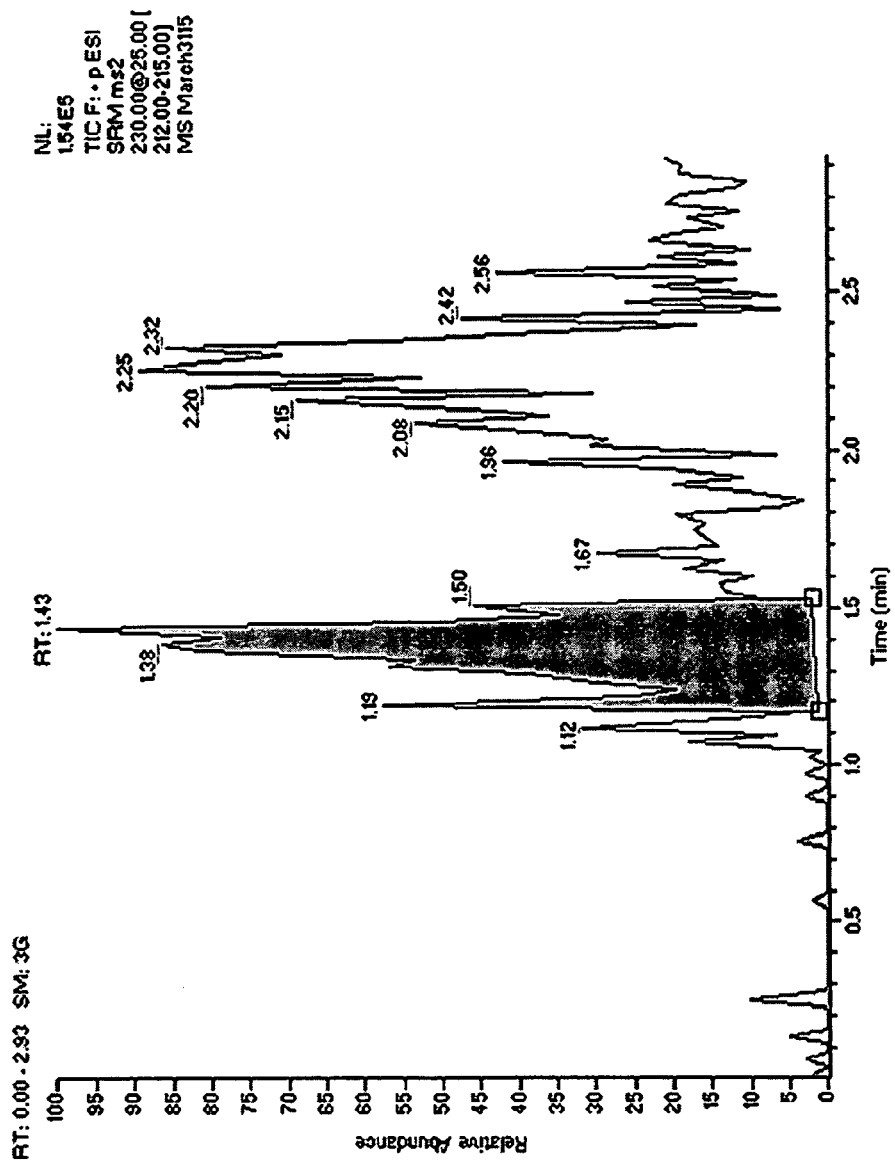
FIG. 17: HPLC trace of serum $T_0$AM in a human sample.

FIG. 17 shows an HPLC chromatogram of an extract of human serum showing a high intensity, broad peak with a retention time characteristic of T₀AM. (1.22-1.40 min)

Figure 18:
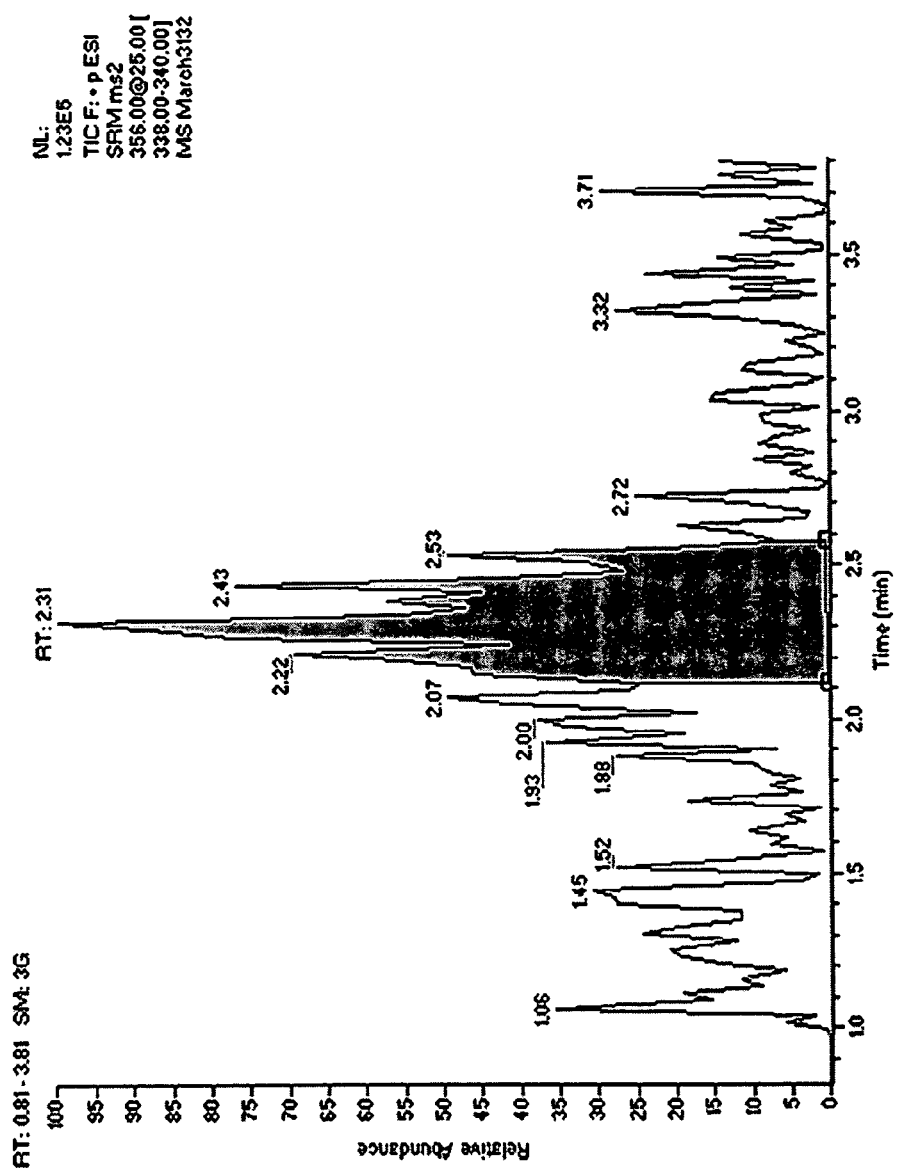
FIG. 18: HPLC trace of plasma $T_1$AM in a human sample.

FIG. 18 shows an HPLC chromatogram of an extract of human plasma showing a high intensity, broad peak with a retention time characteristic of T₁AM. (2.0-2.4 min)

Figure 19:
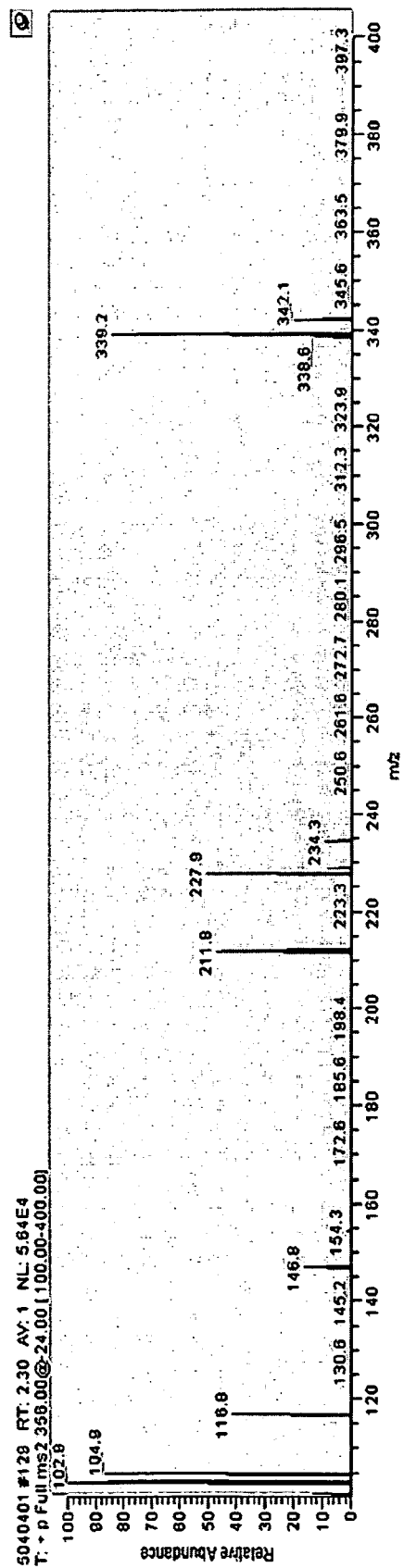
FIG. 19: Fragmentation spectrum for $T_1$AM of a human serum sample.

FIG. 19 shows fragmentation spectrum for T₁AM of a human serum sample. Expected daughter ions (212 & 339) are present following fragmentation of the putative T₁AM peak shown in FIG. 16. Y axis is unitless (relative intensity). X axis is the m/z ratio (mass/charge) for each daughter ion species FIG. 20 shows mass spectrometry peak intensities. No units are shown and is not quantitative. Peak intensities are relative to one another.

Peak plasma T₀AM levels showed a significant correlation with the confusion-bewilderment mood factor score. Significant correlation with Spearman correlation coefficient exists between: Plasma T₁AM and Depression-Dejection factor r=0.6458, p=0.0171 Plasma T1AM and total mood disturbance score r=0.6759, p=0.0112 Plasma T₀AM and Confusion-Bewilderment factor r=0.5540, p=0.0495. Serum peak intensities did not significantly correlate with any POMS factor.

No significant correlation with Pearson correlation coefficient exists between thyronamine peak intensity and any POMS mood factor, hemoglobin levels or blood glucose levels.

No significant correlation with Spearman correlation coefficient between serum thyronamine peak intensity and any POMS mood factor, hemoglobin levels or blood glucose levels.

No significant differences are seen between human males and human females in any of the POMS factor scores, POMS total mood disturbance score, hemoglobin, blood glucose, plasma/serum T₁AM/T₀AM peak intensities When considering personal and/or family history of depression, no significant differences are seen in any of the POMS factor scores, POMS total mood disturbance score, hemoglobin, blood glucose, plasma/serum T₁AM/T₀AM peak intensities.

Thyronamine levels can be detected using mass spectrometry and both T₀AM and T₁AM are present in humans and seems to significantly correlate with mood. The results of this study indicate that measuring an elevated levels of T₀AM and T₁AM in a human subject positively correlate with increased depression in the human subject as measured by the depression-dejection mood factor of POMS, as well as the total mood disturbance score. Our analysis of extracts prepared from spiked blood samples suggested 95% of the synthetic standards were lost in the extraction process. This is most likely due to problems with the extraction method making it difficult to quantify the amount of T₀AM and T₁AM in the human blood. Correlation with mood is limited due to study parameters. The sample size is 17, and the sample population was limited to first year medical students. Furthermore, timing of blood draw may influence mood since the blood was drawn after an 8 hour fast in the early morning, and events occurring within the sample population may have influenced thyronamine levels and mood. These results suggest that further studies of these interesting compounds are warranted.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula IV:

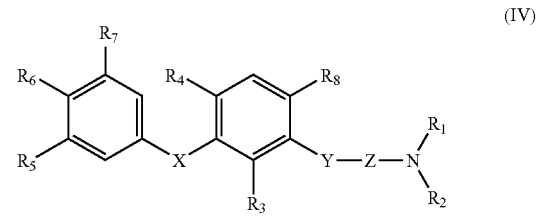

(IV)

or a stereoisomer, prodrug, pharmaceutically acceptable salt, hydrate, solvate, acid salt hydrate, N-oxide or isomorphic crystalline form therof;

wherein independently, $R_1$ and $R_2$ are H, lower alkyl, cyclic alkyl, or benzyl;

Y is —[C(R'R")]$_n$—, where R' is H, and R" is aryl optionally substituted with 1-3 substituents selected from the group consisting of lower alkyl, halo, hydroxyl, and alkoxy; or benzyl wherein the phenyl portion thereof is optionally substituted with 1-3 substituents selected from the group consisting of lower alkyl, halo, hydroxyl, and alkoxy;

Z is —[C(R)$_2$]$_n$—, CHOR, O, S, NR, CONH, or NHCO;

$R_3$, $R_4$, $R_5$, and $R_7$ I, Br, Cl, F, H, $CH_3$, $CF_3$, CN, SR, $OCH_3$, $CH_2CH_3$, or $CH(CH_3)_2$;

$R_6$ is OH, H, SH, F, $CF_3$, lower alkyl, or $N(R)_2$;

$R_8$ is OR, R, $CH_2OR$, $CH_2NR_2$, $CH_2N^+R_3$, SR, or $CH_2SR$;

X is O, S, SO, $SO_2$, NR, $C(R)_2$, -lower alkyl-O—, —O-lower alkyl-, $COCH_2O$, or $OCH_2CO$;

R is H, lower alkyl, aryl optionally substituted with 1-3 substituents selected from the group consisting of lower alkyl, halo, hydroxy, and alkoxy; or benzyl wherein the phenyl portion thereof is optionally substituted with 1-3 substituents selected from the group consisting of lower alkyl, halo, hydroxy, and alkoxy; and n is 1 to 6.

2. The compound of claim 1, wherein $R_1$ and $R_2$ are H or lower alkyl, $R_6$ is H, X is O, Y is O, and Z is alkyl.

3. The compound of claim 1, wherein R" is phenyl optionally substituted with 1-3 substituents selected from the group consisting of lower alkyl, halo, hydroxyl, and alkoxy.

4. A pharmaceutical composition, comprising at least one compound of claim 1 in combination with at least one pharmaceutically acceptable carrier or excipient.

5. A method for alleviating a disease state in a mammal believed to be responsive to treatment with a thyronamine antagonist comprising the step of administering to the mammal a therapeutic amount of a compound of claim 1, or a stereoisomer, prodrug, pharmaceutically acceptable salt, hydrate, solvate, acid salt hydrate, N-oxide or isomorphic crystalline form thereof.

6. The method of claim 5, wherein the disease state is depression, bipolar disorder, schizophrenia, eating disorders, anxiety, seizure, epilepsy, insomnia and sleeping disorders, gastro esophageal reflux disease, diseases involving gastrointestinal motility or asthma.

7. The method of claim 5, wherein the disease state is diabetes, hyperglycemia, hypoglycemia, cardiac arrhythmia, stroke, osteoporosis, obesity, atherosclerosis, hypertension, hyperthyroidism or hypothyroidism.

8. The method of claim 5, wherein the disease state is congestive heart failure.

9. The method of claim 5, wherein the disease state is fever or heatstroke.

10. A method of treating depression in a mammalian subject believed to be responsive to treatment with a thyronamine antagonist comprising administering a therapeutically effective amount of a compound of claim 1, or a stereoisomer, prodrug, pharmaceutically acceptable salt, hydrate, solvate, acid salt hydrate, N-oxide or isomorphic crystalline form thereof, to the subject.

11. The compound of claim 1, wherein $R_1$ through $R_8$ are H.

12. The compound of claim 1, wherein X is O.

13. The compound of claim 3, wherein R" is phenyl.

14. The compound of claim 1, wherein Z is —$CH_2$—.

15. The compound of claim 11, wherein X is O.

16. The compound of claim 15, wherein Y is —CH (phenyl)—.

17. The compound of claim 16, wherein Z is —$CH_2$—.

* * * * *